US008759293B2

(12) United States Patent
Barnett

(10) Patent No.: US 8,759,293 B2

(45) Date of Patent: Jun. 24, 2014

(54) VON WILLEBRAND FACTOR (VWF)-CONTAINING PREPARATIONS, AND METHODS, KITS, AND USES RELATED THERETO

(75) Inventor: Thomas Barnett, Research Triangle Park, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 0 days.

(21) Appl. No.: 13/509,309

(22) PCT Filed: Nov. 12, 2010

(86) PCT No.: PCT/US2010/056496

§ 371 (c)(1), (2), (4) Date: Jul. 31, 2012

(87) PCT Pub. No.: WO2011/060242

PCT Pub. Date: May 19, 2011

(65) Prior Publication Data

US 2012/0289468 A1 Nov. 15, 2012

Related U.S. Application Data

(60) Provisional application No. 61/261,145, filed on Nov. 13, 2009.

(51) Int. Cl.

| | |
|---|---|
| ***A61K 38/37*** | (2006.01) |
| ***C07K 14/755*** | (2006.01) |
| ***A61K 38/16*** | (2006.01) |
| ***C12N 5/00*** | (2006.01) |
| ***C12N 5/02*** | (2006.01) |
| ***C12N 5/07*** | (2010.01) |
| ***C12N 5/16*** | (2006.01) |
| ***C07K 1/00*** | (2006.01) |
| ***C07K 14/00*** | (2006.01) |
| ***C07K 17/00*** | (2006.01) |
| ***A61K 35/14*** | (2006.01) |
| ***C07K 16/00*** | (2006.01) |
| ***C12P 21/08*** | (2006.01) |

(52) U.S. Cl.

USPC ......... 514/14.1; 514/21.2; 435/325; 435/328; 435/337; 530/350; 530/383; 530/387.1; 530/387.3

(58) Field of Classification Search

None

See application file for complete search history.

(56) References Cited

U.S. PATENT DOCUMENTS

| | | | | |
|---|---|---|---|---|
| 4,511,503 | A | 4/1985 | Olson et al. | |
| 4,631,211 | A | 12/1986 | Houghten et al. | |
| 4,652,639 | A | 3/1987 | Stabinsky et al. | |
| 4,965,195 | A | 10/1990 | Namen et al. | |
| 4,968,607 | A | 11/1990 | Dower et al. | |
| 5,043,429 | A | 8/1991 | Zimmerman et al. | |
| 5,073,627 | A | 12/1991 | Curtis et al. | |
| 5,075,371 | A | 12/1991 | Boschetti et al. | |
| 5,149,637 | A | 9/1992 | Scandella et al. | |
| 5,200,510 | A | 4/1993 | Kumar et al. | |
| 5,234,991 | A | 8/1993 | Tayot et al. | |
| 5,250,421 | A | 10/1993 | Kaufman et al. | |
| 5,252,709 | A | 10/1993 | Burnouf et al. | |
| 5,260,274 | A | 11/1993 | Zimmerman et al. | |
| 5,268,097 | A | 12/1993 | Girot et al. | |
| 5,350,683 | A | 9/1994 | Sims et al. | |
| 5,364,771 | A | 11/1994 | Lollar et al. | |
| 5,422,250 | A | 6/1995 | Mignot et al. | |
| 5,539,086 | A * | 7/1996 | Farb et al. | 530/383 |
| 5,597,711 | A | 1/1997 | Zimmerman et al. | |
| 5,633,150 | A | 5/1997 | Wood et al. | |
| 5,661,008 | A | 8/1997 | Almstedt et al. | |
| 5,668,108 | A | 9/1997 | Capon et al. | |
| 5,670,625 | A | 9/1997 | Lyman et al. | |
| 5,683,912 | A | 11/1997 | Elgoyhen et al. | |
| 5,688,912 | A | 11/1997 | Dadd et al. | |
| 5,804,420 | A | 9/1998 | Chan et al. | |
| 5,849,989 | A | 12/1998 | Edlund et al. | |
| 5,880,265 | A | 3/1999 | Fischer et al. | |
| 6,040,143 | A | 3/2000 | Venta et al. | |
| 6,074,832 | A | 6/2000 | Venta et al. | |
| 6,307,032 | B1 | 10/2001 | Schonhofer et al. | |
| 6,312,893 | B1 | 11/2001 | Van Ness et al. | |
| 6,444,422 | B2 | 9/2002 | Van Ness et al. | |
| 6,489,290 | B2 | 12/2002 | Loscalzo et al. | |
| 6,579,723 | B1 | 6/2003 | Mitterer et al. | |
| 6,613,508 | B1 | 9/2003 | Van Ness et al. | |
| 6,623,928 | B2 | 9/2003 | Van Ness et al. | |

(Continued)

FOREIGN PATENT DOCUMENTS

| | | |
|---|---|---|
| EP | 367566 | 5/1997 |
| EP | 460846 | 2/2002 |

(Continued)

OTHER PUBLICATIONS

Bonnefoy et al., "von Willebrand factor A1 domain can adequately substitute for A3 domain in recruitment of flowing platelets to collagen," J. Thrombosis and Haemostasis 4:2151-2161 (2006).*

Blast sequence aligment between US 2005/0147618, SEQ ID No. 2 and presently claimed SEQ ID No. 16 (conducted on Apr. 25, 2013).*

Bonnefoy et al., "von Willebrand factor A1 domain can adequately substitute for A3 domain in recruitment of flowing platelets to collagen," J. Thrombosis & Haemostatis 4:2151-2161 (2006).*

Titani et al., "Amino Acid Sequence of Human von Willebrand Factor," Biochem. 25:3171-3184 (1986).*

Andrews, R.K., "Platelet Adhesion: A Game of Catch and Release," *J. of Clinical Investigation*, 118(9): 3009-3011 (2008).

Arakawa, T., et al., "MEP Chromatography of Antibody and Fc_Fusion Protein Using Aqueous Arginine Solution," *Prot. Expr. Purif.*, 63:158-163 (2009).

(Continued)

*Primary Examiner* — James H Alstrum Acevedo

*Assistant Examiner* — Thea D'Ambrosio

(74) *Attorney, Agent, or Firm* — Womble Carlyle Sandridge & Rice, LLP

(57) ABSTRACT

The present invention relates to methods, compositions and kits for preparing FVIII and employing same. Also provided are vWF polypeptides and nucleic acid molecules encoding same.

10 Claims, 11 Drawing Sheets

(56) References Cited

U.S. PATENT DOCUMENTS 6,664,112 B2 12/2003 Mulligan et al.
6,844,191 B2 1/2005 Gordon et al.
6,855,544 B1 2/2005 Hatteboer et al.
6,953,837 B2 10/2005 Mitterer
7,144,996 B1 12/2006 de Sauvage et al.
7,189,690 B2 3/2007 Rosen et al.
7,211,559 B2 5/2007 Saenko et al.
7,317,091 B2 * 1/2008 Lazar et al. ................ 530/387.1
7,348,004 B2 * 3/2008 Peters et al. ............... 424/178.1
7,404,956 B2 7/2008 Peters et al.
7,439,043 B2 10/2008 DeFrees et al.
7,589,073 B2 9/2009 Diener et al.
7,604,960 B2 10/2009 Hateboer et al.
7,645,609 B2 1/2010 Follstad et al.
7,648,958 B2 1/2010 Mitterer
2002/0032317 A1 3/2002 Blank
2002/0077471 A1 6/2002 Mulligan et al.
2002/0119456 A1 8/2002 Van Ness et al.
2003/0126629 A1 7/2003 Rapp et al.
2004/0087778 A1 * 5/2004 Feige et al. ................ 530/391.1
2004/0249134 A1 12/2004 Lollar et al.
2005/0054568 A1 3/2005 Ling et al.
2005/0074836 A1 4/2005 Lenting et al.
2005/0147618 A1 * 7/2005 Rivera et al. ............... 424/178.1
2005/0153383 A1 7/2005 Montgomery et al.
2005/0164386 A1 7/2005 Uytdehaag et al.
2005/0226864 A1 10/2005 Hinton et al.
2006/0099685 A1 5/2006 Yallop et al.
2006/0211033 A1 9/2006 Callen et al.
2007/0160534 A1 7/2007 Dennis et al.
2008/0096223 A1 4/2008 De Groot et al.
2008/0221032 A1 9/2008 Turecek et al.
2009/0192076 A1 7/2009 Matthiessen et al.
2009/0221100 A1 9/2009 Weber et al.
2010/0055093 A1 3/2010 Shepard et al.
2010/0184141 A1 7/2010 Schroeder et al.
2011/0086362 A1 4/2011 Wang et al.
2011/0262424 A1 10/2011 Sandberg et al.

FOREIGN PATENT DOCUMENTS

EP 1624891 8/2009
WO WO97-27331 7/1997
WO WO99-05322 2/1999
WO WO01-94366 12/2001
WO WO03-54232 7/2003
WO WO 2006-016168 2/2006
WO WO 2007-090584 8/2007
WO WO-2008/077616 7/2008
WO WO 2009-079382 6/2009
WO WO-2009/156137 12/2009
WO WO 2011-060242 5/2011

OTHER PUBLICATIONS

Ashkenazi, A , et al., "Protection against endotoxic shock by a tumor necrosis factor receptor immunoadhesin," *PNAS*, 88:10535 (1991).

Bahou, W.F., et al., "A Monoclonal Antibody to von Willebrand Factor (vWF) Inhibits Factor VIII Binding," *J. Clin. Invest*., 84:56-61 (1989).

Bonnefoy, A., et al., "Shielding the Front-Strand B3 of the von Willebrand Factor A1 Domain Inhibits its Binding to Platelet Glycoprotein Iba," *Blood*, 101:1375-1383 (2003).

Bonnefoy, A., et al., "von Willebrand Factor A1 Domain Can Adequately Substitute for A3 Domain in Recruitment of Flowing Platelets to Collagen," *J. Thrombosis and Haemostasis*, 4(10):2151-2161 (2006).

Bowie, J. U., et al., "Deciphering the Message in Protein Sequences: Tolerance to Amino Acid Substitutions," *Science* 247;1306-1310 (1990).

Byrn, R.A., et al., "Biological Properties of a CD4 Immunoadhesin," *Nature* 344:677 (1990).

Chang, Y., et al., "Structure and Ligand Binding Determinants of the Recombinant Kringle 5 Domain of Human Plasminogen," *Biochemistry* 37:3258-3271 (1998).

Chauhan, A., et al., "Von Willebrand Factor and factor VIII are Independently Required to Form Stable Occlusive Thrombi in Injured Veins," *Blood*, 109(6): 2424-2429 (2007).

Cosman, D., et al., "high Level Stable Expression of Human Interleukin-2 Receptors in Mouse Cells Generates Only Low Affinity Interleukin-2 Binding Sites," *Mol. Immun*., 23(9): 935-941 (1986).

Cosman, D., et al., "Cloning, Sequence and Expression of Human Interleukin-2 Receptor," *Nature* 312: 768-771 (1984).

Cunningham and Wells, "High-Resolution Epitope Mapping of hGH-Receptor Interactions by Alanine-Scanning Mutagenesis," *Science* 244:1081-1085 (1989).

Dayhoff, M.O., et al., "Matrices for Detecting Distant Relationships," *Atlas of Protein Sequence and Structure*, 3:353-358 (1978).

de Vos, A. M., et al. "Human Growth Hormone and Extracellulair Domain of its Receptor: Crystal Structure of the Complex," *Science* 255:306-312 (1992).

Denis, C., et al., "Clearance of von Willebrand Factor," *Thromb. Haemost*, 99: 271-278 (2008).

Ellison, J., et al., "The Nucleotide Sequence of a Human Immunoglobulin Cγ1 Gene," *Nucl. Acid Res*., 10:4071-4079 (1982).

Fischer, B.E., et al., "Structural analysis of recombinant von Willebrand factor produced at industrial scale fermentation of transformed CHO cells co-expressing recombinant furin," *FEBS Lett*. 375:259-262 (1995).

Fischer, et al., "Recombinant von Willebrand Factor: Potential Therapeutic Use," *J. Thromb. Haemost*., 8: 197-205 (1999).

Foster, P.A., et al., "A Major Factor VIII Binding Domain Resides within the Amino-Terminal 272 Amino Acid residues of von Willebrand Factor," *JBC*, 262:8443 (1987).

Fulcher, C.A., et al., "Human Factor VIII Procoagulant Protein," *J. Clin. Invest*., 76:117-124 (1985).

Gillies, S., et al., "Improved Circulating Half-Life and Efficacy of an Antibody-Interleukin 2 Immunocytokine Based on Reduced Intracellular Proteolysis," *Clin. Cancer Res*., 8: 210-216 (2002).

Gregoriadis, G., et al., "Improving the Therapeutic Efficacy of Peptides and Proteins: A Role for Polysialic Acids," *Internat. J. Pharm*. 300: 125-300 (2005).

Gribskov, M., et al., "Sigma Factors from *E. Coli, B. Subtilis*, Phage SP01, and Phage T4 are Homologous Proteins," *Nucl. Acids Res*. 14(6):6745-6763 (1986).

Hannah, M.J., et al., "Differential Kinetics of Cell Surface Loss of von Willebrand factor and Its Propolypeptide After Secretion from Weibel-Palade bodies in Living Human Endothelial Cells," *J. Biological Chem*., 280(24): 22827-22830 (2005).

Harlow, E and Lane, D. Antibodies: A Laboratory Manual, 116-223. (1988).

Hinnen, A., et al., "Transformation of Yeast," *Proc. Natl. Acad. Sci*., 75:1929, 1978.

Houghten, R. A., "General method for the rapid solid-phase synthesis of large numbers of peptides: Specificity of antigen-antibody interaction at the level of individual amino acids," *Proc. Natl. Acad. Sci*., 82:5131-5135 (1985).

Hsu, T-C., et al., "The Factor VIII C1 Domain Contributes to Platelet binding," *Blood*, 111:200-208 (2008).

Hu, S-Z., et al., "Minibody: A Novel Engineered Anti-Carcinoembryonic Antigen Antibody Fragment (Single-Chain Fv-CH3) Which Exhibits Rapid, High-Level Targeting of Xenografts," Cancer res., 56: 3055-3061 (1996).

Kalind, M.P., et al., "The B-domain of Factor VIII reduces cell membrane attachment to host cells under serum free conditions," *J. Biotechnology*, 147:198-204 (2010).

Kaufman, R., et al., "Effect of von Willebrand Factor Coexpression on the Synthesis and Secretion of Factor VIII in Chinese Hamster Ovary Cells," *Mol. Cell. Biol*., 9:1233-1242 (1989).

Konigs c., et al., "A review of current literature on second-generation, sucroseformulated, full-length recombinant factor VIII," *Drugs of Today*, 45(7): 549-561 (2009).

Kontermann, R., et al., "Strategies to Extend Plasma Half-Lives of Recombinant Antibodies," *Biodrugs*, 23: 93-109 (2009).

Laidler, P., et al., "Tumor Cell N-Glycans in Metastasis," *Acta Biochimica Polonica*, 44(2): 343-358 (1997).

(56) References Cited

OTHER PUBLICATIONS

Lenting, J.P., et al., "An Experimental Model to Study the in Vitro Survival of von Willebrand Factor," *J. Biological Chemistry*, 279(13): 12102-12109 (2004).
Lillicrap, D., "Extending Half-Life in Coagulation Factors: Where Do We Stand?" *Thromb. Res.*, 122 Suppl. 4:S2-S8 (2003).
Low, S.C., et al., "Oral and Pulmonary Delivery of FSH-Fc Fusion Proteins via Neonatal Fc receptor-Mediated Transcytosis," *Human Reproduction*, 20(7),1805-1813 (2005).
Luckow, V.A., et al., "Trends in the Development of Baculovirus Expression Vectors," *Bio/Technology* 6:47-55 (1988).
Lusher, J.M., et al., "Evolution of Recombinant Factor VIII Safety: Kogenate and Kogenate FS/Bayer," *Intl. J. Hematol.* 90(4):446-454 (2009).
McMahan, C.J., et al, "A novel IL-1 receptor, cloned from B cells by mammalian expression, is expressed in many cell types," *EMSO J.* 10:2821(1991).
Mordenti, J., et al., "Pharmacokinetics and Interspecies Scaling of Recombinant Human Factor VIII," *Toxicol. Appl. Pharmacol.*, 137:75-78 (1996).
Mori, F., et al., "Progress in Large-Scale Purification of Factor VIII/ von Willebrand Factor Concentrates using Ion-Exchange Chromatography," *Vox Sanginuis*, 95: 298-307 (2008).
Nakayama, J., et al., "A Human Polysialyltransferase Directs in vitro Synthesis of Polysialic Acid," *J. Bio. Chem.*, 271: 1829-1832 (1996).
Nakayama, J., et al., "Polysialic Acid, a Unique Glycan that is Developmentally Regulated by Two Polysialyltransferases. PST and STX, in the Central Nervous System; from Biosynthesis to Function," *Pathol. Inter*. 48:665-677 (1998).
Okayama; H., et al., "A cDNA Cloning Vectror that Permits Expression of cDNA Inserts in Mammalian Cells," *Mol. Cell. Biol.* 3:280-289 (1983).
Pan, J., et al., "Enhanced Efficacy of Recombinant FVIII in Noncovalent Complex with PEGylated Liposome in Hemophilia A Mice," *Blood* 114(13): 2802-2811 (2009).
Raines, G., et al., "Multimeric Analysis of Von Willebrand Factor by Molecular Sieving Electrophoresis in Sodium Dodecyl Sulphate Agarose Gel" *Thrombosis Res.*,60:201-212 (1990).
Ruggeri, Z.M., "The Role of von Willebrand Factor in Thrombus Formation," *Thromb. Res.*, 120(Suppl 1): S5-S9. (2007).
Sadler, J.E., et al., "Cloning and characterization of two cDNAs coding for human von Willebrand factor," *PNAS*, 82:6394-6398 (1985).
Schwartz, H.P., "Recombinant von Willebrand Factor—Insight into Structure and Function Through Infusion Studies in Animals with Severe von Willebrand Disease," *Semin. Thromb. Hemost*. 28: 215-226(2002).
Shen, J., et al., "Single Variable Domain-IgG Fusion a Novel Recombinant Approach to Fc Domain-Containing Bispecific Antibodies," *J. Biological Chem.*, 281(16):10706-10714 (2006).
Shu, L., et al., "Secretion of a Single-Gene-Encoded Immunoglobulin from Myeloma Cells," *PNAS* 90:7995-7999 (1993).
Smith, T,.F. and M.S. Waterman. "Comparison of Biosequences," *Advances in Applied Mathematics* 2:482-489 (1981).
Smith, L.J.. Et al. "Human Interleukin 4 the Solution Structure of a Four helix Bundle Protein," *J. Mol. Biol.* 224:899-904 (1992).
Suiter, T.M., et al., "First and next generation native rFVIII in the treatment of hemophilia A. What has been achieved? Can patients be switched safely?" *Semin Thromb Hemost*., 28(3):277-284 (2002).
Titani, K., et al., "Amino Acid Sequence of Human von Willebrand Factory," *Biochemistry*, 25:3171-84 (1986).
Trail, D., "Minimizing Purification Time with Parallel Purification of Proteins," *Poster*, (2004).
Torecek, P.L., et al., "Development of a plasma-and albumin-free recombinant von Willebrand factor," *Hamostaseologie*, 29: Suppl. 1, S32-S38, (2009).
Valiera, D., et al., "Molecular Modification of a Recombinant, Bivalent Anti-Human CD3 Immunotoxin (Bic3) Results in Reduced in Vivo Toxicity in Mice," *Leukemia Res.*, 29(3): 331-341 (2009).
Van Rooijen, J.M., et al., "Sulfated di-, tri- and tetraantennary N-glycans in human Tamm-Horsfall glycoprotein," *Eur. J. Biochem.*, 256: 471-478 (1998).
van Schooten, C.J., et al., "Microphages Contribute to the Cellular Uptake of von Willebrand Factor and Factor VIII in Vivo," *Blood*, 112: 1704-1712 (2008).
Vlot, A., et al., "Kinetics of Factor VIII—von Willebrand Factor Association," *Blood*, 87: 1809-1816 (1996).
Williams, S.C., et al., "Production and Functional Activity of a Recombinant von Willebrand Factor-A Domain from Human Complement Factor B," *J. Biochem.*, 342:625-632 (1999).
Wise, R.J., et al., "The Polypeptide of von Willebrand Factor Independently Mediates the Assembly of von Willebrand Multimers," *Cell*, 52:229-236 (1988).
Wood, W.I., et al., "Expression of Active Human Factor VIII from Recombinant DNA Clones,"*Nature*, 312:330-7 (1984).
Yee, A., et al., "[P-MO-445] Stabilization of FVIII by VWF Fragments," *Abstract*, presented at ISTH on Monday, Jul. 25—ISTH 2011—XXIII.
Zhou, W., et al., "An Enzyme Immunoassay of ADAMTS14 Distinguishes Patients with Thrombotic Thrombocytopenic Purpura from Normal Individuals and Carriers of ADAMTS13 Mutations," *Thrombosis and Haemostasis*, 91(4): 806-811 (2004).
Extended European Search Report for corresponding European Application No. 10830777.8 dated Aug. 1, 2013.
Hodges, Characterization of the Recombinant Human Factor VIII Expressed in the Milk of Transgenic Swine: Chapter 1., An Introduction to Factor VIII and its Inherent Instability, Jan. 12, 2001, available at http://scholar.lib.vt.edu/theses/available/etd-02232001-144721/.
Invivogen, "Engineered Fc regions reviews," downloaded from website on Jul. 23, 2013: www.invivogen.com/review-engineered-pfuse-chig.
Filpula, D.R., GenBank Accession No. X70421; according to NCBI online revision history, first seen at NCBI on Apr. 21, 1993; pp. 1-2.
Pietu, G., GenBank Accession No. NP000543; according to NCBI online revision history, first seen at NCBI on Mar. 24, 1999; pp. 1-8.
RefSeqGene project, GenBank Accession No. NM000552; according to NCBI online revision history, first seen at NCBI on Mar. 24, 1999; pp. 1-9.
Garfinkel, L., GenBank Accession No. AAE20723; according to NCBI online revision history, first seen at NCBI on Sep. 30, 1999; p. 1.
Sadler, J.E., GenBank Accession No. AAB59512; according to NCBI online revision history, first seen at NCBI on Aug. 3, 1993; pp. 1-3.
UniProtKB, GenBank Accession No. P04275; according to NCBI online revision history, first seen at NCBI on Apr. 24, 1993; pp. -1-30.
Mural R.J., GenBank Accession No. EAW88815; according to NCBI online revision history, first seen at NCBI on Dec. 18, 2006; pp. 1-5.
Cargill, M., GenBank Accession No. ACP57027; according to NCBI online revision history, first seen at NCBI on Apr. 29, 2009; pp. 1-4.
Mural, R.J., GenBank Accession No. EAW88816; according to NCBI online revision history, first seen at NCBI on Dec. 18, 2006; pp. 1-5.
Venta, P.J., GenBank Accession No. AAD04919; according to NCBI online revision history, first seen at NCBI on Jan. 14, 1999; pp. 1-4.
Gitschier, J., GenBank Accession No. AAA52420.1; according to NCBI online revision history, first seen at NCBI on Apr. 27, 1993; pp. 1-3.
Wood, W.I., GenBank Accession No. CAA25619.1; according to NCBI online revision history, first seen at NCBI on Apr. 21, 1993; pp. 1-3.
Toole, J.J., GenBank Accession No. AAA52484.1; according to NCBI online revision history, first seen at NCBI on Apr. 27, 1993; pp. 1-2.
Toole, J.J., GenBank Accession No. 1012298A; according to NCBI online revision history, first seen at NCBI on Apr. 29, 1993; pp. 1-2.
Mural, R.J., GenBank Accession No. EAW72647.1; according to NCBI online revision history, first seen at NCBI on Dec. 18, 2006; pp. 1-3.

(56) References Cited

OTHER PUBLICATIONS

Mural, R.J., Genbank Accession No. EAW72646.1; according to NCBI online revision history, first seen at NCBI on Dec. 18, 2006; pp. 1-3.
GenBank Accession No. XP_001498954.1; according to NCBI online revision history, first seen at NCBI on Jun. 25, 2007; pp. 1-2.
Green, E.D., GenBank Accession No. ACO95359.1; according to NCBI online revision history, first seen at NCBI on Apr. 17, 2009; pp. 1-3.
Khalaj, M., GenBank Accession No. NP_001138980.1; according to NCBI online revision history, first seen at NCBI on Mar. 2, 2009; pp. 1-2.
Greene, E.D., GenBank Accession No. ABZ10503.1; according to NCBI online revision history, first seen at NCBI on Feb. 6, 2008; pp. 1-2.
Herman, G.E., GenBank Accession No. NP_032003.2; according to NCBI online revision history, first seen at NCBI on Jan. 6, 2000; pp. 1-4.
Teledyne ISCO, BioOptix 10 Parallel Protein Purification, 2008.

* cited by examiner

A. Wild type von Willebrand Factor structure

B. vWF polypeptide

A. Wild type von Willebrand Factor structure

B. vWF domain segments with fusion to Fc of $IgG_1$

C. vWF-Fc fusion product monomer

SEQUENCE LISTING

```
<160> NUMBER OF SEQ ID NOS: 43

<210> SEQ ID NO 1
<211> LENGTH: 484
<212> TYPE: PRT
<213> ORGANISM: Artificial Sequence
<220> FEATURE:
<223> OTHER INFORMATION: von Willebrand Factor sequence

<400> SEQUENCE: 1

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335
```

```
Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro


<210> SEQ ID NO 2
<211> LENGTH: 485
<212> TYPE: PRT
<213> ORGANISM: Artificial Sequence
<220> FEATURE:
<223> OTHER INFORMATION: von Willebrand Factor sequence

<400> SEQUENCE: 2

Ala Ser Leu Ser Cys Arg Pro Pro Met Val Lys Leu Val Cys Pro Ala
1               5                   10                  15

Asp Asn Leu Arg Ala Glu Gly Leu Glu Cys Thr Lys Thr Cys Gln Asn
            20                  25                  30

Tyr Asp Leu Glu Cys Met Ser Met Gly Cys Val Ser Gly Cys Leu Cys
        35                  40                  45

Pro Pro Gly Met Val Arg His Glu Asn Arg Cys Val Ala Leu Glu Arg
    50                  55                  60

Cys Pro Cys Phe His Gln Gly Lys Glu Tyr Ala Pro Gly Glu Thr Val
65                  70                  75                  80

Lys Ile Gly Cys Asn Thr Cys Val Cys Arg Asp Arg Lys Trp Asn Cys
                85                  90                  95

Thr Asp His Val Cys Asp Ala Thr Cys Ser Thr Ile Gly Met Ala His
            100                 105                 110

Tyr Leu Thr Phe Asp Gly Leu Lys Tyr Leu Phe Pro Gly Glu Cys Gln
        115                 120                 125

Tyr Val Leu Val Gln Asp Tyr Cys Gly Ser Asn Pro Gly Thr Phe Arg
    130                 135                 140

Ile Leu Val Gly Asn Lys Gly Cys Ser His Pro Ser Val Lys Cys Lys
145                 150                 155                 160

Lys Arg Val Thr Ile Leu Val Glu Gly Gly Glu Ile Glu Leu Phe Asp
                165                 170                 175

Gly Glu Val Asn Val Lys Arg Pro Met Lys Asp Glu Thr His Phe Glu
            180                 185                 190

Val Val Glu Ser Gly Arg Tyr Ile Ile Leu Leu Leu Gly Lys Ala Leu
        195                 200                 205
```

```
Ser Val Val Trp Asp Arg His Leu Ser Ile Ser Val Val Leu Lys Gln
    210                 215                 220

Thr Tyr Gln Glu Lys Val Cys Gly Leu Cys Gly Asn Phe Asp Gly Ile
225                 230                 235                 240

Gln Asn Asn Asp Leu Thr Ser Ser Asn Leu Gln Val Glu Glu Asp Pro
                245                 250                 255

Val Asp Phe Gly Asn Ser Trp Lys Val Ser Ser Gln Cys Ala Asp Thr
            260                 265                 270

Arg Lys Val Pro Leu Asp Ser Ser Pro Ala Thr Cys His Asn Asn Ile
        275                 280                 285

Met Lys Gln Thr Met Val Asp Ser Ser Cys Arg Ile Leu Thr Ser Asp
    290                 295                 300

Val Phe Gln Asp Cys Asn Lys Leu Val Asp Pro Glu Pro Tyr Leu Asp
305                 310                 315                 320

Val Cys Ile Tyr Asp Thr Cys Ser Cys Glu Ser Ile Gly Asp Cys Ala
                325                 330                 335

Cys Phe Cys Asp Thr Ile Ala Ala Tyr Ala His Val Cys Ala Gln His
            340                 345                 350

Gly Lys Val Val Thr Trp Arg Thr Ala Thr Leu Cys Pro Gln Ser Cys
        355                 360                 365

Glu Glu Arg Asn Leu Arg Glu Asn Gly Tyr Glu Cys Glu Trp Arg Tyr
    370                 375                 380

Asn Ser Cys Ala Pro Ala Cys Gln Val Thr Cys Gln His Pro Glu Pro
385                 390                 395                 400

Leu Ala Cys Pro Val Gln Cys Val Glu Gly Cys His Ala His Cys Pro
                405                 410                 415

Pro Gly Lys Ile Leu Asp Glu Leu Leu Gln Thr Cys Val Asp Pro Glu
            420                 425                 430

Asp Cys Pro Val Cys Glu Val Ala Gly Arg Arg Phe Ala Ser Gly Lys
        435                 440                 445

Lys Val Thr Leu Asn Pro Ser Asp Pro Glu His Cys Gln Ile Cys His
    450                 455                 460

Cys Asp Val Val Asn Leu Thr Cys Glu Ala Cys Gln Glu Pro Gly Gly
465                 470                 475                 480

Leu Val Val Pro Pro
                485


<210> SEQ ID NO 3
<211> LENGTH: 507
<212> TYPE: PRT
<213> ORGANISM: Artificial Sequence
<220> FEATURE:
<223> OTHER INFORMATION: von Willebrand Factor sequence

<400> SEQUENCE: 3

Met Ile Pro Ala Arg Phe Ala Gly Val Leu Leu Ala Leu Ala Leu Ile
1               5                   10                  15

Leu Pro Gly Thr Leu Cys Ala Ser Leu Ser Cys Arg Pro Pro Met Val
            20                  25                  30

Lys Leu Val Cys Pro Ala Asp Asn Leu Arg Ala Glu Gly Leu Glu Cys
        35                  40                  45

Thr Lys Thr Cys Gln Asn Tyr Asp Leu Glu Cys Met Ser Met Gly Cys
    50                  55                  60

Val Ser Gly Cys Leu Cys Pro Pro Gly Met Val Arg His Glu Asn Arg
65                  70                  75                  80
```

```
Cys Val Ala Leu Glu Arg Cys Pro Cys Phe His Gln Gly Lys Glu Tyr
                85                  90                  95

Ala Pro Gly Glu Thr Val Lys Ile Gly Cys Asn Thr Cys Val Cys Arg
            100                 105                 110

Asp Arg Lys Trp Asn Cys Thr Asp His Val Cys Asp Ala Thr Cys Ser
        115                 120                 125

Thr Ile Gly Met Ala His Tyr Leu Thr Phe Asp Gly Leu Lys Tyr Leu
    130                 135                 140

Phe Pro Gly Glu Cys Gln Tyr Val Leu Val Gln Asp Tyr Cys Gly Ser
145                 150                 155                 160

Asn Pro Gly Thr Phe Arg Ile Leu Val Gly Asn Lys Gly Cys Ser His
                165                 170                 175

Pro Ser Val Lys Cys Lys Lys Arg Val Thr Ile Leu Val Glu Gly Gly
            180                 185                 190

Glu Ile Glu Leu Phe Asp Gly Glu Val Asn Val Lys Arg Pro Met Lys
        195                 200                 205

Asp Glu Thr His Phe Glu Val Val Glu Ser Gly Arg Tyr Ile Ile Leu
    210                 215                 220

Leu Leu Gly Lys Ala Leu Ser Val Val Trp Asp Arg His Leu Ser Ile
225                 230                 235                 240

Ser Val Val Leu Lys Gln Thr Tyr Gln Glu Lys Val Cys Gly Leu Cys
                245                 250                 255

Gly Asn Phe Asp Gly Ile Gln Asn Asn Asp Leu Thr Ser Ser Asn Leu
            260                 265                 270

Gln Val Glu Glu Asp Pro Val Asp Phe Gly Asn Ser Trp Lys Val Ser
        275                 280                 285

Ser Gln Cys Ala Asp Thr Arg Lys Val Pro Leu Asp Ser Ser Pro Ala
    290                 295                 300

Thr Cys His Asn Asn Ile Met Lys Gln Thr Met Val Asp Ser Ser Cys
305                 310                 315                 320

Arg Ile Leu Thr Ser Asp Val Phe Gln Asp Cys Asn Lys Leu Val Asp
                325                 330                 335

Pro Glu Pro Tyr Leu Asp Val Cys Ile Tyr Asp Thr Cys Ser Cys Glu
            340                 345                 350

Ser Ile Gly Asp Cys Ala Cys Phe Cys Asp Thr Ile Ala Ala Tyr Ala
        355                 360                 365

His Val Cys Ala Gln His Gly Lys Val Val Thr Trp Arg Thr Ala Thr
    370                 375                 380

Leu Cys Pro Gln Ser Cys Glu Glu Arg Asn Leu Arg Glu Asn Gly Tyr
385                 390                 395                 400

Glu Cys Glu Trp Arg Tyr Asn Ser Cys Ala Pro Ala Cys Gln Val Thr
                405                 410                 415

Cys Gln His Pro Glu Pro Leu Ala Cys Pro Val Gln Cys Val Glu Gly
            420                 425                 430

Cys His Ala His Cys Pro Pro Gly Lys Ile Leu Asp Glu Leu Leu Gln
        435                 440                 445

Thr Cys Val Asp Pro Glu Asp Cys Pro Val Cys Glu Val Ala Gly Arg
    450                 455                 460

Arg Phe Ala Ser Gly Lys Lys Val Thr Leu Asn Pro Ser Asp Pro Glu
465                 470                 475                 480

His Cys Gln Ile Cys His Cys Asp Val Val Asn Leu Thr Cys Glu Ala
                485                 490                 495

Cys Gln Glu Pro Gly Gly Leu Val Val Pro Pro
```

```
        500                 505


<210> SEQ ID NO 4
<211> LENGTH: 718
<212> TYPE: PRT
<213> ORGANISM: Artificial Sequence
<220> FEATURE:
<223> OTHER INFORMATION: von Willebrand Factor sequence

<400> SEQUENCE: 4

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
```

```
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
    530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
        595                 600                 605

Ile Asp Arg Pro Glu Ala Ser Arg Ile Ala Leu Leu Leu Met Ala Ser
    610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
        675                 680                 685

Glu Ile Val Ser Tyr Leu Cys Asp Leu Ala Pro Glu Ala Pro Pro Pro
    690                 695                 700

Thr Leu Pro Pro His Met Ala Gln Val Thr Val Gly Pro Gly
705                 710                 715


<210> SEQ ID NO 5
<211> LENGTH: 719
<212> TYPE: PRT
<213> ORGANISM: Artificial Sequence
<220> FEATURE:
<223> OTHER INFORMATION: von Willebrand Factor sequence

<400> SEQUENCE: 5

Ala Ser Leu Ser Cys Arg Pro Pro Met Val Lys Leu Val Cys Pro Ala
```

-continued

```
1               5                   10                  15

Asp Asn Leu Arg Ala Glu Gly Leu Glu Cys Thr Lys Thr Cys Gln Asn
            20                  25                  30

Tyr Asp Leu Glu Cys Met Ser Met Gly Cys Val Ser Gly Cys Leu Cys
        35                  40                  45

Pro Pro Gly Met Val Arg His Glu Asn Arg Cys Val Ala Leu Glu Arg
    50                  55                  60

Cys Pro Cys Phe His Gln Gly Lys Glu Tyr Ala Pro Gly Glu Thr Val
65                  70                  75                  80

Lys Ile Gly Cys Asn Thr Cys Val Cys Arg Asp Arg Lys Trp Asn Cys
                85                  90                  95

Thr Asp His Val Cys Asp Ala Thr Cys Ser Thr Ile Gly Met Ala His
            100                 105                 110

Tyr Leu Thr Phe Asp Gly Leu Lys Tyr Leu Phe Pro Gly Glu Cys Gln
        115                 120                 125

Tyr Val Leu Val Gln Asp Tyr Cys Gly Ser Asn Pro Gly Thr Phe Arg
    130                 135                 140

Ile Leu Val Gly Asn Lys Gly Cys Ser His Pro Ser Val Lys Cys Lys
145                 150                 155                 160

Lys Arg Val Thr Ile Leu Val Glu Gly Gly Glu Ile Glu Leu Phe Asp
                165                 170                 175

Gly Glu Val Asn Val Lys Arg Pro Met Lys Asp Glu Thr His Phe Glu
            180                 185                 190

Val Val Glu Ser Gly Arg Tyr Ile Ile Leu Leu Leu Gly Lys Ala Leu
        195                 200                 205

Ser Val Val Trp Asp Arg His Leu Ser Ile Ser Val Val Leu Lys Gln
    210                 215                 220

Thr Tyr Gln Glu Lys Val Cys Gly Leu Cys Gly Asn Phe Asp Gly Ile
225                 230                 235                 240

Gln Asn Asn Asp Leu Thr Ser Ser Asn Leu Gln Val Glu Glu Asp Pro
                245                 250                 255

Val Asp Phe Gly Asn Ser Trp Lys Val Ser Ser Gln Cys Ala Asp Thr
            260                 265                 270

Arg Lys Val Pro Leu Asp Ser Ser Pro Ala Thr Cys His Asn Asn Ile
        275                 280                 285

Met Lys Gln Thr Met Val Asp Ser Ser Cys Arg Ile Leu Thr Ser Asp
    290                 295                 300

Val Phe Gln Asp Cys Asn Lys Leu Val Asp Pro Glu Pro Tyr Leu Asp
305                 310                 315                 320

Val Cys Ile Tyr Asp Thr Cys Ser Cys Glu Ser Ile Gly Asp Cys Ala
                325                 330                 335

Cys Phe Cys Asp Thr Ile Ala Ala Tyr Ala His Val Cys Ala Gln His
            340                 345                 350

Gly Lys Val Val Thr Trp Arg Thr Ala Thr Leu Cys Pro Gln Ser Cys
        355                 360                 365

Glu Glu Arg Asn Leu Arg Glu Asn Gly Tyr Glu Cys Glu Trp Arg Tyr
    370                 375                 380

Asn Ser Cys Ala Pro Ala Cys Gln Val Thr Cys Gln His Pro Glu Pro
385                 390                 395                 400

Leu Ala Cys Pro Val Gln Cys Val Glu Gly Cys His Ala His Cys Pro
                405                 410                 415

Pro Gly Lys Ile Leu Asp Glu Leu Leu Gln Thr Cys Val Asp Pro Glu
            420                 425                 430
```

-continued

Asp Cys Pro Val Cys Glu Val Ala Gly Arg Arg Phe Ala Ser Gly Lys
435 440 445

Lys Val Thr Leu Asn Pro Ser Asp Pro Glu His Cys Gln Ile Cys His
450 455 460

Cys Asp Val Val Asn Leu Thr Cys Glu Ala Cys Gln Glu Pro Gly Gly
465 470 475 480

Leu Val Val Pro Pro Thr Asp Ala Pro Val Ser Pro Thr Thr Leu Tyr
485 490 495

Val Glu Asp Ile Ser Glu Pro Pro Leu His Asp Phe Tyr Cys Ser Arg
500 505 510

Leu Leu Asp Leu Val Phe Leu Leu Asp Gly Ser Ser Arg Leu Ser Glu
515 520 525

Ala Glu Phe Glu Val Leu Lys Ala Phe Val Val Asp Met Met Glu Arg
530 535 540

Leu Arg Ile Ser Gln Lys Trp Val Arg Val Ala Val Val Glu Tyr His
545 550 555 560

Asp Gly Ser His Ala Tyr Ile Gly Leu Lys Asp Arg Lys Arg Pro Ser
565 570 575

Glu Leu Arg Arg Ile Ala Ser Gln Val Lys Tyr Ala Gly Ser Gln Val
580 585 590

Ala Ser Thr Ser Glu Val Leu Lys Tyr Thr Leu Phe Gln Ile Phe Ser
595 600 605

Lys Ile Asp Arg Pro Glu Ala Ser Arg Ile Ala Leu Leu Leu Met Ala
610 615 620

Ser Gln Glu Pro Gln Arg Met Ser Arg Asn Phe Val Arg Tyr Val Gln
625 630 635 640

Gly Leu Lys Lys Lys Lys Val Ile Val Ile Pro Val Gly Ile Gly Pro
645 650 655

His Ala Asn Leu Lys Gln Ile Arg Leu Ile Glu Lys Gln Ala Pro Glu
660 665 670

Asn Lys Ala Phe Val Leu Ser Ser Val Asp Glu Leu Glu Gln Gln Arg
675 680 685

Asp Glu Ile Val Ser Tyr Leu Cys Asp Leu Ala Pro Glu Ala Pro Pro
690 695 700

Pro Thr Leu Pro Pro His Met Ala Gln Val Thr Val Gly Pro Gly
705 710 715

<210> SEQ ID NO 6
<211> LENGTH: 741
<212> TYPE: PRT
<213> ORGANISM: Artificial Sequence
<220> FEATURE:
<223> OTHER INFORMATION: von Willebrand Factor sequence

<400> SEQUENCE: 6

Met Ile Pro Ala Arg Phe Ala Gly Val Leu Leu Ala Leu Ala Leu Ile
1 5 10 15

Leu Pro Gly Thr Leu Cys Ala Ser Leu Ser Cys Arg Pro Pro Met Val
20 25 30

Lys Leu Val Cys Pro Ala Asp Asn Leu Arg Ala Glu Gly Leu Glu Cys
35 40 45

Thr Lys Thr Cys Gln Asn Tyr Asp Leu Glu Cys Met Ser Met Gly Cys
50 55 60

Val Ser Gly Cys Leu Cys Pro Pro Gly Met Val Arg His Glu Asn Arg
65 70 75 80

```
Cys Val Ala Leu Glu Arg Cys Pro Cys Phe His Gln Gly Lys Glu Tyr
                85                  90                  95

Ala Pro Gly Glu Thr Val Lys Ile Gly Cys Asn Thr Cys Val Cys Arg
            100                 105                 110

Asp Arg Lys Trp Asn Cys Thr Asp His Val Cys Asp Ala Thr Cys Ser
        115                 120                 125

Thr Ile Gly Met Ala His Tyr Leu Thr Phe Asp Gly Leu Lys Tyr Leu
    130                 135                 140

Phe Pro Gly Glu Cys Gln Tyr Val Leu Val Gln Asp Tyr Cys Gly Ser
145                 150                 155                 160

Asn Pro Gly Thr Phe Arg Ile Leu Val Gly Asn Lys Gly Cys Ser His
                165                 170                 175

Pro Ser Val Lys Cys Lys Lys Arg Val Thr Ile Leu Val Glu Gly Gly
            180                 185                 190

Glu Ile Glu Leu Phe Asp Gly Glu Val Asn Val Lys Arg Pro Met Lys
        195                 200                 205

Asp Glu Thr His Phe Glu Val Val Glu Ser Gly Arg Tyr Ile Ile Leu
    210                 215                 220

Leu Leu Gly Lys Ala Leu Ser Val Val Trp Asp Arg His Leu Ser Ile
225                 230                 235                 240

Ser Val Val Leu Lys Gln Thr Tyr Gln Glu Lys Val Cys Gly Leu Cys
                245                 250                 255

Gly Asn Phe Asp Gly Ile Gln Asn Asn Asp Leu Thr Ser Ser Asn Leu
            260                 265                 270

Gln Val Glu Glu Asp Pro Val Asp Phe Gly Asn Ser Trp Lys Val Ser
        275                 280                 285

Ser Gln Cys Ala Asp Thr Arg Lys Val Pro Leu Asp Ser Ser Pro Ala
    290                 295                 300

Thr Cys His Asn Asn Ile Met Lys Gln Thr Met Val Asp Ser Ser Cys
305                 310                 315                 320

Arg Ile Leu Thr Ser Asp Val Phe Gln Asp Cys Asn Lys Leu Val Asp
                325                 330                 335

Pro Glu Pro Tyr Leu Asp Val Cys Ile Tyr Asp Thr Cys Ser Cys Glu
            340                 345                 350

Ser Ile Gly Asp Cys Ala Cys Phe Cys Asp Thr Ile Ala Ala Tyr Ala
        355                 360                 365

His Val Cys Ala Gln His Gly Lys Val Val Thr Trp Arg Thr Ala Thr
    370                 375                 380

Leu Cys Pro Gln Ser Cys Glu Glu Arg Asn Leu Arg Glu Asn Gly Tyr
385                 390                 395                 400

Glu Cys Glu Trp Arg Tyr Asn Ser Cys Ala Pro Ala Cys Gln Val Thr
                405                 410                 415

Cys Gln His Pro Glu Pro Leu Ala Cys Pro Val Gln Cys Val Glu Gly
            420                 425                 430

Cys His Ala His Cys Pro Pro Gly Lys Ile Leu Asp Glu Leu Leu Gln
        435                 440                 445

Thr Cys Val Asp Pro Glu Asp Cys Pro Val Cys Glu Val Ala Gly Arg
    450                 455                 460

Arg Phe Ala Ser Gly Lys Lys Val Thr Leu Asn Pro Ser Asp Pro Glu
465                 470                 475                 480

His Cys Gln Ile Cys His Cys Asp Val Val Asn Leu Thr Cys Glu Ala
                485                 490                 495
```

```
Cys Gln Glu Pro Gly Gly Leu Val Val Pro Pro Thr Asp Ala Pro Val
            500                 505                 510

Ser Pro Thr Thr Leu Tyr Val Glu Asp Ile Ser Glu Pro Pro Leu His
        515                 520                 525

Asp Phe Tyr Cys Ser Arg Leu Leu Asp Leu Val Phe Leu Leu Asp Gly
    530                 535                 540

Ser Ser Arg Leu Ser Glu Ala Glu Phe Glu Val Leu Lys Ala Phe Val
545                 550                 555                 560

Val Asp Met Met Glu Arg Leu Arg Ile Ser Gln Lys Trp Val Arg Val
                565                 570                 575

Ala Val Val Glu Tyr His Asp Gly Ser His Ala Tyr Ile Gly Leu Lys
            580                 585                 590

Asp Arg Lys Arg Pro Ser Glu Leu Arg Arg Ile Ala Ser Gln Val Lys
        595                 600                 605

Tyr Ala Gly Ser Gln Val Ala Ser Thr Ser Glu Val Leu Lys Tyr Thr
    610                 615                 620

Leu Phe Gln Ile Phe Ser Lys Ile Asp Arg Pro Glu Ala Ser Arg Ile
625                 630                 635                 640

Ala Leu Leu Leu Met Ala Ser Gln Glu Pro Gln Arg Met Ser Arg Asn
                645                 650                 655

Phe Val Arg Tyr Val Gln Gly Leu Lys Lys Lys Lys Val Ile Val Ile
            660                 665                 670

Pro Val Gly Ile Gly Pro His Ala Asn Leu Lys Gln Ile Arg Leu Ile
        675                 680                 685

Glu Lys Gln Ala Pro Glu Asn Lys Ala Phe Val Leu Ser Ser Val Asp
    690                 695                 700

Glu Leu Glu Gln Gln Arg Asp Glu Ile Val Ser Tyr Leu Cys Asp Leu
705                 710                 715                 720

Ala Pro Glu Ala Pro Pro Pro Thr Leu Pro Pro His Met Ala Gln Val
                725                 730                 735

Thr Val Gly Pro Gly
            740


<210> SEQ ID NO 7
<211> LENGTH: 1116
<212> TYPE: PRT
<213> ORGANISM: Artificial Sequence
<220> FEATURE:
<223> OTHER INFORMATION: von Willebrand Factor sequence

<400> SEQUENCE: 7

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110
```

```
Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
```

```
    530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
        595                 600                 605

Ile Asp Arg Pro Glu Ala Ser Arg Ile Ala Leu Leu Leu Met Ala Ser
    610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
        675                 680                 685

Glu Ile Val Ser Tyr Leu Cys Asp Leu Ala Pro Glu Ala Pro Pro Pro
    690                 695                 700

Thr Leu Pro Pro His Met Ala Gln Val Thr Val Gly Pro Gly Leu Leu
705                 710                 715                 720

Gly Val Ser Thr Leu Gly Pro Lys Arg Asn Ser Met Val Leu Asp Val
                725                 730                 735

Ala Phe Val Leu Glu Gly Ser Asp Lys Ile Gly Glu Ala Asp Phe Asn
            740                 745                 750

Arg Ser Lys Glu Phe Met Glu Glu Val Ile Gln Arg Met Asp Val Gly
        755                 760                 765

Gln Asp Ser Ile His Val Thr Val Leu Gln Tyr Ser Tyr Met Val Thr
    770                 775                 780

Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                805                 810                 815

Leu Ala Leu Arg Tyr Leu Ser Asp His Ser Phe Leu Val Ser Gln Gly
            820                 825                 830

Asp Arg Glu Gln Ala Pro Asn Leu Val Tyr Met Val Thr Gly Asn Pro
        835                 840                 845

Ala Ser Asp Glu Ile Lys Arg Leu Pro Gly Asp Ile Gln Val Val Pro
    850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                885                 890                 895

Glu Ala Pro Asp Leu Val Leu Gln Arg Cys Cys Ser Gly Glu Gly Leu
            900                 905                 910

Gln Ile Pro Thr Leu Ser Pro Ala Pro Asp Cys Ser Gln Pro Leu Asp
        915                 920                 925

Val Ile Leu Leu Leu Asp Gly Ser Ser Ser Phe Pro Ala Ser Tyr Phe
    930                 935                 940

Asp Glu Met Lys Ser Phe Ala Lys Ala Phe Ile Ser Lys Ala Asn Ile
945                 950                 955                 960
```

```
Gly Pro Arg Leu Thr Gln Val Ser Val Leu Gln Tyr Gly Ser Ile Thr
                965                 970                 975

Thr Ile Asp Val Pro Trp Asn Val Val Pro Glu Lys Ala His Leu Leu
            980                 985                 990

Ser Leu Val Asp Val Met Gln Arg  Glu Gly Gly Pro Ser  Gln Ile Gly
        995                 1000                1005

Asp Ala  Leu Gly Phe Ala Val  Arg Tyr Leu Thr Ser  Glu Met His
    1010                1015                1020

Gly Ala  Arg Pro Gly Ala Ser  Lys Ala Val Val Ile  Leu Val Thr
    1025                1030                1035

Asp Val  Ser Val Asp Ser Val  Asp Ala Ala Ala Asp  Ala Ala Arg
    1040                1045                1050

Ser Asn  Arg Val Thr Val Phe  Pro Ile Gly Ile Gly  Asp Arg Tyr
    1055                1060                1065

Asp Ala  Ala Gln Leu Arg Ile  Leu Ala Gly Pro Ala  Gly Asp Ser
    1070                1075                1080

Asn Val  Val Lys Leu Gln Arg  Ile Glu Asp Leu Pro  Thr Met Val
    1085                1090                1095

Thr Leu  Gly Asn Ser Phe Leu  His Lys Leu Cys Ser  Gly Phe Val
    1100                1105                1110

Arg Ile  Cys
    1115


<210> SEQ ID NO 8
<211> LENGTH: 1117
<212> TYPE: PRT
<213> ORGANISM: Artificial Sequence
<220> FEATURE:
<223> OTHER INFORMATION: von Willebrand Factor sequence

<400> SEQUENCE: 8

Ala Ser Leu Ser Cys Arg Pro Pro Met Val Lys Leu Val Cys Pro Ala
1               5                   10                  15

Asp Asn Leu Arg Ala Glu Gly Leu Glu Cys Thr Lys Thr Cys Gln Asn
            20                  25                  30

Tyr Asp Leu Glu Cys Met Ser Met Gly Cys Val Ser Gly Cys Leu Cys
        35                  40                  45

Pro Pro Gly Met Val Arg His Glu Asn Arg Cys Val Ala Leu Glu Arg
    50                  55                  60

Cys Pro Cys Phe His Gln Gly Lys Glu Tyr Ala Pro Gly Glu Thr Val
65                  70                  75                  80

Lys Ile Gly Cys Asn Thr Cys Val Cys Arg Asp Arg Lys Trp Asn Cys
                85                  90                  95

Thr Asp His Val Cys Asp Ala Thr Cys Ser Thr Ile Gly Met Ala His
            100                 105                 110

Tyr Leu Thr Phe Asp Gly Leu Lys Tyr Leu Phe Pro Gly Glu Cys Gln
        115                 120                 125

Tyr Val Leu Val Gln Asp Tyr Cys Gly Ser Asn Pro Gly Thr Phe Arg
    130                 135                 140

Ile Leu Val Gly Asn Lys Gly Cys Ser His Pro Ser Val Lys Cys Lys
145                 150                 155                 160

Lys Arg Val Thr Ile Leu Val Glu Gly Gly Glu Ile Glu Leu Phe Asp
                165                 170                 175

Gly Glu Val Asn Val Lys Arg Pro Met Lys Asp Glu Thr His Phe Glu
            180                 185                 190
```

```
Val Val Glu Ser Gly Arg Tyr Ile Ile Leu Leu Leu Gly Lys Ala Leu
        195                 200                 205

Ser Val Val Trp Asp Arg His Leu Ser Ile Ser Val Val Leu Lys Gln
    210                 215                 220

Thr Tyr Gln Glu Lys Val Cys Gly Leu Cys Gly Asn Phe Asp Gly Ile
225                 230                 235                 240

Gln Asn Asn Asp Leu Thr Ser Ser Asn Leu Gln Val Glu Glu Asp Pro
                245                 250                 255

Val Asp Phe Gly Asn Ser Trp Lys Val Ser Ser Gln Cys Ala Asp Thr
            260                 265                 270

Arg Lys Val Pro Leu Asp Ser Ser Pro Ala Thr Cys His Asn Asn Ile
        275                 280                 285

Met Lys Gln Thr Met Val Asp Ser Ser Cys Arg Ile Leu Thr Ser Asp
    290                 295                 300

Val Phe Gln Asp Cys Asn Lys Leu Val Asp Pro Glu Pro Tyr Leu Asp
305                 310                 315                 320

Val Cys Ile Tyr Asp Thr Cys Ser Cys Glu Ser Ile Gly Asp Cys Ala
                325                 330                 335

Cys Phe Cys Asp Thr Ile Ala Ala Tyr Ala His Val Cys Ala Gln His
            340                 345                 350

Gly Lys Val Val Thr Trp Arg Thr Ala Thr Leu Cys Pro Gln Ser Cys
        355                 360                 365

Glu Glu Arg Asn Leu Arg Glu Asn Gly Tyr Glu Cys Glu Trp Arg Tyr
    370                 375                 380

Asn Ser Cys Ala Pro Ala Cys Gln Val Thr Cys Gln His Pro Glu Pro
385                 390                 395                 400

Leu Ala Cys Pro Val Gln Cys Val Glu Gly Cys His Ala His Cys Pro
                405                 410                 415

Pro Gly Lys Ile Leu Asp Glu Leu Leu Gln Thr Cys Val Asp Pro Glu
            420                 425                 430

Asp Cys Pro Val Cys Glu Val Ala Gly Arg Arg Phe Ala Ser Gly Lys
        435                 440                 445

Lys Val Thr Leu Asn Pro Ser Asp Pro Glu His Cys Gln Ile Cys His
    450                 455                 460

Cys Asp Val Val Asn Leu Thr Cys Glu Ala Cys Gln Glu Pro Gly Gly
465                 470                 475                 480

Leu Val Val Pro Pro Thr Asp Ala Pro Val Ser Pro Thr Thr Leu Tyr
                485                 490                 495

Val Glu Asp Ile Ser Glu Pro Pro Leu His Asp Phe Tyr Cys Ser Arg
            500                 505                 510

Leu Leu Asp Leu Val Phe Leu Leu Asp Gly Ser Ser Arg Leu Ser Glu
        515                 520                 525

Ala Glu Phe Glu Val Leu Lys Ala Phe Val Val Asp Met Met Glu Arg
    530                 535                 540

Leu Arg Ile Ser Gln Lys Trp Val Arg Val Ala Val Val Glu Tyr His
545                 550                 555                 560

Asp Gly Ser His Ala Tyr Ile Gly Leu Lys Asp Arg Lys Arg Pro Ser
                565                 570                 575

Glu Leu Arg Arg Ile Ala Ser Gln Val Lys Tyr Ala Gly Ser Gln Val
            580                 585                 590

Ala Ser Thr Ser Glu Val Leu Lys Tyr Thr Leu Phe Gln Ile Phe Ser
        595                 600                 605
```

```
Lys Ile Asp Arg Pro Glu Ala Ser Arg Ile Ala Leu Leu Leu Met Ala
    610                 615                 620

Ser Gln Glu Pro Gln Arg Met Ser Arg Asn Phe Val Arg Tyr Val Gln
625                 630                 635                 640

Gly Leu Lys Lys Lys Lys Val Ile Val Ile Pro Val Gly Ile Gly Pro
                645                 650                 655

His Ala Asn Leu Lys Gln Ile Arg Leu Ile Glu Lys Gln Ala Pro Glu
            660                 665                 670

Asn Lys Ala Phe Val Leu Ser Ser Val Asp Glu Leu Glu Gln Gln Arg
        675                 680                 685

Asp Glu Ile Val Ser Tyr Leu Cys Asp Leu Ala Pro Glu Ala Pro Pro
    690                 695                 700

Pro Thr Leu Pro Pro His Met Ala Gln Val Thr Val Gly Pro Gly Leu
705                 710                 715                 720

Leu Gly Val Ser Thr Leu Gly Pro Lys Arg Asn Ser Met Val Leu Asp
                725                 730                 735

Val Ala Phe Val Leu Glu Gly Ser Asp Lys Ile Gly Glu Ala Asp Phe
            740                 745                 750

Asn Arg Ser Lys Glu Phe Met Glu Glu Val Ile Gln Arg Met Asp Val
        755                 760                 765

Gly Gln Asp Ser Ile His Val Thr Val Leu Gln Tyr Ser Tyr Met Val
    770                 775                 780

Thr Val Glu Tyr Pro Phe Ser Glu Ala Gln Ser Lys Gly Asp Ile Leu
785                 790                 795                 800

Gln Arg Val Arg Glu Ile Arg Tyr Gln Gly Gly Asn Arg Thr Asn Thr
                805                 810                 815

Gly Leu Ala Leu Arg Tyr Leu Ser Asp His Ser Phe Leu Val Ser Gln
            820                 825                 830

Gly Asp Arg Glu Gln Ala Pro Asn Leu Val Tyr Met Val Thr Gly Asn
        835                 840                 845

Pro Ala Ser Asp Glu Ile Lys Arg Leu Pro Gly Asp Ile Gln Val Val
    850                 855                 860

Pro Ile Gly Val Gly Pro Asn Ala Asn Val Gln Glu Leu Glu Arg Ile
865                 870                 875                 880

Gly Trp Pro Asn Ala Pro Ile Leu Ile Gln Asp Phe Glu Thr Leu Pro
                885                 890                 895

Arg Glu Ala Pro Asp Leu Val Leu Gln Arg Cys Cys Ser Gly Glu Gly
            900                 905                 910

Leu Gln Ile Pro Thr Leu Ser Pro Ala Pro Asp Cys Ser Gln Pro Leu
        915                 920                 925

Asp Val Ile Leu Leu Leu Asp Gly Ser Ser Ser Phe Pro Ala Ser Tyr
    930                 935                 940

Phe Asp Glu Met Lys Ser Phe Ala Lys Ala Phe Ile Ser Lys Ala Asn
945                 950                 955                 960

Ile Gly Pro Arg Leu Thr Gln Val Ser Val Leu Gln Tyr Gly Ser Ile
                965                 970                 975

Thr Thr Ile Asp Val Pro Trp Asn Val Val Pro Glu Lys Ala His Leu
            980                 985                 990

Leu Ser Leu Val Asp Val Met Gln  Arg Glu Gly Gly Pro  Ser Gln Ile
        995                 1000                1005

Gly Asp  Ala Leu Gly Phe Ala  Val Arg Tyr Leu Thr  Ser Glu Met
    1010                1015                1020

His Gly  Ala Arg Pro Gly Ala  Ser Lys Ala Val Val  Ile Leu Val
```

```
    1025                1030                1035

Thr Asp  Val Ser Val Asp Ser  Val Asp Ala Ala Ala  Asp Ala Ala
    1040                1045                1050

Arg Ser  Asn Arg Val Thr Val  Phe Pro Ile Gly Ile  Gly Asp Arg
    1055                1060                1065

Tyr Asp  Ala Ala Gln Leu Arg  Ile Leu Ala Gly Pro  Ala Gly Asp
    1070                1075                1080

Ser Asn  Val Val Lys Leu Gln  Arg Ile Glu Asp Leu  Pro Thr Met
    1085                1090                1095

Val Thr  Leu Gly Asn Ser Phe  Leu His Lys Leu Cys  Ser Gly Phe
    1100                1105                1110

Val Arg  Ile Cys
    1115


<210> SEQ ID NO 9
<211> LENGTH: 1139
<212> TYPE: PRT
<213> ORGANISM: Artificial Sequence
<220> FEATURE:
<223> OTHER INFORMATION: von Willebrand Factor sequence

<400> SEQUENCE: 9

Met Ile Pro Ala Arg Phe Ala Gly Val Leu Leu Ala Leu Ala Leu Ile
1               5                   10                  15

Leu Pro Gly Thr Leu Cys Ala Ser Leu Ser Cys Arg Pro Pro Met Val
            20                  25                  30

Lys Leu Val Cys Pro Ala Asp Asn Leu Arg Ala Glu Gly Leu Glu Cys
        35                  40                  45

Thr Lys Thr Cys Gln Asn Tyr Asp Leu Glu Cys Met Ser Met Gly Cys
    50                  55                  60

Val Ser Gly Cys Leu Cys Pro Pro Gly Met Val Arg His Glu Asn Arg
65                  70                  75                  80

Cys Val Ala Leu Glu Arg Cys Pro Cys Phe His Gln Gly Lys Glu Tyr
                85                  90                  95

Ala Pro Gly Glu Thr Val Lys Ile Gly Cys Asn Thr Cys Val Cys Arg
            100                 105                 110

Asp Arg Lys Trp Asn Cys Thr Asp His Val Cys Asp Ala Thr Cys Ser
        115                 120                 125

Thr Ile Gly Met Ala His Tyr Leu Thr Phe Asp Gly Leu Lys Tyr Leu
    130                 135                 140

Phe Pro Gly Glu Cys Gln Tyr Val Leu Val Gln Asp Tyr Cys Gly Ser
145                 150                 155                 160

Asn Pro Gly Thr Phe Arg Ile Leu Val Gly Asn Lys Gly Cys Ser His
                165                 170                 175

Pro Ser Val Lys Cys Lys Lys Arg Val Thr Ile Leu Val Glu Gly Gly
            180                 185                 190

Glu Ile Glu Leu Phe Asp Gly Glu Val Asn Val Lys Arg Pro Met Lys
        195                 200                 205

Asp Glu Thr His Phe Glu Val Val Glu Ser Gly Arg Tyr Ile Ile Leu
    210                 215                 220

Leu Leu Gly Lys Ala Leu Ser Val Val Trp Asp Arg His Leu Ser Ile
225                 230                 235                 240

Ser Val Val Leu Lys Gln Thr Tyr Gln Glu Lys Val Cys Gly Leu Cys
                245                 250                 255

Gly Asn Phe Asp Gly Ile Gln Asn Asn Asp Leu Thr Ser Ser Asn Leu
```

-continued

```
            260                 265                 270

Gln Val Glu Glu Asp Pro Val Asp Phe Gly Asn Ser Trp Lys Val Ser
        275                 280                 285

Ser Gln Cys Ala Asp Thr Arg Lys Val Pro Leu Asp Ser Ser Pro Ala
    290                 295                 300

Thr Cys His Asn Asn Ile Met Lys Gln Thr Met Val Asp Ser Ser Cys
305                 310                 315                 320

Arg Ile Leu Thr Ser Asp Val Phe Gln Asp Cys Asn Lys Leu Val Asp
                325                 330                 335

Pro Glu Pro Tyr Leu Asp Val Cys Ile Tyr Asp Thr Cys Ser Cys Glu
            340                 345                 350

Ser Ile Gly Asp Cys Ala Cys Phe Cys Asp Thr Ile Ala Ala Tyr Ala
        355                 360                 365

His Val Cys Ala Gln His Gly Lys Val Val Thr Trp Arg Thr Ala Thr
    370                 375                 380

Leu Cys Pro Gln Ser Cys Glu Glu Arg Asn Leu Arg Glu Asn Gly Tyr
385                 390                 395                 400

Glu Cys Glu Trp Arg Tyr Asn Ser Cys Ala Pro Ala Cys Gln Val Thr
                405                 410                 415

Cys Gln His Pro Glu Pro Leu Ala Cys Pro Val Gln Cys Val Glu Gly
            420                 425                 430

Cys His Ala His Cys Pro Pro Gly Lys Ile Leu Asp Glu Leu Leu Gln
        435                 440                 445

Thr Cys Val Asp Pro Glu Asp Cys Pro Val Cys Glu Val Ala Gly Arg
    450                 455                 460

Arg Phe Ala Ser Gly Lys Lys Val Thr Leu Asn Pro Ser Asp Pro Glu
465                 470                 475                 480

His Cys Gln Ile Cys His Cys Asp Val Val Asn Leu Thr Cys Glu Ala
                485                 490                 495

Cys Gln Glu Pro Gly Gly Leu Val Val Pro Pro Thr Asp Ala Pro Val
            500                 505                 510

Ser Pro Thr Thr Leu Tyr Val Glu Asp Ile Ser Glu Pro Pro Leu His
        515                 520                 525

Asp Phe Tyr Cys Ser Arg Leu Leu Asp Leu Val Phe Leu Leu Asp Gly
    530                 535                 540

Ser Ser Arg Leu Ser Glu Ala Glu Phe Glu Val Leu Lys Ala Phe Val
545                 550                 555                 560

Val Asp Met Met Glu Arg Leu Arg Ile Ser Gln Lys Trp Val Arg Val
                565                 570                 575

Ala Val Val Glu Tyr His Asp Gly Ser His Ala Tyr Ile Gly Leu Lys
            580                 585                 590

Asp Arg Lys Arg Pro Ser Glu Leu Arg Arg Ile Ala Ser Gln Val Lys
        595                 600                 605

Tyr Ala Gly Ser Gln Val Ala Ser Thr Ser Glu Val Leu Lys Tyr Thr
    610                 615                 620

Leu Phe Gln Ile Phe Ser Lys Ile Asp Arg Pro Glu Ala Ser Arg Ile
625                 630                 635                 640

Ala Leu Leu Leu Met Ala Ser Gln Glu Pro Gln Arg Met Ser Arg Asn
                645                 650                 655

Phe Val Arg Tyr Val Gln Gly Leu Lys Lys Lys Lys Val Ile Val Ile
            660                 665                 670

Pro Val Gly Ile Gly Pro His Ala Asn Leu Lys Gln Ile Arg Leu Ile
        675                 680                 685
```

```
Glu Lys Gln Ala Pro Glu Asn Lys Ala Phe Val Leu Ser Ser Val Asp
    690                 695                 700

Glu Leu Glu Gln Gln Arg Asp Glu Ile Val Ser Tyr Leu Cys Asp Leu
705                 710                 715                 720

Ala Pro Glu Ala Pro Pro Pro Thr Leu Pro Pro His Met Ala Gln Val
                725                 730                 735

Thr Val Gly Pro Gly Leu Leu Gly Val Ser Thr Leu Gly Pro Lys Arg
            740                 745                 750

Asn Ser Met Val Leu Asp Val Ala Phe Val Leu Glu Gly Ser Asp Lys
        755                 760                 765

Ile Gly Glu Ala Asp Phe Asn Arg Ser Lys Glu Phe Met Glu Glu Val
    770                 775                 780

Ile Gln Arg Met Asp Val Gly Gln Asp Ser Ile His Val Thr Val Leu
785                 790                 795                 800

Gln Tyr Ser Tyr Met Val Thr Val Glu Tyr Pro Phe Ser Glu Ala Gln
                805                 810                 815

Ser Lys Gly Asp Ile Leu Gln Arg Val Arg Glu Ile Arg Tyr Gln Gly
            820                 825                 830

Gly Asn Arg Thr Asn Thr Gly Leu Ala Leu Arg Tyr Leu Ser Asp His
        835                 840                 845

Ser Phe Leu Val Ser Gln Gly Asp Arg Glu Gln Ala Pro Asn Leu Val
    850                 855                 860

Tyr Met Val Thr Gly Asn Pro Ala Ser Asp Glu Ile Lys Arg Leu Pro
865                 870                 875                 880

Gly Asp Ile Gln Val Val Pro Ile Gly Val Gly Pro Asn Ala Asn Val
                885                 890                 895

Gln Glu Leu Glu Arg Ile Gly Trp Pro Asn Ala Pro Ile Leu Ile Gln
            900                 905                 910

Asp Phe Glu Thr Leu Pro Arg Glu Ala Pro Asp Leu Val Leu Gln Arg
        915                 920                 925

Cys Cys Ser Gly Glu Gly Leu Gln Ile Pro Thr Leu Ser Pro Ala Pro
    930                 935                 940

Asp Cys Ser Gln Pro Leu Asp Val Ile Leu Leu Leu Asp Gly Ser Ser
945                 950                 955                 960

Ser Phe Pro Ala Ser Tyr Phe Asp Glu Met Lys Ser Phe Ala Lys Ala
                965                 970                 975

Phe Ile Ser Lys Ala Asn Ile Gly Pro Arg Leu Thr Gln Val Ser Val
            980                 985                 990

Leu Gln Tyr Gly Ser Ile Thr Thr  Ile Asp Val Pro Trp  Asn Val Val
        995                 1000                 1005

Pro Glu  Lys Ala His Leu Leu  Ser Leu Val Asp Val  Met Gln Arg
    1010                 1015                 1020

Glu Gly  Gly Pro Ser Gln Ile  Gly Asp Ala Leu Gly  Phe Ala Val
    1025                 1030                 1035

Arg Tyr  Leu Thr Ser Glu Met  His Gly Ala Arg Pro  Gly Ala Ser
    1040                 1045                 1050

Lys Ala  Val Val Ile Leu Val  Thr Asp Val Ser Val  Asp Ser Val
    1055                 1060                 1065

Asp Ala  Ala Ala Asp Ala Ala  Arg Ser Asn Arg Val  Thr Val Phe
    1070                 1075                 1080

Pro Ile  Gly Ile Gly Asp Arg  Tyr Asp Ala Ala Gln  Leu Arg Ile
    1085                 1090                 1095
```

```
Leu Ala  Gly Pro Ala Gly Asp  Ser Asn Val Val Lys  Leu Gln Arg
    1100                 1105                 1110

Ile Glu  Asp Leu Pro Thr Met  Val Thr Leu Gly Asn  Ser Phe Leu
    1115                 1120                 1125

His Lys  Leu Cys Ser Gly Phe  Val Arg Ile Cys
    1130                 1135


<210> SEQ ID NO 10
<211> LENGTH: 1225
<212> TYPE: PRT
<213> ORGANISM: Artificial Sequence
<220> FEATURE:
<223> OTHER INFORMATION: von Willebrand Factor sequence

<400> SEQUENCE: 10

Ala Glu Gly Thr Arg Gly Arg Ser Ser Thr Ala Arg Cys Ser Leu Phe
1               5                   10                  15

Gly Ser Asp Phe Val Asn Thr Phe Asp Gly Ser Met Tyr Ser Phe Ala
            20                  25                  30

Gly Tyr Cys Ser Tyr Leu Leu Ala Gly Gly Cys Gln Lys Arg Ser Phe
        35                  40                  45

Ser Ile Ile Gly Asp Phe Gln Asn Gly Lys Arg Val Ser Leu Ser Val
    50                  55                  60

Tyr Leu Gly Glu Phe Phe Asp Ile His Leu Phe Val Asn Gly Thr Val
65                  70                  75                  80

Thr Gln Gly Asp Gln Arg Val Ser Met Pro Tyr Ala Ser Lys Gly Leu
                85                  90                  95

Tyr Leu Glu Thr Glu Ala Gly Tyr Tyr Lys Leu Ser Gly Glu Ala Tyr
            100                 105                 110

Gly Phe Val Ala Arg Ile Asp Gly Ser Gly Asn Phe Gln Val Leu Leu
        115                 120                 125

Ser Asp Arg Tyr Phe Asn Lys Thr Cys Gly Leu Cys Gly Asn Phe Asn
    130                 135                 140

Ile Phe Ala Glu Asp Asp Phe Met Thr Gln Glu Gly Thr Leu Thr Ser
145                 150                 155                 160

Asp Pro Tyr Asp Phe Ala Asn Ser Trp Ala Leu Ser Ser Gly Glu Gln
                165                 170                 175

Trp Cys Glu Arg Ala Ser Pro Pro Ser Ser Ser Cys Asn Ile Ser Ser
            180                 185                 190

Gly Glu Met Gln Lys Gly Leu Trp Glu Gln Cys Gln Leu Leu Lys Ser
        195                 200                 205

Thr Ser Val Phe Ala Arg Cys His Pro Leu Val Asp Pro Glu Pro Phe
    210                 215                 220

Val Ala Leu Cys Glu Lys Thr Leu Cys Glu Cys Ala Gly Gly Leu Glu
225                 230                 235                 240

Cys Ala Cys Pro Ala Leu Leu Glu Tyr Ala Arg Thr Cys Ala Gln Glu
                245                 250                 255

Gly Met Val Leu Tyr Gly Trp Thr Asp His Ser Ala Cys Ser Pro Val
            260                 265                 270

Cys Pro Ala Gly Met Glu Tyr Arg Gln Cys Val Ser Pro Cys Ala Arg
        275                 280                 285

Thr Cys Gln Ser Leu His Ile Asn Glu Met Cys Gln Glu Arg Cys Val
    290                 295                 300

Asp Gly Cys Ser Cys Pro Glu Gly Gln Leu Leu Asp Glu Gly Leu Cys
305                 310                 315                 320
```

```
Val Glu Ser Thr Glu Cys Pro Cys Val His Ser Gly Lys Arg Tyr Pro
                325                 330                 335

Pro Gly Thr Ser Leu Ser Arg Asp Cys Asn Thr Cys Ile Cys Arg Asn
            340                 345                 350

Ser Gln Trp Ile Cys Ser Asn Glu Glu Cys Pro Gly Glu Cys Leu Val
        355                 360                 365

Thr Gly Gln Ser His Phe Lys Ser Phe Asp Asn Arg Tyr Phe Thr Phe
    370                 375                 380

Ser Gly Ile Cys Gln Tyr Leu Leu Ala Arg Asp Cys Gln Asp His Ser
385                 390                 395                 400

Phe Ser Ile Val Ile Glu Thr Val Gln Cys Ala Asp Asp Arg Asp Ala
                405                 410                 415

Val Cys Thr Arg Ser Val Thr Val Arg Leu Pro Gly Leu His Asn Ser
            420                 425                 430

Leu Val Lys Leu Lys His Gly Ala Gly Val Ala Met Asp Gly Gln Asp
        435                 440                 445

Ile Gln Leu Pro Leu Leu Lys Gly Asp Leu Arg Ile Gln His Thr Val
    450                 455                 460

Thr Ala Ser Val Arg Leu Ser Tyr Gly Glu Asp Leu Gln Met Asp Trp
465                 470                 475                 480

Asp Gly Arg Gly Arg Leu Leu Val Lys Leu Ser Pro Val Tyr Ala Gly
                485                 490                 495

Lys Thr Cys Gly Leu Cys Gly Asn Tyr Asn Gly Asn Gln Gly Asp Asp
            500                 505                 510

Phe Leu Thr Pro Ser Gly Leu Ala Glu Pro Arg Val Glu Asp Phe Gly
        515                 520                 525

Asn Ala Trp Lys Leu His Gly Asp Cys Gln Asp Leu Gln Lys Gln His
    530                 535                 540

Ser Asp Pro Cys Ala Leu Asn Pro Arg Met Thr Arg Phe Ser Glu Glu
545                 550                 555                 560

Ala Cys Ala Val Leu Thr Ser Pro Thr Phe Glu Ala Cys His Arg Ala
                565                 570                 575

Val Ser Pro Leu Pro Tyr Leu Arg Asn Cys Arg Tyr Asp Val Cys Ser
            580                 585                 590

Cys Ser Asp Gly Arg Glu Cys Leu Cys Gly Ala Leu Ala Ser Tyr Ala
        595                 600                 605

Ala Ala Cys Ala Gly Arg Gly Val Arg Val Ala Trp Arg Glu Pro Gly
    610                 615                 620

Arg Cys Glu Leu Asn Cys Pro Lys Gly Gln Val Tyr Leu Gln Cys Gly
625                 630                 635                 640

Thr Pro Cys Asn Leu Thr Cys Arg Ser Leu Ser Tyr Pro Asp Glu Glu
                645                 650                 655

Cys Asn Glu Ala Cys Leu Glu Gly Cys Phe Cys Pro Pro Gly Leu Tyr
            660                 665                 670

Met Asp Glu Arg Gly Asp Cys Val Pro Lys Ala Gln Cys Pro Cys Tyr
        675                 680                 685

Tyr Asp Gly Glu Ile Phe Gln Pro Glu Asp Ile Phe Ser Asp His His
    690                 695                 700

Thr Met Cys Tyr Cys Glu Asp Gly Phe Met His Cys Thr Met Ser Gly
705                 710                 715                 720

Val Pro Gly Ser Leu Leu Pro Asp Ala Val Leu Ser Ser Pro Leu Ser
                725                 730                 735

His Arg Ser Lys Arg Ser Leu Ser Cys Arg Pro Pro Met Val Lys Leu
```

```
        740                 745                 750

Val Cys Pro Ala Asp Asn Leu Arg Ala Glu Gly Leu Glu Cys Thr Lys
    755                 760                 765

Thr Cys Gln Asn Tyr Asp Leu Glu Cys Met Ser Met Gly Cys Val Ser
    770                 775                 780

Gly Cys Leu Cys Pro Pro Gly Met Val Arg His Glu Asn Arg Cys Val
785                 790                 795                 800

Ala Leu Glu Arg Cys Pro Cys Phe His Gln Gly Lys Glu Tyr Ala Pro
                805                 810                 815

Gly Glu Thr Val Lys Ile Gly Cys Asn Thr Cys Val Cys Arg Asp Arg
            820                 825                 830

Lys Trp Asn Cys Thr Asp His Val Cys Asp Ala Thr Cys Ser Thr Ile
    835                 840                 845

Gly Met Ala His Tyr Leu Thr Phe Asp Gly Leu Lys Tyr Leu Phe Pro
    850                 855                 860

Gly Glu Cys Gln Tyr Val Leu Val Gln Asp Tyr Cys Gly Ser Asn Pro
865                 870                 875                 880

Gly Thr Phe Arg Ile Leu Val Gly Asn Lys Gly Cys Ser His Pro Ser
                885                 890                 895

Val Lys Cys Lys Lys Arg Val Thr Ile Leu Val Glu Gly Gly Glu Ile
            900                 905                 910

Glu Leu Phe Asp Gly Glu Val Asn Val Lys Arg Pro Met Lys Asp Glu
    915                 920                 925

Thr His Phe Glu Val Val Glu Ser Gly Arg Tyr Ile Ile Leu Leu Leu
    930                 935                 940

Gly Lys Ala Leu Ser Val Val Trp Asp Arg His Leu Ser Ile Ser Val
945                 950                 955                 960

Val Leu Lys Gln Thr Tyr Gln Glu Lys Val Cys Gly Leu Cys Gly Asn
                965                 970                 975

Phe Asp Gly Ile Gln Asn Asn Asp Leu Thr Ser Ser Asn Leu Gln Val
            980                 985                 990

Glu Glu Asp Pro Val Asp Phe Gly  Asn Ser Trp Lys Val  Ser Ser Gln
    995                 1000                1005

Cys Ala  Asp Thr Arg Lys Val  Pro Leu Asp Ser Ser  Pro Ala Thr
    1010                1015                1020

Cys His  Asn Asn Ile Met Lys  Gln Thr Met Val Asp  Ser Ser Cys
    1025                1030                1035

Arg Ile  Leu Thr Ser Asp Val  Phe Gln Asp Cys Asn  Lys Leu Val
    1040                1045                1050

Asp Pro  Glu Pro Tyr Leu Asp  Val Cys Ile Tyr Asp  Thr Cys Ser
    1055                1060                1065

Cys Glu  Ser Ile Gly Asp Cys  Ala Cys Phe Cys Asp  Thr Ile Ala
    1070                1075                1080

Ala Tyr  Ala His Val Cys Ala  Gln His Gly Lys Val  Val Thr Trp
    1085                1090                1095

Arg Thr  Ala Thr Leu Cys Pro  Gln Ser Cys Glu Glu  Arg Asn Leu
    1100                1105                1110

Arg Glu  Asn Gly Tyr Glu Cys  Glu Trp Arg Tyr Asn  Ser Cys Ala
    1115                1120                1125

Pro Ala  Cys Gln Val Thr Cys  Gln His Pro Glu Pro  Leu Ala Cys
    1130                1135                1140

Pro Val  Gln Cys Val Glu Gly  Cys His Ala His Cys  Pro Pro Gly
    1145                1150                1155
```

```
Lys Ile  Leu Asp Glu Leu Leu  Gln Thr Cys Val Asp  Pro Glu Asp
    1160                 1165                 1170

Cys Pro  Val Cys Glu Val Ala  Gly Arg Arg Phe Ala  Ser Gly Lys
    1175                 1180                 1185

Lys Val  Thr Leu Asn Pro Ser  Asp Pro Glu His Cys  Gln Ile Cys
    1190                 1195                 1200

His Cys  Asp Val Val Asn Leu  Thr Cys Glu Ala Cys  Gln Glu Pro
    1205                 1210                 1215

Gly Gly  Leu Val Val Pro Pro
    1220                 1225
```

<210> SEQ ID NO 11
<211> LENGTH: 1247
<212> TYPE: PRT
<213> ORGANISM: Artificial Sequence
<220> FEATURE:
<223> OTHER INFORMATION: von Willebrand Factor sequence

<400> SEQUENCE: 11

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285
```

```
Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700
```

```
Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                 1005

Ser Ser  Asn Leu Gln Val Glu  Glu Asp Pro Val Asp  Phe Gly Asn
    1010                 1015                 1020

Ser Trp  Lys Val Ser Ser Gln  Cys Ala Asp Thr Arg  Lys Val Pro
    1025                 1030                 1035

Leu Asp  Ser Ser Pro Ala Thr  Cys His Asn Asn Ile  Met Lys Gln
    1040                 1045                 1050

Thr Met  Val Asp Ser Ser Cys  Arg Ile Leu Thr Ser  Asp Val Phe
    1055                 1060                 1065

Gln Asp  Cys Asn Lys Leu Val  Asp Pro Glu Pro Tyr  Leu Asp Val
    1070                 1075                 1080

Cys Ile  Tyr Asp Thr Cys Ser  Cys Glu Ser Ile Gly  Asp Cys Ala
    1085                 1090                 1095

Cys Phe  Cys Asp Thr Ile Ala  Ala Tyr Ala His Val  Cys Ala Gln
    1100                 1105                 1110

His Gly  Lys Val Val Thr Trp  Arg Thr Ala Thr Leu  Cys Pro Gln
```

```
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
    1145                1150                1155

His Pro  Glu Pro Leu Ala Cys  Pro Val Gln Cys Val  Glu Gly Cys
    1160                1165                1170

His Ala  His Cys Pro Pro Gly  Lys Ile Leu Asp Glu  Leu Leu Gln
    1175                1180                1185

Thr Cys  Val Asp Pro Glu Asp  Cys Pro Val Cys Glu  Val Ala Gly
    1190                1195                1200

Arg Arg  Phe Ala Ser Gly Lys  Lys Val Thr Leu Asn  Pro Ser Asp
    1205                1210                1215

Pro Glu  His Cys Gln Ile Cys  His Cys Asp Val Val  Asn Leu Thr
    1220                1225                1230

Cys Glu  Ala Cys Gln Glu Pro  Gly Gly Leu Val Val  Pro Pro
    1235                1240                1245


<210> SEQ ID NO 12
<211> LENGTH: 1459
<212> TYPE: PRT
<213> ORGANISM: Artificial Sequence
<220> FEATURE:
<223> OTHER INFORMATION: von Willebrand Factor sequence

<400> SEQUENCE: 12

Ala Glu Gly Thr Arg Gly Arg Ser Ser Thr Ala Arg Cys Ser Leu Phe
1               5                   10                  15

Gly Ser Asp Phe Val Asn Thr Phe Asp Gly Ser Met Tyr Ser Phe Ala
            20                  25                  30

Gly Tyr Cys Ser Tyr Leu Leu Ala Gly Gly Cys Gln Lys Arg Ser Phe
        35                  40                  45

Ser Ile Ile Gly Asp Phe Gln Asn Gly Lys Arg Val Ser Leu Ser Val
    50                  55                  60

Tyr Leu Gly Glu Phe Phe Asp Ile His Leu Phe Val Asn Gly Thr Val
65                  70                  75                  80

Thr Gln Gly Asp Gln Arg Val Ser Met Pro Tyr Ala Ser Lys Gly Leu
                85                  90                  95

Tyr Leu Glu Thr Glu Ala Gly Tyr Tyr Lys Leu Ser Gly Glu Ala Tyr
            100                 105                 110

Gly Phe Val Ala Arg Ile Asp Gly Ser Gly Asn Phe Gln Val Leu Leu
        115                 120                 125

Ser Asp Arg Tyr Phe Asn Lys Thr Cys Gly Leu Cys Gly Asn Phe Asn
    130                 135                 140

Ile Phe Ala Glu Asp Asp Phe Met Thr Gln Glu Gly Thr Leu Thr Ser
145                 150                 155                 160

Asp Pro Tyr Asp Phe Ala Asn Ser Trp Ala Leu Ser Ser Gly Glu Gln
                165                 170                 175

Trp Cys Glu Arg Ala Ser Pro Pro Ser Ser Ser Cys Asn Ile Ser Ser
            180                 185                 190

Gly Glu Met Gln Lys Gly Leu Trp Glu Gln Cys Gln Leu Leu Lys Ser
        195                 200                 205

Thr Ser Val Phe Ala Arg Cys His Pro Leu Val Asp Pro Glu Pro Phe
    210                 215                 220

Val Ala Leu Cys Glu Lys Thr Leu Cys Glu Cys Ala Gly Gly Leu Glu
```

```
225                 230                 235                 240

Cys Ala Cys Pro Ala Leu Leu Glu Tyr Ala Arg Thr Cys Ala Gln Glu
                245                 250                 255

Gly Met Val Leu Tyr Gly Trp Thr Asp His Ser Ala Cys Ser Pro Val
            260                 265                 270

Cys Pro Ala Gly Met Glu Tyr Arg Gln Cys Val Ser Pro Cys Ala Arg
        275                 280                 285

Thr Cys Gln Ser Leu His Ile Asn Glu Met Cys Gln Glu Arg Cys Val
    290                 295                 300

Asp Gly Cys Ser Cys Pro Glu Gly Gln Leu Leu Asp Glu Gly Leu Cys
305                 310                 315                 320

Val Glu Ser Thr Glu Cys Pro Cys Val His Ser Gly Lys Arg Tyr Pro
                325                 330                 335

Pro Gly Thr Ser Leu Ser Arg Asp Cys Asn Thr Cys Ile Cys Arg Asn
            340                 345                 350

Ser Gln Trp Ile Cys Ser Asn Glu Glu Cys Pro Gly Glu Cys Leu Val
        355                 360                 365

Thr Gly Gln Ser His Phe Lys Ser Phe Asp Asn Arg Tyr Phe Thr Phe
    370                 375                 380

Ser Gly Ile Cys Gln Tyr Leu Leu Ala Arg Asp Cys Gln Asp His Ser
385                 390                 395                 400

Phe Ser Ile Val Ile Glu Thr Val Gln Cys Ala Asp Asp Arg Asp Ala
                405                 410                 415

Val Cys Thr Arg Ser Val Thr Val Arg Leu Pro Gly Leu His Asn Ser
            420                 425                 430

Leu Val Lys Leu Lys His Gly Ala Gly Val Ala Met Asp Gly Gln Asp
        435                 440                 445

Ile Gln Leu Pro Leu Leu Lys Gly Asp Leu Arg Ile Gln His Thr Val
    450                 455                 460

Thr Ala Ser Val Arg Leu Ser Tyr Gly Glu Asp Leu Gln Met Asp Trp
465                 470                 475                 480

Asp Gly Arg Gly Arg Leu Leu Val Lys Leu Ser Pro Val Tyr Ala Gly
                485                 490                 495

Lys Thr Cys Gly Leu Cys Gly Asn Tyr Asn Gly Asn Gln Gly Asp Asp
            500                 505                 510

Phe Leu Thr Pro Ser Gly Leu Ala Glu Pro Arg Val Glu Asp Phe Gly
        515                 520                 525

Asn Ala Trp Lys Leu His Gly Asp Cys Gln Asp Leu Gln Lys Gln His
    530                 535                 540

Ser Asp Pro Cys Ala Leu Asn Pro Arg Met Thr Arg Phe Ser Glu Glu
545                 550                 555                 560

Ala Cys Ala Val Leu Thr Ser Pro Thr Phe Glu Ala Cys His Arg Ala
                565                 570                 575

Val Ser Pro Leu Pro Tyr Leu Arg Asn Cys Arg Tyr Asp Val Cys Ser
            580                 585                 590

Cys Ser Asp Gly Arg Glu Cys Leu Cys Gly Ala Leu Ala Ser Tyr Ala
        595                 600                 605

Ala Ala Cys Ala Gly Arg Gly Val Arg Val Ala Trp Arg Glu Pro Gly
    610                 615                 620

Arg Cys Glu Leu Asn Cys Pro Lys Gly Gln Val Tyr Leu Gln Cys Gly
625                 630                 635                 640

Thr Pro Cys Asn Leu Thr Cys Arg Ser Leu Ser Tyr Pro Asp Glu Glu
                645                 650                 655
```

```
Cys Asn Glu Ala Cys Leu Glu Gly Cys Phe Cys Pro Pro Gly Leu Tyr
            660                 665                 670

Met Asp Glu Arg Gly Asp Cys Val Pro Lys Ala Gln Cys Pro Cys Tyr
        675                 680                 685

Tyr Asp Gly Glu Ile Phe Gln Pro Glu Asp Ile Phe Ser Asp His His
    690                 695                 700

Thr Met Cys Tyr Cys Glu Asp Gly Phe Met His Cys Thr Met Ser Gly
705                 710                 715                 720

Val Pro Gly Ser Leu Leu Pro Asp Ala Val Leu Ser Ser Pro Leu Ser
                725                 730                 735

His Arg Ser Lys Arg Ser Leu Ser Cys Arg Pro Pro Met Val Lys Leu
            740                 745                 750

Val Cys Pro Ala Asp Asn Leu Arg Ala Glu Gly Leu Glu Cys Thr Lys
        755                 760                 765

Thr Cys Gln Asn Tyr Asp Leu Glu Cys Met Ser Met Gly Cys Val Ser
    770                 775                 780

Gly Cys Leu Cys Pro Pro Gly Met Val Arg His Glu Asn Arg Cys Val
785                 790                 795                 800

Ala Leu Glu Arg Cys Pro Cys Phe His Gln Gly Lys Glu Tyr Ala Pro
                805                 810                 815

Gly Glu Thr Val Lys Ile Gly Cys Asn Thr Cys Val Cys Arg Asp Arg
            820                 825                 830

Lys Trp Asn Cys Thr Asp His Val Cys Asp Ala Thr Cys Ser Thr Ile
        835                 840                 845

Gly Met Ala His Tyr Leu Thr Phe Asp Gly Leu Lys Tyr Leu Phe Pro
    850                 855                 860

Gly Glu Cys Gln Tyr Val Leu Val Gln Asp Tyr Cys Gly Ser Asn Pro
865                 870                 875                 880

Gly Thr Phe Arg Ile Leu Val Gly Asn Lys Gly Cys Ser His Pro Ser
                885                 890                 895

Val Lys Cys Lys Lys Arg Val Thr Ile Leu Val Glu Gly Gly Glu Ile
            900                 905                 910

Glu Leu Phe Asp Gly Glu Val Asn Val Lys Arg Pro Met Lys Asp Glu
        915                 920                 925

Thr His Phe Glu Val Val Glu Ser Gly Arg Tyr Ile Ile Leu Leu Leu
    930                 935                 940

Gly Lys Ala Leu Ser Val Val Trp Asp Arg His Leu Ser Ile Ser Val
945                 950                 955                 960

Val Leu Lys Gln Thr Tyr Gln Glu Lys Val Cys Gly Leu Cys Gly Asn
                965                 970                 975

Phe Asp Gly Ile Gln Asn Asn Asp Leu Thr Ser Ser Asn Leu Gln Val
            980                 985                 990

Glu Glu Asp Pro Val Asp Phe Gly  Asn Ser Trp Lys Val  Ser Ser Gln
        995                 1000                 1005

Cys Ala  Asp Thr Arg Lys Val  Pro Leu Asp Ser Ser  Pro Ala Thr
    1010                 1015                 1020

Cys His  Asn Asn Ile Met Lys  Gln Thr Met Val Asp  Ser Ser Cys
    1025                 1030                 1035

Arg Ile  Leu Thr Ser Asp Val  Phe Gln Asp Cys Asn  Lys Leu Val
    1040                 1045                 1050

Asp Pro  Glu Pro Tyr Leu Asp  Val Cys Ile Tyr Asp  Thr Cys Ser
    1055                 1060                 1065
```

```
Cys Glu  Ser Ile Gly Asp Cys  Ala Cys Phe Cys Asp  Thr Ile Ala
    1070                 1075                 1080

Ala Tyr  Ala His Val Cys Ala  Gln His Gly Lys Val  Val Thr Trp
    1085                 1090                 1095

Arg Thr  Ala Thr Leu Cys Pro  Gln Ser Cys Glu Glu  Arg Asn Leu
    1100                 1105                 1110

Arg Glu  Asn Gly Tyr Glu Cys  Glu Trp Arg Tyr Asn  Ser Cys Ala
    1115                 1120                 1125

Pro Ala  Cys Gln Val Thr Cys  Gln His Pro Glu Pro  Leu Ala Cys
    1130                 1135                 1140

Pro Val  Gln Cys Val Glu Gly  Cys His Ala His Cys  Pro Pro Gly
    1145                 1150                 1155

Lys Ile  Leu Asp Glu Leu Leu  Gln Thr Cys Val Asp  Pro Glu Asp
    1160                 1165                 1170

Cys Pro  Val Cys Glu Val Ala  Gly Arg Arg Phe Ala  Ser Gly Lys
    1175                 1180                 1185

Lys Val  Thr Leu Asn Pro Ser  Asp Pro Glu His Cys  Gln Ile Cys
    1190                 1195                 1200

His Cys  Asp Val Val Asn Leu  Thr Cys Glu Ala Cys  Gln Glu Pro
    1205                 1210                 1215

Gly Gly  Leu Val Val Pro Pro  Thr Asp Ala Pro Val  Ser Pro Thr
    1220                 1225                 1230

Thr Leu  Tyr Val Glu Asp Ile  Ser Glu Pro Pro Leu  His Asp Phe
    1235                 1240                 1245

Tyr Cys  Ser Arg Leu Leu Asp  Leu Val Phe Leu Leu  Asp Gly Ser
    1250                 1255                 1260

Ser Arg  Leu Ser Glu Ala Glu  Phe Glu Val Leu Lys  Ala Phe Val
    1265                 1270                 1275

Val Asp  Met Met Glu Arg Leu  Arg Ile Ser Gln Lys  Trp Val Arg
    1280                 1285                 1290

Val Ala  Val Val Glu Tyr His  Asp Gly Ser His Ala  Tyr Ile Gly
    1295                 1300                 1305

Leu Lys  Asp Arg Lys Arg Pro  Ser Glu Leu Arg Arg  Ile Ala Ser
    1310                 1315                 1320

Gln Val  Lys Tyr Ala Gly Ser  Gln Val Ala Ser Thr  Ser Glu Val
    1325                 1330                 1335

Leu Lys  Tyr Thr Leu Phe Gln  Ile Phe Ser Lys Ile  Asp Arg Pro
    1340                 1345                 1350

Glu Ala  Ser Arg Ile Ala Leu  Leu Leu Met Ala Ser  Gln Glu Pro
    1355                 1360                 1365

Gln Arg  Met Ser Arg Asn Phe  Val Arg Tyr Val Gln  Gly Leu Lys
    1370                 1375                 1380

Lys Lys  Lys Val Ile Val Ile  Pro Val Gly Ile Gly  Pro His Ala
    1385                 1390                 1395

Asn Leu  Lys Gln Ile Arg Leu  Ile Glu Lys Gln Ala  Pro Glu Asn
    1400                 1405                 1410

Lys Ala  Phe Val Leu Ser Ser  Val Asp Glu Leu Glu  Gln Gln Arg
    1415                 1420                 1425

Asp Glu  Ile Val Ser Tyr Leu  Cys Asp Leu Ala Pro  Glu Ala Pro
    1430                 1435                 1440

Pro Pro  Thr Leu Pro Pro His  Met Ala Gln Val Thr  Val Gly Pro
    1445                 1450                 1455

Gly
```

<210> SEQ ID NO 13
<211> LENGTH: 1481
<212> TYPE: PRT
<213> ORGANISM: Artificial Sequence
<220> FEATURE:
<223> OTHER INFORMATION: von Willebrand Factor sequence

<400> SEQUENCE: 13

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365
```

```
Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780
```

-continued

```
Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
    1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
    1145                1150                1155

His Pro  Glu Pro Leu Ala Cys  Pro Val Gln Cys Val  Glu Gly Cys
    1160                1165                1170

His Ala  His Cys Pro Pro Gly  Lys Ile Leu Asp Glu  Leu Leu Gln
    1175                1180                1185

Thr Cys  Val Asp Pro Glu Asp  Cys Pro Val Cys Glu  Val Ala Gly
```

```
    1190                1195                1200

Arg Arg  Phe Ala Ser Gly Lys  Lys Val Thr Leu Asn  Pro Ser Asp
    1205                1210                1215

Pro Glu  His Cys Gln Ile Cys  His Cys Asp Val Val  Asn Leu Thr
    1220                1225                1230

Cys Glu  Ala Cys Gln Glu Pro  Gly Gly Leu Val Val  Pro Pro Thr
    1235                1240                1245

Asp Ala  Pro Val Ser Pro Thr  Thr Leu Tyr Val Glu  Asp Ile Ser
    1250                1255                1260

Glu Pro  Pro Leu His Asp Phe  Tyr Cys Ser Arg Leu  Leu Asp Leu
    1265                1270                1275

Val Phe  Leu Leu Asp Gly Ser  Ser Arg Leu Ser Glu  Ala Glu Phe
    1280                1285                1290

Glu Val  Leu Lys Ala Phe Val  Val Asp Met Met Glu  Arg Leu Arg
    1295                1300                1305

Ile Ser  Gln Lys Trp Val Arg  Val Ala Val Val Glu  Tyr His Asp
    1310                1315                1320

Gly Ser  His Ala Tyr Ile Gly  Leu Lys Asp Arg Lys  Arg Pro Ser
    1325                1330                1335

Glu Leu  Arg Arg Ile Ala Ser  Gln Val Lys Tyr Ala  Gly Ser Gln
    1340                1345                1350

Val Ala  Ser Thr Ser Glu Val  Leu Lys Tyr Thr Leu  Phe Gln Ile
    1355                1360                1365

Phe Ser  Lys Ile Asp Arg Pro  Glu Ala Ser Arg Ile  Ala Leu Leu
    1370                1375                1380

Leu Met  Ala Ser Gln Glu Pro  Gln Arg Met Ser Arg  Asn Phe Val
    1385                1390                1395

Arg Tyr  Val Gln Gly Leu Lys  Lys Lys Lys Val Ile  Val Ile Pro
    1400                1405                1410

Val Gly  Ile Gly Pro His Ala  Asn Leu Lys Gln Ile  Arg Leu Ile
    1415                1420                1425

Glu Lys  Gln Ala Pro Glu Asn  Lys Ala Phe Val Leu  Ser Ser Val
    1430                1435                1440

Asp Glu  Leu Glu Gln Gln Arg  Asp Glu Ile Val Ser  Tyr Leu Cys
    1445                1450                1455

Asp Leu  Ala Pro Glu Ala Pro  Pro Pro Thr Leu Pro  Pro His Met
    1460                1465                1470

Ala Gln  Val Thr Val Gly Pro  Gly
    1475                1480
```

<210> SEQ ID NO 14
<211> LENGTH: 1857
<212> TYPE: PRT
<213> ORGANISM: Artificial Sequence
<220> FEATURE:
<223> OTHER INFORMATION: von Willebrand Factor sequence

<400> SEQUENCE: 14

```
Ala Glu Gly Thr Arg Gly Arg Ser Ser Thr Ala Arg Cys Ser Leu Phe
1               5                   10                  15

Gly Ser Asp Phe Val Asn Thr Phe Asp Gly Ser Met Tyr Ser Phe Ala
            20                  25                  30

Gly Tyr Cys Ser Tyr Leu Leu Ala Gly Gly Cys Gln Lys Arg Ser Phe
        35                  40                  45

Ser Ile Ile Gly Asp Phe Gln Asn Gly Lys Arg Val Ser Leu Ser Val
```

```
    50                  55                  60

Tyr Leu Gly Glu Phe Phe Asp Ile His Leu Phe Val Asn Gly Thr Val
65                  70                  75                  80

Thr Gln Gly Asp Gln Arg Val Ser Met Pro Tyr Ala Ser Lys Gly Leu
                85                  90                  95

Tyr Leu Glu Thr Glu Ala Gly Tyr Tyr Lys Leu Ser Gly Glu Ala Tyr
            100                 105                 110

Gly Phe Val Ala Arg Ile Asp Gly Ser Gly Asn Phe Gln Val Leu Leu
        115                 120                 125

Ser Asp Arg Tyr Phe Asn Lys Thr Cys Gly Leu Cys Gly Asn Phe Asn
    130                 135                 140

Ile Phe Ala Glu Asp Asp Phe Met Thr Gln Glu Gly Thr Leu Thr Ser
145                 150                 155                 160

Asp Pro Tyr Asp Phe Ala Asn Ser Trp Ala Leu Ser Ser Gly Glu Gln
                165                 170                 175

Trp Cys Glu Arg Ala Ser Pro Pro Ser Ser Ser Cys Asn Ile Ser Ser
            180                 185                 190

Gly Glu Met Gln Lys Gly Leu Trp Glu Gln Cys Gln Leu Leu Lys Ser
        195                 200                 205

Thr Ser Val Phe Ala Arg Cys His Pro Leu Val Asp Pro Glu Pro Phe
    210                 215                 220

Val Ala Leu Cys Glu Lys Thr Leu Cys Glu Cys Ala Gly Gly Leu Glu
225                 230                 235                 240

Cys Ala Cys Pro Ala Leu Leu Glu Tyr Ala Arg Thr Cys Ala Gln Glu
                245                 250                 255

Gly Met Val Leu Tyr Gly Trp Thr Asp His Ser Ala Cys Ser Pro Val
            260                 265                 270

Cys Pro Ala Gly Met Glu Tyr Arg Gln Cys Val Ser Pro Cys Ala Arg
        275                 280                 285

Thr Cys Gln Ser Leu His Ile Asn Glu Met Cys Gln Glu Arg Cys Val
    290                 295                 300

Asp Gly Cys Ser Cys Pro Glu Gly Gln Leu Leu Asp Glu Gly Leu Cys
305                 310                 315                 320

Val Glu Ser Thr Glu Cys Pro Cys Val His Ser Gly Lys Arg Tyr Pro
                325                 330                 335

Pro Gly Thr Ser Leu Ser Arg Asp Cys Asn Thr Cys Ile Cys Arg Asn
            340                 345                 350

Ser Gln Trp Ile Cys Ser Asn Glu Glu Cys Pro Gly Glu Cys Leu Val
        355                 360                 365

Thr Gly Gln Ser His Phe Lys Ser Phe Asp Asn Arg Tyr Phe Thr Phe
    370                 375                 380

Ser Gly Ile Cys Gln Tyr Leu Leu Ala Arg Asp Cys Gln Asp His Ser
385                 390                 395                 400

Phe Ser Ile Val Ile Glu Thr Val Gln Cys Ala Asp Asp Arg Asp Ala
                405                 410                 415

Val Cys Thr Arg Ser Val Thr Val Arg Leu Pro Gly Leu His Asn Ser
            420                 425                 430

Leu Val Lys Leu Lys His Gly Ala Gly Val Ala Met Asp Gly Gln Asp
        435                 440                 445

Ile Gln Leu Pro Leu Leu Lys Gly Asp Leu Arg Ile Gln His Thr Val
    450                 455                 460

Thr Ala Ser Val Arg Leu Ser Tyr Gly Glu Asp Leu Gln Met Asp Trp
465                 470                 475                 480
```

```
Asp Gly Arg Gly Arg Leu Leu Val Lys Leu Ser Pro Val Tyr Ala Gly
                485                 490                 495

Lys Thr Cys Gly Leu Cys Gly Asn Tyr Asn Gly Asn Gln Gly Asp Asp
            500                 505                 510

Phe Leu Thr Pro Ser Gly Leu Ala Glu Pro Arg Val Glu Asp Phe Gly
        515                 520                 525

Asn Ala Trp Lys Leu His Gly Asp Cys Gln Asp Leu Gln Lys Gln His
    530                 535                 540

Ser Asp Pro Cys Ala Leu Asn Pro Arg Met Thr Arg Phe Ser Glu Glu
545                 550                 555                 560

Ala Cys Ala Val Leu Thr Ser Pro Thr Phe Glu Ala Cys His Arg Ala
                565                 570                 575

Val Ser Pro Leu Pro Tyr Leu Arg Asn Cys Arg Tyr Asp Val Cys Ser
            580                 585                 590

Cys Ser Asp Gly Arg Glu Cys Leu Cys Gly Ala Leu Ala Ser Tyr Ala
        595                 600                 605

Ala Ala Cys Ala Gly Arg Gly Val Arg Val Ala Trp Arg Glu Pro Gly
    610                 615                 620

Arg Cys Glu Leu Asn Cys Pro Lys Gly Gln Val Tyr Leu Gln Cys Gly
625                 630                 635                 640

Thr Pro Cys Asn Leu Thr Cys Arg Ser Leu Ser Tyr Pro Asp Glu Glu
                645                 650                 655

Cys Asn Glu Ala Cys Leu Glu Gly Cys Phe Cys Pro Pro Gly Leu Tyr
            660                 665                 670

Met Asp Glu Arg Gly Asp Cys Val Pro Lys Ala Gln Cys Pro Cys Tyr
        675                 680                 685

Tyr Asp Gly Glu Ile Phe Gln Pro Glu Asp Ile Phe Ser Asp His His
    690                 695                 700

Thr Met Cys Tyr Cys Glu Asp Gly Phe Met His Cys Thr Met Ser Gly
705                 710                 715                 720

Val Pro Gly Ser Leu Leu Pro Asp Ala Val Leu Ser Ser Pro Leu Ser
                725                 730                 735

His Arg Ser Lys Arg Ser Leu Ser Cys Arg Pro Pro Met Val Lys Leu
            740                 745                 750

Val Cys Pro Ala Asp Asn Leu Arg Ala Glu Gly Leu Glu Cys Thr Lys
        755                 760                 765

Thr Cys Gln Asn Tyr Asp Leu Glu Cys Met Ser Met Gly Cys Val Ser
    770                 775                 780

Gly Cys Leu Cys Pro Pro Gly Met Val Arg His Glu Asn Arg Cys Val
785                 790                 795                 800

Ala Leu Glu Arg Cys Pro Cys Phe His Gln Gly Lys Glu Tyr Ala Pro
                805                 810                 815

Gly Glu Thr Val Lys Ile Gly Cys Asn Thr Cys Val Cys Arg Asp Arg
            820                 825                 830

Lys Trp Asn Cys Thr Asp His Val Cys Asp Ala Thr Cys Ser Thr Ile
        835                 840                 845

Gly Met Ala His Tyr Leu Thr Phe Asp Gly Leu Lys Tyr Leu Phe Pro
    850                 855                 860

Gly Glu Cys Gln Tyr Val Leu Val Gln Asp Tyr Cys Gly Ser Asn Pro
865                 870                 875                 880

Gly Thr Phe Arg Ile Leu Val Gly Asn Lys Gly Cys Ser His Pro Ser
                885                 890                 895
```

```
Val Lys Cys Lys Lys Arg Val Thr Ile Leu Val Glu Gly Gly Glu Ile
            900                 905                 910

Glu Leu Phe Asp Gly Glu Val Asn Val Lys Arg Pro Met Lys Asp Glu
        915                 920                 925

Thr His Phe Glu Val Val Glu Ser Gly Arg Tyr Ile Ile Leu Leu Leu
    930                 935                 940

Gly Lys Ala Leu Ser Val Val Trp Asp Arg His Leu Ser Ile Ser Val
945                 950                 955                 960

Val Leu Lys Gln Thr Tyr Gln Glu Lys Val Cys Gly Leu Cys Gly Asn
                965                 970                 975

Phe Asp Gly Ile Gln Asn Asn Asp Leu Thr Ser Ser Asn Leu Gln Val
            980                 985                 990

Glu Glu Asp Pro Val Asp Phe Gly  Asn Ser Trp Lys Val  Ser Ser Gln
        995                 1000                1005

Cys Ala  Asp Thr Arg Lys Val  Pro Leu Asp Ser Ser  Pro Ala Thr
    1010                1015                1020

Cys His  Asn Asn Ile Met Lys  Gln Thr Met Val Asp  Ser Ser Cys
    1025                1030                1035

Arg Ile  Leu Thr Ser Asp Val  Phe Gln Asp Cys Asn  Lys Leu Val
    1040                1045                1050

Asp Pro  Glu Pro Tyr Leu Asp  Val Cys Ile Tyr Asp  Thr Cys Ser
    1055                1060                1065

Cys Glu  Ser Ile Gly Asp Cys  Ala Cys Phe Cys Asp  Thr Ile Ala
    1070                1075                1080

Ala Tyr  Ala His Val Cys Ala  Gln His Gly Lys Val  Val Thr Trp
    1085                1090                1095

Arg Thr  Ala Thr Leu Cys Pro  Gln Ser Cys Glu Glu  Arg Asn Leu
    1100                1105                1110

Arg Glu  Asn Gly Tyr Glu Cys  Glu Trp Arg Tyr Asn  Ser Cys Ala
    1115                1120                1125

Pro Ala  Cys Gln Val Thr Cys  Gln His Pro Glu Pro  Leu Ala Cys
    1130                1135                1140

Pro Val  Gln Cys Val Glu Gly  Cys His Ala His Cys  Pro Pro Gly
    1145                1150                1155

Lys Ile  Leu Asp Glu Leu Leu  Gln Thr Cys Val Asp  Pro Glu Asp
    1160                1165                1170

Cys Pro  Val Cys Glu Val Ala  Gly Arg Arg Phe Ala  Ser Gly Lys
    1175                1180                1185

Lys Val  Thr Leu Asn Pro Ser  Asp Pro Glu His Cys  Gln Ile Cys
    1190                1195                1200

His Cys  Asp Val Val Asn Leu  Thr Cys Glu Ala Cys  Gln Glu Pro
    1205                1210                1215

Gly Gly  Leu Val Val Pro Pro  Thr Asp Ala Pro Val  Ser Pro Thr
    1220                1225                1230

Thr Leu  Tyr Val Glu Asp Ile  Ser Glu Pro Pro Leu  His Asp Phe
    1235                1240                1245

Tyr Cys  Ser Arg Leu Leu Asp  Leu Val Phe Leu Leu  Asp Gly Ser
    1250                1255                1260

Ser Arg  Leu Ser Glu Ala Glu  Phe Glu Val Leu Lys  Ala Phe Val
    1265                1270                1275

Val Asp  Met Met Glu Arg Leu  Arg Ile Ser Gln Lys  Trp Val Arg
    1280                1285                1290

Val Ala  Val Val Glu Tyr His  Asp Gly Ser His Ala  Tyr Ile Gly
```

```
    1295                1300                1305

Leu Lys  Asp Arg Lys Arg Pro  Ser Glu Leu Arg Arg  Ile Ala Ser
    1310                1315                1320

Gln Val  Lys Tyr Ala Gly Ser  Gln Val Ala Ser Thr  Ser Glu Val
    1325                1330                1335

Leu Lys  Tyr Thr Leu Phe Gln  Ile Phe Ser Lys Ile  Asp Arg Pro
    1340                1345                1350

Glu Ala  Ser Arg Ile Ala Leu  Leu Leu Met Ala Ser  Gln Glu Pro
    1355                1360                1365

Gln Arg  Met Ser Arg Asn Phe  Val Arg Tyr Val Gln  Gly Leu Lys
    1370                1375                1380

Lys Lys  Lys Val Ile Val Ile  Pro Val Gly Ile Gly  Pro His Ala
    1385                1390                1395

Asn Leu  Lys Gln Ile Arg Leu  Ile Glu Lys Gln Ala  Pro Glu Asn
    1400                1405                1410

Lys Ala  Phe Val Leu Ser Ser  Val Asp Glu Leu Glu  Gln Gln Arg
    1415                1420                1425

Asp Glu  Ile Val Ser Tyr Leu  Cys Asp Leu Ala Pro  Glu Ala Pro
    1430                1435                1440

Pro Pro  Thr Leu Pro Pro His  Met Ala Gln Val Thr  Val Gly Pro
    1445                1450                1455

Gly Leu  Leu Gly Val Ser Thr  Leu Gly Pro Lys Arg  Asn Ser Met
    1460                1465                1470

Val Leu  Asp Val Ala Phe Val  Leu Glu Gly Ser Asp  Lys Ile Gly
    1475                1480                1485

Glu Ala  Asp Phe Asn Arg Ser  Lys Glu Phe Met Glu  Glu Val Ile
    1490                1495                1500

Gln Arg  Met Asp Val Gly Gln  Asp Ser Ile His Val  Thr Val Leu
    1505                1510                1515

Gln Tyr  Ser Tyr Met Val Thr  Val Glu Tyr Pro Phe  Ser Glu Ala
    1520                1525                1530

Gln Ser  Lys Gly Asp Ile Leu  Gln Arg Val Arg Glu  Ile Arg Tyr
    1535                1540                1545

Gln Gly  Gly Asn Arg Thr Asn  Thr Gly Leu Ala Leu  Arg Tyr Leu
    1550                1555                1560

Ser Asp  His Ser Phe Leu Val  Ser Gln Gly Asp Arg  Glu Gln Ala
    1565                1570                1575

Pro Asn  Leu Val Tyr Met Val  Thr Gly Asn Pro Ala  Ser Asp Glu
    1580                1585                1590

Ile Lys  Arg Leu Pro Gly Asp  Ile Gln Val Val Pro  Ile Gly Val
    1595                1600                1605

Gly Pro  Asn Ala Asn Val Gln  Glu Leu Glu Arg Ile  Gly Trp Pro
    1610                1615                1620

Asn Ala  Pro Ile Leu Ile Gln  Asp Phe Glu Thr Leu  Pro Arg Glu
    1625                1630                1635

Ala Pro  Asp Leu Val Leu Gln  Arg Cys Cys Ser Gly  Glu Gly Leu
    1640                1645                1650

Gln Ile  Pro Thr Leu Ser Pro  Ala Pro Asp Cys Ser  Gln Pro Leu
    1655                1660                1665

Asp Val  Ile Leu Leu Leu Asp  Gly Ser Ser Ser Phe  Pro Ala Ser
    1670                1675                1680

Tyr Phe  Asp Glu Met Lys Ser  Phe Ala Lys Ala Phe  Ile Ser Lys
    1685                1690                1695
```

```
Ala Asn  Ile Gly Pro Arg Leu  Thr Gln Val Ser Val  Leu Gln Tyr
    1700                 1705                 1710

Gly Ser  Ile Thr Thr Ile Asp  Val Pro Trp Asn Val  Val Pro Glu
    1715                 1720                 1725

Lys Ala  His Leu Leu Ser Leu  Val Asp Val Met Gln  Arg Glu Gly
    1730                 1735                 1740

Gly Pro  Ser Gln Ile Gly Asp  Ala Leu Gly Phe Ala  Val Arg Tyr
    1745                 1750                 1755

Leu Thr  Ser Glu Met His Gly  Ala Arg Pro Gly Ala  Ser Lys Ala
    1760                 1765                 1770

Val Val  Ile Leu Val Thr Asp  Val Ser Val Asp Ser  Val Asp Ala
    1775                 1780                 1785

Ala Ala  Asp Ala Ala Arg Ser  Asn Arg Val Thr Val  Phe Pro Ile
    1790                 1795                 1800

Gly Ile  Gly Asp Arg Tyr Asp  Ala Ala Gln Leu Arg  Ile Leu Ala
    1805                 1810                 1815

Gly Pro  Ala Gly Asp Ser Asn  Val Val Lys Leu Gln  Arg Ile Glu
    1820                 1825                 1830

Asp Leu  Pro Thr Met Val Thr  Leu Gly Asn Ser Phe  Leu His Lys
    1835                 1840                 1845

Leu Cys  Ser Gly Phe Val Arg  Ile Cys
    1850                 1855


<210> SEQ ID NO 15
<211> LENGTH: 1879
<212> TYPE: PRT
<213> ORGANISM: Artificial Sequence
<220> FEATURE:
<223> OTHER INFORMATION: von Willebrand Factor sequence

<400> SEQUENCE: 15

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190
```

```
Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605
```

```
Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
```

```
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
    1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
    1145                1150                1155

His Pro  Glu Pro Leu Ala Cys  Pro Val Gln Cys Val  Glu Gly Cys
    1160                1165                1170

His Ala  His Cys Pro Pro Gly  Lys Ile Leu Asp Glu  Leu Leu Gln
    1175                1180                1185

Thr Cys  Val Asp Pro Glu Asp  Cys Pro Val Cys Glu  Val Ala Gly
    1190                1195                1200

Arg Arg  Phe Ala Ser Gly Lys  Lys Val Thr Leu Asn  Pro Ser Asp
    1205                1210                1215

Pro Glu  His Cys Gln Ile Cys  His Cys Asp Val Val  Asn Leu Thr
    1220                1225                1230

Cys Glu  Ala Cys Gln Glu Pro  Gly Gly Leu Val Val  Pro Pro Thr
    1235                1240                1245

Asp Ala  Pro Val Ser Pro Thr  Thr Leu Tyr Val Glu  Asp Ile Ser
    1250                1255                1260

Glu Pro  Pro Leu His Asp Phe  Tyr Cys Ser Arg Leu  Leu Asp Leu
    1265                1270                1275

Val Phe  Leu Leu Asp Gly Ser  Ser Arg Leu Ser Glu  Ala Glu Phe
    1280                1285                1290

Glu Val  Leu Lys Ala Phe Val  Val Asp Met Met Glu  Arg Leu Arg
    1295                1300                1305

Ile Ser  Gln Lys Trp Val Arg  Val Ala Val Val Glu  Tyr His Asp
    1310                1315                1320

Gly Ser  His Ala Tyr Ile Gly  Leu Lys Asp Arg Lys  Arg Pro Ser
    1325                1330                1335

Glu Leu  Arg Arg Ile Ala Ser  Gln Val Lys Tyr Ala  Gly Ser Gln
    1340                1345                1350

Val Ala  Ser Thr Ser Glu Val  Leu Lys Tyr Thr Leu  Phe Gln Ile
    1355                1360                1365

Phe Ser  Lys Ile Asp Arg Pro  Glu Ala Ser Arg Ile  Ala Leu Leu
    1370                1375                1380

Leu Met  Ala Ser Gln Glu Pro  Gln Arg Met Ser Arg  Asn Phe Val
    1385                1390                1395

Arg Tyr  Val Gln Gly Leu Lys  Lys Lys Lys Val Ile  Val Ile Pro
    1400                1405                1410

Val Gly  Ile Gly Pro His Ala  Asn Leu Lys Gln Ile  Arg Leu Ile
    1415                1420                1425
```

```
Glu Lys  Gln Ala Pro Glu Asn  Lys Ala Phe Val Leu  Ser Ser Val
    1430                 1435                 1440

Asp Glu  Leu Glu Gln Gln Arg  Asp Glu Ile Val Ser  Tyr Leu Cys
    1445                 1450                 1455

Asp Leu  Ala Pro Glu Ala Pro  Pro Pro Thr Leu Pro  Pro His Met
    1460                 1465                 1470

Ala Gln  Val Thr Val Gly Pro  Gly Leu Leu Gly Val  Ser Thr Leu
    1475                 1480                 1485

Gly Pro  Lys Arg Asn Ser Met  Val Leu Asp Val Ala  Phe Val Leu
    1490                 1495                 1500

Glu Gly  Ser Asp Lys Ile Gly  Glu Ala Asp Phe Asn  Arg Ser Lys
    1505                 1510                 1515

Glu Phe  Met Glu Glu Val Ile  Gln Arg Met Asp Val  Gly Gln Asp
    1520                 1525                 1530

Ser Ile  His Val Thr Val Leu  Gln Tyr Ser Tyr Met  Val Thr Val
    1535                 1540                 1545

Glu Tyr  Pro Phe Ser Glu Ala  Gln Ser Lys Gly Asp  Ile Leu Gln
    1550                 1555                 1560

Arg Val  Arg Glu Ile Arg Tyr  Gln Gly Gly Asn Arg  Thr Asn Thr
    1565                 1570                 1575

Gly Leu  Ala Leu Arg Tyr Leu  Ser Asp His Ser Phe  Leu Val Ser
    1580                 1585                 1590

Gln Gly  Asp Arg Glu Gln Ala  Pro Asn Leu Val Tyr  Met Val Thr
    1595                 1600                 1605

Gly Asn  Pro Ala Ser Asp Glu  Ile Lys Arg Leu Pro  Gly Asp Ile
    1610                 1615                 1620

Gln Val  Val Pro Ile Gly Val  Gly Pro Asn Ala Asn  Val Gln Glu
    1625                 1630                 1635

Leu Glu  Arg Ile Gly Trp Pro  Asn Ala Pro Ile Leu  Ile Gln Asp
    1640                 1645                 1650

Phe Glu  Thr Leu Pro Arg Glu  Ala Pro Asp Leu Val  Leu Gln Arg
    1655                 1660                 1665

Cys Cys  Ser Gly Glu Gly Leu  Gln Ile Pro Thr Leu  Ser Pro Ala
    1670                 1675                 1680

Pro Asp  Cys Ser Gln Pro Leu  Asp Val Ile Leu Leu  Leu Asp Gly
    1685                 1690                 1695

Ser Ser  Ser Phe Pro Ala Ser  Tyr Phe Asp Glu Met  Lys Ser Phe
    1700                 1705                 1710

Ala Lys  Ala Phe Ile Ser Lys  Ala Asn Ile Gly Pro  Arg Leu Thr
    1715                 1720                 1725

Gln Val  Ser Val Leu Gln Tyr  Gly Ser Ile Thr Thr  Ile Asp Val
    1730                 1735                 1740

Pro Trp  Asn Val Val Pro Glu  Lys Ala His Leu Leu  Ser Leu Val
    1745                 1750                 1755

Asp Val  Met Gln Arg Glu Gly  Gly Pro Ser Gln Ile  Gly Asp Ala
    1760                 1765                 1770

Leu Gly  Phe Ala Val Arg Tyr  Leu Thr Ser Glu Met  His Gly Ala
    1775                 1780                 1785

Arg Pro  Gly Ala Ser Lys Ala  Val Val Ile Leu Val  Thr Asp Val
    1790                 1795                 1800

Ser Val  Asp Ser Val Asp Ala  Ala Ala Asp Ala Ala  Arg Ser Asn
    1805                 1810                 1815
```

```
Arg Val  Thr Val Phe Pro Ile  Gly Ile Gly Asp Arg  Tyr Asp Ala
    1820                 1825                 1830

Ala Gln  Leu Arg Ile Leu Ala  Gly Pro Ala Gly Asp  Ser Asn Val
    1835                 1840                 1845

Val Lys  Leu Gln Arg Ile Glu  Asp Leu Pro Thr Met  Val Thr Leu
    1850                 1855                 1860

Gly Asn  Ser Phe Leu His Lys  Leu Cys Ser Gly Phe  Val Arg Ile
    1865                 1870                 1875

Cys


<210> SEQ ID NO 16
<211> LENGTH: 227
<212> TYPE: PRT
<213> ORGANISM: Artificial Sequence
<220> FEATURE:
<223> OTHER INFORMATION: IgG1 derivved Fc

<400> SEQUENCE: 16

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 17
<211> LENGTH: 734
<212> TYPE: PRT
<213> ORGANISM: Artificial Sequence
<220> FEATURE:
<223> OTHER INFORMATION: von Willebrand Factor sequence

<400> SEQUENCE: 17
```

```
Met Ile Pro Ala Arg Phe Ala Gly Val Leu Leu Ala Leu Ala Leu Ile
1               5                   10                  15

Leu Pro Gly Thr Leu Cys Ala Ser Leu Ser Cys Arg Pro Pro Met Val
            20                  25                  30

Lys Leu Val Cys Pro Ala Asp Asn Leu Arg Ala Glu Gly Leu Glu Cys
        35                  40                  45

Thr Lys Thr Cys Gln Asn Tyr Asp Leu Glu Cys Met Ser Met Gly Cys
    50                  55                  60

Val Ser Gly Cys Leu Cys Pro Pro Gly Met Val Arg His Glu Asn Arg
65                  70                  75                  80

Cys Val Ala Leu Glu Arg Cys Pro Cys Phe His Gln Gly Lys Glu Tyr
                85                  90                  95

Ala Pro Gly Glu Thr Val Lys Ile Gly Cys Asn Thr Cys Val Cys Arg
            100                 105                 110

Asp Arg Lys Trp Asn Cys Thr Asp His Val Cys Asp Ala Thr Cys Ser
        115                 120                 125

Thr Ile Gly Met Ala His Tyr Leu Thr Phe Asp Gly Leu Lys Tyr Leu
    130                 135                 140

Phe Pro Gly Glu Cys Gln Tyr Val Leu Val Gln Asp Tyr Cys Gly Ser
145                 150                 155                 160

Asn Pro Gly Thr Phe Arg Ile Leu Val Gly Asn Lys Gly Cys Ser His
                165                 170                 175

Pro Ser Val Lys Cys Lys Lys Arg Val Thr Ile Leu Val Glu Gly Gly
            180                 185                 190

Glu Ile Glu Leu Phe Asp Gly Glu Val Asn Val Lys Arg Pro Met Lys
        195                 200                 205

Asp Glu Thr His Phe Glu Val Val Glu Ser Gly Arg Tyr Ile Ile Leu
    210                 215                 220

Leu Leu Gly Lys Ala Leu Ser Val Val Trp Asp Arg His Leu Ser Ile
225                 230                 235                 240

Ser Val Val Leu Lys Gln Thr Tyr Gln Glu Lys Val Cys Gly Leu Cys
                245                 250                 255

Gly Asn Phe Asp Gly Ile Gln Asn Asn Asp Leu Thr Ser Ser Asn Leu
            260                 265                 270

Gln Val Glu Glu Asp Pro Val Asp Phe Gly Asn Ser Trp Lys Val Ser
        275                 280                 285

Ser Gln Cys Ala Asp Thr Arg Lys Val Pro Leu Asp Ser Ser Pro Ala
    290                 295                 300

Thr Cys His Asn Asn Ile Met Lys Gln Thr Met Val Asp Ser Ser Cys
305                 310                 315                 320

Arg Ile Leu Thr Ser Asp Val Phe Gln Asp Cys Asn Lys Leu Val Asp
                325                 330                 335

Pro Glu Pro Tyr Leu Asp Val Cys Ile Tyr Asp Thr Cys Ser Cys Glu
            340                 345                 350

Ser Ile Gly Asp Cys Ala Cys Phe Cys Asp Thr Ile Ala Ala Tyr Ala
        355                 360                 365

His Val Cys Ala Gln His Gly Lys Val Val Thr Trp Arg Thr Ala Thr
    370                 375                 380

Leu Cys Pro Gln Ser Cys Glu Glu Arg Asn Leu Arg Glu Asn Gly Tyr
385                 390                 395                 400

Glu Cys Glu Trp Arg Tyr Asn Ser Cys Ala Pro Ala Cys Gln Val Thr
                405                 410                 415

Cys Gln His Pro Glu Pro Leu Ala Cys Pro Val Gln Cys Val Glu Gly
```

```
            420                 425                 430

Cys His Ala His Cys Pro Pro Gly Lys Ile Leu Asp Glu Leu Leu Gln
        435                 440                 445

Thr Cys Val Asp Pro Glu Asp Cys Pro Val Cys Glu Val Ala Gly Arg
    450                 455                 460

Arg Phe Ala Ser Gly Lys Lys Val Thr Leu Asn Pro Ser Asp Pro Glu
465                 470                 475                 480

His Cys Gln Ile Cys His Cys Asp Val Val Asn Leu Thr Cys Glu Ala
                485                 490                 495

Cys Gln Glu Pro Gly Gly Leu Val Val Pro Pro Asp Lys Thr His Thr
            500                 505                 510

Cys Pro Pro Cys Pro Ala Pro Glu Leu Leu Gly Gly Pro Ser Val Phe
        515                 520                 525

Leu Phe Pro Pro Lys Pro Lys Asp Thr Leu Met Ile Ser Arg Thr Pro
    530                 535                 540

Glu Val Thr Cys Val Val Val Asp Val Ser His Glu Asp Pro Glu Val
545                 550                 555                 560

Lys Phe Asn Trp Tyr Val Asp Gly Val Glu Val His Asn Ala Lys Thr
                565                 570                 575

Lys Pro Arg Glu Glu Gln Tyr Asn Ser Thr Tyr Arg Val Val Ser Val
            580                 585                 590

Leu Thr Val Leu His Gln Asp Trp Leu Asn Gly Lys Glu Tyr Lys Cys
        595                 600                 605

Lys Val Ser Asn Lys Ala Leu Pro Ala Pro Ile Glu Lys Thr Ile Ser
    610                 615                 620

Lys Ala Lys Gly Gln Pro Arg Glu Pro Gln Val Tyr Thr Leu Pro Pro
625                 630                 635                 640

Ser Arg Asp Glu Leu Thr Lys Asn Gln Val Ser Leu Thr Cys Leu Val
                645                 650                 655

Lys Gly Phe Tyr Pro Ser Asp Ile Ala Val Glu Trp Glu Ser Asn Gly
            660                 665                 670

Gln Pro Glu Asn Asn Tyr Lys Thr Thr Pro Pro Val Leu Asp Ser Asp
        675                 680                 685

Gly Ser Phe Phe Leu Tyr Ser Lys Leu Thr Val Asp Lys Ser Arg Trp
    690                 695                 700

Gln Gln Gly Asn Val Phe Ser Cys Ser Val Met His Glu Ala Leu His
705                 710                 715                 720

Asn His Tyr Thr Gln Lys Ser Leu Ser Leu Ser Pro Gly Lys
                725                 730


<210> SEQ ID NO 18
<211> LENGTH: 968
<212> TYPE: PRT
<213> ORGANISM: Artificial Sequence
<220> FEATURE:
<223> OTHER INFORMATION: von Willebrand Factor sequence

<400> SEQUENCE: 18

Met Ile Pro Ala Arg Phe Ala Gly Val Leu Leu Ala Leu Ala Leu Ile
1               5                   10                  15

Leu Pro Gly Thr Leu Cys Ala Ser Leu Ser Cys Arg Pro Pro Met Val
            20                  25                  30

Lys Leu Val Cys Pro Ala Asp Asn Leu Arg Ala Glu Gly Leu Glu Cys
        35                  40                  45

Thr Lys Thr Cys Gln Asn Tyr Asp Leu Glu Cys Met Ser Met Gly Cys
```

```
    50                  55                  60

Val Ser Gly Cys Leu Cys Pro Pro Gly Met Val Arg His Glu Asn Arg
65                  70                  75                  80

Cys Val Ala Leu Glu Arg Cys Pro Cys Phe His Gln Gly Lys Glu Tyr
                85                  90                  95

Ala Pro Gly Glu Thr Val Lys Ile Gly Cys Asn Thr Cys Val Cys Arg
            100                 105                 110

Asp Arg Lys Trp Asn Cys Thr Asp His Val Cys Asp Ala Thr Cys Ser
        115                 120                 125

Thr Ile Gly Met Ala His Tyr Leu Thr Phe Asp Gly Leu Lys Tyr Leu
    130                 135                 140

Phe Pro Gly Glu Cys Gln Tyr Val Leu Val Gln Asp Tyr Cys Gly Ser
145                 150                 155                 160

Asn Pro Gly Thr Phe Arg Ile Leu Val Gly Asn Lys Gly Cys Ser His
                165                 170                 175

Pro Ser Val Lys Cys Lys Lys Arg Val Thr Ile Leu Val Glu Gly Gly
            180                 185                 190

Glu Ile Glu Leu Phe Asp Gly Glu Val Asn Val Lys Arg Pro Met Lys
        195                 200                 205

Asp Glu Thr His Phe Glu Val Val Glu Ser Gly Arg Tyr Ile Ile Leu
    210                 215                 220

Leu Leu Gly Lys Ala Leu Ser Val Val Trp Asp Arg His Leu Ser Ile
225                 230                 235                 240

Ser Val Val Leu Lys Gln Thr Tyr Gln Glu Lys Val Cys Gly Leu Cys
                245                 250                 255

Gly Asn Phe Asp Gly Ile Gln Asn Asn Asp Leu Thr Ser Ser Asn Leu
            260                 265                 270

Gln Val Glu Glu Asp Pro Val Asp Phe Gly Asn Ser Trp Lys Val Ser
        275                 280                 285

Ser Gln Cys Ala Asp Thr Arg Lys Val Pro Leu Asp Ser Ser Pro Ala
    290                 295                 300

Thr Cys His Asn Asn Ile Met Lys Gln Thr Met Val Asp Ser Ser Cys
305                 310                 315                 320

Arg Ile Leu Thr Ser Asp Val Phe Gln Asp Cys Asn Lys Leu Val Asp
                325                 330                 335

Pro Glu Pro Tyr Leu Asp Val Cys Ile Tyr Asp Thr Cys Ser Cys Glu
            340                 345                 350

Ser Ile Gly Asp Cys Ala Cys Phe Cys Asp Thr Ile Ala Ala Tyr Ala
        355                 360                 365

His Val Cys Ala Gln His Gly Lys Val Val Thr Trp Arg Thr Ala Thr
    370                 375                 380

Leu Cys Pro Gln Ser Cys Glu Glu Arg Asn Leu Arg Glu Asn Gly Tyr
385                 390                 395                 400

Glu Cys Glu Trp Arg Tyr Asn Ser Cys Ala Pro Ala Cys Gln Val Thr
                405                 410                 415

Cys Gln His Pro Glu Pro Leu Ala Cys Pro Val Gln Cys Val Glu Gly
            420                 425                 430

Cys His Ala His Cys Pro Pro Gly Lys Ile Leu Asp Glu Leu Leu Gln
        435                 440                 445

Thr Cys Val Asp Pro Glu Asp Cys Pro Val Cys Glu Val Ala Gly Arg
    450                 455                 460

Arg Phe Ala Ser Gly Lys Lys Val Thr Leu Asn Pro Ser Asp Pro Glu
465                 470                 475                 480
```

```
His Cys Gln Ile Cys His Cys Asp Val Val Asn Leu Thr Cys Glu Ala
                485                 490                 495

Cys Gln Glu Pro Gly Gly Leu Val Val Pro Pro Thr Asp Ala Pro Val
            500                 505                 510

Ser Pro Thr Thr Leu Tyr Val Glu Asp Ile Ser Glu Pro Pro Leu His
        515                 520                 525

Asp Phe Tyr Cys Ser Arg Leu Leu Asp Leu Val Phe Leu Leu Asp Gly
    530                 535                 540

Ser Ser Arg Leu Ser Glu Ala Glu Phe Glu Val Leu Lys Ala Phe Val
545                 550                 555                 560

Val Asp Met Met Glu Arg Leu Arg Ile Ser Gln Lys Trp Val Arg Val
                565                 570                 575

Ala Val Val Glu Tyr His Asp Gly Ser His Ala Tyr Ile Gly Leu Lys
            580                 585                 590

Asp Arg Lys Arg Pro Ser Glu Leu Arg Arg Ile Ala Ser Gln Val Lys
        595                 600                 605

Tyr Ala Gly Ser Gln Val Ala Ser Thr Ser Glu Val Leu Lys Tyr Thr
    610                 615                 620

Leu Phe Gln Ile Phe Ser Lys Ile Asp Arg Pro Glu Ala Ser Arg Ile
625                 630                 635                 640

Ala Leu Leu Leu Met Ala Ser Gln Glu Pro Gln Arg Met Ser Arg Asn
                645                 650                 655

Phe Val Arg Tyr Val Gln Gly Leu Lys Lys Lys Lys Val Ile Val Ile
            660                 665                 670

Pro Val Gly Ile Gly Pro His Ala Asn Leu Lys Gln Ile Arg Leu Ile
        675                 680                 685

Glu Lys Gln Ala Pro Glu Asn Lys Ala Phe Val Leu Ser Ser Val Asp
    690                 695                 700

Glu Leu Glu Gln Gln Arg Asp Glu Ile Val Ser Tyr Leu Cys Asp Leu
705                 710                 715                 720

Ala Pro Glu Ala Pro Pro Pro Thr Leu Pro Pro His Met Ala Gln Val
                725                 730                 735

Thr Val Gly Pro Gly Asp Lys Thr His Thr Cys Pro Pro Cys Pro Ala
            740                 745                 750

Pro Glu Leu Leu Gly Gly Pro Ser Val Phe Leu Phe Pro Pro Lys Pro
        755                 760                 765

Lys Asp Thr Leu Met Ile Ser Arg Thr Pro Glu Val Thr Cys Val Val
    770                 775                 780

Val Asp Val Ser His Glu Asp Pro Glu Val Lys Phe Asn Trp Tyr Val
785                 790                 795                 800

Asp Gly Val Glu Val His Asn Ala Lys Thr Lys Pro Arg Glu Glu Gln
                805                 810                 815

Tyr Asn Ser Thr Tyr Arg Val Val Ser Val Leu Thr Val Leu His Gln
            820                 825                 830

Asp Trp Leu Asn Gly Lys Glu Tyr Lys Cys Lys Val Ser Asn Lys Ala
        835                 840                 845

Leu Pro Ala Pro Ile Glu Lys Thr Ile Ser Lys Ala Lys Gly Gln Pro
    850                 855                 860

Arg Glu Pro Gln Val Tyr Thr Leu Pro Pro Ser Arg Asp Glu Leu Thr
865                 870                 875                 880

Lys Asn Gln Val Ser Leu Thr Cys Leu Val Lys Gly Phe Tyr Pro Ser
                885                 890                 895
```

```
Asp Ile Ala Val Glu Trp Glu Ser Asn Gly Gln Pro Glu Asn Asn Tyr
            900                 905                 910

Lys Thr Thr Pro Pro Val Leu Asp Ser Asp Gly Ser Phe Phe Leu Tyr
        915                 920                 925

Ser Lys Leu Thr Val Asp Lys Ser Arg Trp Gln Gln Gly Asn Val Phe
    930                 935                 940

Ser Cys Ser Val Met His Glu Ala Leu His Asn His Tyr Thr Gln Lys
945                 950                 955                 960

Ser Leu Ser Leu Ser Pro Gly Lys
                965


<210> SEQ ID NO 19
<211> LENGTH: 1366
<212> TYPE: PRT
<213> ORGANISM: Artificial Sequence
<220> FEATURE:
<223> OTHER INFORMATION: von Willebrand Factor sequence

<400> SEQUENCE: 19

Met Ile Pro Ala Arg Phe Ala Gly Val Leu Leu Ala Leu Ala Leu Ile
1               5                   10                  15

Leu Pro Gly Thr Leu Cys Ala Ser Leu Ser Cys Arg Pro Pro Met Val
            20                  25                  30

Lys Leu Val Cys Pro Ala Asp Asn Leu Arg Ala Glu Gly Leu Glu Cys
        35                  40                  45

Thr Lys Thr Cys Gln Asn Tyr Asp Leu Glu Cys Met Ser Met Gly Cys
    50                  55                  60

Val Ser Gly Cys Leu Cys Pro Pro Gly Met Val Arg His Glu Asn Arg
65                  70                  75                  80

Cys Val Ala Leu Glu Arg Cys Pro Cys Phe His Gln Gly Lys Glu Tyr
                85                  90                  95

Ala Pro Gly Glu Thr Val Lys Ile Gly Cys Asn Thr Cys Val Cys Arg
            100                 105                 110

Asp Arg Lys Trp Asn Cys Thr Asp His Val Cys Asp Ala Thr Cys Ser
        115                 120                 125

Thr Ile Gly Met Ala His Tyr Leu Thr Phe Asp Gly Leu Lys Tyr Leu
    130                 135                 140

Phe Pro Gly Glu Cys Gln Tyr Val Leu Val Gln Asp Tyr Cys Gly Ser
145                 150                 155                 160

Asn Pro Gly Thr Phe Arg Ile Leu Val Gly Asn Lys Gly Cys Ser His
                165                 170                 175

Pro Ser Val Lys Cys Lys Lys Arg Val Thr Ile Leu Val Glu Gly Gly
            180                 185                 190

Glu Ile Glu Leu Phe Asp Gly Glu Val Asn Val Lys Arg Pro Met Lys
        195                 200                 205

Asp Glu Thr His Phe Glu Val Val Glu Ser Gly Arg Tyr Ile Ile Leu
    210                 215                 220

Leu Leu Gly Lys Ala Leu Ser Val Val Trp Asp Arg His Leu Ser Ile
225                 230                 235                 240

Ser Val Val Leu Lys Gln Thr Tyr Gln Glu Lys Val Cys Gly Leu Cys
                245                 250                 255

Gly Asn Phe Asp Gly Ile Gln Asn Asn Asp Leu Thr Ser Ser Asn Leu
            260                 265                 270

Gln Val Glu Glu Asp Pro Val Asp Phe Gly Asn Ser Trp Lys Val Ser
        275                 280                 285
```

```
Ser Gln Cys Ala Asp Thr Arg Lys Val Pro Leu Asp Ser Ser Pro Ala
    290                 295                 300

Thr Cys His Asn Asn Ile Met Lys Gln Thr Met Val Asp Ser Ser Cys
305                 310                 315                 320

Arg Ile Leu Thr Ser Asp Val Phe Gln Asp Cys Asn Lys Leu Val Asp
                325                 330                 335

Pro Glu Pro Tyr Leu Asp Val Cys Ile Tyr Asp Thr Cys Ser Cys Glu
            340                 345                 350

Ser Ile Gly Asp Cys Ala Cys Phe Cys Asp Thr Ile Ala Ala Tyr Ala
        355                 360                 365

His Val Cys Ala Gln His Gly Lys Val Val Thr Trp Arg Thr Ala Thr
    370                 375                 380

Leu Cys Pro Gln Ser Cys Glu Glu Arg Asn Leu Arg Glu Asn Gly Tyr
385                 390                 395                 400

Glu Cys Glu Trp Arg Tyr Asn Ser Cys Ala Pro Ala Cys Gln Val Thr
                405                 410                 415

Cys Gln His Pro Glu Pro Leu Ala Cys Pro Val Gln Cys Val Glu Gly
            420                 425                 430

Cys His Ala His Cys Pro Pro Gly Lys Ile Leu Asp Glu Leu Leu Gln
        435                 440                 445

Thr Cys Val Asp Pro Glu Asp Cys Pro Val Cys Glu Val Ala Gly Arg
    450                 455                 460

Arg Phe Ala Ser Gly Lys Lys Val Thr Leu Asn Pro Ser Asp Pro Glu
465                 470                 475                 480

His Cys Gln Ile Cys His Cys Asp Val Val Asn Leu Thr Cys Glu Ala
                485                 490                 495

Cys Gln Glu Pro Gly Gly Leu Val Val Pro Pro Thr Asp Ala Pro Val
            500                 505                 510

Ser Pro Thr Thr Leu Tyr Val Glu Asp Ile Ser Glu Pro Pro Leu His
        515                 520                 525

Asp Phe Tyr Cys Ser Arg Leu Leu Asp Leu Val Phe Leu Leu Asp Gly
    530                 535                 540

Ser Ser Arg Leu Ser Glu Ala Glu Phe Glu Val Leu Lys Ala Phe Val
545                 550                 555                 560

Val Asp Met Met Glu Arg Leu Arg Ile Ser Gln Lys Trp Val Arg Val
                565                 570                 575

Ala Val Val Glu Tyr His Asp Gly Ser His Ala Tyr Ile Gly Leu Lys
            580                 585                 590

Asp Arg Lys Arg Pro Ser Glu Leu Arg Arg Ile Ala Ser Gln Val Lys
        595                 600                 605

Tyr Ala Gly Ser Gln Val Ala Ser Thr Ser Glu Val Leu Lys Tyr Thr
    610                 615                 620

Leu Phe Gln Ile Phe Ser Lys Ile Asp Arg Pro Glu Ala Ser Arg Ile
625                 630                 635                 640

Ala Leu Leu Leu Met Ala Ser Gln Glu Pro Gln Arg Met Ser Arg Asn
                645                 650                 655

Phe Val Arg Tyr Val Gln Gly Leu Lys Lys Lys Lys Val Ile Val Ile
            660                 665                 670

Pro Val Gly Ile Gly Pro His Ala Asn Leu Lys Gln Ile Arg Leu Ile
        675                 680                 685

Glu Lys Gln Ala Pro Glu Asn Lys Ala Phe Val Leu Ser Ser Val Asp
    690                 695                 700

Glu Leu Glu Gln Gln Arg Asp Glu Ile Val Ser Tyr Leu Cys Asp Leu
```

```
705                 710                 715                 720

Ala Pro Glu Ala Pro Pro Pro Thr Leu Pro Pro His Met Ala Gln Val
                725                 730                 735

Thr Val Gly Pro Gly Leu Leu Gly Val Ser Thr Leu Gly Pro Lys Arg
            740                 745                 750

Asn Ser Met Val Leu Asp Val Ala Phe Val Leu Glu Gly Ser Asp Lys
        755                 760                 765

Ile Gly Glu Ala Asp Phe Asn Arg Ser Lys Glu Phe Met Glu Glu Val
    770                 775                 780

Ile Gln Arg Met Asp Val Gly Gln Asp Ser Ile His Val Thr Val Leu
785                 790                 795                 800

Gln Tyr Ser Tyr Met Val Thr Val Glu Tyr Pro Phe Ser Glu Ala Gln
                805                 810                 815

Ser Lys Gly Asp Ile Leu Gln Arg Val Arg Glu Ile Arg Tyr Gln Gly
            820                 825                 830

Gly Asn Arg Thr Asn Thr Gly Leu Ala Leu Arg Tyr Leu Ser Asp His
        835                 840                 845

Ser Phe Leu Val Ser Gln Gly Asp Arg Glu Gln Ala Pro Asn Leu Val
    850                 855                 860

Tyr Met Val Thr Gly Asn Pro Ala Ser Asp Glu Ile Lys Arg Leu Pro
865                 870                 875                 880

Gly Asp Ile Gln Val Val Pro Ile Gly Val Gly Pro Asn Ala Asn Val
                885                 890                 895

Gln Glu Leu Glu Arg Ile Gly Trp Pro Asn Ala Pro Ile Leu Ile Gln
            900                 905                 910

Asp Phe Glu Thr Leu Pro Arg Glu Ala Pro Asp Leu Val Leu Gln Arg
        915                 920                 925

Cys Cys Ser Gly Glu Gly Leu Gln Ile Pro Thr Leu Ser Pro Ala Pro
    930                 935                 940

Asp Cys Ser Gln Pro Leu Asp Val Ile Leu Leu Leu Asp Gly Ser Ser
945                 950                 955                 960

Ser Phe Pro Ala Ser Tyr Phe Asp Glu Met Lys Ser Phe Ala Lys Ala
                965                 970                 975

Phe Ile Ser Lys Ala Asn Ile Gly Pro Arg Leu Thr Gln Val Ser Val
            980                 985                 990

Leu Gln Tyr Gly Ser Ile Thr Thr  Ile Asp Val Pro Trp  Asn Val Val
        995                 1000                1005

Pro Glu  Lys Ala His Leu Leu  Ser Leu Val Asp Val  Met Gln Arg
    1010                1015                1020

Glu Gly  Gly Pro Ser Gln Ile  Gly Asp Ala Leu Gly  Phe Ala Val
    1025                1030                1035

Arg Tyr  Leu Thr Ser Glu Met  His Gly Ala Arg Pro  Gly Ala Ser
    1040                1045                1050

Lys Ala  Val Val Ile Leu Val  Thr Asp Val Ser Val  Asp Ser Val
    1055                1060                1065

Asp Ala  Ala Ala Asp Ala Ala  Arg Ser Asn Arg Val  Thr Val Phe
    1070                1075                1080

Pro Ile  Gly Ile Gly Asp Arg  Tyr Asp Ala Ala Gln  Leu Arg Ile
    1085                1090                1095

Leu Ala  Gly Pro Ala Gly Asp  Ser Asn Val Val Lys  Leu Gln Arg
    1100                1105                1110

Ile Glu  Asp Leu Pro Thr Met  Val Thr Leu Gly Asn  Ser Phe Leu
    1115                1120                1125
```

```
His Lys Leu Cys Ser Gly Phe Val Arg Ile Cys Asp Lys Thr His
    1130                1135                1140

Thr Cys Pro Pro Cys Pro Ala Pro Glu Leu Leu Gly Gly Pro Ser
    1145                1150                1155

Val Phe Leu Phe Pro Pro Lys Pro Lys Asp Thr Leu Met Ile Ser
    1160                1165                1170

Arg Thr Pro Glu Val Thr Cys Val Val Val Asp Val Ser His Glu
    1175                1180                1185

Asp Pro Glu Val Lys Phe Asn Trp Tyr Val Asp Gly Val Glu Val
    1190                1195                1200

His Asn Ala Lys Thr Lys Pro Arg Glu Glu Gln Tyr Asn Ser Thr
    1205                1210                1215

Tyr Arg Val Val Ser Val Leu Thr Val Leu His Gln Asp Trp Leu
    1220                1225                1230

Asn Gly Lys Glu Tyr Lys Cys Lys Val Ser Asn Lys Ala Leu Pro
    1235                1240                1245

Ala Pro Ile Glu Lys Thr Ile Ser Lys Ala Lys Gly Gln Pro Arg
    1250                1255                1260

Glu Pro Gln Val Tyr Thr Leu Pro Pro Ser Arg Asp Glu Leu Thr
    1265                1270                1275

Lys Asn Gln Val Ser Leu Thr Cys Leu Val Lys Gly Phe Tyr Pro
    1280                1285                1290

Ser Asp Ile Ala Val Glu Trp Glu Ser Asn Gly Gln Pro Glu Asn
    1295                1300                1305

Asn Tyr Lys Thr Thr Pro Pro Val Leu Asp Ser Asp Gly Ser Phe
    1310                1315                1320

Phe Leu Tyr Ser Lys Leu Thr Val Asp Lys Ser Arg Trp Gln Gln
    1325                1330                1335

Gly Asn Val Phe Ser Cys Ser Val Met His Glu Ala Leu His Asn
    1340                1345                1350

His Tyr Thr Gln Lys Ser Leu Ser Leu Ser Pro Gly Lys
    1355                1360                1365


<210> SEQ ID NO 20
<211> LENGTH: 1474
<212> TYPE: PRT
<213> ORGANISM: Artificial Sequence
<220> FEATURE:
<223> OTHER INFORMATION: von Willebrand Factor sequence

<400> SEQUENCE: 20

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110
```

-continued

```
Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525
```

```
Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
```

```
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                 1005

Ser Ser  Asn Leu Gln Val Glu  Glu Asp Pro Val Asp  Phe Gly Asn
    1010                 1015                 1020

Ser Trp  Lys Val Ser Ser Gln  Cys Ala Asp Thr Arg  Lys Val Pro
    1025                 1030                 1035

Leu Asp  Ser Ser Pro Ala Thr  Cys His Asn Asn Ile  Met Lys Gln
    1040                 1045                 1050

Thr Met  Val Asp Ser Ser Cys  Arg Ile Leu Thr Ser  Asp Val Phe
    1055                 1060                 1065

Gln Asp  Cys Asn Lys Leu Val  Asp Pro Glu Pro Tyr  Leu Asp Val
    1070                 1075                 1080

Cys Ile  Tyr Asp Thr Cys Ser  Cys Glu Ser Ile Gly  Asp Cys Ala
    1085                 1090                 1095

Cys Phe  Cys Asp Thr Ile Ala  Ala Tyr Ala His Val  Cys Ala Gln
    1100                 1105                 1110

His Gly  Lys Val Val Thr Trp  Arg Thr Ala Thr Leu  Cys Pro Gln
    1115                 1120                 1125

Ser Cys  Glu Glu Arg Asn Leu  Arg Glu Asn Gly Tyr  Glu Cys Glu
    1130                 1135                 1140

Trp Arg  Tyr Asn Ser Cys Ala  Pro Ala Cys Gln Val  Thr Cys Gln
    1145                 1150                 1155

His Pro  Glu Pro Leu Ala Cys  Pro Val Gln Cys Val  Glu Gly Cys
    1160                 1165                 1170

His Ala  His Cys Pro Pro Gly  Lys Ile Leu Asp Glu  Leu Leu Gln
    1175                 1180                 1185

Thr Cys  Val Asp Pro Glu Asp  Cys Pro Val Cys Glu  Val Ala Gly
    1190                 1195                 1200

Arg Arg  Phe Ala Ser Gly Lys  Lys Val Thr Leu Asn  Pro Ser Asp
    1205                 1210                 1215

Pro Glu  His Cys Gln Ile Cys  His Cys Asp Val Val  Asn Leu Thr
    1220                 1225                 1230

Cys Glu  Ala Cys Gln Glu Pro  Gly Gly Leu Val Val  Pro Pro Asp
    1235                 1240                 1245

Lys Thr  His Thr Cys Pro Pro  Cys Pro Ala Pro Glu  Leu Leu Gly
    1250                 1255                 1260

Gly Pro  Ser Val Phe Leu Phe  Pro Pro Lys Pro Lys  Asp Thr Leu
    1265                 1270                 1275

Met Ile  Ser Arg Thr Pro Glu  Val Thr Cys Val Val  Val Asp Val
    1280                 1285                 1290

Ser His  Glu Asp Pro Glu Val  Lys Phe Asn Trp Tyr  Val Asp Gly
    1295                 1300                 1305

Val Glu  Val His Asn Ala Lys  Thr Lys Pro Arg Glu  Glu Gln Tyr
    1310                 1315                 1320

Asn Ser  Thr Tyr Arg Val Val  Ser Val Leu Thr Val  Leu His Gln
    1325                 1330                 1335

Asp Trp  Leu Asn Gly Lys Glu  Tyr Lys Cys Lys Val  Ser Asn Lys
    1340                 1345                 1350
```

```
Ala Leu  Pro Ala Pro Ile Glu  Lys Thr Ile Ser Lys  Ala Lys Gly
    1355                 1360                 1365

Gln Pro  Arg Glu Pro Gln Val  Tyr Thr Leu Pro Pro  Ser Arg Asp
    1370                 1375                 1380

Glu Leu  Thr Lys Asn Gln Val  Ser Leu Thr Cys Leu  Val Lys Gly
    1385                 1390                 1395

Phe Tyr  Pro Ser Asp Ile Ala  Val Glu Trp Glu Ser  Asn Gly Gln
    1400                 1405                 1410

Pro Glu  Asn Asn Tyr Lys Thr  Thr Pro Pro Val Leu  Asp Ser Asp
    1415                 1420                 1425

Gly Ser  Phe Phe Leu Tyr Ser  Lys Leu Thr Val Asp  Lys Ser Arg
    1430                 1435                 1440

Trp Gln  Gln Gly Asn Val Phe  Ser Cys Ser Val Met  His Glu Ala
    1445                 1450                 1455

Leu His  Asn His Tyr Thr Gln  Lys Ser Leu Ser Leu  Ser Pro Gly
    1460                 1465                 1470

Lys


<210> SEQ ID NO 21
<211> LENGTH: 1708
<212> TYPE: PRT
<213> ORGANISM: Artificial Sequence
<220> FEATURE:
<223> OTHER INFORMATION: von Willebrand Factor sequence

<400> SEQUENCE: 21

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220
```

```
Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
```

```
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065
```

```
Gln Asp  Cys Asn Lys Leu Val  Asp Pro Glu Pro Tyr  Leu Asp Val
    1070                  1075                  1080

Cys Ile  Tyr Asp Thr Cys Ser  Cys Glu Ser Ile Gly  Asp Cys Ala
    1085                  1090                  1095

Cys Phe  Cys Asp Thr Ile Ala  Ala Tyr Ala His Val  Cys Ala Gln
    1100                  1105                  1110

His Gly  Lys Val Val Thr Trp  Arg Thr Ala Thr Leu  Cys Pro Gln
    1115                  1120                  1125

Ser Cys  Glu Glu Arg Asn Leu  Arg Glu Asn Gly Tyr  Glu Cys Glu
    1130                  1135                  1140

Trp Arg  Tyr Asn Ser Cys Ala  Pro Ala Cys Gln Val  Thr Cys Gln
    1145                  1150                  1155

His Pro  Glu Pro Leu Ala Cys  Pro Val Gln Cys Val  Glu Gly Cys
    1160                  1165                  1170

His Ala  His Cys Pro Pro Gly  Lys Ile Leu Asp Glu  Leu Leu Gln
    1175                  1180                  1185

Thr Cys  Val Asp Pro Glu Asp  Cys Pro Val Cys Glu  Val Ala Gly
    1190                  1195                  1200

Arg Arg  Phe Ala Ser Gly Lys  Lys Val Thr Leu Asn  Pro Ser Asp
    1205                  1210                  1215

Pro Glu  His Cys Gln Ile Cys  His Cys Asp Val Val  Asn Leu Thr
    1220                  1225                  1230

Cys Glu  Ala Cys Gln Glu Pro  Gly Gly Leu Val Val  Pro Pro Thr
    1235                  1240                  1245

Asp Ala  Pro Val Ser Pro Thr  Thr Leu Tyr Val Glu  Asp Ile Ser
    1250                  1255                  1260

Glu Pro  Pro Leu His Asp Phe  Tyr Cys Ser Arg Leu  Leu Asp Leu
    1265                  1270                  1275

Val Phe  Leu Leu Asp Gly Ser  Ser Arg Leu Ser Glu  Ala Glu Phe
    1280                  1285                  1290

Glu Val  Leu Lys Ala Phe Val  Val Asp Met Met Glu  Arg Leu Arg
    1295                  1300                  1305

Ile Ser  Gln Lys Trp Val Arg  Val Ala Val Val Glu  Tyr His Asp
    1310                  1315                  1320

Gly Ser  His Ala Tyr Ile Gly  Leu Lys Asp Arg Lys  Arg Pro Ser
    1325                  1330                  1335

Glu Leu  Arg Arg Ile Ala Ser  Gln Val Lys Tyr Ala  Gly Ser Gln
    1340                  1345                  1350

Val Ala  Ser Thr Ser Glu Val  Leu Lys Tyr Thr Leu  Phe Gln Ile
    1355                  1360                  1365

Phe Ser  Lys Ile Asp Arg Pro  Glu Ala Ser Arg Ile  Ala Leu Leu
    1370                  1375                  1380

Leu Met  Ala Ser Gln Glu Pro  Gln Arg Met Ser Arg  Asn Phe Val
    1385                  1390                  1395

Arg Tyr  Val Gln Gly Leu Lys  Lys Lys Lys Val Ile  Val Ile Pro
    1400                  1405                  1410

Val Gly  Ile Gly Pro His Ala  Asn Leu Lys Gln Ile  Arg Leu Ile
    1415                  1420                  1425

Glu Lys  Gln Ala Pro Glu Asn  Lys Ala Phe Val Leu  Ser Ser Val
    1430                  1435                  1440

Asp Glu  Leu Glu Gln Gln Arg  Asp Glu Ile Val Ser  Tyr Leu Cys
    1445                  1450                  1455
```

```
Asp Leu  Ala Pro Glu Ala Pro  Pro Pro Thr Leu Pro  Pro His Met
    1460                 1465                 1470

Ala Gln  Val Thr Val Gly Pro  Gly Asp Lys Thr His  Thr Cys Pro
    1475                 1480                 1485

Pro Cys  Pro Ala Pro Glu Leu  Leu Gly Gly Pro Ser  Val Phe Leu
    1490                 1495                 1500

Phe Pro  Pro Lys Pro Lys Asp  Thr Leu Met Ile Ser  Arg Thr Pro
    1505                 1510                 1515

Glu Val  Thr Cys Val Val Val  Asp Val Ser His Glu  Asp Pro Glu
    1520                 1525                 1530

Val Lys  Phe Asn Trp Tyr Val  Asp Gly Val Glu Val  His Asn Ala
    1535                 1540                 1545

Lys Thr  Lys Pro Arg Glu Glu  Gln Tyr Asn Ser Thr  Tyr Arg Val
    1550                 1555                 1560

Val Ser  Val Leu Thr Val Leu  His Gln Asp Trp Leu  Asn Gly Lys
    1565                 1570                 1575

Glu Tyr  Lys Cys Lys Val Ser  Asn Lys Ala Leu Pro  Ala Pro Ile
    1580                 1585                 1590

Glu Lys  Thr Ile Ser Lys Ala  Lys Gly Gln Pro Arg  Glu Pro Gln
    1595                 1600                 1605

Val Tyr  Thr Leu Pro Pro Ser  Arg Asp Glu Leu Thr  Lys Asn Gln
    1610                 1615                 1620

Val Ser  Leu Thr Cys Leu Val  Lys Gly Phe Tyr Pro  Ser Asp Ile
    1625                 1630                 1635

Ala Val  Glu Trp Glu Ser Asn  Gly Gln Pro Glu Asn  Asn Tyr Lys
    1640                 1645                 1650

Thr Thr  Pro Pro Val Leu Asp  Ser Asp Gly Ser Phe  Phe Leu Tyr
    1655                 1660                 1665

Ser Lys  Leu Thr Val Asp Lys  Ser Arg Trp Gln Gln  Gly Asn Val
    1670                 1675                 1680

Phe Ser  Cys Ser Val Met His  Glu Ala Leu His Asn  His Tyr Thr
    1685                 1690                 1695

Gln Lys  Ser Leu Ser Leu Ser  Pro Gly Lys
    1700                 1705


<210> SEQ ID NO 22
<211> LENGTH: 2106
<212> TYPE: PRT
<213> ORGANISM: Artificial Sequence
<220> FEATURE:
<223> OTHER INFORMATION: von Willebrand Factor sequence

<400> SEQUENCE: 22

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95
```

```
Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
```

```
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940
```

```
Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                 1005

Ser Ser  Asn Leu Gln Val Glu  Glu Asp Pro Val Asp  Phe Gly Asn
    1010                 1015                 1020

Ser Trp  Lys Val Ser Ser Gln  Cys Ala Asp Thr Arg  Lys Val Pro
    1025                 1030                 1035

Leu Asp  Ser Ser Pro Ala Thr  Cys His Asn Asn Ile  Met Lys Gln
    1040                 1045                 1050

Thr Met  Val Asp Ser Ser Cys  Arg Ile Leu Thr Ser  Asp Val Phe
    1055                 1060                 1065

Gln Asp  Cys Asn Lys Leu Val  Asp Pro Glu Pro Tyr  Leu Asp Val
    1070                 1075                 1080

Cys Ile  Tyr Asp Thr Cys Ser  Cys Glu Ser Ile Gly  Asp Cys Ala
    1085                 1090                 1095

Cys Phe  Cys Asp Thr Ile Ala  Ala Tyr Ala His Val  Cys Ala Gln
    1100                 1105                 1110

His Gly  Lys Val Val Thr Trp  Arg Thr Ala Thr Leu  Cys Pro Gln
    1115                 1120                 1125

Ser Cys  Glu Glu Arg Asn Leu  Arg Glu Asn Gly Tyr  Glu Cys Glu
    1130                 1135                 1140

Trp Arg  Tyr Asn Ser Cys Ala  Pro Ala Cys Gln Val  Thr Cys Gln
    1145                 1150                 1155

His Pro  Glu Pro Leu Ala Cys  Pro Val Gln Cys Val  Glu Gly Cys
    1160                 1165                 1170

His Ala  His Cys Pro Pro Gly  Lys Ile Leu Asp Glu  Leu Leu Gln
    1175                 1180                 1185

Thr Cys  Val Asp Pro Glu Asp  Cys Pro Val Cys Glu  Val Ala Gly
    1190                 1195                 1200

Arg Arg  Phe Ala Ser Gly Lys  Lys Val Thr Leu Asn  Pro Ser Asp
    1205                 1210                 1215

Pro Glu  His Cys Gln Ile Cys  His Cys Asp Val Val  Asn Leu Thr
    1220                 1225                 1230

Cys Glu  Ala Cys Gln Glu Pro  Gly Gly Leu Val Val  Pro Pro Thr
    1235                 1240                 1245

Asp Ala  Pro Val Ser Pro Thr  Thr Leu Tyr Val Glu  Asp Ile Ser
    1250                 1255                 1260

Glu Pro  Pro Leu His Asp Phe  Tyr Cys Ser Arg Leu  Leu Asp Leu
    1265                 1270                 1275

Val Phe  Leu Leu Asp Gly Ser  Ser Arg Leu Ser Glu  Ala Glu Phe
    1280                 1285                 1290

Glu Val  Leu Lys Ala Phe Val  Val Asp Met Met Glu  Arg Leu Arg
    1295                 1300                 1305

Ile Ser  Gln Lys Trp Val Arg  Val Ala Val Val Glu  Tyr His Asp
    1310                 1315                 1320

Gly Ser  His Ala Tyr Ile Gly  Leu Lys Asp Arg Lys  Arg Pro Ser
    1325                 1330                 1335
```

```
Glu Leu  Arg Arg Ile Ala Ser  Gln Val Lys Tyr Ala  Gly Ser Gln
    1340                 1345                 1350

Val Ala  Ser Thr Ser Glu Val  Leu Lys Tyr Thr Leu  Phe Gln Ile
    1355                 1360                 1365

Phe Ser  Lys Ile Asp Arg Pro  Glu Ala Ser Arg Ile  Ala Leu Leu
    1370                 1375                 1380

Leu Met  Ala Ser Gln Glu Pro  Gln Arg Met Ser Arg  Asn Phe Val
    1385                 1390                 1395

Arg Tyr  Val Gln Gly Leu Lys  Lys Lys Lys Val Ile  Val Ile Pro
    1400                 1405                 1410

Val Gly  Ile Gly Pro His Ala  Asn Leu Lys Gln Ile  Arg Leu Ile
    1415                 1420                 1425

Glu Lys  Gln Ala Pro Glu Asn  Lys Ala Phe Val Leu  Ser Ser Val
    1430                 1435                 1440

Asp Glu  Leu Glu Gln Gln Arg  Asp Glu Ile Val Ser  Tyr Leu Cys
    1445                 1450                 1455

Asp Leu  Ala Pro Glu Ala Pro  Pro Pro Thr Leu Pro  Pro His Met
    1460                 1465                 1470

Ala Gln  Val Thr Val Gly Pro  Gly Leu Leu Gly Val  Ser Thr Leu
    1475                 1480                 1485

Gly Pro  Lys Arg Asn Ser Met  Val Leu Asp Val Ala  Phe Val Leu
    1490                 1495                 1500

Glu Gly  Ser Asp Lys Ile Gly  Glu Ala Asp Phe Asn  Arg Ser Lys
    1505                 1510                 1515

Glu Phe  Met Glu Glu Val Ile  Gln Arg Met Asp Val  Gly Gln Asp
    1520                 1525                 1530

Ser Ile  His Val Thr Val Leu  Gln Tyr Ser Tyr Met  Val Thr Val
    1535                 1540                 1545

Glu Tyr  Pro Phe Ser Glu Ala  Gln Ser Lys Gly Asp  Ile Leu Gln
    1550                 1555                 1560

Arg Val  Arg Glu Ile Arg Tyr  Gln Gly Gly Asn Arg  Thr Asn Thr
    1565                 1570                 1575

Gly Leu  Ala Leu Arg Tyr Leu  Ser Asp His Ser Phe  Leu Val Ser
    1580                 1585                 1590

Gln Gly  Asp Arg Glu Gln Ala  Pro Asn Leu Val Tyr  Met Val Thr
    1595                 1600                 1605

Gly Asn  Pro Ala Ser Asp Glu  Ile Lys Arg Leu Pro  Gly Asp Ile
    1610                 1615                 1620

Gln Val  Val Pro Ile Gly Val  Gly Pro Asn Ala Asn  Val Gln Glu
    1625                 1630                 1635

Leu Glu  Arg Ile Gly Trp Pro  Asn Ala Pro Ile Leu  Ile Gln Asp
    1640                 1645                 1650

Phe Glu  Thr Leu Pro Arg Glu  Ala Pro Asp Leu Val  Leu Gln Arg
    1655                 1660                 1665

Cys Cys  Ser Gly Glu Gly Leu  Gln Ile Pro Thr Leu  Ser Pro Ala
    1670                 1675                 1680

Pro Asp  Cys Ser Gln Pro Leu  Asp Val Ile Leu Leu  Leu Asp Gly
    1685                 1690                 1695

Ser Ser  Ser Phe Pro Ala Ser  Tyr Phe Asp Glu Met  Lys Ser Phe
    1700                 1705                 1710

Ala Lys  Ala Phe Ile Ser Lys  Ala Asn Ile Gly Pro  Arg Leu Thr
    1715                 1720                 1725

Gln Val  Ser Val Leu Gln Tyr  Gly Ser Ile Thr Thr  Ile Asp Val
```

```
    1730                1735                1740

Pro Trp  Asn Val Val Pro Glu  Lys Ala His Leu Leu  Ser Leu Val
    1745                1750                1755

Asp Val  Met Gln Arg Glu Gly  Gly Pro Ser Gln Ile  Gly Asp Ala
    1760                1765                1770

Leu Gly  Phe Ala Val Arg Tyr  Leu Thr Ser Glu Met  His Gly Ala
    1775                1780                1785

Arg Pro  Gly Ala Ser Lys Ala  Val Val Ile Leu Val  Thr Asp Val
    1790                1795                1800

Ser Val  Asp Ser Val Asp Ala  Ala Ala Asp Ala Ala  Arg Ser Asn
    1805                1810                1815

Arg Val  Thr Val Phe Pro Ile  Gly Ile Gly Asp Arg  Tyr Asp Ala
    1820                1825                1830

Ala Gln  Leu Arg Ile Leu Ala  Gly Pro Ala Gly Asp  Ser Asn Val
    1835                1840                1845

Val Lys  Leu Gln Arg Ile Glu  Asp Leu Pro Thr Met  Val Thr Leu
    1850                1855                1860

Gly Asn  Ser Phe Leu His Lys  Leu Cys Ser Gly Phe  Val Arg Ile
    1865                1870                1875

Cys Asp  Lys Thr His Thr Cys  Pro Pro Cys Pro Ala  Pro Glu Leu
    1880                1885                1890

Leu Gly  Gly Pro Ser Val Phe  Leu Phe Pro Pro Lys  Pro Lys Asp
    1895                1900                1905

Thr Leu  Met Ile Ser Arg Thr  Pro Glu Val Thr Cys  Val Val Val
    1910                1915                1920

Asp Val  Ser His Glu Asp Pro  Glu Val Lys Phe Asn  Trp Tyr Val
    1925                1930                1935

Asp Gly  Val Glu Val His Asn  Ala Lys Thr Lys Pro  Arg Glu Glu
    1940                1945                1950

Gln Tyr  Asn Ser Thr Tyr Arg  Val Val Ser Val Leu  Thr Val Leu
    1955                1960                1965

His Gln  Asp Trp Leu Asn Gly  Lys Glu Tyr Lys Cys  Lys Val Ser
    1970                1975                1980

Asn Lys  Ala Leu Pro Ala Pro  Ile Glu Lys Thr Ile  Ser Lys Ala
    1985                1990                1995

Lys Gly  Gln Pro Arg Glu Pro  Gln Val Tyr Thr Leu  Pro Pro Ser
    2000                2005                2010

Arg Asp  Glu Leu Thr Lys Asn  Gln Val Ser Leu Thr  Cys Leu Val
    2015                2020                2025

Lys Gly  Phe Tyr Pro Ser Asp  Ile Ala Val Glu Trp  Glu Ser Asn
    2030                2035                2040

Gly Gln  Pro Glu Asn Asn Tyr  Lys Thr Thr Pro Pro  Val Leu Asp
    2045                2050                2055

Ser Asp  Gly Ser Phe Phe Leu  Tyr Ser Lys Leu Thr  Val Asp Lys
    2060                2065                2070

Ser Arg  Trp Gln Gln Gly Asn  Val Phe Ser Cys Ser  Val Met His
    2075                2080                2085

Glu Ala  Leu His Asn His Tyr  Thr Gln Lys Ser Leu  Ser Leu Ser
    2090                2095                2100

Pro Gly  Lys
    2105

<210> SEQ ID NO 23
```

<211> LENGTH: 6318
<212> TYPE: DNA
<213> ORGANISM: Artificial Sequence
<220> FEATURE:
<223> OTHER INFORMATION: von Willebrand Factor sequence

<400> SEQUENCE: 23

```
atgatccccg ccagattcgc cggcgtgctg ctggccctgg ccctgatcct gcccggcacc     60

ctgtgcgccg agggcaccag aggcagatcc agcaccgccc ggtgcagcct gttcggcagc    120

gacttcgtga acaccttcga cggcagcatg tacagcttcg ccggctactg tagctacctg    180

ctggctggcg gctgccagaa gcggagcttc agcatcatcg gcgacttcca gaacggcaag    240

cgggtgtccc tgagcgtgta cctgggcgag ttcttcgaca tccacctgtt cgtgaacggc    300

accgtgaccc agggcgatca gagggtgtcc atgccctacg ccagcaaggg cctgtacctg    360

gaaaccgagg ccggctacta caagctgtcc ggcgaggcct acggcttcgt ggcccggatc    420

gacggctccg gcaacttcca ggtgctgctg tccgaccggt acttcaacaa gacctgcggc    480

ctgtgcggca acttcaacat cttcgccgag gacgacttca tgacccagga aggcaccctg    540

accagcgacc cctacgactt cgccaacagc tgggccctga gcagcggcga gcagtggtgc    600

gagagagcca gcccccccag cagcagctgc aacatcagct ccggcgagat gcagaaaggc    660

ctgtgggagc agtgccagct gctgaagtcc acctccgtgt tcgcccggtg ccaccccctg    720

gtggaccccg agccctttgt ggccctgtgc gaaaagaccc tgtgcgagtg cgctggcggc    780

ctggaatgcg cctgccctgc cctgctggaa tacgcccgga cctgcgccca agaagggatg    840

gtcctgtacg gctggaccga ccacagcgcc tgcagccccg tctgccctgc cggcatggaa    900

taccggcagt gcgtgagccc ctgcgccaga acctgccaga gcctgcacat caacgagatg    960

tgccaggaaa gatgcgtcga cggctgctct tgtcccgagg gacagctcct ggacgagggc   1020

ctctgcgtgg agagcaccga gtgcccctgc gtgcacagcg gcaagagata ccccccctggc   1080

accagcctga gccgggactg caacacctgc atttgccgga acagccagtg gatctgcagc   1140

aacgaggaat gcccaggcga gtgcctggtc accggccaga gccacttcaa gagcttcgac   1200

aacagatact tcaccttcag cggcatctgc cagtatctgc tggccagaga ctgccaggac   1260

cacagcttct ccatcgtgat cgagacagtg cagtgcgccg acgaccggga cgccgtgtgc   1320

accagatccg tgaccgtgag actgcccggc ctgcacaaca gcctggtcaa gctgaagcat   1380

ggcgctggcg tggccatgga cggccaggac atccagctgc ctctgctgaa gggcgacctg   1440

cggatccagc acaccgtgac cgccagcgtg agactgtcct acggcgagga cctgcagatg   1500

gactgggacg gcagaggccg gctgctcgtg aagctgtccc ccgtgtacgc cggcaagaca   1560

tgtggcctgt gtgggaacta caacggcaac cagggcgacg actttctgac ccccagcggc   1620

ctggccgagc ccagagtgga ggacttcggc aacgcctgga agctgcacgg cgattgccag   1680

gatctgcaga aacagcactc cgacccctgc gccctgaacc cccggatgac ccggttcagc   1740

gaagaggctt gcgccgtgct gaccagcccc accttcgagg cctgccaccg ggccgtgagc   1800

cccctgccct acctgcggaa ctgcagatac gatgtgtgta gctgctctga cggccgggag   1860

tgcctgtgtg gcgccctggc cagctatgcc gctgcctgcg ccggacgcgg tgtgagagtg   1920

gcttggcggg agcctggcag atgcgagctg aactgcccca agggccaggt gtacctgcag   1980

tgcggcaccc cctgcaacct gacctgccgg tccctgagct accccgacga agagtgcaac   2040

gaggcctgtc tcgaaggctg cttctgcccc cctggcctgt acatggacga gcggggcgac   2100

tgcgtgccca aggcccagtg cccctgttac tacgacggcg agatcttcca gcccgaggac   2160
```

```
atcttcagcg accaccacac catgtgctac tgcgaggacg gctttatgca ctgcaccatg   2220
agcggcgtgc ccggcagcct gctgccagac gccgtgctgt cctccccccct gagccaccgg   2280
tccaagcgga gcctgagctg cagacccccc atggtcaagc tcgtgtgccc agccgacaat   2340
ctgcgggccg aggggctgga atgcaccaag acctgccaga actacgacct ggaatgcatg   2400
agcatgggct gcgtgagcgg ctgcctgtgc ccacccggca tggtccggca cgagaacaga   2460
tgcgtggccc tggaacggtg cccatgcttc caccagggca aagagtacgc ccctggcgag   2520
acagtgaaga tcggctgcaa tacctgcgtg tgccgggacc ggaagtggaa ctgcaccgac   2580
cacgtgtgcg acgccacatg cagcaccatc ggcatggccc actacctgac ctttgacggc   2640
ctgaagtacc tgttccccgg cgagtgccag tacgtgctgg tgcaggacta ctgcggcagc   2700
aaccccggca ccttccggat cctcgtgggc aacaagggat gcagccaccc cagcgtgaag   2760
tgcaagaaac gcgtgaccat cctggtggag ggcggcgaga tcgagctgtt cgacggcgaa   2820
gtgaacgtga agcggcccat gaaggacgag acacacttcg aggtggtgga gagcggccgg   2880
tacatcatcc tgctgctggg caaggctctg agcgtcgtgt gggaccggca cctgagcatc   2940
agcgtggtgc tgaagcagac ctaccaggaa aaagtctgcg gcctctgtgg caatttcgac   3000
ggcatccaga acaacgatct gaccagcagc aacctgcagg tggaagagga ccccgtggac   3060
tttggcaata gctggaaggt gtccagccag tgtgccgaca ccagaaaagt gcccctggac   3120
tctagccccg ccacctgcca caacaacatc atgaagcaga caatggtgga cagctcctgc   3180
cggatcctga cctccgacgt gttccaggac tgtaacaaac tggtggatcc tgagccttac   3240
ctggacgtgt gcatctacga cacctgcagc tgcgagagca tcggcgattg cgcctgcttc   3300
tgcgacacaa tcgccgccta cgcccatgtg tgcgcccagc acggcaaggt ggtcacctgg   3360
cggaccgcaa ccctgtgccc ccagagctgc gaggaacgga acctgcggga gaacggctac   3420
gagtgcgagt ggcggtacaa cagctgcgcc ccagcctgcc aggtcacctg ccagcacccc   3480
gagcctctgg cctgccccgt gcagtgcgtg gagggctgcc acgcccactg ccctccaggc   3540
aagatcctgg acgagctgct gcagacctgc gtggaccctg aggactgccc tgtgtgcgag   3600
gtggccggca ggcggttcgc ctccggcaag aaagtgaccc tgaaccctag cgaccccgag   3660
cactgccaga tctgccactg cgacgtggtc aatctgacct gcgaggcttg ccaggaacca   3720
ggcggcctcg tcgtgccccc taccgacgcc cctgtgtccc caaccaccct gtacgtggag   3780
gacatcagcg agcccccct gcacgacttc tactgctctc ggctgctgga cctggtgttc   3840
ctgctggacg gcagttctag actgagcgag gccgagttcg aggtgctgaa ggccttcgtc   3900
gtggacatga tggaacggct gcggatcagc cagaaatggg tccgggtggc cgtggtggag   3960
taccacgacg gcagccacgc ctacatcggc ctgaaggacc ggaagcggcc ctccgaactc   4020
cggcggatcg ccagccaggt caagtacgcc ggatcccagg tggccagcac cagcgaagtg   4080
ctgaagtaca ccctgttcca gatcttcagc aagatcgacc ggcccgaggc cagccggatc   4140
gcactgctgc tgatggccag ccaagaaccc cagcggatga gccggaactt cgtgagatac   4200
gtgcagggcc tgaagaaaaa gaaagtgatc gtgatccccg tgggcatcgg cccccacgcc   4260
aacctgaagc agatccggct gatcgagaag caggcacccg agaacaaggc ctttgtgctg   4320
tccagcgtgg atgagctgga acagcagcgg gacgagatcg tgtcctacct gtgcgacctg   4380
gcccctgagg cccctcctcc cacactgccc ccccacatgg ctcaggtcac cgtgggacca   4440
ggcctgctgg gagtgagcac actgggcccc aagcggaaca gcatggtgct ggacgtggcc   4500
```

```
ttcgtgctcg agggcagcga caagatcggc gaggccgact tcaaccggtc caaagaattc   4560

atggaagagg tcatccagcg gatggacgtg ggccaggaca gcatccacgt gacagtgctg   4620

cagtacagct acatggtcac agtggagtac cccttcagcg aggcccagag caagggcgac   4680

atcctgcaga gagtgcggga gatcagatac cagggcggca accggaccaa caccggcctg   4740

gccctgcgct acctgagcga ccactccttt ctggtgtctc agggcgatcg ggagcaggcc   4800

cctaacctgg tgtatatggt cacaggcaac cccgctagcg acgagatcaa gagactgccc   4860

ggcgacatcc aggtggtgcc catcggcgtg ggccccaacg ctaatgtgca ggaactggaa   4920

cggatcggct ggcccaacgc ccccatcctg atccaggact tcgagacact gcccagagaa   4980

gcccccgacc tggtgctgca gcggtgctgt agcggcgagg ggctgcagat ccccaccctg   5040

agccctgccc ccgactgcag ccagcccctg gacgtgatcc tgctcctgga cggctccagc   5100

tccttccccg ccagctactt cgacgagatg aagtccttcg ccaaggcctt catcagcaag   5160

gccaacatcg gccccagact gacccaggtg tccgtgctcc agtacggcag catcaccacc   5220

atcgacgtgc cctggaatgt ggtccccgag aaggcccacc tgctgtccct ggtggatgtg   5280

atgcagcggg agggcggacc cagccagatc ggcgacgccc tgggcttcgc cgtgagatac   5340

ctgacaagcg agatgcacgg agccagacct ggagcctcca aggccgtggt catcctcgtg   5400

accgacgtgt ccgtggacag cgtggacgct gccgccgacg ccgccagatc caacagagtg   5460

accgtgttcc ctatcggcat cggcgaccgc tacgacgccg cccagctgag aatcctggcc   5520

ggacctgccg gcgacagcaa cgtggtcaaa ctgcagcgga tcgaggatct gcccaccatg   5580

gtcaccctgg gcaacagctt tctgcacaag ctgtgtagcg gcttcgtgcg gatctgcgac   5640

aaaactcaca catgcccacc gtgcccagca cctgaactcc tggggggacc gtcagtcttc   5700

ctcttccccc caaaacccaa ggacaccctc atgatctccc ggacccctga ggtcacatgc   5760

gtggtggtgg acgtgagcca cgaagaccct gaggtcaagt tcaactggta cgtggacggc   5820

gtggaggtgc ataatgccaa gacaaagccg cgggaggagc agtacaacag cacgtaccgt   5880

gtggtcagcg tcctcaccgt cctgcaccag gactggctga atggcaagga gtacaagtgc   5940

aaggtctcca acaaagccct cccagccccc atcgagaaaa ccatctccaa agccaaaggg   6000

cagccccgag agccacaggt gtacaccctg cccccatccc gggatgagct gaccaagaac   6060

caggtcagcc tgacctgcct ggtcaaaggc ttctatccca gcgacatcgc cgtggagtgg   6120

gagagcaatg ggcagccgga gaacaactac aagaccacgc ctcccgtgct ggactccgac   6180

ggctccttct tcctctacag caagctcacc gtggacaaga gcaggtggca gcaggggaac   6240

gtcttctcat gctccgtgat gcatgaggct ctgcacaacc actacacgca gaagagcctc   6300

tccctgtctc cgggtaaa                                                 6318
```

<210> SEQ ID NO 24
<211> LENGTH: 4422
<212> TYPE: DNA
<213> ORGANISM: Artificial Sequence
<220> FEATURE:
<223> OTHER INFORMATION: von Willebrand Factor sequence

<400> SEQUENCE: 24

```
atgatccccg ccagattcgc cggcgtgctg ctggccctgg ccctgatcct gcccggcacc     60

ctgtgcgccg agggcaccag aggcagatcc agcaccgccc ggtgcagcct gttcggcagc    120

gacttcgtga acaccttcga cggcagcatg tacagcttcg ccggctactg tagctacctg    180

ctggctggcg gctgccagaa gcggagcttc agcatcatcg gcgacttcca gaacggcaag    240
```

```
cgggtgtccc tgagcgtgta cctgggcgag ttcttcgaca tccacctgtt cgtgaacggc    300
accgtgaccc agggcgatca gagggtgtcc atgccctacg ccagcaaggg cctgtacctg    360
gaaaccgagg ccggctacta caagctgtcc ggcgaggcct acggcttcgt ggcccggatc    420
gacggctccg gcaacttcca ggtgctgctg tccgaccggt acttcaacaa gacctgcggc    480
ctgtgcggca acttcaacat cttcgccgag gacgacttca tgacccagga aggcaccctg    540
accagcgacc cctacgactt cgccaacagc tgggccctga gcagcggcga gcagtggtgc    600
gagagagcca gcccccccag cagcagctgc aacatcagct ccggcgagat gcagaaaggc    660
ctgtgggagc agtgccagct gctgaagtcc acctccgtgt tcgcccggtg ccaccccctg    720
gtggaccccg agccctttgt ggccctgtgc gaaaagaccc tgtgcgagtg cgctggcggc    780
ctggaatgcg cctgccctgc cctgctggaa tacgcccgga cctgcgccca agaagggatg    840
gtcctgtacg gctggaccga ccacagcgcc tgcagccccg tctgccctgc cggcatggaa    900
taccggcagt gcgtgagccc ctgcgccaga acctgccaga gcctgcacat caacgagatg    960
tgccaggaaa gatgcgtcga cggctgctct tgtcccgagg gacagctcct ggacgagggc   1020
ctctgcgtgg agagcaccga gtgcccctgc gtgcacagcg gcaagagata cccccctggc   1080
accagcctga gccgggactg caacacctgc atttgccgga acagccagtg gatctgcagc   1140
aacgaggaat gcccaggcga gtgcctggtc accggccaga gccacttcaa gagcttcgac   1200
aacagatact tcaccttcag cggcatctgc cagtatctgc tggccagaga ctgccaggac   1260
cacagcttct ccatcgtgat cgagacagtg cagtgcgccg acgaccggga cgccgtgtgc   1320
accagatccg tgaccgtgag actgcccggc ctgcacaaca gcctggtcaa gctgaagcat   1380
ggcgctggcg tggccatgga cggccaggac atccagctgc ctctgctgaa gggcgacctg   1440
cggatccagc acaccgtgac cgccagcgtg agactgtcct acggcgagga cctgcagatg   1500
gactgggacg gcagaggccg gctgctcgtg aagctgtccc ccgtgtacgc cggcaagaca   1560
tgtggcctgt gtgggaacta caacggcaac cagggcgacg actttctgac ccccagcggc   1620
ctggccgagc ccagagtgga ggacttcggc aacgcctgga agctgcacgg cgattgccag   1680
gatctgcaga aacagcactc cgacccctgc gccctgaacc cccggatgac ccggttcagc   1740
gaagaggctt gcgccgtgct gaccagcccc accttcgagg cctgccaccg ggccgtgagc   1800
cccctgccct acctgcggaa ctgcagatac gatgtgtgta gctgctctga cggccgggag   1860
tgcctgtgtg gcgccctggc cagctatgcc gctgcctgcg ccggacgcgg tgtgagagtg   1920
gcttggcggg agcctggcag atgcgagctg aactgcccca agggccaggt gtacctgcag   1980
tgcggcaccc cctgcaacct gacctgccgg tccctgagct accccgacga agagtgcaac   2040
gaggcctgtc tcgaaggctg cttctgcccc cctggcctgt acatggacga gcggggcgac   2100
tgcgtgccca aggcccagtg cccctgttac tacgacggcg agatcttcca gcccgaggac   2160
atcttcagcg accaccacac catgtgctac tgcgaggacg gctttatgca ctgcaccatg   2220
agcggcgtgc ccggcagcct gctgccagac gccgtgctgt cctcccccct gagccaccgg   2280
tccaagcgga gcctgagctg cagacccccc atggtcaagc tcgtgtgccc agccgacaat   2340
ctgcgggccg aggggctgga atgcaccaag acctgccaga actacgacct ggaatgcatg   2400
agcatgggct gcgtgagcgg ctgcctgtgc ccacccggca tggtccggca cgagaacaga   2460
tgcgtggccc tggaacggtg cccatgcttc caccagggca aagagtacgc ccctggcgag   2520
acagtgaaga tcggctgcaa tacctgcgtg tgccgggacc ggaagtggaa ctgcaccgac   2580
```

```
cacgtgtgcg acgccacatg cagcaccatc ggcatggccc actacctgac ctttgacggc   2640

ctgaagtacc tgttccccgg cgagtgccag tacgtgctgg tgcaggacta ctgcggcagc   2700

aaccccggca ccttccggat cctcgtgggc aacaagggat gcagccaccc cagcgtgaag   2760

tgcaagaaac gcgtgaccat cctggtggag ggcggcgaga tcgagctgtt cgacggcgaa   2820

gtgaacgtga agcggcccat gaaggacgag acacacttcg aggtggtgga gagcggccgg   2880

tacatcatcc tgctgctggg caaggctctg agcgtcgtgt gggaccggca cctgagcatc   2940

agcgtggtgc tgaagcagac ctaccaggaa aaagtctgcg gcctctgtgg caatttcgac   3000

ggcatccaga acaacgatct gaccagcagc aacctgcagg tggaagagga ccccgtggac   3060

tttggcaata gctggaaggt gtccagccag tgtgccgaca ccagaaaagt gcccctggac   3120

tctagccccg ccacctgcca caacaacatc atgaagcaga caatggtgga cagctcctgc   3180

cggatcctga cctccgacgt gttccaggac tgtaacaaac tggtggatcc tgagccttac   3240

ctggacgtgt gcatctacga cacctgcagc tgcgagagca tcggcgattg cgcctgcttc   3300

tgcgacacaa tcgccgccta cgcccatgtg tgcgcccagc acggcaaggt ggtcacctgg   3360

cggaccgcaa ccctgtgccc ccagagctgc gaggaacgga acctgcggga gaacggctac   3420

gagtgcgagt ggcggtacaa cagctgcgcc ccagcctgcc aggtcacctg ccagcacccc   3480

gagcctctgg cctgccccgt gcagtgcgtg gagggctgcc acgcccactg ccctccaggc   3540

aagatcctgg acgagctgct gcagacctgc gtggaccctg aggactgccc tgtgtgcgag   3600

gtggccggca ggcggttcgc ctccggcaag aaagtgaccc tgaaccctag cgaccccgag   3660

cactgccaga tctgccactg cgacgtggtc aatctgacct gcgaggcttg ccaggaacca   3720

ggcggcctcg tcgtgccccc tgacaaaact cacacatgcc caccgtgccc agcacctgaa   3780

ctcctggggg gaccgtcagt cttcctcttc cccccaaaac ccaaggacac cctcatgatc   3840

tcccggaccc ctgaggtcac atgcgtggtg gtggacgtga gccacgaaga ccctgaggtc   3900

aagttcaact ggtacgtgga cggcgtggag gtgcataatg ccaagacaaa gccgcgggag   3960

gagcagtaca acagcacgta ccgtgtggtc agcgtcctca ccgtcctgca ccaggactgg   4020

ctgaatggca aggagtacaa gtgcaaggtc tccaacaaag ccctcccagc ccccatcgag   4080

aaaaccatct ccaaagccaa agggcagccc cgagagccac aggtgtacac cctgccccca   4140

tcccgggatg agctgaccaa gaaccaggtc agcctgacct gcctggtcaa aggcttctat   4200

cccagcgaca tcgccgtgga gtgggagagc aatgggcagc cggagaacaa ctacaagacc   4260

acgcctcccg tgctggactc cgacggctcc ttcttcctct acagcaagct caccgtggac   4320

aagagcaggt ggcagcaggg gaacgtcttc tcatgctccg tgatgcatga ggctctgcac   4380

aaccactaca cgcagaagag cctctccctg tctccgggta aa                      4422
```

<210> SEQ ID NO 25
<211> LENGTH: 4098
<212> TYPE: DNA
<213> ORGANISM: Artificial Sequence
<220> FEATURE:
<223> OTHER INFORMATION: von Willebrand Factor sequence

<400> SEQUENCE: 25

```
atgatccccg ccagattcgc cggcgtgctg ctggccctgg ccctgatcct gcccggcacc     60

ctgtgcgcca gcctgagctg cagacccccc atggtcaagc tcgtgtgccc agccgacaat    120

ctgcgggccg aggggctgga atgcaccaag acctgccaga actacgacct ggaatgcatg    180

agcatgggct gcgtgagcgg ctgcctgtgc ccacccggca tggtccggca cgagaacaga    240
```

```
tgcgtggccc tggaacggtg cccatgcttc caccagggca aagagtacgc ccctggcgag    300
acagtgaaga tcggctgcaa tacctgcgtg tgccgggacc ggaagtggaa ctgcaccgac    360
cacgtgtgcg acgccacatg cagcaccatc ggcatggccc actacctgac ctttgacggc    420
ctgaagtacc tgttccccgg cgagtgccag tacgtgctgg tgcaggacta ctgcggcagc    480
aaccccggca ccttccggat cctcgtgggc aacaagggat gcagccaccc cagcgtgaag    540
tgcaagaaac gcgtgaccat cctggtggag ggcggcgaga tcgagctgtt cgacggcgaa    600
gtgaacgtga agcggcccat gaaggacgag acacacttcg aggtggtgga gagcggccgg    660
tacatcatcc tgctgctggg caaggctctg agcgtcgtgt gggaccggca cctgagcatc    720
agcgtggtgc tgaagcagac ctaccaggaa aaagtctgcg gcctctgtgg caatttcgac    780
ggcatccaga acaacgatct gaccagcagc aacctgcagg tggaagagga ccccgtggac    840
tttggcaata gctggaaggt gtccagccag tgtgccgaca ccagaaaagt gcccctggac    900
tctagccccg ccacctgcca caacaacatc atgaagcaga caatggtgga cagctcctgc    960
cggatcctga cctccgacgt gttccaggac tgtaacaaac tggtggatcc tgagccttac   1020
ctggacgtgt gcatctacga cacctgcagc tgcgagagca tcggcgattg cgcctgcttc   1080
tgcgacacaa tcgccgccta cgcccatgtg tgcgcccagc acggcaaggt ggtcacctgg   1140
cggaccgcaa ccctgtgccc ccagagctgc gaggaacgga acctgcggga gaacggctac   1200
gagtgcgagt ggcggtacaa cagctgcgcc ccagcctgcc aggtcacctg ccagcacccc   1260
gagcctctgg cctgccccgt gcagtgcgtg gagggctgcc acgcccactg ccctccaggc   1320
aagatcctgg acgagctgct gcagacctgc gtggaccctg aggactgccc tgtgtgcgag   1380
gtggccggca ggcggttcgc ctccggcaag aaagtgaccc tgaaccctag cgaccccgag   1440
cactgccaga tctgccactg cgacgtggtc aatctgacct gcgaggcttg ccaggaacca   1500
ggcggcctcg tcgtgccccc taccgacgcc cctgtgtccc caaccaccct gtacgtggag   1560
gacatcagcg agcccccccct gcacgacttc tactgctctc ggctgctgga cctggtgttc   1620
ctgctggacg gcagttctag actgagcgag gccgagttcg aggtgctgaa ggccttcgtc   1680
gtggacatga tggaacggct gcggatcagc cagaaatggg tccgggtggc cgtggtggag   1740
taccacgacg gcagccacgc ctacatcggc ctgaaggacc ggaagcggcc ctccgaactc   1800
cggcggatcg ccagccaggt caagtacgcc ggatcccagg tggccagcac cagcgaagtg   1860
ctgaagtaca ccctgttcca gatcttcagc aagatcgacc ggcccgaggc cagccggatc   1920
gcactgctgc tgatggccag ccaagaaccc cagcggatga gccggaactt cgtgagatac   1980
gtgcagggcc tgaagaaaaa gaaagtgatc gtgatccccg tgggcatcgg cccccacgcc   2040
aacctgaagc agatccggct gatcgagaag caggcacccg agaacaaggc ctttgtgctg   2100
tccagcgtgg atgagctgga acagcagcgg gacgagatcg tgtcctacct gtgcgacctg   2160
gcccctgagg cccctcctcc cacactgccc ccccacatgg ctcaggtcac cgtgggacca   2220
ggcctgctgg gagtgagcac actgggcccc aagcggaaca gcatggtgct ggacgtggcc   2280
ttcgtgctcg agggcagcga caagatcggc gaggccgact tcaaccggtc caaagaattc   2340
atggaagagg tcatccagcg gatggacgtg ggccaggaca gcatccacgt gacagtgctg   2400
cagtacagct acatggtcac agtggagtac cccttcagcg aggcccagag caagggcgac   2460
atcctgcaga gagtgcggga gatcagatac cagggcggca accggaccaa caccggcctg   2520
gccctgcgct acctgagcga ccactccttt ctggtgtctc agggcgatcg ggagcaggcc   2580
```

```
cctaacctgg tgtatatggt cacaggcaac cccgctagcg acgagatcaa gagactgccc   2640

ggcgacatcc aggtggtgcc catcggcgtg ggccccaacg ctaatgtgca ggaactggaa   2700

cggatcggct ggcccaacgc ccccatcctg atccaggact tcgagacact gcccagagaa   2760

gcccccgacc tggtgctgca gcggtgctgt agcggcgagg ggctgcagat ccccaccctg   2820

agccctgccc ccgactgcag ccagcccctg gacgtgatcc tgctcctgga cggctccagc   2880

tccttccccg ccagctactt cgacgagatg aagtccttcg ccaaggcctt catcagcaag   2940

gccaacatcg gccccagact gacccaggtg tccgtgctcc agtacggcag catcaccacc   3000

atcgacgtgc cctggaatgt ggtccccgag aaggcccacc tgctgtccct ggtggatgtg   3060

atgcagcggg agggcggacc cagccagatc ggcgacgccc tgggcttcgc cgtgagatac   3120

ctgacaagcg agatgcacgg agccagacct ggagcctcca aggccgtggt catcctcgtg   3180

accgacgtgt ccgtggacag cgtggacgct gccgccgacg ccgccagatc caacagagtg   3240

accgtgttcc ctatcggcat cggcgaccgc tacgacgccg cccagctgag aatcctggcc   3300

ggacctgccg gcgacagcaa cgtggtcaaa ctgcagcgga tcgaggatct gcccaccatg   3360

gtcaccctgg gcaacagctt tctgcacaag ctgtgtagcg gcttcgtgcg gatctgcgac   3420

aaaactcaca catgcccacc gtgcccagca cctgaactcc tggggggacc gtcagtcttc   3480

ctcttccccc caaaacccaa ggacaccctc atgatctccc ggacccctga ggtcacatgc   3540

gtggtggtgg acgtgagcca cgaagaccct gaggtcaagt tcaactggta cgtggacggc   3600

gtggaggtgc ataatgccaa gacaaagccg cgggaggagc agtacaacag cacgtaccgt   3660

gtggtcagcg tcctcaccgt cctgcaccag gactggctga atggcaagga gtacaagtgc   3720

aaggtctcca acaaagccct cccagccccc atcgagaaaa ccatctccaa agccaaaggg   3780

cagccccgag agccacaggt gtacaccctg cccccatccc gggatgagct gaccaagaac   3840

caggtcagcc tgacctgcct ggtcaaaggc ttctatccca gcgacatcgc cgtggagtgg   3900

gagagcaatg ggcagccgga gaacaactac aagaccacgc ctcccgtgct ggactccgac   3960

ggctccttct tcctctacag caagctcacc gtggacaaga gcaggtggca gcaggggaac   4020

gtcttctcat gctccgtgat gcatgaggct ctgcacaacc actacacgca gaagagcctc   4080

tccctgtctc cgggtaaa                                                 4098
```

<210> SEQ ID NO 26
<211> LENGTH: 2202
<212> TYPE: DNA
<213> ORGANISM: Artificial Sequence
<220> FEATURE:
<223> OTHER INFORMATION: von Willebrand Factor sequence

<400> SEQUENCE: 26

```
atgatccccg ccagattcgc cggcgtgctg ctggccctgg ccctgatcct gcccggcacc     60

ctgtgcgcca gcctgagctg cagacccccc atggtcaagc tcgtgtgccc agccgacaat    120

ctgcgggccg aggggctgga atgcaccaag acctgccaga actacgacct ggaatgcatg    180

agcatgggct gcgtgagcgg ctgcctgtgc ccacccggca tggtccggca cgagaacaga    240

tgcgtggccc tggaacggtg cccatgcttc caccagggca aagagtacgc ccctggcgag    300

acagtgaaga tcggctgcaa tacctgcgtg tgccgggacc ggaagtggaa ctgcaccgac    360

cacgtgtgcg acgccacatg cagcaccatc ggcatggccc actacctgac ctttgacggc    420

ctgaagtacc tgttccccgg cgagtgccag tacgtgctgg tgcaggacta ctgcggcagc    480

aaccccggca ccttccggat cctcgtgggc aacaagggat gcagccaccc cagcgtgaag    540
```

```
tgcaagaaac gcgtgaccat cctggtggag ggcggcgaga tcgagctgtt cgacggcgaa    600
gtgaacgtga agcggcccat gaaggacgag acacacttcg aggtggtgga gagcggccgg    660
tacatcatcc tgctgctggg caaggctctg agcgtcgtgt gggaccggca cctgagcatc    720
agcgtggtgc tgaagcagac ctaccaggaa aaagtctgcg gcctctgtgg caatttcgac    780
ggcatccaga acaacgatct gaccagcagc aacctgcagg tggaagagga ccccgtggac    840
tttggcaata gctggaaggt gtccagccag tgtgccgaca ccagaaaagt gcccctggac    900
tctagccccg ccacctgcca caacaacatc atgaagcaga caatggtgga cagctcctgc    960
cggatcctga cctccgacgt gttccaggac tgtaacaaac tggtggatcc tgagccttac   1020
ctggacgtgt gcatctacga cacctgcagc tgcgagagca tcggcgattg cgcctgcttc   1080
tgcgacacaa tcgccgccta cgcccatgtg tgcgcccagc acggcaaggt ggtcacctgg   1140
cggaccgcaa ccctgtgccc ccagagctgc gaggaacgga acctgcggga gaacggctac   1200
gagtgcgagt ggcggtacaa cagctgcgcc ccagcctgcc aggtcacctg ccagcacccc   1260
gagcctctgg cctgccccgt gcagtgcgtg gagggctgcc acgcccactg ccctccaggc   1320
aagatcctgg acgagctgct gcagacctgc gtggaccctg aggactgccc tgtgtgcgag   1380
gtggccggca ggcggttcgc ctccggcaag aaagtgaccc tgaaccctag cgaccccgag   1440
cactgccaga tctgccactg cgacgtggtc aatctgacct gcgaggcttg ccaggaacca   1500
ggcggcctcg tcgtgccccc tgacaaaact cacacatgcc caccgtgccc agcacctgaa   1560
ctcctggggg gaccgtcagt cttcctcttc cccccaaaac ccaaggacac cctcatgatc   1620
tcccggaccc ctgaggtcac atgcgtggtg gtggacgtga gccacgaaga ccctgaggtc   1680
aagttcaact ggtacgtgga cggcgtggag gtgcataatg ccaagacaaa gccgcgggag   1740
gagcagtaca acagcacgta ccgtgtggtc agcgtcctca ccgtcctgca ccaggactgg   1800
ctgaatggca aggagtacaa gtgcaaggtc tccaacaaag ccctcccagc ccccatcgag   1860
aaaaccatct ccaaagccaa agggcagccc cgagagccac aggtgtacac cctgccccca   1920
tcccgggatg agctgaccaa gaaccaggtc agcctgacct gcctggtcaa aggcttctat   1980
cccagcgaca tcgccgtgga gtgggagagc aatgggcagc cggagaacaa ctacaagacc   2040
acgcctcccg tgctggactc cgacggctcc ttcttcctct acagcaagct caccgtggac   2100
aagagcaggt ggcagcaggg gaacgtcttc tcatgctccg tgatgcatga ggctctgcac   2160
aaccactaca cgcagaagag cctctccctg tctccgggta aa                      2202
```

<210> SEQ ID NO 27
<211> LENGTH: 2904
<212> TYPE: DNA
<213> ORGANISM: Artificial Sequence
<220> FEATURE:
<223> OTHER INFORMATION: von Willebrand Factor sequence

<400> SEQUENCE: 27

```
atgatccccg ccagattcgc cggcgtgctg ctggccctgg ccctgatcct gcccggcacc     60
ctgtgcgcca gcctgagctg cagacccccc atggtcaagc tcgtgtgccc agccgacaat    120
ctgcgggccg aggggctgga atgcaccaag acctgccaga actacgacct ggaatgcatg    180
agcatgggct gcgtgagcgg ctgcctgtgc ccacccggca tggtccggca cgagaacaga    240
tgcgtggccc tggaacggtg cccatgcttc caccagggca aagagtacgc ccctggcgag    300
acagtgaaga tcggctgcaa tacctgcgtg tgccgggacc ggaagtggaa ctgcaccgac    360
```

```
cacgtgtgcg acgccacatg cagcaccatc ggcatggccc actacctgac ctttgacggc    420
ctgaagtacc tgttccccgg cgagtgccag tacgtgctgg tgcaggacta ctgcggcagc    480
aaccccggca ccttccggat cctcgtgggc aacaagggat gcagccaccc cagcgtgaag    540
tgcaagaaac gcgtgaccat cctggtggag ggcggcgaga tcgagctgtt cgacggcgaa    600
gtgaacgtga agcggcccat gaaggacgag acacacttcg aggtggtgga gagcggccgg    660
tacatcatcc tgctgctggg caaggctctg agcgtcgtgt gggaccggca cctgagcatc    720
agcgtggtgc tgaagcagac ctaccaggaa aaagtctgcg gcctctgtgg caatttcgac    780
ggcatccaga acaacgatct gaccagcagc aacctgcagg tggaagagga ccccgtggac    840
tttggcaata gctggaaggt gtccagccag tgtgccgaca ccagaaaagt gcccctggac    900
tctagccccg ccacctgcca caacaacatc atgaagcaga caatggtgga cagctcctgc    960
cggatcctga cctccgacgt gttccaggac tgtaacaaac tggtggatcc tgagccttac   1020
ctggacgtgt gcatctacga cacctgcagc tgcgagagca tcggcgattg cgcctgcttc   1080
tgcgacacaa tcgccgccta cgcccatgtg tgcgcccagc acggcaaggt ggtcacctgg   1140
cggaccgcaa ccctgtgccc ccagagctgc gaggaacgga acctgcggga gaacggctac   1200
gagtgcgagt ggcggtacaa cagctgcgcc ccagcctgcc aggtcacctg ccagcacccc   1260
gagcctctgg cctgccccgt gcagtgcgtg gagggctgcc acgcccactg ccctccaggc   1320
aagatcctgg acgagctgct gcagacctgc gtggaccctg aggactgccc tgtgtgcgag   1380
gtggccggca ggcggttcgc ctccggcaag aaagtgaccc tgaaccctag cgaccccgag   1440
cactgccaga tctgccactg cgacgtggtc aatctgacct gcgaggcttg ccaggaacca   1500
ggcggcctcg tcgtgccccc taccgacgcc cctgtgtccc caaccaccct gtacgtggag   1560
gacatcagcg agccccccct gcacgacttc tactgctctc ggctgctgga cctggtgttc   1620
ctgctggacg gcagttctag actgagcgag gccgagttcg aggtgctgaa ggccttcgtc   1680
gtggacatga tggaacggct gcggatcagc cagaaatggg tccgggtggc cgtggtggag   1740
taccacgacg gcagccacgc ctacatcggc ctgaaggacc ggaagcggcc ctccgaactc   1800
cggcggatcg ccagccaggt caagtacgcc ggatcccagg tggccagcac cagcgaagtg   1860
ctgaagtaca ccctgttcca gatcttcagc aagatcgacc ggcccgaggc cagccggatc   1920
gcactgctgc tgatggccag ccaagaaccc cagcggatga gccggaactt cgtgagatac   1980
gtgcagggcc tgaagaaaaa gaaagtgatc gtgatccccg tgggcatcgg cccccacgcc   2040
aacctgaagc agatccggct gatcgagaag caggcacccg agaacaaggc ctttgtgctg   2100
tccagcgtgg atgagctgga acagcagcgg gacgagatcg tgtcctacct gtgcgacctg   2160
gcccctgagg cccctcctcc cacactgccc ccccacatgg ctcaggtcac cgtgggacca   2220
ggcgacaaaa ctcacacatg cccaccgtgc ccagcacctg aactcctggg gggaccgtca   2280
gtcttcctct tccccccaaa acccaaggac accctcatga tctcccggac ccctgaggtc   2340
acatgcgtgg tggtggacgt gagccacgaa gaccctgagg tcaagttcaa ctggtacgtg   2400
gacggcgtgg aggtgcataa tgccaagaca aagccgcggg aggagcagta caacagcacg   2460
taccgtgtgg tcagcgtcct caccgtcctg caccaggact ggctgaatgg caaggagtac   2520
aagtgcaagg tctccaacaa agccctccca gcccccatcg agaaaaccat ctccaaagcc   2580
aaagggcagc cccgagagcc acaggtgtac accctgcccc catcccggga tgagctgacc   2640
aagaaccagg tcagcctgac ctgcctggtc aaaggcttct atcccagcga catcgccgtg   2700
gagtgggaga gcaatgggca gccggagaac aactacaaga ccacgcctcc cgtgctggac   2760
```

```
tccgacggct ccttcttcct ctacagcaag ctcaccgtgg acaagagcag gtggcagcag   2820

gggaacgtct tctcatgctc cgtgatgcat gaggctctgc acaaccacta cacgcagaag   2880

agcctctccc tgtctccggg taaa                                           2904


<210> SEQ ID NO 28
<211> LENGTH: 5124
<212> TYPE: DNA
<213> ORGANISM: Artificial Sequence
<220> FEATURE:
<223> OTHER INFORMATION: von Willebrand Factor sequence

<400> SEQUENCE: 28

atgatccccg ccagattcgc cggcgtgctg ctggccctgg ccctgatcct gcccggcacc     60

ctgtgcgccg agggcaccag aggcagatcc agcaccgccc ggtgcagcct gttcggcagc    120

gacttcgtga acaccttcga cggcagcatg tacagcttcg ccggctactg tagctacctg    180

ctggctggcg gctgccagaa gcggagcttc agcatcatcg gcgacttcca gaacggcaag    240

cgggtgtccc tgagcgtgta cctgggcgag ttcttcgaca tccacctgtt cgtgaacggc    300

accgtgaccc agggcgatca gagggtgtcc atgccctacg ccagcaaggg cctgtacctg    360

gaaaccgagg ccggctacta caagctgtcc ggcgaggcct acggcttcgt ggcccggatc    420

gacggctccg gcaacttcca ggtgctgctg tccgaccggt acttcaacaa gacctgcggc    480

ctgtgcggca acttcaacat cttcgccgag gacgacttca tgacccagga aggcaccctg    540

accagcgacc cctacgactt cgccaacagc tgggccctga gcagcggcga gcagtggtgc    600

gagagagcca gcccccccag cagcagctgc aacatcagct ccggcgagat gcagaaaggc    660

ctgtgggagc agtgccagct gctgaagtcc acctccgtgt tcgcccggtg ccacccccctg   720

gtggaccccg agccctttgt ggccctgtgc gaaaagaccc tgtgcgagtg cgctggcggc    780

ctggaatgcg cctgccctgc cctgctggaa tacgcccgga cctgcgccca agaagggatg    840

gtcctgtacg gctggaccga ccacagcgcc tgcagccccg tctgccctgc cggcatggaa    900

taccggcagt gcgtgagccc ctgcgccaga acctgccaga gcctgcacat caacgagatg    960

tgccaggaaa gatgcgtcga cggctgctct tgtcccgagg gacagctcct ggacgagggc   1020

ctctgcgtgg agagcaccga gtgcccctgc gtgcacagcg gcaagagata ccccccctggc  1080

accagcctga gccgggactg caacacctgc atttgccgga acagccagtg gatctgcagc   1140

aacgaggaat gcccaggcga gtgcctggtc accggccaga gccacttcaa gagcttcgac   1200

aacagatact tcaccttcag cggcatctgc cagtatctgc tggccagaga ctgccaggac   1260

cacagcttct ccatcgtgat cgagacagtg cagtgcgccg acgaccggga cgccgtgtgc   1320

accagatccg tgaccgtgag actgcccggc ctgcacaaca gcctggtcaa gctgaagcat   1380

ggcgctggcg tggccatgga cggccaggac atccagctgc ctctgctgaa gggcgacctg   1440

cggatccagc acaccgtgac cgccagcgtg agactgtcct acggcgagga cctgcagatg   1500

gactgggacg gcagaggccg gctgctcgtg aagctgtccc ccgtgtacgc cggcaagaca   1560

tgtggcctgt gtgggaacta caacggcaac cagggcgacg actttctgac cccccagcggc  1620

ctggccgagc ccagagtgga ggacttcggc aacgcctgga agctgcacgg cgattgccag   1680

gatctgcaga aacagcactc cgacccctgc gccctgaacc cccggatgac ccggttcagc   1740

gaagaggctt gcgccgtgct gaccagcccc accttcgagg cctgccaccg ggccgtgagc   1800

cccctgccct acctgcggaa ctgcagatac gatgtgtgta gctgctctga cggccgggag   1860
```

-continued

```
tgcctgtgtg gcgccctggc cagctatgcc gctgcctgcg ccggacgcgg tgtgagagtg   1920
gcttggcggg agcctggcag atgcgagctg aactgcccca agggccaggt gtacctgcag   1980
tgcggcaccc cctgcaacct gacctgccgg tccctgagct accccgacga agagtgcaac   2040
gaggcctgtc tcgaaggctg cttctgcccc cctggcctgt acatggacga gcggggcgac   2100
tgcgtgccca aggcccagtg cccctgttac tacgacggcg agatcttcca gcccgaggac   2160
atcttcagcg accaccacac catgtgctac tgcgaggacg gctttatgca ctgcaccatg   2220
agcggcgtgc ccggcagcct gctgccagac gccgtgctgt cctccccccct gagccaccgg   2280
tccaagcgga gcctgagctg cagacccccc atggtcaagc tcgtgtgccc agccgacaat   2340
ctgcgggccg aggggctgga atgcaccaag acctgccaga actacgacct ggaatgcatg   2400
agcatgggct gcgtgagcgg ctgcctgtgc ccacccggca tggtccggca cgagaacaga   2460
tgcgtggccc tggaacggtg cccatgcttc caccagggca aagagtacgc ccctggcgag   2520
acagtgaaga tcggctgcaa tacctgcgtg tgccgggacc ggaagtggaa ctgcaccgac   2580
cacgtgtgcg acgccacatg cagcaccatc ggcatggccc actacctgac ctttgacggc   2640
ctgaagtacc tgttccccgg cgagtgccag tacgtgctgg tgcaggacta ctgcggcagc   2700
aaccccggca ccttccggat cctcgtgggc aacaagggat gcagccaccc cagcgtgaag   2760
tgcaagaaac gcgtgaccat cctggtggag ggcggcgaga tcgagctgtt cgacggcgaa   2820
gtgaacgtga agcggcccat gaaggacgag acacacttcg aggtggtgga gagcggccgg   2880
tacatcatcc tgctgctggg caaggctctg agcgtcgtgt gggaccggca cctgagcatc   2940
agcgtggtgc tgaagcagac ctaccaggaa aaagtctgcg gcctctgtgg caatttcgac   3000
ggcatccaga acaacgatct gaccagcagc aacctgcagg tggaagagga ccccgtggac   3060
tttggcaata gctggaaggt gtccagccag tgtgccgaca ccagaaaagt gcccctggac   3120
tctagccccg ccacctgcca caacaacatc atgaagcaga caatggtgga cagctcctgc   3180
cggatcctga cctccgacgt gttccaggac tgtaacaaac tggtggatcc tgagccttac   3240
ctggacgtgt gcatctacga cacctgcagc tgcgagagca tcggcgattg cgcctgcttc   3300
tgcgacacaa tcgccgccta cgcccatgtg tgcgcccagc acggcaaggt ggtcacctgg   3360
cggaccgcaa ccctgtgccc ccagagctgc gaggaacgga acctgcggga gaacggctac   3420
gagtgcgagt ggcggtacaa cagctgcgcc ccagcctgcc aggtcacctg ccagcacccc   3480
gagcctctgg cctgccccgt gcagtgcgtg gagggctgcc acgcccactg ccctccaggc   3540
aagatcctgg acgagctgct gcagacctgc gtggaccctg aggactgccc tgtgtgcgag   3600
gtggccggca ggcggttcgc ctccggcaag aaagtgaccc tgaaccctag cgaccccgag   3660
cactgccaga tctgccactg cgacgtggtc aatctgacct gcgaggcttg ccaggaacca   3720
ggcggcctcg tcgtgccccc taccgacgcc cctgtgtccc caaccaccct gtacgtggag   3780
gacatcagcg agcccccccct gcacgacttc tactgctctc ggctgctgga cctggtgttc   3840
ctgctggacg gcagttctag actgagcgag gccgagttcg aggtgctgaa ggccttcgtc   3900
gtggacatga tggaacggct gcggatcagc cagaaatggg tccgggtggc cgtggtggag   3960
taccacgacg gcagccacgc ctacatcggc ctgaaggacc ggaagcggcc ctccgaactc   4020
cggcggatcg ccagccaggt caagtacgcc ggatcccagg tggccagcac cagcgaagtg   4080
ctgaagtaca ccctgttcca gatcttcagc aagatcgacc ggcccgaggc cagccggatc   4140
gcactgctgc tgatggccag ccaagaaccc cagcggatga gccggaactt cgtgagatac   4200
gtgcagggcc tgaagaaaaa gaaagtgatc gtgatccccg tgggcatcgg cccccacgcc   4260
```

```
aacctgaagc agatccggct gatcgagaag caggcacccg agaacaaggc ctttgtgctg   4320

tccagcgtgg atgagctgga acagcagcgg gacgagatcg tgtcctacct gtgcgacctg   4380

gcccctgagg cccctcctcc cacactgccc ccccacatgg ctcaggtcac cgtgggacca   4440

ggcgacaaaa ctcacacatg cccaccgtgc ccagcacctg aactcctggg gggaccgtca   4500

gtcttcctct tcccccccaaa acccaaggac accctcatga tctcccggac ccctgaggtc   4560

acatgcgtgg tggtggacgt gagccacgaa gaccctgagg tcaagttcaa ctggtacgtg   4620

gacggcgtgg aggtgcataa tgccaagaca aagccgcggg aggagcagta caacagcacg   4680

taccgtgtgg tcagcgtcct caccgtcctg caccaggact ggctgaatgg caaggagtac   4740

aagtgcaagg tctccaacaa agccctccca gcccccatcg agaaaaccat ctccaaagcc   4800

aaagggcagc cccgagagcc acaggtgtac accctgcccc catcccggga tgagctgacc   4860

aagaaccagg tcagcctgac ctgcctggtc aaaggcttct atcccagcga catcgccgtg   4920

gagtgggaga gcaatgggca gccggagaac aactacaaga ccacgcctcc cgtgctggac   4980

tccgacggct ccttcttcct ctacagcaag ctcaccgtgg acaagagcag gtggcagcag   5040

gggaacgtct tctcatgctc cgtgatgcat gaggctctgc acaaccacta cacgcagaag   5100

agcctctccc tgtctccggg taaa                                          5124
```

<210> SEQ ID NO 29
<211> LENGTH: 2813
<212> TYPE: PRT
<213> ORGANISM: Artificial Sequence
<220> FEATURE:
<223> OTHER INFORMATION: von Willebrand Factor sequence

<400> SEQUENCE: 29

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205
```

```
Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620
```

```
Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                 1005

Ser Ser  Asn Leu Gln Val Glu  Glu Asp Pro Val Asp  Phe Gly Asn
    1010                 1015                 1020

Ser Trp  Lys Val Ser Ser Gln  Cys Ala Asp Thr Arg  Lys Val Pro
    1025                 1030                 1035

Leu Asp  Ser Ser Pro Ala Thr  Cys His Asn Asn Ile  Met Lys Gln
```

```
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
    1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
    1145                1150                1155

His Pro  Glu Pro Leu Ala Cys  Pro Val Gln Cys Val  Glu Gly Cys
    1160                1165                1170

His Ala  His Cys Pro Pro Gly  Lys Ile Leu Asp Glu  Leu Leu Gln
    1175                1180                1185

Thr Cys  Val Asp Pro Glu Asp  Cys Pro Val Cys Glu  Val Ala Gly
    1190                1195                1200

Arg Arg  Phe Ala Ser Gly Lys  Lys Val Thr Leu Asn  Pro Ser Asp
    1205                1210                1215

Pro Glu  His Cys Gln Ile Cys  His Cys Asp Val Val  Asn Leu Thr
    1220                1225                1230

Cys Glu  Ala Cys Gln Glu Pro  Gly Gly Leu Val Val  Pro Pro Thr
    1235                1240                1245

Asp Ala  Pro Val Ser Pro Thr  Thr Leu Tyr Val Glu  Asp Ile Ser
    1250                1255                1260

Glu Pro  Pro Leu His Asp Phe  Tyr Cys Ser Arg Leu  Leu Asp Leu
    1265                1270                1275

Val Phe  Leu Leu Asp Gly Ser  Ser Arg Leu Ser Glu  Ala Glu Phe
    1280                1285                1290

Glu Val  Leu Lys Ala Phe Val  Val Asp Met Met Glu  Arg Leu Arg
    1295                1300                1305

Ile Ser  Gln Lys Trp Val Arg  Val Ala Val Val Glu  Tyr His Asp
    1310                1315                1320

Gly Ser  His Ala Tyr Ile Gly  Leu Lys Asp Arg Lys  Arg Pro Ser
    1325                1330                1335

Glu Leu  Arg Arg Ile Ala Ser  Gln Val Lys Tyr Ala  Gly Ser Gln
    1340                1345                1350

Val Ala  Ser Thr Ser Glu Val  Leu Lys Tyr Thr Leu  Phe Gln Ile
    1355                1360                1365

Phe Ser  Lys Ile Asp Arg Pro  Glu Ala Ser Arg Ile  Ala Leu Leu
    1370                1375                1380

Leu Met  Ala Ser Gln Glu Pro  Gln Arg Met Ser Arg  Asn Phe Val
    1385                1390                1395

Arg Tyr  Val Gln Gly Leu Lys  Lys Lys Lys Val Ile  Val Ile Pro
    1400                1405                1410

Val Gly  Ile Gly Pro His Ala  Asn Leu Lys Gln Ile  Arg Leu Ile
    1415                1420                1425

Glu Lys  Gln Ala Pro Glu Asn  Lys Ala Phe Val Leu  Ser Ser Val
    1430                1435                1440
```

```
Asp Glu  Leu Glu Gln Gln Arg  Asp Glu Ile Val Ser  Tyr Leu Cys
    1445                 1450                 1455

Asp Leu  Ala Pro Glu Ala Pro  Pro Pro Thr Leu Pro  Pro His Met
    1460                 1465                 1470

Ala Gln  Val Thr Val Gly Pro  Gly Leu Leu Gly Val  Ser Thr Leu
    1475                 1480                 1485

Gly Pro  Lys Arg Asn Ser Met  Val Leu Asp Val Ala  Phe Val Leu
    1490                 1495                 1500

Glu Gly  Ser Asp Lys Ile Gly  Glu Ala Asp Phe Asn  Arg Ser Lys
    1505                 1510                 1515

Glu Phe  Met Glu Glu Val Ile  Gln Arg Met Asp Val  Gly Gln Asp
    1520                 1525                 1530

Ser Ile  His Val Thr Val Leu  Gln Tyr Ser Tyr Met  Val Thr Val
    1535                 1540                 1545

Glu Tyr  Pro Phe Ser Glu Ala  Gln Ser Lys Gly Asp  Ile Leu Gln
    1550                 1555                 1560

Arg Val  Arg Glu Ile Arg Tyr  Gln Gly Gly Asn Arg  Thr Asn Thr
    1565                 1570                 1575

Gly Leu  Ala Leu Arg Tyr Leu  Ser Asp His Ser Phe  Leu Val Ser
    1580                 1585                 1590

Gln Gly  Asp Arg Glu Gln Ala  Pro Asn Leu Val Tyr  Met Val Thr
    1595                 1600                 1605

Gly Asn  Pro Ala Ser Asp Glu  Ile Lys Arg Leu Pro  Gly Asp Ile
    1610                 1615                 1620

Gln Val  Val Pro Ile Gly Val  Gly Pro Asn Ala Asn  Val Gln Glu
    1625                 1630                 1635

Leu Glu  Arg Ile Gly Trp Pro  Asn Ala Pro Ile Leu  Ile Gln Asp
    1640                 1645                 1650

Phe Glu  Thr Leu Pro Arg Glu  Ala Pro Asp Leu Val  Leu Gln Arg
    1655                 1660                 1665

Cys Cys  Ser Gly Glu Gly Leu  Gln Ile Pro Thr Leu  Ser Pro Ala
    1670                 1675                 1680

Pro Asp  Cys Ser Gln Pro Leu  Asp Val Ile Leu Leu  Leu Asp Gly
    1685                 1690                 1695

Ser Ser  Ser Phe Pro Ala Ser  Tyr Phe Asp Glu Met  Lys Ser Phe
    1700                 1705                 1710

Ala Lys  Ala Phe Ile Ser Lys  Ala Asn Ile Gly Pro  Arg Leu Thr
    1715                 1720                 1725

Gln Val  Ser Val Leu Gln Tyr  Gly Ser Ile Thr Thr  Ile Asp Val
    1730                 1735                 1740

Pro Trp  Asn Val Val Pro Glu  Lys Ala His Leu Leu  Ser Leu Val
    1745                 1750                 1755

Asp Val  Met Gln Arg Glu Gly  Gly Pro Ser Gln Ile  Gly Asp Ala
    1760                 1765                 1770

Leu Gly  Phe Ala Val Arg Tyr  Leu Thr Ser Glu Met  His Gly Ala
    1775                 1780                 1785

Arg Pro  Gly Ala Ser Lys Ala  Val Val Ile Leu Val  Thr Asp Val
    1790                 1795                 1800

Ser Val  Asp Ser Val Asp Ala  Ala Ala Asp Ala Ala  Arg Ser Asn
    1805                 1810                 1815

Arg Val  Thr Val Phe Pro Ile  Gly Ile Gly Asp Arg  Tyr Asp Ala
    1820                 1825                 1830
```

```
Ala Gln  Leu Arg Ile Leu Ala  Gly Pro Ala Gly Asp  Ser Asn Val
    1835                 1840                 1845

Val Lys  Leu Gln Arg Ile Glu  Asp Leu Pro Thr Met  Val Thr Leu
    1850                 1855                 1860

Gly Asn  Ser Phe Leu His Lys  Leu Cys Ser Gly Phe  Val Arg Ile
    1865                 1870                 1875

Cys Met  Asp Glu Asp Gly Asn  Glu Lys Arg Pro Gly  Asp Val Trp
    1880                 1885                 1890

Thr Leu  Pro Asp Gln Cys His  Thr Val Thr Cys Gln  Pro Asp Gly
    1895                 1900                 1905

Gln Thr  Leu Leu Lys Ser His  Arg Val Asn Cys Asp  Arg Gly Leu
    1910                 1915                 1920

Arg Pro  Ser Cys Pro Asn Ser  Gln Ser Pro Val Lys  Val Glu Glu
    1925                 1930                 1935

Thr Cys  Gly Cys Arg Trp Thr  Cys Pro Cys Val Cys  Thr Gly Ser
    1940                 1945                 1950

Ser Thr  Arg His Ile Val Thr  Phe Asp Gly Gln Asn  Phe Lys Leu
    1955                 1960                 1965

Thr Gly  Ser Cys Ser Tyr Val  Leu Phe Gln Asn Lys  Glu Gln Asp
    1970                 1975                 1980

Leu Glu  Val Ile Leu His Asn  Gly Ala Cys Ser Pro  Gly Ala Arg
    1985                 1990                 1995

Gln Gly  Cys Met Lys Ser Ile  Glu Val Lys His Ser  Ala Leu Ser
    2000                 2005                 2010

Val Glu  Leu His Ser Asp Met  Glu Val Thr Val Asn  Gly Arg Leu
    2015                 2020                 2025

Val Ser  Val Pro Tyr Val Gly  Gly Asn Met Glu Val  Asn Val Tyr
    2030                 2035                 2040

Gly Ala  Ile Met His Glu Val  Arg Phe Asn His Leu  Gly His Ile
    2045                 2050                 2055

Phe Thr  Phe Thr Pro Gln Asn  Asn Glu Phe Gln Leu  Gln Leu Ser
    2060                 2065                 2070

Pro Lys  Thr Phe Ala Ser Lys  Thr Tyr Gly Leu Cys  Gly Ile Cys
    2075                 2080                 2085

Asp Glu  Asn Gly Ala Asn Asp  Phe Met Leu Arg Asp  Gly Thr Val
    2090                 2095                 2100

Thr Thr  Asp Trp Lys Thr Leu  Val Gln Glu Trp Thr  Val Gln Arg
    2105                 2110                 2115

Pro Gly  Gln Thr Cys Gln Pro  Ile Leu Glu Glu Gln  Cys Leu Val
    2120                 2125                 2130

Pro Asp  Ser Ser His Cys Gln  Val Leu Leu Leu Pro  Leu Phe Ala
    2135                 2140                 2145

Glu Cys  His Lys Val Leu Ala  Pro Ala Thr Phe Tyr  Ala Ile Cys
    2150                 2155                 2160

Gln Gln  Asp Ser Cys His Gln  Glu Gln Val Cys Glu  Val Ile Ala
    2165                 2170                 2175

Ser Tyr  Ala His Leu Cys Arg  Thr Asn Gly Val Cys  Val Asp Trp
    2180                 2185                 2190

Arg Thr  Pro Asp Phe Cys Ala  Met Ser Cys Pro Pro  Ser Leu Val
    2195                 2200                 2205

Tyr Asn  His Cys Glu His Gly  Cys Pro Arg His Cys  Asp Gly Asn
    2210                 2215                 2220

Val Ser  Ser Cys Gly Asp His  Pro Ser Glu Gly Cys  Phe Cys Pro
```

```
    2225                2230                2235

Pro Asp  Lys Val Met Leu Glu  Gly Ser Cys Val Pro  Glu Glu Ala
    2240                2245                2250

Cys Thr  Gln Cys Ile Gly Glu  Asp Gly Val Gln His  Gln Phe Leu
    2255                2260                2265

Glu Ala  Trp Val Pro Asp His  Gln Pro Cys Gln Ile  Cys Thr Cys
    2270                2275                2280

Leu Ser  Gly Arg Lys Val Asn  Cys Thr Thr Gln Pro  Cys Pro Thr
    2285                2290                2295

Ala Lys  Ala Pro Thr Cys Gly  Leu Cys Glu Val Ala  Arg Leu Arg
    2300                2305                2310

Gln Asn  Ala Asp Gln Cys Cys  Pro Glu Tyr Glu Cys  Val Cys Asp
    2315                2320                2325

Pro Val  Ser Cys Asp Leu Pro  Pro Val Pro His Cys  Glu Arg Gly
    2330                2335                2340

Leu Gln  Pro Thr Leu Thr Asn  Pro Gly Glu Cys Arg  Pro Asn Phe
    2345                2350                2355

Thr Cys  Ala Cys Arg Lys Glu  Glu Cys Lys Arg Val  Ser Pro Pro
    2360                2365                2370

Ser Cys  Pro Pro His Arg Leu  Pro Thr Leu Arg Lys  Thr Gln Cys
    2375                2380                2385

Cys Asp  Glu Tyr Glu Cys Ala  Cys Asn Cys Val Asn  Ser Thr Val
    2390                2395                2400

Ser Cys  Pro Leu Gly Tyr Leu  Ala Ser Thr Ala Thr  Asn Asp Cys
    2405                2410                2415

Gly Cys  Thr Thr Thr Thr Cys  Leu Pro Asp Lys Val  Cys Val His
    2420                2425                2430

Arg Ser  Thr Ile Tyr Pro Val  Gly Gln Phe Trp Glu  Glu Gly Cys
    2435                2440                2445

Asp Val  Cys Thr Cys Thr Asp  Met Glu Asp Ala Val  Met Gly Leu
    2450                2455                2460

Arg Val  Ala Gln Cys Ser Gln  Lys Pro Cys Glu Asp  Ser Cys Arg
    2465                2470                2475

Ser Gly  Phe Thr Tyr Val Leu  His Glu Gly Glu Cys  Cys Gly Arg
    2480                2485                2490

Cys Leu  Pro Ser Ala Cys Glu  Val Val Thr Gly Ser  Pro Arg Gly
    2495                2500                2505

Asp Ser  Gln Ser Ser Trp Lys  Ser Val Gly Ser Gln  Trp Ala Ser
    2510                2515                2520

Pro Glu  Asn Pro Cys Leu Ile  Asn Glu Cys Val Arg  Val Lys Glu
    2525                2530                2535

Glu Val  Phe Ile Gln Gln Arg  Asn Val Ser Cys Pro  Gln Leu Glu
    2540                2545                2550

Val Pro  Val Cys Pro Ser Gly  Phe Gln Leu Ser Cys  Lys Thr Ser
    2555                2560                2565

Ala Cys  Cys Pro Ser Cys Arg  Cys Glu Arg Met Glu  Ala Cys Met
    2570                2575                2580

Leu Asn  Gly Thr Val Ile Gly  Pro Gly Lys Thr Val  Met Ile Asp
    2585                2590                2595

Val Cys  Thr Thr Cys Arg Cys  Met Val Gln Val Gly  Val Ile Ser
    2600                2605                2610

Gly Phe  Lys Leu Glu Cys Arg  Lys Thr Thr Cys Asn  Pro Cys Pro
    2615                2620                2625
```

```
Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810
```

<210> SEQ ID NO 30
<211> LENGTH: 8833
<212> TYPE: DNA
<213> ORGANISM: Artificial Sequence
<220> FEATURE:
<223> OTHER INFORMATION: von Willebrand Factor sequence

<400> SEQUENCE: 30

```
agctcacagc tattgtggtg ggaaagggag ggtggttggt ggatgtcaca gcttgggctt      60

tatctccccc agcagtgggg actccacagc ccctgggcta cataacagca agacagtccg     120

gagctgtagc agacctgatt gagcctttgc agcagctgag agcatggcct agggtgggcg     180

gcaccattgt ccagcagctg agtttcccag ggaccttgga gatagccgca gccctcattt     240

gcaggggaag atgattcctg ccagatttgc cggggtgctg cttgctctgg ccctcatttt     300

gccagggacc ctttgtgcag aaggaactcg cggcaggtca tccacggccc gatgcagcct     360

ttcggaagt gacttcgtca acacctttga tgggagcatg tacagctttg cgggatactg     420

cagttacctc ctggcagggg gctgccagaa acgctccttc tcgattattg gggacttcca     480

gaatggcaag agagtgagcc tctccgtgta tcttggggaa ttttttgaca tccatttgtt     540

tgtcaatggt accgtgacac agggggacca aagagtctcc atgccctatg cctccaaagg     600

gctgtatcta gaaactgagg ctgggtacta caagctgtcc ggtgaggcct atggctttgt     660

ggccaggatc gatggcagcg gcaactttca agtcctgctg tcagacagat acttcaacaa     720

gacctgcggg ctgtgtggca actttaacat ctttgctgaa gatgacttta tgacccaaga     780

agggaccttg acctcggacc cttatgactt tgccaactca tgggctctga gcagtggaga     840

acagtggtgt gaacgggcat ctcctcccag cagctcatgc aacatctcct ctggggaaat     900
```

```
gcagaagggc ctgtgggagc agtgccagct tctgaagagc acctcggtgt ttgcccgctg    960
ccaccctctg gtggaccccg agccttttgt ggccctgtgt gagaagactt tgtgtgagtg   1020
tgctgggggg ctggagtgcg cctgccctgc cctcctggag tacgcccgga cctgtgccca   1080
ggagggaatg gtgctgtacg gctggaccga ccacagcgcg tgcagcccag tgtgccctgc   1140
tggtatggag tataggcagt gtgtgtcccc ttgcgccagg acctgccaga gcctgcacat   1200
caatgaaatg tgtcaggagc gatgcgtgga tggctgcagc tgccctgagg gacagctcct   1260
ggatgaaggc ctctgcgtgg agagcaccga gtgtccctgc gtgcattccg gaaagcgcta   1320
ccctcccggc acctccctct ctcgagactg caacacctgc atttgccgaa acagccagtg   1380
gatctgcagc aatgaagaat gtccagggga gtgccttgtc acaggtcaat cacacttcaa   1440
gagctttgac aacagatact tcaccttcag tgggatctgc cagtacctgc tggcccggga   1500
ttgccaggac cactccttct ccattgtcat tgagactgtc cagtgtgctg atgaccgcga   1560
cgctgtgtgc acccgctccg tcaccgtccg gctgcctggc ctgcacaaca gccttgtgaa   1620
actgaagcat ggggcaggag ttgccatgga tggccaggac gtccagctcc ccctcctgaa   1680
aggtgacctc cgcatccagc atacagtgac ggcctccgtg cgcctcagct acggggagga   1740
cctgcagatg gactgggatg gccgcgggag gctgctggtg aagctgtccc ccgtctatgc   1800
cgggaagacc tgcggcctgt gtgggaatta caatggcaac cagggcgacg acttccttac   1860
cccctctggg ctggcggagc cccgggtgga ggacttcggg aacgcctgga agctgcacgg   1920
ggactgccag gacctgcaga agcagcacag cgatccctgc gccctcaacc cgcgcatgac   1980
caggttctcc gaggaggcgt gcgcggtcct gacgtccccc acattcgagg cctgccatcg   2040
tgccgtcagc ccgctgccct acctgcggaa ctgccgctac gacgtgtgct cctgctcgga   2100
cggccgcgag tgcctgtgcg gcgccctggc cagctatgcc gcggcctgcg cggggagagg   2160
cgtgcgcgtc gcgtggcgcg agccaggccg ctgtgagctg aactgcccga aaggccaggt   2220
gtacctgcag tgcgggaccc cctgcaacct gacctgccgc tctctctctt acccggatga   2280
ggaatgcaat gaggcctgcc tggagggctg cttctgcccc ccagggctct acatggatga   2340
gaggggggac tgcgtgccca aggcccagtg cccctgttac tatgacggtg agatcttcca   2400
gccagaagac atcttctcag accatcacac catgtgctac tgtgaggatg gcttcatgca   2460
ctgtaccatg agtggagtcc ccggaagctt gctgcctgac gctgtcctca gcagtcccct   2520
gtctcatcgc agcaaaagga gcctatcctg tcggcccccc atggtcaagc tggtgtgtcc   2580
cgctgacaac ctgcgggctg aagggctcga gtgtaccaaa acgtgccaga actatgacct   2640
ggagtgcatg agcatgggct gtgtctctgg ctgcctctgc cccccgggca tggtccggca   2700
tgagaacaga tgtgtggccc tggaaaggtg tccctgcttc catcagggca aggagtatgc   2760
ccctggagaa acagtgaaga ttggctgcaa cacttgtgtc tgtcgggacc ggaagtggaa   2820
ctgcacagac catgtgtgtg atgccacgtg ctccacgatc ggcatggccc actacctcac   2880
cttcgacggg ctcaaatacc tgttccccgg ggagtgccag tacgttctgg tgcaggatta   2940
ctgcggcagt aaccctggga cctttcggat cctagtgggg aataagggat gcagccaccc   3000
ctcagtgaaa tgcaagaaac gggtcaccat cctggtggag ggaggagaga ttgagctgtt   3060
tgacggggag gtgaatgtga agaggcccat gaaggatgag actcactttg aggtggtgga   3120
gtctggccgg tacatcattc tgctgctggg caaagccctc tccgtggtct gggaccgcca   3180
cctgagcatc tccgtggtcc tgaagcagac ataccaggag aaagtgtgtg gcctgtgtgg   3240
```

```
gaattttgat ggcatccaga acaatgacct caccagcagc aacctccaag tggaggaaga   3300
ccctgtggac tttgggaact cctggaaagt gagctcgcag tgtgctgaca ccagaaaagt   3360
gcctctggac tcatcccctg ccacctgcca taacaacatc atgaagcaga cgatggtgga   3420
ttcctcctgt agaatcctta ccagtgacgt cttccaggac tgcaacaagc tggtggaccc   3480
cgagccatat ctggatgtct gcatttacga cacctgctcc tgtgagtcca ttggggactg   3540
cgcctgcttc tgcgacacca ttgctgccta tgcccacgtg tgtgcccagc atggcaaggt   3600
ggtgacctgg aggacggcca cattgtgccc ccagagctgc gaggagagga atctccggga   3660
gaacgggtat gagtgtgagt ggcgctataa cagctgtgca cctgcctgtc aagtcacgtg   3720
tcagcaccct gagccactgg cctgccctgt gcagtgtgtg gagggctgcc atgcccactg   3780
ccctccaggg aaaatcctgg atgagctttt gcagacctgc gttgaccctg aagactgtcc   3840
agtgtgtgag gtggctggcc ggcgttttgc ctcaggaaag aaagtcacct tgaatcccag   3900
tgaccctgag cactgccaga tttgccactg tgatgttgtc aacctcacct gtgaagcctg   3960
ccaggagccg ggaggcctgg tggtgcctcc cacagatgcc ccggtgagcc ccaccactct   4020
gtatgtggag gacatctcgg aaccgccgtt gcacgatttc tactgcagca ggctactgga   4080
cctggtcttc ctgctggatg gctcctccag gctgtccgag gctgagtttg aagtgctgaa   4140
ggcctttgtg gtggacatga tggagcggct gcgcatctcc cagaagtggg tccgcgtggc   4200
cgtggtggag taccacgacg gctcccacgc ctacatcggg ctcaaggacc ggaagcgacc   4260
gtcagagctg cggcgcattg ccagccaggt gaagtatgcg ggcagccagg tggcctccac   4320
cagcgaggtc ttgaaataca cactgttcca aatcttcagc aagatcgacc gccctgaagc   4380
ctcccgcatc accctgctcc tgatggccag ccaggagccc caacggatgt cccggaactt   4440
tgtccgctac gtccagggcc tgaagaagaa gaaggtcatt gtgatcccgg tgggcattgg   4500
gccccatgcc aacctcaagc agatccgcct catcgagaag caggcccctg agaacaaggc   4560
cttcgtgctg agcagtgtgg atgagctgga gcagcaaagg gacgagatcg ttagctacct   4620
ctgtgacctt gccccctgaag cccctcctcc tactctgccc cccgacatgg cacaagtcac   4680
tgtgggcccg gggctcttgg gggtttcgac cctggggccc aagaggaact ccatggttct   4740
ggatgtggcg ttcgtcctgg aaggatcgga caaaattggt gaagccgact tcaacaggag   4800
caaggagttc atggaggagg tgattcagcg gatggatgtg ggccaggaca gcatccacgt   4860
cacggtgctg cagtactcct acatggtgac tgtggagtac cccttcagcg aggcacagtc   4920
caaaggggac atcctgcagc gggtgcgaga gatccgctac cagggcggca acaggaccaa   4980
cactgggctg gccctgcggt acctctctga ccacagcttc ttggtcagcc agggtgaccg   5040
ggagcaggcg cccaacctgg tctacatggt caccggaaat cctgcctctg atgagatcaa   5100
gaggctgcct ggagacatcc aggtggtgcc cattggagtg ggccctaatg ccaacgtgca   5160
ggagctggag aggattggct ggcccaatgc ccctatcctc atccaggact ttgagacgct   5220
cccccgagag gctcctgacc tggtgctgca gaggtgctgc tccggagagg ggctgcagat   5280
ccccaccctc tcccctgcac ctgactgcag ccagcccctg gacgtgatcc ttctcctgga   5340
tggctcctcc agtttcccag cttcttattt tgatgaaatg aagagtttcg ccaaggcttt   5400
catttcaaaa gccaatatag ggcctcgtct cactcaggtg tcagtgctgc agtatggaag   5460
catcaccacc attgacgtgc catggaacgt ggtcccggag aaagcccatt tgctgagcct   5520
tgtggacgtc atgcagcggg agggaggccc cagccaaatc ggggatgcct tgggctttgc   5580
tgtgcgatac ttgacttcag aaatgcatgg tgccaggccg ggagcctcaa aggcggtggt   5640
```

```
catcctggtc acggacgtct ctgtggattc agtggatgca gcagctgatg ccgccaggtc   5700
caacagagtg acagtgttcc ctattggaat tggagatcgc tacgatgcag cccagctacg   5760
gatcttggca ggcccagcag gcgactccaa cgtggtgaag ctccagcgaa tcgaagacct   5820
ccctaccatg gtcaccttgg gcaattcctt cctccacaaa ctgtgctctg gatttgttag   5880
gatttgcatg gatgaggatg ggaatgagaa gaggcccggg gacgtctgga ccttgccaga   5940
ccagtgccac accgtgactt gccagccaga tggccagacc ttgctgaaga gtcatcgggt   6000
caactgtgac cgggggctga ggccttcgtg ccctaacagc cagtcccctg ttaaagtgga   6060
agagacctgt ggctgccgct ggacctgccc ctgcgtgtgc acaggcagct ccactcggca   6120
catcgtgacc tttgatgggc agaatttcaa gctgactggc agctgttctt atgtcctatt   6180
tcaaaacaag gagcaggacc tggaggtgat tctccataat ggtgcctgca gccctggagc   6240
aaggcagggc tgcatgaaat ccatcgaggt gaagcacagt gccctctccg tcgagctgca   6300
cagtgacatg gaggtgacgg tgaatgggag actggtctct gttccttacg tgggtgggaa   6360
catggaagtc aacgtttatg gtgccatcat gcatgaggtc agattcaatc accttggtca   6420
catcttcaca ttcactccac aaaacaatga gttccaactg cagctcagcc ccaagacttt   6480
tgcttcaaag acgtatggtc tgtgtgggat ctgtgatgag aacggagcca atgacttcat   6540
gctgagggat ggcacagtca ccacagactg gaaaacactt gttcaggaat ggactgtgca   6600
gcggccaggg cagacgtgcc agcccatcct ggaggagcag tgtcttgtcc ccgacagctc   6660
ccactgccag gtcctcctct taccactgtt tgctgaatgc cacaaggtcc tggctccagc   6720
cacattctat gccatctgcc agcaggacag ttgccaccag gagcaagtgt gtgaggtgat   6780
cgcctcttat gcccacctct gtcggaccaa cggggtctgc gttgactgga ggacacctga   6840
tttctgtgct atgtcatgcc caccatctct ggtctacaac cactgtgagc atggctgtcc   6900
ccggcactgt gatggcaacg tgagctcctg tggggaccat ccctccgaag gctgtttctg   6960
ccctccagat aaagtcatgt tggaaggcag ctgtgtccct gaagaggcct gcactcagtg   7020
cattggtgag gatggagtcc agcaccagtt cctggaagcc tgggtcccgg accaccagcc   7080
ctgtcagatc tgcacatgcc tcagcgggcg gaaggtcaac tgcacaacgc agccctgccc   7140
cacggccaaa gctcccacgt gtggcctgtg tgaagtagcc cgcctccgcc agaatgcaga   7200
ccagtgctgc cccgagtatg agtgtgtgtg tgacccagtg agctgtgacc tgcccccagt   7260
gcctcactgt gaacgtggcc tccagcccac actgaccaac cctggcgagt gcagacccaa   7320
cttcacctgc gcctgcagga aggaggagtg caaaagagtg tccccaccct cctgcccccc   7380
gcaccgtttg cccacccttc ggaagaccca gtgctgtgat gagtatgagt gtgcctgcaa   7440
ctgtgtcaac tccacagtga gctgtcccct tgggtacttg gcctcaactg ccaccaatga   7500
ctgtggctgt accacaacca cctgccttcc cgacaaggtg tgtgtccacc gaagcaccat   7560
ctaccctgtg ggccagttct gggaggaggg ctgcgatgtg tgcacctgca ccgacatgga   7620
ggatgccgtg atgggcctcc gcgtggccca gtgctcccag aagccctgtg aggacagctg   7680
tcggtcgggc ttcacttacg ttctgcatga aggcgagtgc tgtggaaggt gcctgccatc   7740
tgcctgtgag gtggtgactg gctcaccgcg gggggactcc cagtcttcct ggaagagtgt   7800
cggctcccag tgggcctccc cggagaaccc ctgcctcatc aatgagtgtg tccgagtgaa   7860
ggaggaggtc tttatacaac aaaggaacgt ctcctgcccc cagctggagg tccctgtctg   7920
cccctcgggc tttcagctga gctgtaagac ctcagcgtgc tgcccaagct gtcgctgtga   7980
```

```
gcgcatggag gcctgcatgc tcaatggcac tgtcattggg cccgggaaga ctgtgatgat   8040

cgatgtgtgc acgacctgcc gctgcatggt gcaggtgggg gtcatctctg gattcaagct   8100

ggagtgcagg aagaccacct gcaacccctg ccccctgggt tacaaggaag aaaataacac   8160

aggtgaatgt tgtgggagat gtttgcctac ggcttgcacc attcagctaa gaggaggaca   8220

gatcatgaca ctgaagcgtg atgagacgct ccaggatggc tgtgatactc acttctgcaa   8280

ggtcaatgag agaggagagt acttctggga gaagagggtc acaggctgcc caccctttga   8340

tgaacacaag tgtctggctg agggaggtaa aattatgaaa attccaggca cctgctgtga   8400

cacatgtgag gagcctgagt gcaacgacat cactgccagg ctgcagtatg tcaaggtggg   8460

aagctgtaag tctgaagtag aggtggatat ccactactgc cagggcaaat gtgccagcaa   8520

agccatgtac tccattgaca tcaacgatgt gcaggaccag tgctcctgct gctctccgac   8580

acggacggag cccatgcagg tggccctgca ctgcaccaat ggctctgttg tgtaccatga   8640

ggttctcaat gccatggagt gcaaatgctc ccccaggaag tgcagcaagt gaggctgctg   8700

cagctgcatg ggtgcctgct gctgcctgcc ttggcctgat ggccaggcca gagtgctgcc   8760

agtcctctgc atgttctgct cttgtgccct tctgagccca caataaaggc tgagctctta   8820

tcttgcaaaa ggc                                                      8833
```

```
<210> SEQ ID NO 31
<211> LENGTH: 763
<212> TYPE: PRT
<213> ORGANISM: Artificial Sequence
<220> FEATURE:
<223> OTHER INFORMATION: von Willebrand Factor sequence

<400> SEQUENCE: 31

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205
```

```
Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
```

625 630 635 640

Ala Trp Arg Glu Pro Gly Arg Cys Glu Leu Asn Cys Pro Lys Gly Gln
645 650 655

Val Tyr Leu Gln Cys Gly Thr Pro Cys Asn Leu Thr Cys Arg Ser Leu
660 665 670

Ser Tyr Pro Asp Glu Glu Cys Asn Glu Ala Cys Leu Glu Gly Cys Phe
675 680 685

Cys Pro Pro Gly Leu Tyr Met Asp Glu Arg Gly Asp Cys Val Pro Lys
690 695 700

Ala Gln Cys Pro Cys Tyr Tyr Asp Gly Glu Ile Phe Gln Pro Glu Asp
705 710 715 720

Ile Phe Ser Asp His His Thr Met Cys Tyr Cys Glu Asp Gly Phe Met
725 730 735

His Cys Thr Met Ser Gly Val Pro Gly Ser Leu Leu Pro Asp Ala Val
740 745 750

Leu Ser Ser Pro Leu Ser His Arg Ser Lys Arg
755 760

<210> SEQ ID NO 32
<211> LENGTH: 2289
<212> TYPE: DNA
<213> ORGANISM: Artificial Sequence
<220> FEATURE:
<223> OTHER INFORMATION: von Willebrand Factor sequence

<400> SEQUENCE: 32
atgatccccg ccagattcgc cggcgtgctg ctggccctgg ccctgatcct gcccggcacc 60
ctgtgcgccg agggcaccag aggcagatcc agcaccgccc ggtgcagcct gttcggcagc 120
gacttcgtga acaccttcga cggcagcatg tacagcttcg ccggctactg tagctacctg 180
ctggctggcg gctgccagaa gcggagcttc agcatcatcg gcgacttcca gaacggcaag 240
cgggtgtccc tgagcgtgta cctgggcgag ttcttcgaca tccacctgtt cgtgaacggc 300
accgtgaccc agggcgatca gagggtgtcc atgccctacg ccagcaaggg cctgtacctg 360
gaaaccgagg ccggctacta caagctgtcc ggcgaggcct acggcttcgt ggcccggatc 420
gacggctccg gcaacttcca ggtgctgctg tccgaccggt acttcaacaa gacctgcggc 480
ctgtgcggca acttcaacat cttcgccgag gacgacttca tgacccagga aggcaccctg 540
accagcgacc cctacgactt cgccaacagc tgggccctga gcagcggcga gcagtggtgc 600
gagagagcca gcccccccag cagcagctgc aacatcagct ccggcgagat gcagaaaggc 660
ctgtgggagc agtgccagct gctgaagtcc acctccgtgt tcgcccggtg ccaccccctg 720
gtggaccccg agccctttgt ggccctgtgc gaaaagaccc tgtgcgagtg cgctggcggc 780
ctggaatgcg cctgccctgc cctgctggaa tacgcccgga cctgcgccca agaagggatg 840
gtcctgtacg gctggaccga ccacagcgcc tgcagccccg tctgccctgc cggcatggaa 900
taccggcagt gcgtgagccc ctgcgccaga acctgccaga gcctgcacat caacgagatg 960
tgccaggaaa gatgcgtcga cggctgctct tgtcccgagg gacagctcct ggacgagggc 1020
ctctgcgtgg agagcaccga gtgcccctgc gtgcacagcg gcaagagata ccccccctggc 1080 accagcctga gccgggactg caacacctgc atttgccgga acagccagtg gatctgcagc 1140
aacgaggaat gcccaggcga gtgcctggtc accggccaga gccacttcaa gagcttcgac 1200
aacagatact tcaccttcag cggcatctgc cagtatctgc tggccagaga ctgccaggac 1260
cacagcttct ccatcgtgat cgagacagtg cagtgcgccg acgaccggga cgccgtgtgc 1320

```
accagatccg tgaccgtgag actgcccggc ctgcacaaca gcctggtcaa gctgaagcat   1380

ggcgctggcg tggccatgga cggccaggac gtgcagctgc ctctgctgaa gggcgacctg   1440

cggatccagc acaccgtgac cgccagcgtg agactgtcct acggcgagga cctgcagatg   1500

gactgggacg gcagaggccg gctgctcgtg aagctgtccc ccgtgtacgc cggcaagaca   1560

tgtggcctgt gtgggaacta caacggcaac cagggcgacg actttctgac ccccagcggc   1620

ctggccgagc ccagagtgga ggacttcggc aacgcctgga agctgcacgg cgattgccag   1680

gatctgcaga aacagcactc cgacccctgc gccctgaacc cccggatgac ccggttcagc   1740

gaagaggctt gcgccgtgct gaccagcccc accttcgagg cctgccaccg ggccgtgagc   1800

cccctgccct acctgcggaa ctgcagatac gatgtgtgta gctgctctga cggccgggag   1860

tgcctgtgtg gcgccctggc cagctatgcc gctgcctgcg ccggacgcgg tgtgagagtg   1920

gcttggcggg agcctggcag atgcgagctg aactgcccca agggccaggt gtacctgcag   1980

tgcggcaccc cctgcaacct gacctgccgg tccctgagct accccgacga agagtgcaac   2040

gaggcctgtc tcgaaggctg cttctgcccc cctggcctgt acatggacga gcggggcgac   2100

tgcgtgccca aggcccagtg cccctgttac tacgacggcg agatcttcca gcccgaggac   2160

atcttcagcg accaccacac catgtgctac tgcgaggacg gctttatgca ctgcaccatg   2220

agcggcgtgc ccggcagcct gctgccagac gccgtgctgt cctccccccct gagccaccgg   2280

tccaagcgg                                                           2289
```

<210> SEQ ID NO 33
<211> LENGTH: 506
<212> TYPE: PRT
<213> ORGANISM: Artificial Sequence
<220> FEATURE:
<223> OTHER INFORMATION: von Willebrand Factor sequence

<400> SEQUENCE: 33

```
Met Ile Pro Ala Arg Phe Ala Gly Val Leu Leu Ala Leu Ala Leu Ile
1               5                   10                  15

Leu Pro Gly Thr Leu Cys Ser Leu Ser Cys Arg Pro Pro Met Val Lys
            20                  25                  30

Leu Val Cys Pro Ala Asp Asn Leu Arg Ala Glu Gly Leu Glu Cys Thr
        35                  40                  45

Lys Thr Cys Gln Asn Tyr Asp Leu Glu Cys Met Ser Met Gly Cys Val
    50                  55                  60

Ser Gly Cys Leu Cys Pro Pro Gly Met Val Arg His Glu Asn Arg Cys
65                  70                  75                  80

Val Ala Leu Glu Arg Cys Pro Cys Phe His Gln Gly Lys Glu Tyr Ala
                85                  90                  95

Pro Gly Glu Thr Val Lys Ile Gly Cys Asn Thr Cys Val Cys Arg Asp
            100                 105                 110

Arg Lys Trp Asn Cys Thr Asp His Val Cys Asp Ala Thr Cys Ser Thr
        115                 120                 125

Ile Gly Met Ala His Tyr Leu Thr Phe Asp Gly Leu Lys Tyr Leu Phe
    130                 135                 140

Pro Gly Glu Cys Gln Tyr Val Leu Val Gln Asp Tyr Cys Gly Ser Asn
145                 150                 155                 160

Pro Gly Thr Phe Arg Ile Leu Val Gly Asn Lys Gly Cys Ser His Pro
                165                 170                 175

Ser Val Lys Cys Lys Lys Arg Val Thr Ile Leu Val Glu Gly Gly Glu
```

```
            180                 185                 190

Ile Glu Leu Phe Asp Gly Glu Val Asn Val Lys Arg Pro Met Lys Asp
        195                 200                 205

Glu Thr His Phe Glu Val Val Glu Ser Gly Arg Tyr Ile Ile Leu Leu
    210                 215                 220

Leu Gly Lys Ala Leu Ser Val Val Trp Asp Arg His Leu Ser Ile Ser
225                 230                 235                 240

Val Val Leu Lys Gln Thr Tyr Gln Glu Lys Val Cys Gly Leu Cys Gly
                245                 250                 255

Asn Phe Asp Gly Ile Gln Asn Asn Asp Leu Thr Ser Ser Asn Leu Gln
            260                 265                 270

Val Glu Glu Asp Pro Val Asp Phe Gly Asn Ser Trp Lys Val Ser Ser
        275                 280                 285

Gln Cys Ala Asp Thr Arg Lys Val Pro Leu Asp Ser Ser Pro Ala Thr
    290                 295                 300

Cys His Asn Asn Ile Met Lys Gln Thr Met Val Asp Ser Ser Cys Arg
305                 310                 315                 320

Ile Leu Thr Ser Asp Val Phe Gln Asp Cys Asn Lys Leu Val Asp Pro
                325                 330                 335

Glu Pro Tyr Leu Asp Val Cys Ile Tyr Asp Thr Cys Ser Cys Glu Ser
            340                 345                 350

Ile Gly Asp Cys Ala Cys Phe Cys Asp Thr Ile Ala Ala Tyr Ala His
        355                 360                 365

Val Cys Ala Gln His Gly Lys Val Val Thr Trp Arg Thr Ala Thr Leu
    370                 375                 380

Cys Pro Gln Ser Cys Glu Glu Arg Asn Leu Arg Glu Asn Gly Tyr Glu
385                 390                 395                 400

Cys Glu Trp Arg Tyr Asn Ser Cys Ala Pro Ala Cys Gln Val Thr Cys
                405                 410                 415

Gln His Pro Glu Pro Leu Ala Cys Pro Val Gln Cys Val Glu Gly Cys
            420                 425                 430

His Ala His Cys Pro Pro Gly Lys Ile Leu Asp Glu Leu Leu Gln Thr
        435                 440                 445

Cys Val Asp Pro Glu Asp Cys Pro Val Cys Glu Val Ala Gly Arg Arg
    450                 455                 460

Phe Ala Ser Gly Lys Lys Val Thr Leu Asn Pro Ser Asp Pro Glu His
465                 470                 475                 480

Cys Gln Ile Cys His Cys Asp Val Val Asn Leu Thr Cys Glu Ala Cys
                485                 490                 495

Gln Glu Pro Gly Gly Leu Val Val Pro Pro
            500                 505
```

<210> SEQ ID NO 34
<211> LENGTH: 740
<212> TYPE: PRT
<213> ORGANISM: Artificial Sequence
<220> FEATURE:
<223> OTHER INFORMATION: von Willebrand Factor sequence

<400> SEQUENCE: 34

```
Met Ile Pro Ala Arg Phe Ala Gly Val Leu Leu Ala Leu Ala Leu Ile
1               5                   10                  15

Leu Pro Gly Thr Leu Cys Ser Leu Ser Cys Arg Pro Pro Met Val Lys
            20                  25                  30

Leu Val Cys Pro Ala Asp Asn Leu Arg Ala Glu Gly Leu Glu Cys Thr
```

```
        35                  40                  45

Lys Thr Cys Gln Asn Tyr Asp Leu Glu Cys Met Ser Met Gly Cys Val
    50                  55                  60

Ser Gly Cys Leu Cys Pro Pro Gly Met Val Arg His Glu Asn Arg Cys
65                  70                  75                  80

Val Ala Leu Glu Arg Cys Pro Cys Phe His Gln Gly Lys Glu Tyr Ala
                85                  90                  95

Pro Gly Glu Thr Val Lys Ile Gly Cys Asn Thr Cys Val Cys Arg Asp
            100                 105                 110

Arg Lys Trp Asn Cys Thr Asp His Val Cys Asp Ala Thr Cys Ser Thr
        115                 120                 125

Ile Gly Met Ala His Tyr Leu Thr Phe Asp Gly Leu Lys Tyr Leu Phe
    130                 135                 140

Pro Gly Glu Cys Gln Tyr Val Leu Val Gln Asp Tyr Cys Gly Ser Asn
145                 150                 155                 160

Pro Gly Thr Phe Arg Ile Leu Val Gly Asn Lys Gly Cys Ser His Pro
                165                 170                 175

Ser Val Lys Cys Lys Lys Arg Val Thr Ile Leu Val Glu Gly Gly Glu
            180                 185                 190

Ile Glu Leu Phe Asp Gly Glu Val Asn Val Lys Arg Pro Met Lys Asp
        195                 200                 205

Glu Thr His Phe Glu Val Val Glu Ser Gly Arg Tyr Ile Ile Leu Leu
    210                 215                 220

Leu Gly Lys Ala Leu Ser Val Val Trp Asp Arg His Leu Ser Ile Ser
225                 230                 235                 240

Val Val Leu Lys Gln Thr Tyr Gln Glu Lys Val Cys Gly Leu Cys Gly
                245                 250                 255

Asn Phe Asp Gly Ile Gln Asn Asn Asp Leu Thr Ser Ser Asn Leu Gln
            260                 265                 270

Val Glu Glu Asp Pro Val Asp Phe Gly Asn Ser Trp Lys Val Ser Ser
        275                 280                 285

Gln Cys Ala Asp Thr Arg Lys Val Pro Leu Asp Ser Ser Pro Ala Thr
    290                 295                 300

Cys His Asn Asn Ile Met Lys Gln Thr Met Val Asp Ser Ser Cys Arg
305                 310                 315                 320

Ile Leu Thr Ser Asp Val Phe Gln Asp Cys Asn Lys Leu Val Asp Pro
                325                 330                 335

Glu Pro Tyr Leu Asp Val Cys Ile Tyr Asp Thr Cys Ser Cys Glu Ser
            340                 345                 350

Ile Gly Asp Cys Ala Cys Phe Cys Asp Thr Ile Ala Ala Tyr Ala His
        355                 360                 365

Val Cys Ala Gln His Gly Lys Val Val Thr Trp Arg Thr Ala Thr Leu
    370                 375                 380

Cys Pro Gln Ser Cys Glu Glu Arg Asn Leu Arg Glu Asn Gly Tyr Glu
385                 390                 395                 400

Cys Glu Trp Arg Tyr Asn Ser Cys Ala Pro Ala Cys Gln Val Thr Cys
                405                 410                 415

Gln His Pro Glu Pro Leu Ala Cys Pro Val Gln Cys Val Glu Gly Cys
            420                 425                 430

His Ala His Cys Pro Pro Gly Lys Ile Leu Asp Glu Leu Leu Gln Thr
        435                 440                 445

Cys Val Asp Pro Glu Asp Cys Pro Val Cys Glu Val Ala Gly Arg Arg
    450                 455                 460
```

```
Phe Ala Ser Gly Lys Lys Val Thr Leu Asn Pro Ser Asp Pro Glu His
465                 470                 475                 480

Cys Gln Ile Cys His Cys Asp Val Val Asn Leu Thr Cys Glu Ala Cys
                485                 490                 495

Gln Glu Pro Gly Gly Leu Val Val Pro Pro Thr Asp Ala Pro Val Ser
            500                 505                 510

Pro Thr Thr Leu Tyr Val Glu Asp Ile Ser Glu Pro Pro Leu His Asp
        515                 520                 525

Phe Tyr Cys Ser Arg Leu Leu Asp Leu Val Phe Leu Leu Asp Gly Ser
    530                 535                 540

Ser Arg Leu Ser Glu Ala Glu Phe Glu Val Leu Lys Ala Phe Val Val
545                 550                 555                 560

Asp Met Met Glu Arg Leu Arg Ile Ser Gln Lys Trp Val Arg Val Ala
                565                 570                 575

Val Val Glu Tyr His Asp Gly Ser His Ala Tyr Ile Gly Leu Lys Asp
            580                 585                 590

Arg Lys Arg Pro Ser Glu Leu Arg Arg Ile Ala Ser Gln Val Lys Tyr
        595                 600                 605

Ala Gly Ser Gln Val Ala Ser Thr Ser Glu Val Leu Lys Tyr Thr Leu
    610                 615                 620

Phe Gln Ile Phe Ser Lys Ile Asp Arg Pro Glu Ala Ser Arg Ile Ala
625                 630                 635                 640

Leu Leu Leu Met Ala Ser Gln Glu Pro Gln Arg Met Ser Arg Asn Phe
                645                 650                 655

Val Arg Tyr Val Gln Gly Leu Lys Lys Lys Lys Val Ile Val Ile Pro
            660                 665                 670

Val Gly Ile Gly Pro His Ala Asn Leu Lys Gln Ile Arg Leu Ile Glu
        675                 680                 685

Lys Gln Ala Pro Glu Asn Lys Ala Phe Val Leu Ser Ser Val Asp Glu
    690                 695                 700

Leu Glu Gln Gln Arg Asp Glu Ile Val Ser Tyr Leu Cys Asp Leu Ala
705                 710                 715                 720

Pro Glu Ala Pro Pro Pro Thr Leu Pro Pro His Met Ala Gln Val Thr
                725                 730                 735

Val Gly Pro Gly
            740
```

<210> SEQ ID NO 35
<211> LENGTH: 1138
<212> TYPE: PRT
<213> ORGANISM: Artificial Sequence
<220> FEATURE:
<223> OTHER INFORMATION: von Willebrand Factor sequence

<400> SEQUENCE: 35

```
Met Ile Pro Ala Arg Phe Ala Gly Val Leu Leu Ala Leu Ala Leu Ile
1               5                   10                  15

Leu Pro Gly Thr Leu Cys Ser Leu Ser Cys Arg Pro Pro Met Val Lys
            20                  25                  30

Leu Val Cys Pro Ala Asp Asn Leu Arg Ala Glu Gly Leu Glu Cys Thr
        35                  40                  45

Lys Thr Cys Gln Asn Tyr Asp Leu Glu Cys Met Ser Met Gly Cys Val
    50                  55                  60

Ser Gly Cys Leu Cys Pro Pro Gly Met Val Arg His Glu Asn Arg Cys
65                  70                  75                  80
```

```
Val Ala Leu Glu Arg Cys Pro Cys Phe His Gln Gly Lys Glu Tyr Ala
                85                  90                  95

Pro Gly Glu Thr Val Lys Ile Gly Cys Asn Thr Cys Val Cys Arg Asp
            100                 105                 110

Arg Lys Trp Asn Cys Thr Asp His Val Cys Asp Ala Thr Cys Ser Thr
        115                 120                 125

Ile Gly Met Ala His Tyr Leu Thr Phe Asp Gly Leu Lys Tyr Leu Phe
    130                 135                 140

Pro Gly Glu Cys Gln Tyr Val Leu Val Gln Asp Tyr Cys Gly Ser Asn
145                 150                 155                 160

Pro Gly Thr Phe Arg Ile Leu Val Gly Asn Lys Gly Cys Ser His Pro
                165                 170                 175

Ser Val Lys Cys Lys Lys Arg Val Thr Ile Leu Val Glu Gly Gly Glu
            180                 185                 190

Ile Glu Leu Phe Asp Gly Glu Val Asn Val Lys Arg Pro Met Lys Asp
        195                 200                 205

Glu Thr His Phe Glu Val Val Glu Ser Gly Arg Tyr Ile Ile Leu Leu
    210                 215                 220

Leu Gly Lys Ala Leu Ser Val Val Trp Asp Arg His Leu Ser Ile Ser
225                 230                 235                 240

Val Val Leu Lys Gln Thr Tyr Gln Glu Lys Val Cys Gly Leu Cys Gly
                245                 250                 255

Asn Phe Asp Gly Ile Gln Asn Asn Asp Leu Thr Ser Ser Asn Leu Gln
            260                 265                 270

Val Glu Glu Asp Pro Val Asp Phe Gly Asn Ser Trp Lys Val Ser Ser
        275                 280                 285

Gln Cys Ala Asp Thr Arg Lys Val Pro Leu Asp Ser Ser Pro Ala Thr
    290                 295                 300

Cys His Asn Asn Ile Met Lys Gln Thr Met Val Asp Ser Ser Cys Arg
305                 310                 315                 320

Ile Leu Thr Ser Asp Val Phe Gln Asp Cys Asn Lys Leu Val Asp Pro
                325                 330                 335

Glu Pro Tyr Leu Asp Val Cys Ile Tyr Asp Thr Cys Ser Cys Glu Ser
            340                 345                 350

Ile Gly Asp Cys Ala Cys Phe Cys Asp Thr Ile Ala Ala Tyr Ala His
        355                 360                 365

Val Cys Ala Gln His Gly Lys Val Val Thr Trp Arg Thr Ala Thr Leu
    370                 375                 380

Cys Pro Gln Ser Cys Glu Glu Arg Asn Leu Arg Glu Asn Gly Tyr Glu
385                 390                 395                 400

Cys Glu Trp Arg Tyr Asn Ser Cys Ala Pro Ala Cys Gln Val Thr Cys
                405                 410                 415

Gln His Pro Glu Pro Leu Ala Cys Pro Val Gln Cys Val Glu Gly Cys
            420                 425                 430

His Ala His Cys Pro Pro Gly Lys Ile Leu Asp Glu Leu Leu Gln Thr
        435                 440                 445

Cys Val Asp Pro Glu Asp Cys Pro Val Cys Glu Val Ala Gly Arg Arg
    450                 455                 460

Phe Ala Ser Gly Lys Lys Val Thr Leu Asn Pro Ser Asp Pro Glu His
465                 470                 475                 480

Cys Gln Ile Cys His Cys Asp Val Val Asn Leu Thr Cys Glu Ala Cys
                485                 490                 495
```

```
Gln Glu Pro Gly Gly Leu Val Val Pro Pro Thr Asp Ala Pro Val Ser
            500                 505                 510

Pro Thr Thr Leu Tyr Val Glu Asp Ile Ser Glu Pro Pro Leu His Asp
        515                 520                 525

Phe Tyr Cys Ser Arg Leu Leu Asp Leu Val Phe Leu Leu Asp Gly Ser
    530                 535                 540

Ser Arg Leu Ser Glu Ala Glu Phe Glu Val Leu Lys Ala Phe Val Val
545                 550                 555                 560

Asp Met Met Glu Arg Leu Arg Ile Ser Gln Lys Trp Val Arg Val Ala
                565                 570                 575

Val Val Glu Tyr His Asp Gly Ser His Ala Tyr Ile Gly Leu Lys Asp
            580                 585                 590

Arg Lys Arg Pro Ser Glu Leu Arg Arg Ile Ala Ser Gln Val Lys Tyr
        595                 600                 605

Ala Gly Ser Gln Val Ala Ser Thr Ser Glu Val Leu Lys Tyr Thr Leu
    610                 615                 620

Phe Gln Ile Phe Ser Lys Ile Asp Arg Pro Glu Ala Ser Arg Ile Ala
625                 630                 635                 640

Leu Leu Leu Met Ala Ser Gln Glu Pro Gln Arg Met Ser Arg Asn Phe
                645                 650                 655

Val Arg Tyr Val Gln Gly Leu Lys Lys Lys Lys Val Ile Val Ile Pro
            660                 665                 670

Val Gly Ile Gly Pro His Ala Asn Leu Lys Gln Ile Arg Leu Ile Glu
        675                 680                 685

Lys Gln Ala Pro Glu Asn Lys Ala Phe Val Leu Ser Ser Val Asp Glu
    690                 695                 700

Leu Glu Gln Gln Arg Asp Glu Ile Val Ser Tyr Leu Cys Asp Leu Ala
705                 710                 715                 720

Pro Glu Ala Pro Pro Pro Thr Leu Pro Pro His Met Ala Gln Val Thr
                725                 730                 735

Val Gly Pro Gly Leu Leu Gly Val Ser Thr Leu Gly Pro Lys Arg Asn
            740                 745                 750

Ser Met Val Leu Asp Val Ala Phe Val Leu Glu Gly Ser Asp Lys Ile
        755                 760                 765

Gly Glu Ala Asp Phe Asn Arg Ser Lys Glu Phe Met Glu Glu Val Ile
    770                 775                 780

Gln Arg Met Asp Val Gly Gln Asp Ser Ile His Val Thr Val Leu Gln
785                 790                 795                 800

Tyr Ser Tyr Met Val Thr Val Glu Tyr Pro Phe Ser Glu Ala Gln Ser
                805                 810                 815

Lys Gly Asp Ile Leu Gln Arg Val Arg Glu Ile Arg Tyr Gln Gly Gly
            820                 825                 830

Asn Arg Thr Asn Thr Gly Leu Ala Leu Arg Tyr Leu Ser Asp His Ser
        835                 840                 845

Phe Leu Val Ser Gln Gly Asp Arg Glu Gln Ala Pro Asn Leu Val Tyr
    850                 855                 860

Met Val Thr Gly Asn Pro Ala Ser Asp Glu Ile Lys Arg Leu Pro Gly
865                 870                 875                 880

Asp Ile Gln Val Val Pro Ile Gly Val Gly Pro Asn Ala Asn Val Gln
                885                 890                 895

Glu Leu Glu Arg Ile Gly Trp Pro Asn Ala Pro Ile Leu Ile Gln Asp
            900                 905                 910

Phe Glu Thr Leu Pro Arg Glu Ala Pro Asp Leu Val Leu Gln Arg Cys
```

```
        915                 920                 925

Cys Ser Gly Glu Gly Leu Gln Ile Pro Thr Leu Ser Pro Ala Pro Asp
    930                 935                 940

Cys Ser Gln Pro Leu Asp Val Ile Leu Leu Leu Asp Gly Ser Ser Ser
945                 950                 955                 960

Phe Pro Ala Ser Tyr Phe Asp Glu Met Lys Ser Phe Ala Lys Ala Phe
                965                 970                 975

Ile Ser Lys Ala Asn Ile Gly Pro Arg Leu Thr Gln Val Ser Val Leu
            980                 985                 990

Gln Tyr Gly Ser Ile Thr Thr Ile  Asp Val Pro Trp Asn  Val Val Pro
        995                 1000                1005

Glu Lys  Ala His Leu Leu Ser  Leu Val Asp Val Met  Gln Arg Glu
    1010                1015                1020

Gly Gly  Pro Ser Gln Ile Gly  Asp Ala Leu Gly Phe  Ala Val Arg
    1025                1030                1035

Tyr Leu  Thr Ser Glu Met His  Gly Ala Arg Pro Gly  Ala Ser Lys
    1040                1045                1050

Ala Val  Val Ile Leu Val Thr  Asp Val Ser Val Asp  Ser Val Asp
    1055                1060                1065

Ala Ala  Ala Asp Ala Ala Arg  Ser Asn Arg Val Thr  Val Phe Pro
    1070                1075                1080

Ile Gly  Ile Gly Asp Arg Tyr  Asp Ala Ala Gln Leu  Arg Ile Leu
    1085                1090                1095

Ala Gly  Pro Ala Gly Asp Ser  Asn Val Val Lys Leu  Gln Arg Ile
    1100                1105                1110

Glu Asp  Leu Pro Thr Met Val  Thr Leu Gly Asn Ser  Phe Leu His
    1115                1120                1125

Lys Leu  Cys Ser Gly Phe Val  Arg Ile Cys
    1130                1135
```

<210> SEQ ID NO 36
<211> LENGTH: 733
<212> TYPE: PRT
<213> ORGANISM: Artificial Sequence
<220> FEATURE:
<223> OTHER INFORMATION: von Willebrand Factor sequence

<400> SEQUENCE: 36

```
Met Ile Pro Ala Arg Phe Ala Gly Val Leu Leu Ala Leu Ala Leu Ile
1               5                   10                  15

Leu Pro Gly Thr Leu Cys Ser Leu Ser Cys Arg Pro Pro Met Val Lys
            20                  25                  30

Leu Val Cys Pro Ala Asp Asn Leu Arg Ala Glu Gly Leu Glu Cys Thr
        35                  40                  45

Lys Thr Cys Gln Asn Tyr Asp Leu Glu Cys Met Ser Met Gly Cys Val
    50                  55                  60

Ser Gly Cys Leu Cys Pro Pro Gly Met Val Arg His Glu Asn Arg Cys
65                  70                  75                  80

Val Ala Leu Glu Arg Cys Pro Cys Phe His Gln Gly Lys Glu Tyr Ala
                85                  90                  95

Pro Gly Glu Thr Val Lys Ile Gly Cys Asn Thr Cys Val Cys Arg Asp
            100                 105                 110

Arg Lys Trp Asn Cys Thr Asp His Val Cys Asp Ala Thr Cys Ser Thr
        115                 120                 125

Ile Gly Met Ala His Tyr Leu Thr Phe Asp Gly Leu Lys Tyr Leu Phe
```

```
    130                 135                 140

Pro Gly Glu Cys Gln Tyr Val Leu Val Gln Asp Tyr Cys Gly Ser Asn
145                 150                 155                 160

Pro Gly Thr Phe Arg Ile Leu Val Gly Asn Lys Gly Cys Ser His Pro
                165                 170                 175

Ser Val Lys Cys Lys Lys Arg Val Thr Ile Leu Val Glu Gly Gly Glu
            180                 185                 190

Ile Glu Leu Phe Asp Gly Glu Val Asn Val Lys Arg Pro Met Lys Asp
        195                 200                 205

Glu Thr His Phe Glu Val Val Glu Ser Gly Arg Tyr Ile Ile Leu Leu
    210                 215                 220

Leu Gly Lys Ala Leu Ser Val Val Trp Asp Arg His Leu Ser Ile Ser
225                 230                 235                 240

Val Val Leu Lys Gln Thr Tyr Gln Glu Lys Val Cys Gly Leu Cys Gly
                245                 250                 255

Asn Phe Asp Gly Ile Gln Asn Asn Asp Leu Thr Ser Ser Asn Leu Gln
            260                 265                 270

Val Glu Glu Asp Pro Val Asp Phe Gly Asn Ser Trp Lys Val Ser Ser
        275                 280                 285

Gln Cys Ala Asp Thr Arg Lys Val Pro Leu Asp Ser Ser Pro Ala Thr
    290                 295                 300

Cys His Asn Asn Ile Met Lys Gln Thr Met Val Asp Ser Ser Cys Arg
305                 310                 315                 320

Ile Leu Thr Ser Asp Val Phe Gln Asp Cys Asn Lys Leu Val Asp Pro
                325                 330                 335

Glu Pro Tyr Leu Asp Val Cys Ile Tyr Asp Thr Cys Ser Cys Glu Ser
            340                 345                 350

Ile Gly Asp Cys Ala Cys Phe Cys Asp Thr Ile Ala Ala Tyr Ala His
        355                 360                 365

Val Cys Ala Gln His Gly Lys Val Val Thr Trp Arg Thr Ala Thr Leu
    370                 375                 380

Cys Pro Gln Ser Cys Glu Glu Arg Asn Leu Arg Glu Asn Gly Tyr Glu
385                 390                 395                 400

Cys Glu Trp Arg Tyr Asn Ser Cys Ala Pro Ala Cys Gln Val Thr Cys
                405                 410                 415

Gln His Pro Glu Pro Leu Ala Cys Pro Val Gln Cys Val Glu Gly Cys
            420                 425                 430

His Ala His Cys Pro Pro Gly Lys Ile Leu Asp Glu Leu Leu Gln Thr
        435                 440                 445

Cys Val Asp Pro Glu Asp Cys Pro Val Cys Glu Val Ala Gly Arg Arg
    450                 455                 460

Phe Ala Ser Gly Lys Lys Val Thr Leu Asn Pro Ser Asp Pro Glu His
465                 470                 475                 480

Cys Gln Ile Cys His Cys Asp Val Val Asn Leu Thr Cys Glu Ala Cys
                485                 490                 495

Gln Glu Pro Gly Gly Leu Val Val Pro Pro Asp Lys Thr His Thr Cys
            500                 505                 510

Pro Pro Cys Pro Ala Pro Glu Leu Leu Gly Gly Pro Ser Val Phe Leu
        515                 520                 525

Phe Pro Pro Lys Pro Lys Asp Thr Leu Met Ile Ser Arg Thr Pro Glu
    530                 535                 540

Val Thr Cys Val Val Val Asp Val Ser His Glu Asp Pro Glu Val Lys
545                 550                 555                 560
```

```
Phe Asn Trp Tyr Val Asp Gly Val Glu Val His Asn Ala Lys Thr Lys
                565                 570                 575

Pro Arg Glu Glu Gln Tyr Asn Ser Thr Tyr Arg Val Val Ser Val Leu
            580                 585                 590

Thr Val Leu His Gln Asp Trp Leu Asn Gly Lys Glu Tyr Lys Cys Lys
        595                 600                 605

Val Ser Asn Lys Ala Leu Pro Ala Pro Ile Glu Lys Thr Ile Ser Lys
    610                 615                 620

Ala Lys Gly Gln Pro Arg Glu Pro Gln Val Tyr Thr Leu Pro Pro Ser
625                 630                 635                 640

Arg Asp Glu Leu Thr Lys Asn Gln Val Ser Leu Thr Cys Leu Val Lys
                645                 650                 655

Gly Phe Tyr Pro Ser Asp Ile Ala Val Glu Trp Glu Ser Asn Gly Gln
            660                 665                 670

Pro Glu Asn Asn Tyr Lys Thr Thr Pro Pro Val Leu Asp Ser Asp Gly
        675                 680                 685

Ser Phe Phe Leu Tyr Ser Lys Leu Thr Val Asp Lys Ser Arg Trp Gln
    690                 695                 700

Gln Gly Asn Val Phe Ser Cys Ser Val Met His Glu Ala Leu His Asn
705                 710                 715                 720

His Tyr Thr Gln Lys Ser Leu Ser Leu Ser Pro Gly Lys
                725                 730
```

<210> SEQ ID NO 37
<211> LENGTH: 2199
<212> TYPE: DNA
<213> ORGANISM: Artificial Sequence
<220> FEATURE:
<223> OTHER INFORMATION: von Willebrand Factor sequence

<400> SEQUENCE: 37

```
atgatccccg ccagattcgc cggcgtgctg ctggccctgg ccctgatcct gcccggcacc     60

ctgtgcagcc tgagctgcag accccccatg gtcaagctcg tgtgcccagc cgacaatctg    120

cgggccgagg ggctggaatg caccaagacc tgccagaact acgacctgga atgcatgagc    180

atgggctgcg tgagcggctg cctgtgccca cccggcatgg tccggcacga gaacagatgc    240

gtggccctgg aacggtgccc atgcttccac cagggcaaag agtacgcccc tggcgagaca    300

gtgaagatcg gctgcaatac ctgcgtgtgc cgggaccgga agtggaactg caccgaccac    360

gtgtgcgacg ccacatgcag caccatcggc atggcccact acctgacctt tgacggcctg    420

aagtacctgt tccccggcga gtgccagtac gtgctggtgc aggactactg cggcagcaac    480

cccggcacct tccggatcct cgtgggcaac aagggatgca gccaccccag cgtgaagtgc    540

aagaaacgcg tgaccatcct ggtggagggc ggcgagatcg agctgttcga cggcgaagtg    600

aacgtgaagc ggcccatgaa ggacgagaca cacttcgagg tggtggagag cggccggtac    660

atcatcctgc tgctgggcaa ggctctgagc gtcgtgtggg accggcacct gagcatcagc    720

gtggtgctga agcagaccta ccaggaaaaa gtctgcggcc tctgtggcaa tttcgacggc    780

atccagaaca acgatctgac cagcagcaac ctgcaggtgg aagaggaccc cgtggacttt    840

ggcaatagct ggaaggtgtc cagccagtgt gccgacacca gaaaagtgcc cctggactct    900

agccccgcca cctgccacaa caacatcatg aagcagacaa tggtggacag ctcctgccgg    960

atcctgacct ccgacgtgtt ccaggactgt aacaaactgg tggatcctga gccttacctg   1020

gacgtgtgca tctacgacac ctgcagctgc gagagcatcg gcgattgcgc ctgcttctgc   1080
```

```
gacacaatcg ccgcctacgc ccatgtgtgc gcccagcacg gcaaggtggt cacctggcgg   1140

accgcaaccc tgtgccccca gagctgcgag gaacggaacc tgcgggagaa cggctacgag   1200

tgcgagtggc ggtacaacag ctgcgcccca gcctgccagg tcacctgcca gcaccccgag   1260

cctctggcct gccccgtgca gtgcgtggag ggctgccacg cccactgccc tccaggcaag   1320

atcctggacg agctgctgca gacctgcgtg gaccctgagg actgccctgt gtgcgaggtg   1380

gccggcaggc ggttcgcctc cggcaagaaa gtgaccctga accctagcga ccccgagcac   1440

tgccagatct gccactgcga cgtggtcaat ctgacctgcg aggcttgcca ggaaccaggc   1500

ggcctcgtcg tgcccccctga caaaactcac acatgcccac cgtgcccagc acctgaactc   1560

ctggggggac cgtcagtctt cctcttcccc ccaaaaccca aggacaccct catgatctcc   1620

cggacccctg aggtcacatg cgtggtggtg gacgtgagcc acgaagaccc tgaggtcaag   1680

ttcaactggt acgtggacgg cgtggaggtg cataatgcca agacaaagcc gcgggaggag   1740

cagtacaaca gcacgtaccg tgtggtcagc gtcctcaccg tcctgcacca ggactggctg   1800

aatggcaagg agtacaagtg caaggtctcc aacaaagccc tcccagcccc catcgagaaa   1860

accatctcca aagccaaagg gcagccccga gagccacagg tgtacaccct gcccccatcc   1920

cgggatgagc tgaccaagaa ccaggtcagc ctgacctgcc tggtcaaagg cttctatccc   1980

agcgacatcg ccgtggagtg ggagagcaat gggcagccgg agaacaacta caagaccacg   2040

cctcccgtgc tggactccga cggctccttc ttcctctaca gcaagctcac cgtggacaag   2100

agcaggtggc agcaggggaa cgtcttctca tgctccgtga tgcatgaggc tctgcacaac   2160

cactacacgc agaagagcct ctccctgtct ccgggtaaa                          2199
```

<210> SEQ ID NO 38
<211> LENGTH: 967
<212> TYPE: PRT
<213> ORGANISM: Artificial Sequence
<220> FEATURE:
<223> OTHER INFORMATION: von Willebrand Factor sequence

<400> SEQUENCE: 38

```
Met Ile Pro Ala Arg Phe Ala Gly Val Leu Leu Ala Leu Ala Leu Ile
1               5                   10                  15

Leu Pro Gly Thr Leu Cys Ser Leu Ser Cys Arg Pro Pro Met Val Lys
            20                  25                  30

Leu Val Cys Pro Ala Asp Asn Leu Arg Ala Glu Gly Leu Glu Cys Thr
        35                  40                  45

Lys Thr Cys Gln Asn Tyr Asp Leu Glu Cys Met Ser Met Gly Cys Val
    50                  55                  60

Ser Gly Cys Leu Cys Pro Pro Gly Met Val Arg His Glu Asn Arg Cys
65                  70                  75                  80

Val Ala Leu Glu Arg Cys Pro Cys Phe His Gln Gly Lys Glu Tyr Ala
                85                  90                  95

Pro Gly Glu Thr Val Lys Ile Gly Cys Asn Thr Cys Val Cys Arg Asp
            100                 105                 110

Arg Lys Trp Asn Cys Thr Asp His Val Cys Asp Ala Thr Cys Ser Thr
        115                 120                 125

Ile Gly Met Ala His Tyr Leu Thr Phe Asp Gly Leu Lys Tyr Leu Phe
    130                 135                 140

Pro Gly Glu Cys Gln Tyr Val Leu Val Gln Asp Tyr Cys Gly Ser Asn
145                 150                 155                 160
```

```
Pro Gly Thr Phe Arg Ile Leu Val Gly Asn Lys Gly Cys Ser His Pro
                165                 170                 175

Ser Val Lys Cys Lys Lys Arg Val Thr Ile Leu Val Glu Gly Gly Glu
            180                 185                 190

Ile Glu Leu Phe Asp Gly Glu Val Asn Val Lys Arg Pro Met Lys Asp
        195                 200                 205

Glu Thr His Phe Glu Val Val Glu Ser Gly Arg Tyr Ile Ile Leu Leu
    210                 215                 220

Leu Gly Lys Ala Leu Ser Val Val Trp Asp Arg His Leu Ser Ile Ser
225                 230                 235                 240

Val Val Leu Lys Gln Thr Tyr Gln Glu Lys Val Cys Gly Leu Cys Gly
                245                 250                 255

Asn Phe Asp Gly Ile Gln Asn Asn Asp Leu Thr Ser Ser Asn Leu Gln
            260                 265                 270

Val Glu Glu Asp Pro Val Asp Phe Gly Asn Ser Trp Lys Val Ser Ser
        275                 280                 285

Gln Cys Ala Asp Thr Arg Lys Val Pro Leu Asp Ser Ser Pro Ala Thr
    290                 295                 300

Cys His Asn Asn Ile Met Lys Gln Thr Met Val Asp Ser Ser Cys Arg
305                 310                 315                 320

Ile Leu Thr Ser Asp Val Phe Gln Asp Cys Asn Lys Leu Val Asp Pro
                325                 330                 335

Glu Pro Tyr Leu Asp Val Cys Ile Tyr Asp Thr Cys Ser Cys Glu Ser
            340                 345                 350

Ile Gly Asp Cys Ala Cys Phe Cys Asp Thr Ile Ala Ala Tyr Ala His
        355                 360                 365

Val Cys Ala Gln His Gly Lys Val Val Thr Trp Arg Thr Ala Thr Leu
    370                 375                 380

Cys Pro Gln Ser Cys Glu Glu Arg Asn Leu Arg Glu Asn Gly Tyr Glu
385                 390                 395                 400

Cys Glu Trp Arg Tyr Asn Ser Cys Ala Pro Ala Cys Gln Val Thr Cys
                405                 410                 415

Gln His Pro Glu Pro Leu Ala Cys Pro Val Gln Cys Val Glu Gly Cys
            420                 425                 430

His Ala His Cys Pro Pro Gly Lys Ile Leu Asp Glu Leu Leu Gln Thr
        435                 440                 445

Cys Val Asp Pro Glu Asp Cys Pro Val Cys Glu Val Ala Gly Arg Arg
    450                 455                 460

Phe Ala Ser Gly Lys Lys Val Thr Leu Asn Pro Ser Asp Pro Glu His
465                 470                 475                 480

Cys Gln Ile Cys His Cys Asp Val Val Asn Leu Thr Cys Glu Ala Cys
                485                 490                 495

Gln Glu Pro Gly Gly Leu Val Val Pro Pro Thr Asp Ala Pro Val Ser
            500                 505                 510

Pro Thr Thr Leu Tyr Val Glu Asp Ile Ser Glu Pro Pro Leu His Asp
        515                 520                 525

Phe Tyr Cys Ser Arg Leu Leu Asp Leu Val Phe Leu Leu Asp Gly Ser
    530                 535                 540

Ser Arg Leu Ser Glu Ala Glu Phe Glu Val Leu Lys Ala Phe Val Val
545                 550                 555                 560

Asp Met Met Glu Arg Leu Arg Ile Ser Gln Lys Trp Val Arg Val Ala
                565                 570                 575

Val Val Glu Tyr His Asp Gly Ser His Ala Tyr Ile Gly Leu Lys Asp
```

```
            580                 585                 590

Arg Lys Arg Pro Ser Glu Leu Arg Arg Ile Ala Ser Gln Val Lys Tyr
        595                 600                 605

Ala Gly Ser Gln Val Ala Ser Thr Ser Glu Val Leu Lys Tyr Thr Leu
    610                 615                 620

Phe Gln Ile Phe Ser Lys Ile Asp Arg Pro Glu Ala Ser Arg Ile Ala
625                 630                 635                 640

Leu Leu Leu Met Ala Ser Gln Glu Pro Gln Arg Met Ser Arg Asn Phe
                645                 650                 655

Val Arg Tyr Val Gln Gly Leu Lys Lys Lys Lys Val Ile Val Ile Pro
            660                 665                 670

Val Gly Ile Gly Pro His Ala Asn Leu Lys Gln Ile Arg Leu Ile Glu
        675                 680                 685

Lys Gln Ala Pro Glu Asn Lys Ala Phe Val Leu Ser Ser Val Asp Glu
    690                 695                 700

Leu Glu Gln Gln Arg Asp Glu Ile Val Ser Tyr Leu Cys Asp Leu Ala
705                 710                 715                 720

Pro Glu Ala Pro Pro Pro Thr Leu Pro Pro His Met Ala Gln Val Thr
                725                 730                 735

Val Gly Pro Gly Asp Lys Thr His Thr Cys Pro Pro Cys Pro Ala Pro
            740                 745                 750

Glu Leu Leu Gly Gly Pro Ser Val Phe Leu Phe Pro Pro Lys Pro Lys
        755                 760                 765

Asp Thr Leu Met Ile Ser Arg Thr Pro Glu Val Thr Cys Val Val Val
    770                 775                 780

Asp Val Ser His Glu Asp Pro Glu Val Lys Phe Asn Trp Tyr Val Asp
785                 790                 795                 800

Gly Val Glu Val His Asn Ala Lys Thr Lys Pro Arg Glu Glu Gln Tyr
                805                 810                 815

Asn Ser Thr Tyr Arg Val Val Ser Val Leu Thr Val Leu His Gln Asp
            820                 825                 830

Trp Leu Asn Gly Lys Glu Tyr Lys Cys Lys Val Ser Asn Lys Ala Leu
        835                 840                 845

Pro Ala Pro Ile Glu Lys Thr Ile Ser Lys Ala Lys Gly Gln Pro Arg
    850                 855                 860

Glu Pro Gln Val Tyr Thr Leu Pro Pro Ser Arg Asp Glu Leu Thr Lys
865                 870                 875                 880

Asn Gln Val Ser Leu Thr Cys Leu Val Lys Gly Phe Tyr Pro Ser Asp
                885                 890                 895

Ile Ala Val Glu Trp Glu Ser Asn Gly Gln Pro Glu Asn Asn Tyr Lys
            900                 905                 910

Thr Thr Pro Pro Val Leu Asp Ser Asp Gly Ser Phe Phe Leu Tyr Ser
        915                 920                 925

Lys Leu Thr Val Asp Lys Ser Arg Trp Gln Gln Gly Asn Val Phe Ser
    930                 935                 940

Cys Ser Val Met His Glu Ala Leu His Asn His Tyr Thr Gln Lys Ser
945                 950                 955                 960

Leu Ser Leu Ser Pro Gly Lys
                965


<210> SEQ ID NO 39
<211> LENGTH: 1365
<212> TYPE: PRT
<213> ORGANISM: Artificial Sequence
```

<220> FEATURE:
<223> OTHER INFORMATION: von Willebrand Factor sequence

<400> SEQUENCE: 39

```
Met Ile Pro Ala Arg Phe Ala Gly Val Leu Leu Ala Leu Ala Leu Ile
1               5                   10                  15

Leu Pro Gly Thr Leu Cys Ser Leu Ser Cys Arg Pro Pro Met Val Lys
            20                  25                  30

Leu Val Cys Pro Ala Asp Asn Leu Arg Ala Glu Gly Leu Glu Cys Thr
        35                  40                  45

Lys Thr Cys Gln Asn Tyr Asp Leu Glu Cys Met Ser Met Gly Cys Val
    50                  55                  60

Ser Gly Cys Leu Cys Pro Pro Gly Met Val Arg His Glu Asn Arg Cys
65                  70                  75                  80

Val Ala Leu Glu Arg Cys Pro Cys Phe His Gln Gly Lys Glu Tyr Ala
                85                  90                  95

Pro Gly Glu Thr Val Lys Ile Gly Cys Asn Thr Cys Val Cys Arg Asp
            100                 105                 110

Arg Lys Trp Asn Cys Thr Asp His Val Cys Asp Ala Thr Cys Ser Thr
        115                 120                 125

Ile Gly Met Ala His Tyr Leu Thr Phe Asp Gly Leu Lys Tyr Leu Phe
    130                 135                 140

Pro Gly Glu Cys Gln Tyr Val Leu Val Gln Asp Tyr Cys Gly Ser Asn
145                 150                 155                 160

Pro Gly Thr Phe Arg Ile Leu Val Gly Asn Lys Gly Cys Ser His Pro
                165                 170                 175

Ser Val Lys Cys Lys Lys Arg Val Thr Ile Leu Val Glu Gly Gly Glu
            180                 185                 190

Ile Glu Leu Phe Asp Gly Glu Val Asn Val Lys Arg Pro Met Lys Asp
        195                 200                 205

Glu Thr His Phe Glu Val Val Glu Ser Gly Arg Tyr Ile Ile Leu Leu
    210                 215                 220

Leu Gly Lys Ala Leu Ser Val Val Trp Asp Arg His Leu Ser Ile Ser
225                 230                 235                 240

Val Val Leu Lys Gln Thr Tyr Gln Glu Lys Val Cys Gly Leu Cys Gly
                245                 250                 255

Asn Phe Asp Gly Ile Gln Asn Asn Asp Leu Thr Ser Ser Asn Leu Gln
            260                 265                 270

Val Glu Glu Asp Pro Val Asp Phe Gly Asn Ser Trp Lys Val Ser Ser
        275                 280                 285

Gln Cys Ala Asp Thr Arg Lys Val Pro Leu Asp Ser Ser Pro Ala Thr
    290                 295                 300

Cys His Asn Asn Ile Met Lys Gln Thr Met Val Asp Ser Ser Cys Arg
305                 310                 315                 320

Ile Leu Thr Ser Asp Val Phe Gln Asp Cys Asn Lys Leu Val Asp Pro
                325                 330                 335

Glu Pro Tyr Leu Asp Val Cys Ile Tyr Asp Thr Cys Ser Cys Glu Ser
            340                 345                 350

Ile Gly Asp Cys Ala Cys Phe Cys Asp Thr Ile Ala Ala Tyr Ala His
        355                 360                 365

Val Cys Ala Gln His Gly Lys Val Val Thr Trp Arg Thr Ala Thr Leu
    370                 375                 380

Cys Pro Gln Ser Cys Glu Glu Arg Asn Leu Arg Glu Asn Gly Tyr Glu
385                 390                 395                 400
```

```
Cys Glu Trp Arg Tyr Asn Ser Cys Ala Pro Ala Cys Gln Val Thr Cys
                405                 410                 415

Gln His Pro Glu Pro Leu Ala Cys Pro Val Gln Cys Val Glu Gly Cys
            420                 425                 430

His Ala His Cys Pro Pro Gly Lys Ile Leu Asp Glu Leu Leu Gln Thr
        435                 440                 445

Cys Val Asp Pro Glu Asp Cys Pro Val Cys Glu Val Ala Gly Arg Arg
    450                 455                 460

Phe Ala Ser Gly Lys Lys Val Thr Leu Asn Pro Ser Asp Pro Glu His
465                 470                 475                 480

Cys Gln Ile Cys His Cys Asp Val Val Asn Leu Thr Cys Glu Ala Cys
                485                 490                 495

Gln Glu Pro Gly Gly Leu Val Val Pro Pro Thr Asp Ala Pro Val Ser
            500                 505                 510

Pro Thr Thr Leu Tyr Val Glu Asp Ile Ser Glu Pro Pro Leu His Asp
        515                 520                 525

Phe Tyr Cys Ser Arg Leu Leu Asp Leu Val Phe Leu Leu Asp Gly Ser
    530                 535                 540

Ser Arg Leu Ser Glu Ala Glu Phe Glu Val Leu Lys Ala Phe Val Val
545                 550                 555                 560

Asp Met Met Glu Arg Leu Arg Ile Ser Gln Lys Trp Val Arg Val Ala
                565                 570                 575

Val Val Glu Tyr His Asp Gly Ser His Ala Tyr Ile Gly Leu Lys Asp
            580                 585                 590

Arg Lys Arg Pro Ser Glu Leu Arg Arg Ile Ala Ser Gln Val Lys Tyr
        595                 600                 605

Ala Gly Ser Gln Val Ala Ser Thr Ser Glu Val Leu Lys Tyr Thr Leu
    610                 615                 620

Phe Gln Ile Phe Ser Lys Ile Asp Arg Pro Glu Ala Ser Arg Ile Ala
625                 630                 635                 640

Leu Leu Leu Met Ala Ser Gln Glu Pro Gln Arg Met Ser Arg Asn Phe
                645                 650                 655

Val Arg Tyr Val Gln Gly Leu Lys Lys Lys Lys Val Ile Val Ile Pro
            660                 665                 670

Val Gly Ile Gly Pro His Ala Asn Leu Lys Gln Ile Arg Leu Ile Glu
        675                 680                 685

Lys Gln Ala Pro Glu Asn Lys Ala Phe Val Leu Ser Ser Val Asp Glu
    690                 695                 700

Leu Glu Gln Gln Arg Asp Glu Ile Val Ser Tyr Leu Cys Asp Leu Ala
705                 710                 715                 720

Pro Glu Ala Pro Pro Pro Thr Leu Pro Pro His Met Ala Gln Val Thr
                725                 730                 735

Val Gly Pro Gly Leu Leu Gly Val Ser Thr Leu Gly Pro Lys Arg Asn
            740                 745                 750

Ser Met Val Leu Asp Val Ala Phe Val Leu Glu Gly Ser Asp Lys Ile
        755                 760                 765

Gly Glu Ala Asp Phe Asn Arg Ser Lys Glu Phe Met Glu Glu Val Ile
    770                 775                 780

Gln Arg Met Asp Val Gly Gln Asp Ser Ile His Val Thr Val Leu Gln
785                 790                 795                 800

Tyr Ser Tyr Met Val Thr Val Glu Tyr Pro Phe Ser Glu Ala Gln Ser
                805                 810                 815
```

```
Lys Gly Asp Ile Leu Gln Arg Val Arg Glu Ile Arg Tyr Gln Gly Gly
            820                 825                 830

Asn Arg Thr Asn Thr Gly Leu Ala Leu Arg Tyr Leu Ser Asp His Ser
        835                 840                 845

Phe Leu Val Ser Gln Gly Asp Arg Glu Gln Ala Pro Asn Leu Val Tyr
    850                 855                 860

Met Val Thr Gly Asn Pro Ala Ser Asp Glu Ile Lys Arg Leu Pro Gly
865                 870                 875                 880

Asp Ile Gln Val Val Pro Ile Gly Val Gly Pro Asn Ala Asn Val Gln
                885                 890                 895

Glu Leu Glu Arg Ile Gly Trp Pro Asn Ala Pro Ile Leu Ile Gln Asp
            900                 905                 910

Phe Glu Thr Leu Pro Arg Glu Ala Pro Asp Leu Val Leu Gln Arg Cys
        915                 920                 925

Cys Ser Gly Glu Gly Leu Gln Ile Pro Thr Leu Ser Pro Ala Pro Asp
    930                 935                 940

Cys Ser Gln Pro Leu Asp Val Ile Leu Leu Leu Asp Gly Ser Ser Ser
945                 950                 955                 960

Phe Pro Ala Ser Tyr Phe Asp Glu Met Lys Ser Phe Ala Lys Ala Phe
                965                 970                 975

Ile Ser Lys Ala Asn Ile Gly Pro Arg Leu Thr Gln Val Ser Val Leu
            980                 985                 990

Gln Tyr Gly Ser Ile Thr Thr Ile  Asp Val Pro Trp Asn  Val Val Pro
        995                 1000                 1005

Glu Lys  Ala His Leu Leu Ser  Leu Val Asp Val Met  Gln Arg Glu
    1010                 1015                 1020

Gly Gly  Pro Ser Gln Ile Gly  Asp Ala Leu Gly Phe  Ala Val Arg
    1025                 1030                 1035

Tyr Leu  Thr Ser Glu Met His  Gly Ala Arg Pro Gly  Ala Ser Lys
    1040                 1045                 1050

Ala Val  Val Ile Leu Val Thr  Asp Val Ser Val Asp  Ser Val Asp
    1055                 1060                 1065

Ala Ala  Ala Asp Ala Ala Arg  Ser Asn Arg Val Thr  Val Phe Pro
    1070                 1075                 1080

Ile Gly  Ile Gly Asp Arg Tyr  Asp Ala Ala Gln Leu  Arg Ile Leu
    1085                 1090                 1095

Ala Gly  Pro Ala Gly Asp Ser  Asn Val Val Lys Leu  Gln Arg Ile
    1100                 1105                 1110

Glu Asp  Leu Pro Thr Met Val  Thr Leu Gly Asn Ser  Phe Leu His
    1115                 1120                 1125

Lys Leu  Cys Ser Gly Phe Val  Arg Ile Cys Asp Lys  Thr His Thr
    1130                 1135                 1140

Cys Pro  Pro Cys Pro Ala Pro  Glu Leu Leu Gly Gly  Pro Ser Val
    1145                 1150                 1155

Phe Leu  Phe Pro Pro Lys Pro  Lys Asp Thr Leu Met  Ile Ser Arg
    1160                 1165                 1170

Thr Pro  Glu Val Thr Cys Val  Val Val Asp Val Ser  His Glu Asp
    1175                 1180                 1185

Pro Glu  Val Lys Phe Asn Trp  Tyr Val Asp Gly Val  Glu Val His
    1190                 1195                 1200

Asn Ala  Lys Thr Lys Pro Arg  Glu Glu Gln Tyr Asn  Ser Thr Tyr
    1205                 1210                 1215

Arg Val  Val Ser Val Leu Thr  Val Leu His Gln Asp  Trp Leu Asn
```

```
    1220                1225                1230

Gly Lys  Glu Tyr Lys Cys Lys  Val Ser Asn Lys Ala  Leu Pro Ala
    1235                1240                1245

Pro Ile  Glu Lys Thr Ile Ser  Lys Ala Lys Gly Gln  Pro Arg Glu
    1250                1255                1260

Pro Gln  Val Tyr Thr Leu Pro  Pro Ser Arg Asp Glu  Leu Thr Lys
    1265                1270                1275

Asn Gln  Val Ser Leu Thr Cys  Leu Val Lys Gly Phe  Tyr Pro Ser
    1280                1285                1290

Asp Ile  Ala Val Glu Trp Glu  Ser Asn Gly Gln Pro  Glu Asn Asn
    1295                1300                1305

Tyr Lys  Thr Thr Pro Pro Val  Leu Asp Ser Asp Gly  Ser Phe Phe
    1310                1315                1320

Leu Tyr  Ser Lys Leu Thr Val  Asp Lys Ser Arg Trp  Gln Gln Gly
    1325                1330                1335

Asn Val  Phe Ser Cys Ser Val  Met His Glu Ala Leu  His Asn His
    1340                1345                1350

Tyr Thr  Gln Lys Ser Leu Ser  Leu Ser Pro Gly Lys
    1355                1360                1365


<210> SEQ ID NO 40
<211> LENGTH: 22
<212> TYPE: PRT
<213> ORGANISM: Artificial Sequence
<220> FEATURE:
<223> OTHER INFORMATION: von Willebrand Factor signal peptide

<400> SEQUENCE: 40

Met Ile Pro Ala Arg Phe Ala Gly Val Leu Leu Ala Leu Ala Leu Ile
1               5                   10                  15

Leu Pro Gly Thr Leu Cys
            20


<210> SEQ ID NO 41
<211> LENGTH: 741
<212> TYPE: PRT
<213> ORGANISM: Artificial Sequence
<220> FEATURE:
<223> OTHER INFORMATION: von Willebrand Factor propeptide

<400> SEQUENCE: 41

Ala Glu Gly Thr Arg Gly Arg Ser Ser Thr Ala Arg Cys Ser Leu Phe
1               5                   10                  15

Gly Ser Asp Phe Val Asn Thr Phe Asp Gly Ser Met Tyr Ser Phe Ala
            20                  25                  30

Gly Tyr Cys Ser Tyr Leu Leu Ala Gly Gly Cys Gln Lys Arg Ser Phe
        35                  40                  45

Ser Ile Ile Gly Asp Phe Gln Asn Gly Lys Arg Val Ser Leu Ser Val
    50                  55                  60

Tyr Leu Gly Glu Phe Phe Asp Ile His Leu Phe Val Asn Gly Thr Val
65                  70                  75                  80

Thr Gln Gly Asp Gln Arg Val Ser Met Pro Tyr Ala Ser Lys Gly Leu
                85                  90                  95

Tyr Leu Glu Thr Glu Ala Gly Tyr Tyr Lys Leu Ser Gly Glu Ala Tyr
            100                 105                 110

Gly Phe Val Ala Arg Ile Asp Gly Ser Gly Asn Phe Gln Val Leu Leu
        115                 120                 125
```

```
Ser Asp Arg Tyr Phe Asn Lys Thr Cys Gly Leu Cys Gly Asn Phe Asn
    130                 135                 140

Ile Phe Ala Glu Asp Asp Phe Met Thr Gln Glu Gly Thr Leu Thr Ser
145                 150                 155                 160

Asp Pro Tyr Asp Phe Ala Asn Ser Trp Ala Leu Ser Ser Gly Glu Gln
                165                 170                 175

Trp Cys Glu Arg Ala Ser Pro Pro Ser Ser Ser Cys Asn Ile Ser Ser
            180                 185                 190

Gly Glu Met Gln Lys Gly Leu Trp Glu Gln Cys Gln Leu Leu Lys Ser
        195                 200                 205

Thr Ser Val Phe Ala Arg Cys His Pro Leu Val Asp Pro Glu Pro Phe
    210                 215                 220

Val Ala Leu Cys Glu Lys Thr Leu Cys Glu Cys Ala Gly Gly Leu Glu
225                 230                 235                 240

Cys Ala Cys Pro Ala Leu Leu Glu Tyr Ala Arg Thr Cys Ala Gln Glu
                245                 250                 255

Gly Met Val Leu Tyr Gly Trp Thr Asp His Ser Ala Cys Ser Pro Val
            260                 265                 270

Cys Pro Ala Gly Met Glu Tyr Arg Gln Cys Val Ser Pro Cys Ala Arg
        275                 280                 285

Thr Cys Gln Ser Leu His Ile Asn Glu Met Cys Gln Glu Arg Cys Val
    290                 295                 300

Asp Gly Cys Ser Cys Pro Glu Gly Gln Leu Leu Asp Glu Gly Leu Cys
305                 310                 315                 320

Val Glu Ser Thr Glu Cys Pro Cys Val His Ser Gly Lys Arg Tyr Pro
                325                 330                 335

Pro Gly Thr Ser Leu Ser Arg Asp Cys Asn Thr Cys Ile Cys Arg Asn
            340                 345                 350

Ser Gln Trp Ile Cys Ser Asn Glu Glu Cys Pro Gly Glu Cys Leu Val
        355                 360                 365

Thr Gly Gln Ser His Phe Lys Ser Phe Asp Asn Arg Tyr Phe Thr Phe
    370                 375                 380

Ser Gly Ile Cys Gln Tyr Leu Leu Ala Arg Asp Cys Gln Asp His Ser
385                 390                 395                 400

Phe Ser Ile Val Ile Glu Thr Val Gln Cys Ala Asp Asp Arg Asp Ala
                405                 410                 415

Val Cys Thr Arg Ser Val Thr Val Arg Leu Pro Gly Leu His Asn Ser
            420                 425                 430

Leu Val Lys Leu Lys His Gly Ala Gly Val Ala Met Asp Gly Gln Asp
        435                 440                 445

Ile Gln Leu Pro Leu Leu Lys Gly Asp Leu Arg Ile Gln His Thr Val
    450                 455                 460

Thr Ala Ser Val Arg Leu Ser Tyr Gly Glu Asp Leu Gln Met Asp Trp
465                 470                 475                 480

Asp Gly Arg Gly Arg Leu Leu Val Lys Leu Ser Pro Val Tyr Ala Gly
                485                 490                 495

Lys Thr Cys Gly Leu Cys Gly Asn Tyr Asn Gly Asn Gln Gly Asp Asp
            500                 505                 510

Phe Leu Thr Pro Ser Gly Leu Ala Glu Pro Arg Val Glu Asp Phe Gly
        515                 520                 525

Asn Ala Trp Lys Leu His Gly Asp Cys Gln Asp Leu Gln Lys Gln His
    530                 535                 540

Ser Asp Pro Cys Ala Leu Asn Pro Arg Met Thr Arg Phe Ser Glu Glu
```

```
545                 550                 555                 560

Ala Cys Ala Val Leu Thr Ser Pro Thr Phe Glu Ala Cys His Arg Ala
                565                 570                 575

Val Ser Pro Leu Pro Tyr Leu Arg Asn Cys Arg Tyr Asp Val Cys Ser
            580                 585                 590

Cys Ser Asp Gly Arg Glu Cys Leu Cys Gly Ala Leu Ala Ser Tyr Ala
        595                 600                 605

Ala Ala Cys Ala Gly Arg Gly Val Arg Val Ala Trp Arg Glu Pro Gly
    610                 615                 620

Arg Cys Glu Leu Asn Cys Pro Lys Gly Gln Val Tyr Leu Gln Cys Gly
625                 630                 635                 640

Thr Pro Cys Asn Leu Thr Cys Arg Ser Leu Ser Tyr Pro Asp Glu Glu
                645                 650                 655

Cys Asn Glu Ala Cys Leu Glu Gly Cys Phe Cys Pro Pro Gly Leu Tyr
            660                 665                 670

Met Asp Glu Arg Gly Asp Cys Val Pro Lys Ala Gln Cys Pro Cys Tyr
        675                 680                 685

Tyr Asp Gly Glu Ile Phe Gln Pro Glu Asp Ile Phe Ser Asp His His
    690                 695                 700

Thr Met Cys Tyr Cys Glu Asp Gly Phe Met His Cys Thr Met Ser Gly
705                 710                 715                 720

Val Pro Gly Ser Leu Leu Pro Asp Ala Val Leu Ser Ser Pro Leu Ser
                725                 730                 735

His Arg Ser Lys Arg
            740


<210> SEQ ID NO 42
<211> LENGTH: 2904
<212> TYPE: DNA
<213> ORGANISM: Artificial Sequence
<220> FEATURE:
<223> OTHER INFORMATION: von Willebrand Factor sequence

<400> SEQUENCE: 42

atgatccccg ccagattcgc cggcgtgctg ctggccctgg ccctgatcct gcccggcacc      60

ctgtgcagcc tgagctgcag accccccatg gtcaagctcg tgtgcccagc cgacaatctg     120

cgggccgagg ggctggaatg caccaagacc tgccagaact acgacctgga atgcatgagc     180

atgggctgcg tgagcggctg cctgtgccca cccggcatgg tccggcacga gaacagatgc     240

gtggccctgg aacggtgccc atgcttccac cagggcaaag agtacgcccc tggcgagaca     300

gtgaagatcg gctgcaatac ctgcgtgtgc cgggaccgga agtggaactg caccgaccac     360

gtgtgcgacg ccacatgcag caccatcggc atggcccact acctgacctt tgacggcctg     420

aagtacctgt tccccggcga gtgccagtac gtgctggtgc aggactactg cggcagcaac     480

cccggcacct tccggatcct cgtgggcaac aagggatgca gccaccccag cgtgaagtgc     540

aagaaacgcg tgaccatcct ggtggagggc ggcgagatcg agctgttcga cggcgaagtg     600

aacgtgaagc ggcccatgaa ggacgagaca cacttcgagg tggtggagag cggccggtac     660

atcatcctgc tgctgggcaa ggctctgagc gtcgtgtggg accggcacct gagcatcagc     720

gtggtgctga agcagaccta ccaggaaaaa gtctgcggcc tctgtggcaa tttcgacggc     780

atccagaaca acgatctgac cagcagcaac ctgcaggtgg aagaggaccc cgtggacttt     840

ggcaatagct ggaaggtgtc cagccagtgt gccgacacca gaaaagtgcc cctggactct     900

agccccgcca cctgccacaa caacatcatg aagcagacaa tggtggacag ctcctgccgg     960
```

```
atcctgacct ccgacgtgtt ccaggactgt aacaaactgg tggatcctga gccttacctg   1020

gacgtgtgca tctacgacac ctgcagctgc gagagcatcg gcgattgcgc ctgcttctgc   1080

gacacaatcg ccgcctacgc ccatgtgtgc gcccagcacg gcaaggtggt cacctggcgg   1140

accgcaaccc tgtgccccca gagctgcgag gaacggaacc tgcgggagaa cggctacgag   1200

tgcgagtggc ggtacaacag ctgcgcccca gcctgccagg tcacctgcca gcaccccgag   1260

cctctggcct gccccgtgca gtgcgtggag ggctgccacg cccactgccc tccaggcaag   1320

atcctggacg agctgctgca gacctgcgtg gaccctgagg actgccctgt gtgcgaggtg   1380

gccggcaggc ggttcgcctc cggcaagaaa gtgaccctga accctagcga ccccgagcac   1440

tgccagatct gccactgcga cgtggtcaat ctgacctgcg aggcttgcca ggaaccaggc   1500

ggcctcgtcg tgcccctac cgacgcccct gtgtccccaa ccaccctgta cgtggaggac   1560

atcagcgagc ccccctgca cgacttctac tgctctcggc tgctggacct ggtgttcctg   1620

ctggacggca gttctagact gagcgaggcc gagttcgagg tgctgaaggc cttcgtcgtg   1680

gacatgatgg aacggctgcg gatcagccag aaatgggtcc gggtggccgt ggtggagtac   1740

cacgacggca gccacgccta catcggcctg aaggaccgga agcggccctc cgaactccgg   1800

cggatcgcca gccaggtcaa gtacgccgga tcccaggtgg ccagcaccag cgaagtgctg   1860

aagtacaccc tgttccagat cttcagcaag atcgaccggc ccgaggccag ccggatcgca   1920

ctgctgctga tggccagcca agaaccccag cggatgagcc ggaacttcgt gagatacgtg   1980

cagggcctga agaaaaagaa agtgatcgtg atccccgtgg gcatcggccc ccacgccaac   2040

ctgaagcaga tccggctgat cgagaagcag gcacccgaga acaaggcctt tgtgctgtcc   2100

agcgtggatg agctggaaca gcagcgggac gagatcgtgt cctacctgtg cgacctggcc   2160

cctgaggccc ctcctcccac actgccccc cacatggctc aggtcaccgt gggaccaggc   2220

gacaaaactc acacatgccc accgtgccca gcacctgaac tcctgggggg accgtcagtc   2280

ttcctcttcc ccccaaaacc caaggacacc ctcatgatct cccggacccc tgaggtcaca   2340

tgcgtggtgg tggacgtgag ccacgaagac cctgaggtca agttcaactg gtacgtggac   2400

ggcgtggagg tgcataatgc caagacaaag ccgcgggagg agcagtacaa cagcacgtac   2460

cgtgtggtca gcgtcctcac cgtcctgcac caggactggc tgaatggcaa ggagtacaag   2520

tgcaaggtct ccaacaaagc cctcccagcc cccatcgaga aaaccatctc caaagccaaa   2580

gggcagcccc gagagccaca ggtgtacacc ctgcccccat cccgggatga gctgaccaag   2640

aaccaggtca gcctgacctg cctggtcaaa ggcttctatc ccagcgacat cgccgtggag   2700

tgggagagca atgggcagcc ggagaacaac tacaagacca cgcctcccgt gctggactcc   2760

gacggctcct tcttcctcta cagcaagctc accgtggaca agagcaggtg gcagcagggg   2820

aacgtcttct catgctccgt gatgcatgag gctctgcaca accactacac gcagaagagc   2880

ctctccctgt ctccgggtaa atga                                          2904
```

<210> SEQ ID NO 43
<211> LENGTH: 4098
<212> TYPE: DNA
<213> ORGANISM: Artificial Sequence
<220> FEATURE:
<223> OTHER INFORMATION: von Willebrand Factor sequence

<400> SEQUENCE: 43

```
atgatccccg ccagattcgc cggcgtgctg ctggccctgg ccctgatcct gcccggcacc     60
```

```
ctgtgcagcc tgagctgcag accccccatg gtcaagctcg tgtgcccagc cgacaatctg    120
cgggccgagg ggctggaatg caccaagacc tgccagaact acgacctgga atgcatgagc    180
atgggctgcg tgagcggctg cctgtgccca cccggcatgg tccggcacga gaacagatgc    240
gtggccctgg aacggtgccc atgcttccac cagggcaaag agtacgcccc tggcgagaca    300
gtgaagatcg gctgcaatac ctgcgtgtgc cgggaccgga agtggaactg caccgaccac    360
gtgtgcgacg ccacatgcag caccatcggc atggcccact acctgacctt tgacggcctg    420
aagtacctgt tccccggcga gtgccagtac gtgctggtgc aggactactg cggcagcaac    480
cccggcacct tccggatcct cgtgggcaac aagggatgca gccaccccag cgtgaagtgc    540
aagaaacgcg tgaccatcct ggtggagggc ggcgagatcg agctgttcga cggcgaagtg    600
aacgtgaagc ggcccatgaa ggacgagaca cacttcgagg tggtggagag cggccggtac    660
atcatcctgc tgctgggcaa ggctctgagc gtcgtgtggg accggcacct gagcatcagc    720
gtggtgctga agcagaccta ccaggaaaaa gtctgcggcc tctgtggcaa tttcgacggc    780
atccagaaca acgatctgac cagcagcaac ctgcaggtgg aagaggaccc cgtggacttt    840
ggcaatagct ggaaggtgtc cagccagtgt gccgacacca gaaaagtgcc cctggactct    900
agccccgcca cctgccacaa caacatcatg aagcagacaa tggtggacag ctcctgccgg    960
atcctgacct ccgacgtgtt ccaggactgt aacaaactgg tggatcctga gccttacctg   1020
gacgtgtgca tctacgacac ctgcagctgc gagagcatcg gcgattgcgc ctgcttctgc   1080
gacacaatcg ccgcctacgc ccatgtgtgc gcccagcacg gcaaggtggt cacctggcgg   1140
accgcaaccc tgtgccccca gagctgcgag gaacggaacc tgcgggagaa cggctacgag   1200
tgcgagtggc ggtacaacag ctgcgcccca gcctgccagg tcacctgcca gcaccccgag   1260
cctctggcct gccccgtgca gtgcgtggag ggctgccacg cccactgccc tccaggcaag   1320
atcctggacg agctgctgca gacctgcgtg gaccctgagg actgccctgt gtgcgaggtg   1380
gccggcaggc ggttcgcctc cggcaagaaa gtgaccctga accctagcga ccccgagcac   1440
tgccagatct gccactgcga cgtggtcaat ctgacctgcg aggcttgcca ggaaccaggc   1500
ggcctcgtcg tgcccctac cgacgcccct gtgtccccaa ccaccctgta cgtggaggac   1560
atcagcgagc cccccctgca cgacttctac tgctctcggc tgctggacct ggtgttcctg   1620
ctggacggca gttctagact gagcgaggcc gagttcgagg tgctgaaggc cttcgtcgtg   1680
gacatgatgg aacggctgcg gatcagccag aaatgggtcc gggtggccgt ggtggagtac   1740
cacgacggca gccacgccta catcggcctg aaggaccgga agcggccctc cgaactccgg   1800
cggatcgcca gccaggtcaa gtacgccgga tcccaggtgg ccagcaccag cgaagtgctg   1860
aagtacaccc tgttccagat cttcagcaag atcgaccggc ccgaggccag ccggatcgca   1920
ctgctgctga tggccagcca agaaccccag cggatgagcc ggaacttcgt gagatacgtg   1980
cagggcctga agaaaaagaa agtgatcgtg atccccgtgg gcatcggccc ccacgccaac   2040
ctgaagcaga tccggctgat cgagaagcag gcacccgaga acaaggcctt tgtgctgtcc   2100
agcgtggatg agctggaaca gcagcgggac gagatcgtgt cctacctgtg cgacctggcc   2160
cctgaggccc ctcctcccac actgcccccc cacatggctc aggtcaccgt gggaccaggc   2220
ctgctgggag tgagcacact gggccccaag cggaacagca tggtgctgga cgtggccttc   2280
gtgctcgagg gcagcgacaa gatcggcgag gccgacttca accggtccaa agaattcatg   2340
gaagaggtca tccagcggat ggacgtgggc caggacagca tccacgtgac agtgctgcag   2400
tacagctaca tggtcacagt ggagtacccc ttcagcgagg cccagagcaa gggcgacatc   2460
```

-continued

```
ctgcagagag tgcgggagat cagataccag ggcggcaacc ggaccaacac cggcctggcc   2520
ctgcgctacc tgagcgacca ctcctttctg gtgtctcagg gcgatcggga gcaggcccct   2580
aacctggtgt atatggtcac aggcaacccc gctagcgacg agatcaagag actgcccggc   2640
gacatccagg tggtgcccat cggcgtgggc cccaacgcta atgtgcagga actggaacgg   2700
atcggctggc ccaacgcccc catcctgatc caggacttcg agacactgcc cagagaagcc   2760
cccgacctgg tgctgcagcg gtgctgtagc ggcgaggggc tgcagatccc caccctgagc   2820
cctgcccccg actgcagcca gcccctggac gtgatcctgc tcctggacgg ctccagctcc   2880
ttccccgcca gctacttcga cgagatgaag tccttcgcca aggccttcat cagcaaggcc   2940
aacatcggcc ccagactgac ccaggtgtcc gtgctccagt acggcagcat caccaccatc   3000
gacgtgccct ggaatgtggt ccccgagaag gcccacctgc tgtccctggt ggatgtgatg   3060
cagcgggagg gcggacccag ccagatcggc gacgccctgg gcttcgccgt gagatacctg   3120
acaagcgaga tgcacggagc cagacctgga gcctccaagg ccgtggtcat cctcgtgacc   3180
gacgtgtccg tggacagcgt ggacgctgcc gccgacgccg ccagatccaa cagagtgacc   3240
gtgttcccta tcggcatcgg cgaccgctac gacgccgccc agctgagaat cctggccgga   3300
cctgccggcg acagcaacgt ggtcaaactg cagcggatcg aggatctgcc caccatggtc   3360
accctgggca acagctttct gcacaagctg tgtagcggct tcgtgcggat ctgcgacaaa   3420
actcacacat gcccaccgtg cccagcacct gaactcctgg ggggaccgtc agtcttcctc   3480
ttccccccaa aacccaagga caccctcatg atctcccgga cccctgaggt cacatgcgtg   3540
gtggtggacg tgagccacga agaccctgag gtcaagttca actggtacgt ggacggcgtg   3600
gaggtgcata atgccaagac aaagccgcgg gaggagcagt acaacagcac gtaccgtgtg   3660
gtcagcgtcc tcaccgtcct gcaccaggac tggctgaatg gcaaggagta caagtgcaag   3720
gtctccaaca aagccctccc agcccccatc gagaaaacca tctccaaagc caaagggcag   3780
ccccgagagc cacaggtgta caccctgccc ccatcccggg atgagctgac caagaaccag   3840
gtcagcctga cctgcctggt caaaggcttc tatcccagcg acatcgccgt ggagtgggag   3900
agcaatgggc agccggagaa caactacaag accacgcctc ccgtgctgga ctccgacggc   3960
tccttcttcc tctacagcaa gctcaccgtg gacaagagca ggtggcagca ggggaacgtc   4020
ttctcatgct ccgtgatgca tgaggctctg cacaaccact acacgcagaa gagcctctcc   4080
ctgtctccgg gtaaatga                                                 4098
```

VON WILLEBRAND FACTOR (VWF)-CONTAINING PREPARATIONS, AND METHODS, KITS, AND USES RELATED THERETO

CROSS-REFERENCE TO RELATED APPLICATIONS

The present application is a national phase of International Application PCT/US10/056496, filed Nov. 12, 2010, which claims the benefit of priority under 35 USC §119 to U.S. Provisional Application No. 61/261,145 filed Nov. 13, 2009, each of which is herein incorporated by reference in its entirety.

FIELD OF THE INVENTION

Methods, compositions and kits are provided for vWF-containing preparations, including methods, kits and use of such preparations for preparing Factor VIII (FVIII). Also provided are vWF polypeptides and nucleic acid molecules encoding same.

BACKGROUND OF THE INVENTION

FVIII expressed by mammalian cells is often specifically or non-specifically absorbed onto cell surfaces by interaction with surface components (e.g. proteoglycans) or by receptor-mediated events (e.g. interaction with LRP receptor). It is also possible that expressed FVIII is enzymatically cleaved and/or degraded in the media of cultured cells. Over time in culture, expressed FVIII concentration decreases in media unless the secreted material is rapidly removed after expression (e.g. by perfusion techniques).

Under ordinary circumstances, the FVIII-vWF complex may be removed from media by conventional chromatographic methods including absorption onto charge matrices or by pseudo-affinity chromatography. FVIII can then be purified away from the FVIII:vWF complex by selective washing steps to yield an enriched population of FVIII molecules, minimally contaminated by vWF.

vWF is formed in the vascular endothelial cells, which are the main source of this plasma protein, by constitutive or stimulated liberation, but it is also synthesized in smaller amounts by the megakaryocytes. It is believed that the primary product of translation is comprised of 2813 amino acids. After cleaving off the signal peptide (22 amino acids), dimerization takes place. Further processing is effected in the Golgi apparatus, the dimers polymerizing after cleavage and removal of the propeptide (741 amino acids). The propeptide plays an important role in the further linking of the dimers, where it catalyses the formation of disulfide bridges at the amino-terminal end. Thus, differently sized oligomers ranging in size from a dimer of 500,000 daltons to large multimers of up to 20 million daltons may form. In addition to the proteolytic procedures, vWF is subject to other post-translational modifications, including glycosylation and sulfation.

SUMMARY OF THE INVENTION

In one aspect, the present invention provides a polypeptide comprising a first amino acid sequence present in a vWF polypeptide and a second amino acid sequence heterologous to the first, wherein the polypeptide is capable of binding a FVIII.

In another aspect, the present invention provides a composition comprising the polypeptide comprising the first and the second amino acid sequence.

In some aspects, the present invention provides a protein complex comprising the polypeptide and the FVIII.

In other aspects, the present invention provides a composition comprising the protein complex.

In still further aspects, the present invention provides a nucleotide sequence encoding the polypeptide comprising the first and the second amino acid sequence.

In one aspect, the present invention provides an expression vector comprising the nucleotide sequence.

In another aspect, the present invention provides a cell expressing the polypeptide comprising the first and the second amino acid sequence.

In some aspects, the present invention provides a cell expressing the protein complex comprising the polypeptide and the FVIII.

In other aspects, the present invention provides a method for preparing the protein complex, the method comprising contacting the polypeptide with the FVIII.

In one aspect, the present invention provides a method for preparing a FVIII, the method comprising: contacting the FVIII with the polypeptide comprising the first and the second amino acid sequence to form a protein complex comprising the polypeptide and the FVIII.

In another aspect, the present invention provides a method for enhancing a plasma pharmacokinetic property of a FVIII, the method comprising administering to a subject a composition comprising the protein complex comprising the polypeptide and the FVIII.

In some aspects, the present invention provides a composition comprising the protein complex, and a pharmaceutically acceptable carrier.

In other aspects, the present invention provides a method for treating a blood condition, the method comprising administering the composition comprising the protein complex comprising the polypeptide and the FVIII, wherein the polypeptide comprises the first and the second amino acid sequence.

In still further aspects, a kit is provided.

DETAILED DESCRIPTION

Figure 1:
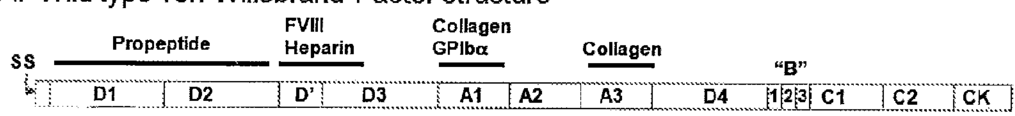
FIG. 1 shows a schematic representation of human von Willebrand Factor protein structure, processing and maturation. (A) Domain structure of the primary von Willebrand Factor polypeptide: SS=signal peptide; D1 and D2=propeptide sequence; D'-D3=includes nominal Factor VIII binding region; A1 and A3=collagen binding domains (and other interactions); (B) During secretion and processing, the signal peptide is removed and the propeptide is later cleaved from the vWF polypeptide by a furin-like processing step to yield a mature vWF polypeptide that initiates normally at the junction of the D' domain; (C) Propeptide associated with the mature vWF polypeptide promotes increased FVIII binding and multimerization; and (D) Cysteine residues provided by the propeptide-matured vWF complex provide covalent bridges that allow for intra- and inter-molecular multimer formation.
Figure 1:
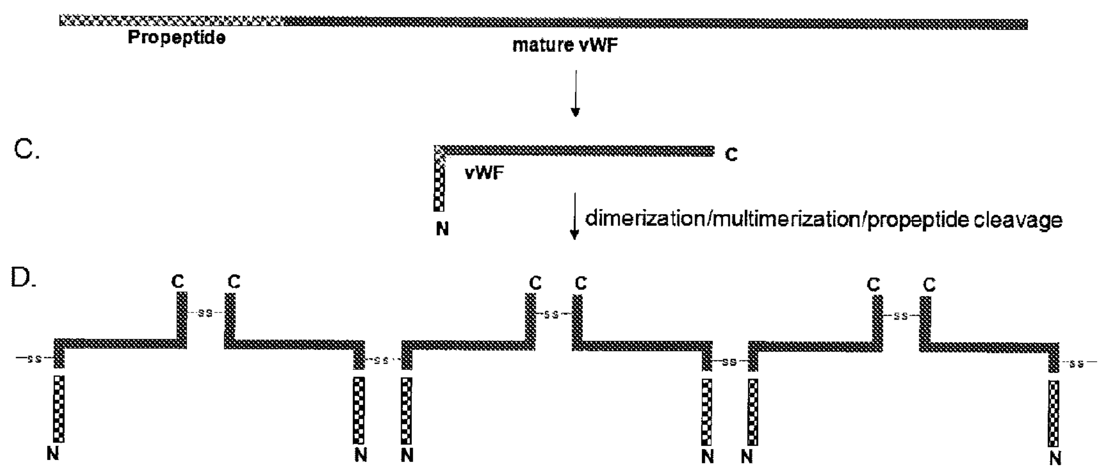
Figure 2:
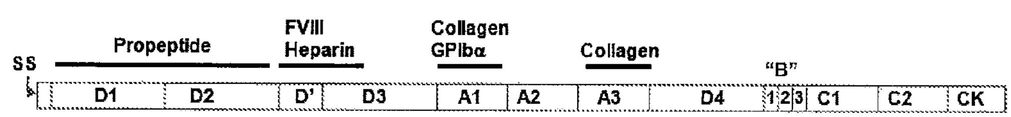
FIG. 2 shows a schematic representation of human von Willebrand Factor domain truncations with covalent fusion to $IgG_1$ Fc. (A) Domain structure of the primary von Willebrand Factor polypeptide: SS=signal peptide; D1 and D2=propeptide sequence; D'-D3=includes the nominal Factor VIII binding region; A1 and A3=collagen binding domains (and other interactions); (B) The primary vWF truncation polypeptides with Fc are diagrammed, showing the expected domain structure after signal peptide cleavage. Sequences include the propeptide followed by either the D'-D3, the D'-A1 or the D'-A3 domain, each in turn fused covalently at the hinge region of the constant region of $IgG_1$; and (C) Propeptide associated with vWF truncation polypeptide-Fc fusions (i.e., D'-D3-Fc, D'-A1-Fc, or D'A3-Fc) promotes increased FVIII binding and multimerization, just as occurs in mature vWF processing.
Figure 2:
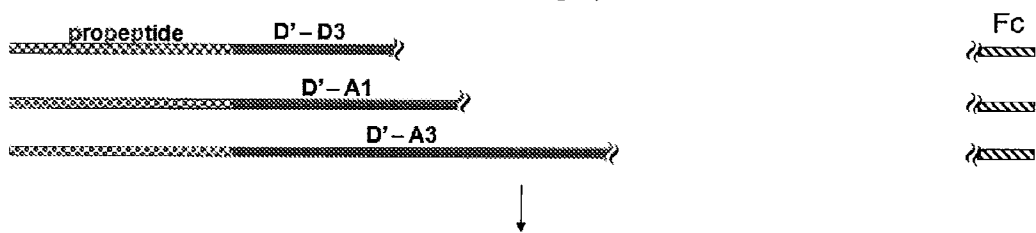
Figure 2:
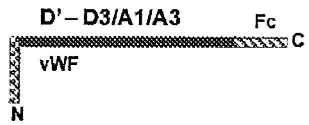
Figure 3:
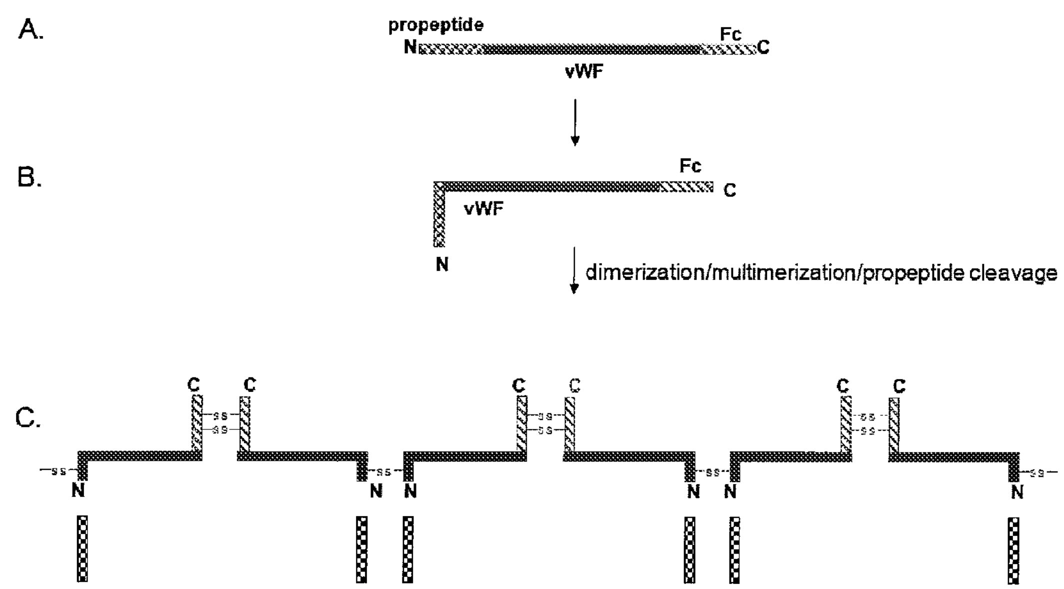
FIG. 3 shows a schematic representation of truncated vWF-Fc fusion processing, maturation and multimerization of the primary translation product. (A) Representation of propeptide and truncated vWF domain-Fc fusion after signal peptide cleavage. In this representation, the polypeptides are derived from a single primary translation product as depicted in FIG. 1, for example; (B) Representation showing propeptide and vWF domain-Fc fusion monomer after processing of primary translation product and association of propeptide with truncated vWF domain-Fc polypeptide to promote proper folding; and (C) Cysteine residues contained within the hinge region of the $IgG_1$ Fc provide the intra-molecular bridging to help create a functional vWF-Fc dimer that also binds FVIII, in a manner similar to that found in plasma-derived vWF; vWF propeptides, in turn, promote multimerization of the fusion polypeptides.
Figure 4:
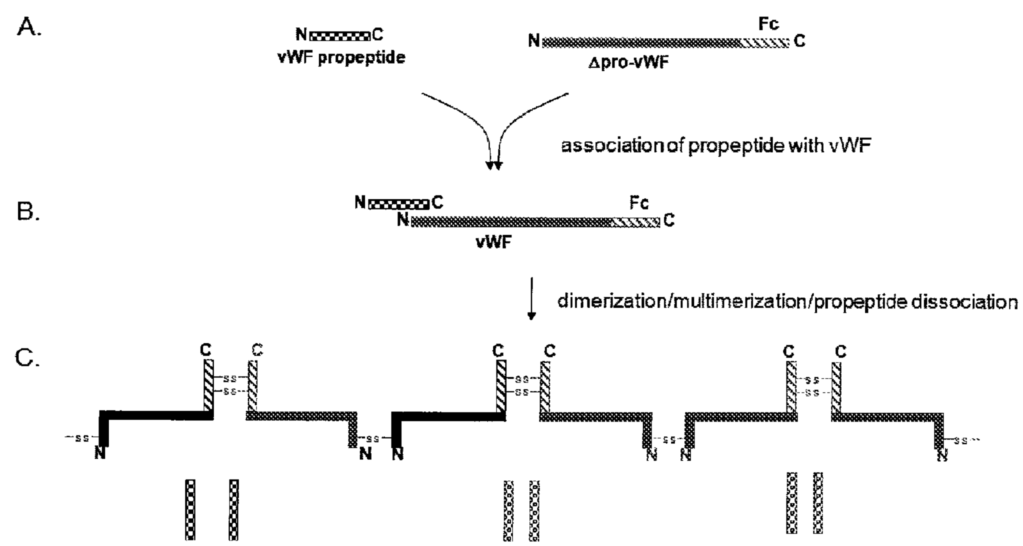
FIG. 4 shows a schematic representation of truncated vWF-Fc fusion processing, maturation and multimerization of two primary translation products from independent coding regions. (A) Representation of separate and independent primary translation products of propeptide and of truncated vWF domain-Fe fusion polypeptides after signal peptide cleavage; no furin-like processing is needed as in normal vWF processing. In this representation, the polypeptides are derived from two independent primary translation products from two independent promoter cassettes either transcribed from one expression vector or from two expression vectors co-expressed in the same cell, the former expression mode depicted in FIG. 6, for example; (B) Representation showing propeptide and vWF domain-Fc fusion monomer after processing of primary translation product and association of co-expressed propeptide with truncated vWF domain-Fe polypeptide to promote proper folding; and (C) Cysteine residues contained within the hinge region of the $IgG_1$ Fc provide the intra-molecular bridging to help create a functional vWF-Fc dimer that also binds FVIII, in a manner similar to that found in plasma-derived vWF; vWF propeptides, in turn, promote multimerization of the fusion polypeptides.
Figure 5:
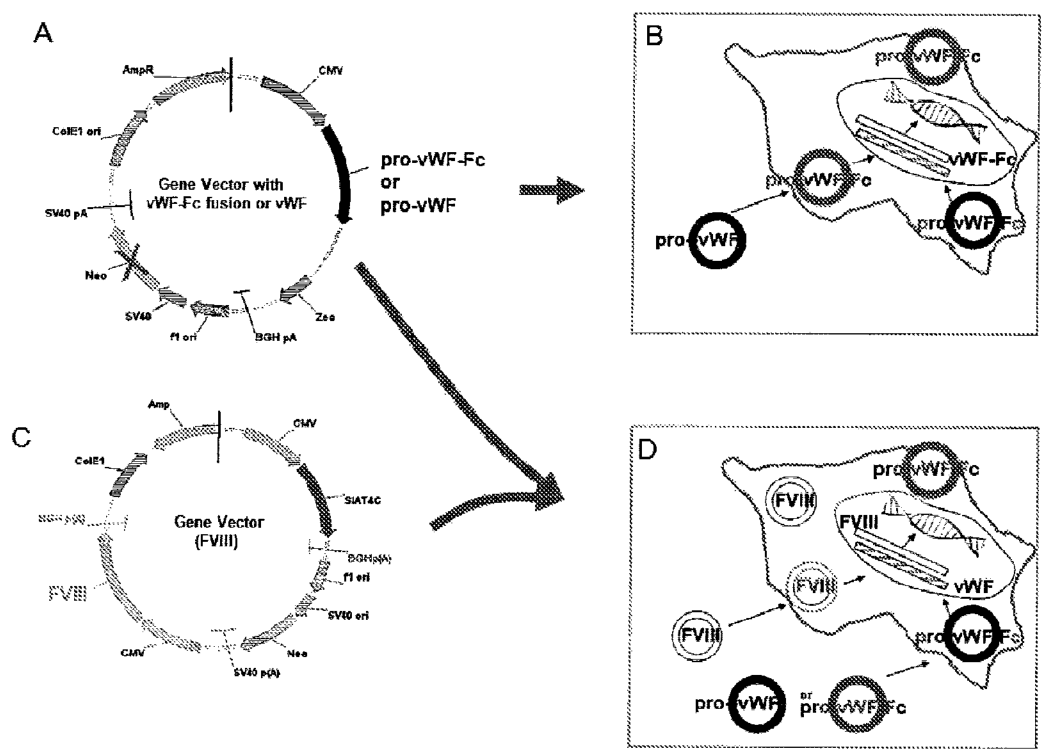
FIG. 5 is a schematic illustrating, in some embodiments, transfection of plasmid expression vectors into mammalian cells that express mature vWF or truncated vWF domain-Fc fusion polypeptides. (A) Expression plasmid with coding sequence for vWF or truncated vWF domain-Fc fusion proteins, each containing signal peptide sequences and propeptide domains as part of the primary translation product; (B) Representation of plasmids transfected and taken up into mammalian cells under selection to create a stable expressing cell line; (C) Expression plasmid with coding cassette for Factor VIII using a different selectable marker (neomycin) than in (A); and (D) Representation of FVIII (C) and vWF or vWF-Fc (D) plasmids co-transfected and taken up into mammalian cells under selection to create a stable cell line that expresses FVIII and vWF-Fc (or vWF).
Figure 6:
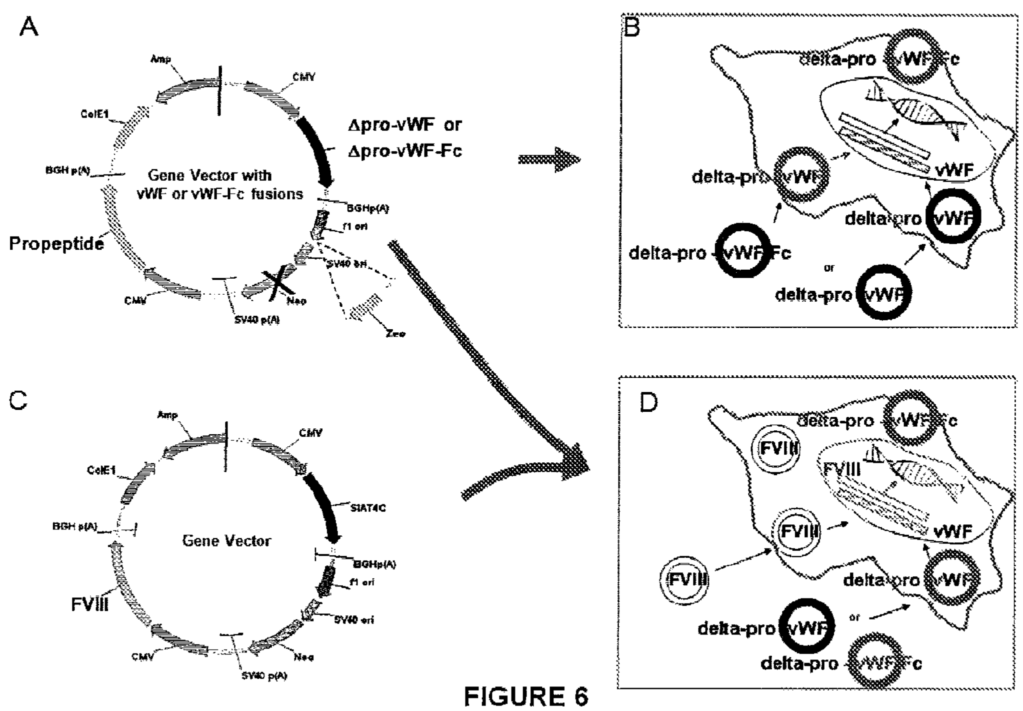
FIG. 6 is a schematic illustrating, in other embodiments, transfection of plasmid expression vectors into mammalian cells that express mature vWF or truncated vWF domain-Fc fusion polypeptides and propeptide sequences from independent promoters, either on the same or different plasmid vectors. (A) Expression plasmid with coding cassettes for vWF or truncated vWF domain-Fc fusion proteins that do not express a propeptide domain as part of their primary translation product, and for the vWF propeptide domain expression cassette (each with respective signal peptide sequences) from independent promoters; (B) Representation of propeptide-minus vWF or vWF-Fc fusion polypeptides and propeptide polypeptide plasmids transfected and taken up into mammalian cells under selection to create a stable cell line that co-expresses both the vWF or vWF-Fc proteins as well as the propeptide polypeptide; (C) Expression plasmid with coding cassette for Factor VIII using a different selectable marker (neomycin) than in (A); and (D) Representation of FVIII (C) and vWF or vWF-Fc with propeptide (D) plasmids co-transfected and taken up into mammalian cells under selection to create a stable cell line that expresses FVIII, and either vWF-Fc or vWF, and independently, the vWF propeptide.
Figure 7:
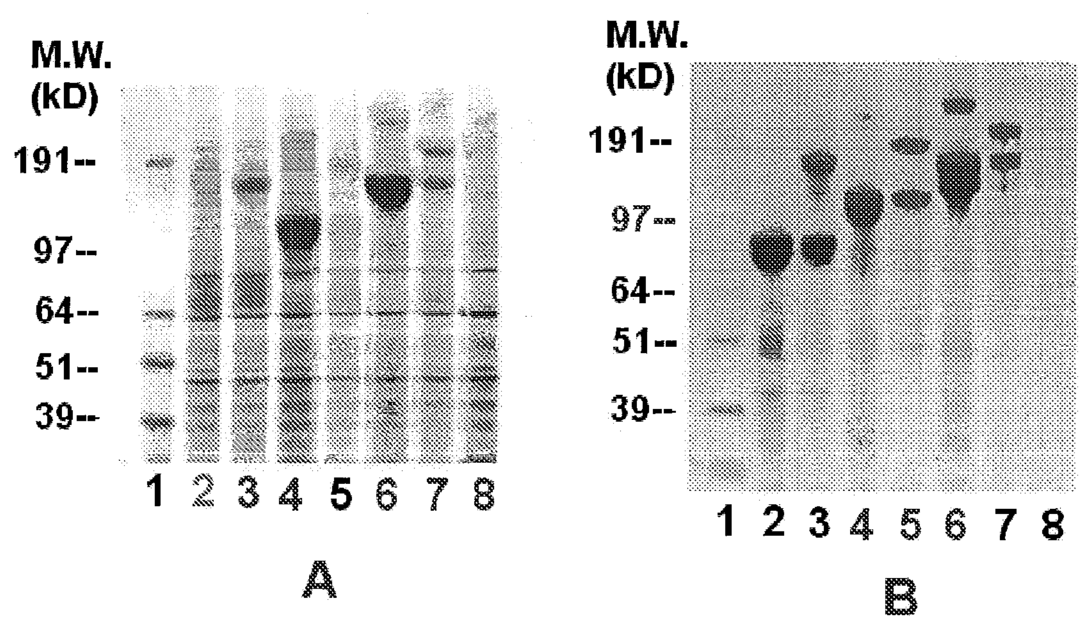
FIG. 7 shows Coomassie stained proteins of expressed proteins electrophoresed on 4-12% Bis-Tris PAGE gels under reducing and denaturing conditions, either directly from expressed culture supernatants (A) or from Protein G immunopreciptations (B) of the proteins present in the cultured supernatants from (A). PER.C6 cells transfected with plasmids containing a truncated vWF-Fc construct were selected for stable cultures as pool using antibiotic selection. For direct supernatant samples, 20 microliters were loaded onto a gel. For immunoprecipitation, 20 microliters of Protein G beads were added to either 1 ml of medium with D'-D3-Fc, or to 0.2 ml of medium with D'-A1-Fc or D'-A3-Fc. Lanes on both gels represent: Lane 1: Molecular weight standard; Lane 2: D'-D3-Fc; Lane 3: pro-D'-D3-Fc; Lane 4: D'-A1-Fc; Lane 5: pro-D'-A1-Fc; Lane 6: D'-A3-Fc; Lane 7: pro-D'-A3-Fc; and Lane 8: untransfected PER.C6 conditioned medium as control. Higher molecular weight bands in lanes 3, 5 and 8 represent unprocessed propeptide still attached to the corresponding vWF domains.

In one aspect, the present invention provides a polypeptide comprising a first amino acid sequence present in a vWF polypeptide and a second amino acid sequence heterologous to the first, wherein the polypeptide is capable of binding a FVIII.

As used herein, the term "capable of binding" contemplates embodiments wherein the capability of the polypeptide to bind to the FVIII is effected by higher order protein assembly and/or one or more post-translational modifications such as, for example, signal peptide cleavage, propeptide cleavage, propeptide association, phosphorylation, glycosylation, and such like. For example, in some embodiments, the polypeptide is "capable of binding" to the FVIII as a dimer, trimer, tetramer, or higher order multimeric complex that forms subsequent to multimerization of the polypeptide. Or, for example, in other embodiments, the polypeptide is "capable of binding" the FVIII following multimerization of the polypeptide subsequent to association of a propeptide with the polypeptide. "Multimerization" and "oligomerization" are used interchangeably herein and refer to the association two or more protein molecules, mediated by covalent (e.g., intermolecular disulfide bonds) and/or non-covalent interactions. Accordingly, "multimer(s)" and "oligomer(s)" also are used interchangeably herein.

vWF and FVIII polypeptides of human and non-human (e.g., primates, dogs, cats, horses, pigs, mice, rats, guinea pigs, rabbits, cows, other vertebrates) origin are contemplated by the present invention including natural, synthetic, and recombinant proteins. Also within the scope of the present invention are vWF and FVIII polypeptides corresponding to wild-type proteins, or mutants, variants, and/or truncations thereof. For example, in some embodiments, the first amino acid sequence corresponds to a fragment of a vWF polypeptide of human origin, wherein the heterologous second amino acid sequence comprises or consists of a sequence not present in any vWF protein, human or otherwise. FVIII and/or vWF include native proteins, as well as derivative thereof, e.g. proteins mutated by deletion, substitution or insertion, or a chemical derivative or fragment thereof.

I. First Amino Acid Sequence

In one embodiment, the first amino acid sequence defines a structure or domain that reacts with a monoclonal anti-vWF antibody capable of specifically binding to a region of a VWF polypeptide comprising a FVIII binding domain In one embodiment, the monoclonal antibody is monoclonal antibody C3 as described by, e.g., Foster et al., JBC, 262:8443 (1987) and Fulcher et al., J. Clin. Invest., 76:117 (1985), each of which is herein incorporated by reference for its teaching of monoclonal antibody C3 and method of preparing monoclonal antibodies, in particular monoclonal antibody C3.

Non-limiting examples of vWF amino acid sequences and nucleic acid sequences encoding vWF or a portion thereof are disclosed by, e.g., GenBank Accession Nos.: NP_000543, NM_000552, AAE20723, AAB59512, P04275, EAW88815, ACP57027, EAW88816, and AAD04919; U.S. Pat. No. 5,260,274; Titani et al., Biochemistry, 25:3171-84 (1986); and Sadler et al., PNAS, 82:6391-6398 (1985), each of which is herein incorporated by reference for its teaching of amino acid and nucleic acid sequences corresponding to vWF.

A person of ordinary skill in the art knows that the prototypical preprop-vWF is a polypeptide of 2813 amino acids with a signal peptide of 22 amino acids and repetitive functional domains, A, B, C, D and CK, which are distributed from the amino terminal in the order "D1," "D2," "D'," "D3," "A1," "A2," "A3," "D4," "B1," "B2," "B3 (the latter three collectively considered "B"), "C1," "C2," and "CK." The "mature" vWF subunit is composed of, from the N- to the C-terminus in the order, the domains D'-D3-A1-A2-A3-D4-B1-B2-B3-C1-C2-CK.

An amino acid sequence of an exemplary full-length human vWF is shown by SEQ ID NO:29, which is encoded by nucleotides 251-8689 of SEQ ID NO:30. With reference to SEQ ID NO:29, the "signal peptide" portion of vWF spans amino acid positions 1 though Cys-22, the "propeptide" portion (D1-D2) spans amino acid positions 23 through Arg-763, and the "mature" vWF protein spans amino acid positions 764 through 2813. The individual domains have also been approximately mapped as D': 764-865; D3: 866-1242; A1: 1260-1479; A2: 1480-1672; A3: 1673-1874; D4: 1947-2298; B: 2296-2399; C1: 2400-2516; C2: 2544-2663; and CK: 2720-2813. An alternative vWF domain mapping and naming system has been used by the EXPASY Protein Database convention (worldwideweb.uniprot.org/uniprot/P04275) as D1: 34-240; D2: 387-598; D': 776-827; D3: 866-1074; A1: 1277-1453; A2: 1498-1665; A3: 1691-1871; D4: 1949-2153; B: 2255-2328 (which is named C1 in EXPASY); C1: 2429-2495 (named C2 in EXPASY); C2: 2580-2645 (named C3 in EXPASY); and CK: 2724-2812.

Non-limiting examples of FVIII amino acid and nucleic acid sequences are disclosed by, e.g., GenBank Accession nos. 1012296A AAA52420.1, CAA25619.1, AAA52484.1, 1012298A, EAW72647.1, EAW72646.1, XP_001498954.1, ACK44290.1, AC095359.1, NP_001138980.1, ABZ10503.1, NP_032003.2, U.S. Pat. No. 6,307,032, and Wood et al., Nature, 312:330-7 (1984), each of which is herein incorporated by reference for its teaching of FVIII sequences. Variants, derivatives, modifications, and complexes of FVIII also are known in the art, and are encompassed in the present invention. For example, variants of Factor VIII, as described in, U.S. Pat. No. 5,668,108 discloses variants of FVIII whereby the aspartic acid at position 1241 is replaced by a glutamic acid with the accompanying nucleic acid changes as well; U.S. Pat. No. 5,149,637 describes FVIII variants comprising the C-terminal fraction, either glycosylated or unglycosylated; and U.S. Pat. No. 5,661,008 describes a FVIII variant comprising amino acids 1-740 linked to amino acids 1649 to 2332 by at least 3 amino acid residues; each of which is herein incorporated by reference for each teaching of FVIII variant sequences.

In one embodiment, the FVIII is plasma- or serum-derived FVIII. In another embodiment, the FVIII is recombinant FVIII, e.g. active human FVIII expressed in cultured mammalian cells from recombinant DNA clones. Expression systems for the production of Factor VIII are known in the art, and include prokaryotic and eukaryotic cells, as exemplified by U.S. Pat. Nos. 5,633,150, 5,804,420, and 5,422,250, each of which is incorporated herein for its teaching of production of FVIII.

One of ordinary skill in the art knows that the ability of the polypeptide to bind FVIII may be determined in a variety of ways. In particular, the polypeptide of the present invention may be assayed for its ability to bind the FVIII using techniques described herein and/or adapting techniques known in the art. For example, to analyze/determine binding, immunoassays can be employed including, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, etc. (see, e.g., Ausubel et al., eds, 1994, Current Protocols in Molecular Biology, Vol. 1, John Wiley & Sons, Inc., New York, which is herein incorporated by reference in its entirety).

For example, the polypeptide comprising the first and the second amino acid sequences can be contacted with the FVIII in a suitable buffer such as TBS in the presence of a monoclonal antibody coupled to Sepharose. The antibody can be directed against a region of the polypeptide such that binding of the antibody to the polypeptide does not interfere with binding of the polypeptide with the FVIII (e.g., the antibody may be directed against the second amino acid sequence or an "A1", or "A2" or "A3" repeat region of vWF where such region also is present on the polypeptide Following contact, FVIII bound to the polypeptide/antibody and unbound FVIII can be separated, e.g. by centrifugation, and FVIII can be measured, e.g. using a chromogenic substrate assay (Factor VIII Coatest; Chromogenix, Mölndal, Sweden).

In preferred embodiments, the first amino acid sequence of the polypeptides of the present invention is a truncated vWF polypeptide. For example, truncated forms of vWF, in some embodiments, include (i) truncated vWF polypeptides that lack the "propeptide" sequence; and (ii) truncated vWF polypeptides that lack the "A1," "A2," "A3," "D4," "B" (also known as "B1", "B2", and "B3"), "C1," "C2," and/or "CK" domain of the mature sequence. Other truncated or otherwise modified forms of vWF also are contemplated.

In one embodiment, the first amino acid sequence is as set forth in SEQ ID NO:1, SEQ. ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:33, SEQ ID NO:34, or SEQ ID NO:35.

II. Second Amino Acid Sequence

In other embodiments, the second amino acid sequence of the polypeptide provides a structure or domain having affinity for a binding partner.

The second amino acid sequence is heterologous to the first. In one embodiment, the heterologous second amino acid sequence comprises or consists of a sequence not present in any vWF protein. In one embodiment, at least a portion (e.g., a contiguous portion) of the heterologous second amino acid sequence corresponds to a sequence not present in any vWF polypeptide.

Preferably, in some embodiment, the second amino acid sequence corresponds to an antibody Fc polypeptide such as, e.g., a human IgG1 Fc region. For example, the second amino acid sequence can correspond to the amino acid residues that extend from the N-terminal hinge region to the native C-terminus, i.e., is an essentially full-length antibody Fc region. Fragments of Fc regions, e.g., those that are truncated at the C-terminal end, also may be employed. In some embodiments, the fragments preferably contain one or more cysteine residues (at least the cysteine residues in the hinge region) to permit interchain disulfide bonds to form between the Fc polypeptide portions of two separate polypeptides of the present invention, forming dimers.

Other antibody Fc regions may be substituted for the human IgG1 Fc region. For example, other suitable Fc regions are those that can bind with affinity to protein A or protein G or other similar Fc-binding matrices, and include the Fc regions of murine IgG, IgA, IgE, IgD, IgM or fragments of the human IgG IgA, IgE, IgD, IgM Fc region, e.g., fragments comprising at least the hinge region so that interchain disulfide bonds will form.

$IgG_1$ Fc region is disclosed by, for example, GenBank Accession no. X70421, which is herein incorporated by reference in its entirety.

In one embodiment, the second amino acid sequence comprises the sequence set forth in SEQ ID NO:16.

In some embodiments, the second amino acid sequence preferably is C-terminus to the first amino acid sequence. Preparation of fusion polypeptides comprising a heterologous amino acid sequence fused to various portions of another amino acid sequence is described, e.g., by Ashkenazi et al., PNAS, 88:10535 (1991) and Byrn et al., Nature 344: 677 (1990), each of which is herein incorporated by reference in its entirety. For example, a gene fusion encoding the polypeptide comprising the first and the second amino acid sequences can be inserted into an appropriate expression vector. The expressed fusion proteins can be allowed to assemble, whereby interchain disulfide bonds can form between the polypeptides, yielding dimers. In other embodiments, the fusion polymers of the present invention can be expressed with or without spacer amino acid linking groups. For example, in some embodiments, the polypeptides of the present invention can further comprise a linker between the first and the second amino acid sequence, wherein the linker comprises one or more amino acid residues separating the first and second sequences.

In another embodiment, the polypeptide of the present invention comprises the amino acid sequence set forth in SEQ ID NO:17, SEQ ID NO:18, SEQ ID NO:19, SEQ ID NO:20, SEQ ID NO:21, SEQ ID NO:22, SEQ ID NO:36, SEQ ID NO:38, or SEQ ID NO:39.

In one embodiment, the polypeptide is encoded by a nucleic acid molecule having the nucleotide sequence set forth in SEQ ID NO:23, SEQ ID NO:24, SEQ ID NO:25, SEQ ID NO:26, SEQ ID NO:27, SEQ ID NO:28, SEQ ID NO:37, SEQ ID NO:42, or SEQ ID NO:43.

Variants of the sequences disclosed herein also are within the scope of the present invention. A variant of a polypeptide may refer to an amino acid sequence that is altered by one or more amino acids. The variant can have "conservative" changes, wherein a substituted amino acid has similar structural or chemical properties, e.g., replacement of leucine with isoleucine. Alternatively, a variant can have "non-conservative" changes, e.g., replacement of a glycine with a tryptophan. Analogous minor variation can also include amino acid deletion or insertion, or both. A particular form of a "variant" polypeptide is a "functionally equivalent" polypeptide, i.e., a polypeptide which exhibits substantially similar in vivo or in vitro activity and/or binding as the examples of the polypeptide of invention. Guidance in determining which amino acid residues can be substituted, inserted, or deleted without eliminating biological or immunological activity can be found using computer programs well-known in the art, for example, DNASTAR software (DNASTAR, Inc., Madison, Wis.). Further, specific guidance is provided below, including that provided within the cited references which are herein incorporated by reference.

In other embodiments, the specific positions of the named residues can vary somewhat while still being present in the polypeptide at structurally and functionally analogous positions (see Chang, Y., et al., *Biochemistry* 37:3258-3271 (1998).

Further, particular embodiments of the invention can be characterized functionally relative to a vWF polypeptide, or a fragment thereof, in terms of FVIII binding ability. In some embodiments, a polypeptide of the invention exhibits a binding capacity towards a FVIII that is less than, about equal to, or greater than the binding capacity of a reference vWF protein (e.g., a wild-type endogenous vWF), or a fragment thereof, that is capable of binding to a FVIII protein (e.g., a wild-type endogenous FVIII).

Thus, the invention includes such variations of the polypeptides disclosed herein. Such variants include deletions, insertions, inversions, repeats, and substitutions. Further guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, fragments, derivatives or analogs of the polypeptides of the present invention include fragments, derivatives or analogs having sequences that have, as compared to the polypeptides of the present invention, (i) one or more of the amino acid residues (e.g., 1, 3, 5, 8, 10, 15 or 20 residues) substituted with a conserved or non-conserved amino acid residue (preferably a conserved amino acid residue). Such substituted amino acid residues may or may not be one encoded by the genetic code; or (ii) one or more of the amino acid residues (e.g., 1, 3, 5, 8, 10, 15 or 20 residues) include a substituent group. In other embodiments, fragments, derivatives or analogs of a polypeptide of the present invention include the polypeptide of the present invention that is coupled with another compound, such as a compound to increase the half-life of the polypeptide (for example, polyethylene glycol), or that is one in which additional amino acids are fused to the polypeptide. Such fragments, derivatives and analogs are deemed to be within the scope of those skilled in the art from the teachings herein.

As indicated, changes are preferably of a minor nature, such as conservative amino acid substitutions that do not significantly affect the folding or FVIII binding capacity. Of course, the number of amino acid substitutions a skilled artisan would make depends on many factors, including those described above. In some embodiments, the number of substitutions for any given polypeptide will not be more than 50, 40, 30, 25, 20, 15, 10, 5, 3, 2, or 1.

Amino acids residues (of the polypeptides of the present invention) that are essential for binding to FVIII can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for binding to FVIII, e.g., as described herein. Sites that are critical for binding to FVIII can also be determined by structural analysis such as crystallization, nuclear magnetic resonance or photoaffinity labeling (Smith, et al., *J. Mol. Biol.* 224:399-904 (1992) and de Vos, et al. *Science* 255:306-312 (1992)).

In one embodiment, the recombinant polypeptide has an amino acid sequences that is at least 70%, 80%, 90%, 95%, 98%, or greater identical to any one of the amino acid sequences set forth herein.

In another embodiment, the first amino acid sequence is present in a vWF polypeptide comprising the amino acid sequence set forth in SEQ ID NO:29 or a variant or fragment thereof.

In other embodiments, the first amino acid sequence is present in a vWF polypeptide encoded by a nucleic acid sequence set forth in SEQ ID NO:30 or a variant or fragment thereof.

In other aspects, the present invention provides a recombinant vWF-Fc fusion protein, wherein the vWF portion of the fusion protein is a truncated vWF that lacks at least one domain of a mature full-length vWF polypeptide, wherein the fusion protein is capable of forming multimers that are capable of binding a FVIII protein. In one embodiment, the truncated vWF has domains D' and D3, with the proviso that the truncated vWF lacks domain A1, A2, A3, D4, B1, B2, B3, C1, C2, CK, or a combination thereof. In another embodiment, the truncated vWF has domains D', D3, and A1, with the proviso that the truncated vWF lacks domains A2, A3, D4, B1, B2, B3, C1, C2, and CK. In some embodiments, the truncated vWF has domains D', D3, A1, and A2, with the proviso that the truncated vWF lacks domains A3, D4, B1, B2, B3, C1, C2, and CK. In other embodiments, the truncated vWF has domains D', D3, A1, A2, and A3, with the proviso that the truncated vWF lacks domains D4, B1, B2, B3, C1, C2, and CK. In still further embodiments, the truncated vWF lacks domains D4, B1, B2, B3, C1, C2, and CK.

III. Nucleic Acids, Vectors, and Expression Systems

In other aspects, the present invention provides recombinant expression vectors for expression of the polypeptide comprising the first and the second amino acid sequences, and host cells transformed with the expression vectors. Any suitable expression system may be employed. The vectors comprise a first and a second DNA sequence encoding the first and the second amino acid sequences, respectively, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the encoding DNA sequence. Thus, a promoter nucleotide sequence is operably linked to the encoding DNA sequence if the promoter nucleotide sequence controls the transcription of the encoding DNA sequence. The ability to replicate in the desired host cells, usually conferred by an origin of replication, and a selection gene by which transformants are identified, may additionally be incorporated into the expression vector.

In still further embodiments, DNA sequences encoding appropriate signal peptides that may or may not be native to the first amino acid sequence can be incorporated into expression vectors. For example, a DNA sequence for a signal peptide (secretory leader) may be provided in frame to the first sequence so that the expressed polypeptide is initially translated as a fusion protein comprising the signal peptide. A signal peptide that is functional in the intended host cells enhances extracellular secretion of the polypeptide comprising the first and the second amino acid sequences. In some embodiments, the signal peptide is cleaved from the polypeptide upon secretion of the polypeptide from the cell. In other embodiments, appropriate signal peptides that are not native to the first amino acid sequence can be provided as an alternative to or in addition to a native signal sequence.

In some embodiments, the signal peptide has the amino acid sequence shown as SEQ ID NO:40.

Suitable host cells for expression of the polypeptides of the present invention include prokaryotes, yeast, filamentous fungi, or higher eukaryotic cells. Appropriate cloning and expression vectors for use with bacterial, fungal, yeast, and mammalian cellular hosts are described, for example, in Pouwels et al. Cloning Vectors: A Laboratory Manual, Elsevier, New York, (1985). Cell-free translation systems could also be employed to produce the polypeptides of the present invention using RNAs derived from DNA constructs.

Prokaryotes include gram negative or gram positive organisms, for example, *E. coli*. Suitable prokaryotic host cells for transformation include, for example, *E. coli, Bacillus subtilis, Salmonella typhimurium*, and various other species within the genera *Pseudomonas, Streptomyces*, and *Staphylococcus*.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Among vectors preferred for use in bacteria include e.g., pET24b or pET22b available from Novagen, Madison, Wis. (pET-24b(+) and pET-22b(+)=pET Expression System 24b (Cat. No. 69750) and 22b (Cat. No. 70765), respectively, EMD Biosciences, Inc., Novagen Brand, Madison, Wis.; see http://worldwideweb.emdbiosciences.com product information section regarding pET-24b and pET-22b for details regarding vector), pQE70, pQE60 and pQE-9, available from Qiagen Inc., Valencia, Calif.; pBS vectors, PHAGESCRIPT vectors, BLUESCRIPT vectors, pNH8A, pNH16a, pNH18A, pNH46A, available from Stratagene, LaJolla, Calif.; and ptrc99a, pKK223-3, pKK233-3, pDR540, pRIT5 available from Pharmacia (now Pfizer, Inc., New York, N.Y.). Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Bacterial promoters suitable for use in the present invention include the *E. coli* lacI and lacZ promoters, the T3 and T7 promoters, the gpt promoter, the lambda PR and PL promoters, and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter. For example, promoter sequences used for recombinant prokaryotic host cell expression vectors include, but are not limited to, β-lactamase (penicillinase), lactose promoter, tryptophan (trp) promoter system, and tac promoter (Maniatis, Molecular Cloning: A Laboratory Manual, Cold Spring Harbor Laboratory, 1982). A particularly useful prokaryotic host cell expression system employs a phage λPL promoter and a cI857ts thermolabile repressor sequence. Plasmid vectors available from the American Type Culture Collection which incorporate derivatives of the λPL promoter include plasmid pHUB2 (resident in *E. coli* strain JMB9 (ATCC 37092)) and pPLc28 (resident in *E. coli* RR1 (ATCC 53082)).

The polypeptides of the present invention also may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression include the glucose-repressible ADH2 promoter. Shuttle vectors replicable in both yeast and *E. coli* may be constructed by inserting DNA sequences from pBR322 for selection and replication in *E. coli* ($Amp^r$ gene and origin of replication) into the yeast vectors.

In some embodiments, the yeast α-factor leader sequence may be employed to direct secretion of the polypeptide. The α-factor leader sequence can be inserted between the promoter sequence and the structural gene sequence. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., Proc. Natl. Acad. Sci. USA 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 μ/ml adenine and 20 μg/ml uracil. Yeast host cells transformed by vectors containing ADH2 promoter sequence may be grown for inducing expression in a rich medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems also can be employed to express recombinant polypeptides. Baculovirus systems for production of heterologous proteins in insect cells are reviewed by Luckow et al., Bio/Technology 6:47 (1988). Established cell lines of mammalian origin also may be employed. Examples of suitable mammalian host cell lines include the COS-7 line of monkey kidney cells (ATCC CRL 1651), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al., EMBO J. 10:2821 (1991).

Other suitable cell lines include, but are not limited to, HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice and a number of other cell lines. Another suitable mammalian cell line is the CV-1 cell line. Normal diploid cells, cell strains derived from in vitro culture of primary tissue, as well as primary explants, are also suitable. Candidate cells may be genotypically deficient in the selection gene, or may contain a dominantly acting selection gene.

In some embodiments, introduction of a vector construct into the cultured host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology, 2$^{nd}$ Edition (1995).

For example, the host cells can be transformed with the one or more vectors carrying the DNA comprising a nucleotide sequence encoding the polypeptide of the present invention, e.g. by methods known in the art, and can then be cultured under suitable conditions if desired, with amplification of one or both introduced genes. The expressed polypeptide can then be recovered and purified from the culture medium (or from the cell, for example if expressed intracellularly) by methods known to one of skill in the art. In some embodiments, the expressed polypeptide can be prepared as a protein complex, e.g. as a homodimer by virtue of one or more inter-chain disulfide bonds between two separate polypeptides with or without the FVIII.

Transcriptional and translational control sequences for mammalian host cell expression vectors may derive from viral genomes. Commonly used promoter sequences and enhancer sequences are derived from Polyoma virus, Adenovirus 2, Simian Virus 40 (SV40), and cytomegalovirus (CMV). DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication.

Vectors suitable for replication in mammalian cells can include viral replicons, or sequences that ensure integration of the sequence encoding the polypeptide into the host genome. Suitable vectors can include, for example, those derived from simian virus SV40, retroviruses, bovine papilloma virus, vaccinia virus, and adenovirus. The components of the vectors, e.g. replicons, selection genes, enhancers, promoters, and the like, may be obtained from natural sources or synthesized by known procedures.

A suitable vector, for example, can be one derived from vaccinia viruses. In this case, the heterologous DNA is inserted into the vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker.

Thus, mammalian expression vectors can comprise one or more eukaryotic transcription units that are capable of expression in mammalian cells. For example, the transcription unit can comprise at least a promoter element to mediate transcription of foreign DNA sequences. In some embodiments, promoters for mammalian cells include viral promoters such as that from SV40, CMV, Rous sarcoma virus (RSV), adenovirus (ADV), and bovine papilloma virus (BPV).

The transcription unit also can comprise a termination sequence and poly(A) addition sequences operably linked to the sequence encoding the polypeptide. The transcription unit also can comprise an enhancer sequence for increasing expression.

Optionally, sequences that allow for amplification of the gene also can be included, as can sequences encoding selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin. Or, for example, the vector DNA can comprise all or part of the bovine papilloma virus genome and be carried in cell lines such as C127 mouse cells as a stable episomal element.

Non-limiting examples of expression vectors and systems for use in mammalian host cells can be constructed, e.g., as disclosed by Okayama et al., Mol. Cell. Biol. 3:280 (1983), Cosman et al., Mol. Immunol. 23:935 (1986) (system for stable high level expression of DNAs in C127 murine mammary epithelial cells), Cosman et al., Nature 312:768 (1984) (expression vector PMLSV N1/N4; ATCC 39890), EP-A-0367566, and U.S. Pat. No. 5,350,683, each of which is herein incorporated by reference for its teaching of expression vectors and/or systems. Vectors may be derived from retroviruses. In some embodiments, in place of the native signal sequence, a heterologous signal sequence may be included, such as the signal sequence for interleukin-7 (IL-7) described by, e.g., U.S. Pat. No. 4,965,195; the signal sequence for interleukin-2 receptor described by, e.g., Cosman et al., Nature 312:768 (1984); the interleukin-4 signal peptide described by, e.g., EP 367,566; the type I interleukin-1 receptor signal peptide described by, e.g., U.S. Pat. No. 4,968,607; and the type II interleukin-1 receptor signal peptide described by, e.g., EP 460,846, each of which is incorporated herein by reference for its teaching of signal sequences.

In one embodiment, the recombinant polypeptide can be prepared using the PER.C6® technology (Crucell, Holland, The Netherlands). Expression of recombinant proteins is disclosed by, e.g., U.S. Pat. No. 6,855,544, which is herein incorporated by reference for its teaching of methods and compositions for the production of recombinant proteins in a human cell line.

It is also contemplated that the polypeptides of the present invention can be prepared by solid phase synthetic methods. See Houghten, R. A., *Proc. Natl. Acad. Sci. USA* 82:5131-5135 (1985); and U.S. Pat. No. 4,631,211 to Houghten et al. (1986).

In other embodiments, the present invention also encompasses recombinant polypeptides comprising the first and the second amino acid sequences, wherein the polypetides are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques, including but not limited, to specific chemical cleavage by cyanogen bromide, trypsin, chymotrypsin, papain, *S. aureus* V8 protease, $NaBH_4$; acetylation, deamidation, formylation, methylation, oxidation, reduction; metabolic synthesis in the presence of tunicamycin; etc. Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition of an N-terminal methionine residue as a result of vectors and constructs adapted for expression of the recombinant polypeptides, for example for expression in prokaryotic cultured host cells.

In some embodiments, wherein insoluble polypeptides are isolated from a host cell (e.g. a prokaryotic host cell), the host cell can be exposed to a buffer of suitable ionic strength to solubilize most host proteins, but in which aggregated polypeptides of interest may be substantially insoluble, and disrupting the cells so as to release the inclusion bodies and make them available for recovery by, for example, centrifugation. This technique is known to one of ordinary skill in the art, and a variation is described, for example, in U.S. Pat. No. 4,511,503, which is incorporated by reference herein for its teaching of a method of solubilizing heterologous protein, produced in an insoluble refractile form in a recombinant host cell culture. Without being held to a particular theory, it is believed that expression of a recombinant protein, in e.g. *E. coli*, may result in the intracellular deposition of the recombinant protein in insoluble aggregates called inclusion bodies. Deposition of recombinant proteins in inclusion bodies can be advantageous both because the inclusion bodies accumulate highly purified recombinant protein and because protein sequestered in inclusion bodies is protected from the action of bacterial proteases.

Generally, host cells (e.g., *E. coli* cells) are harvested after an appropriate amount of growth and suspended in a suitable buffer prior to disruption by lysis using techniques such as, for example, mechanical methods (e.g., sonic oscillator) or by chemical or enzymatic methods. Examples of chemical or enzymatic methods of cell disruption include spheroplasting, which comprises the use of lysozyme to lyse bacterial wall, and osmotic shock, which involves treatment of viable cells with a solution of high tonicity and with a cold-water wash of low tonicity to release the polypeptides.

Following host cell disruption, the suspension is typically centrifuged to pellet the inclusion bodies. The resulting pellet contains substantially all of the insoluble polypeptide fraction, but if the cell disruption process is not complete, it may also contain intact cells or broken cell fragments. Completeness of cell disruption can be assayed by resuspending the pellet in a small amount of the same buffer solution and examining the suspension with a phase-contrast microscope. The presence of broken cell fragments or whole cells indicates that additional disruption is necessary to remove the fragments or cells and the associated non-refractile polypeptides. After such further disruption, if required, the suspension can be again centrifuged and the pellet recovered, resuspended, and analyzed. The process can be repeated until visual examination reveals the absence of broken cell fragments in the pelleted material or until further treatment fails to reduce the size of the resulting pellet. Once obtained from the solubilized inclusion bodies or at a later stage of purification, the polypeptide can be suitably refolded in a suitable refolding buffer such as those known in the art. The degree of any unfolding can be determined by chromatography including reversed phase-high performance liquid chromatography (RP-HPLC).

If the recombinantly expressed polypeptides of the present invention are not already in soluble form before they are to be refolded, they may be solubilized by incubation in a solubilization buffer comprising chaotropic agent (e.g., urea, guanidine) and reducing agent (e.g., glutathione, dithiothreitol (DTT), cysteine) in amounts necessary to substantially solubilize the polypeptides. This incubation takes place under conditions of polypeptide concentration, incubation time, and incubation temperature that will allow solubilization of the polypeptide to occur. Measurement of the degree of solubilization can be carried out by turbidity determination, by analyzing polypeptide fractionation between the supernatant and pellet after centrifugation on reduced SDS gels, by protein assay (e.g., the Bio-Rad protein assay kit), or by high performance liquid chromatography (HPLC).

The pH of the solubilization buffer can be alkaline, preferably at least about pH 7.5, with the preferred range being about pH 7.5 to about pH 11. The concentration of the polypeptide of the present invention in the buffered solution for solubilization must be such that the polypeptide will be substantially solubilized and partially or fully reduced and denatured. Alternatively, the recombinant polypeptide may be initially insoluble. The exact amount to employ will depend, e.g., on the concentrations and types of other ingredients in the buffered solution, particularly the type and amount of reducing agent, the type and amount of chaotropic agent, and the pH of the buffer. For example, the concentration of recombinant polypeptide can be increased if the concentration of reducing agent, e.g., glutathione, is concurrently increased.

In still further embodiments, the present invention provides homogenous or substantially homogeneous polypeptides comprising the first and the second amino acid sequences. In one embodiment, the present invention provides an isolated polypeptide comprising the first amino acid sequence present in the vWF polypeptide and the second amino acid sequence heterologous to the first, wherein the polypeptide is capable of binding the FVIII. In other embodiments, the polypeptide is purified to substantial homogeneity, as indicated by a single protein band upon analysis by SDS-polyacrylamide gel electrophoresis (SDS-PAGE).

As the skilled artisan will recognize, procedures for purifying recombinant proteins will vary according to such factors as the type of host cells employed and whether or not the proteins are secreted into the culture medium. For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify the recombinantly expressed polypeptide. Some or all of the foregoing purification steps, in various combinations, can be employed to provide a substantially homogeneous recombinant protein.

In some embodiments, an affinity column comprising a binding partner of the structure or domain defined by the second amino acid sequence is employed to affinity-purify expressed recombinant polypeptides or protein complexes comprising them. For example, wherein the second amino acid sequence corresponds to an antibody Fc polypeptide, an affinity column comprising protein A or protein G can be used for affinity purification of the polypeptide or protein complexes comprising them. In some embodiments, bound polypeptides and/or complexes can be removed from an affinity column in a high salt elution buffer and then dialyzed into a lower salt buffer for use. By way of another example, the affinity column may comprise an antibody that binds the polypeptide or protein complexes comprising them, e.g., an antibody against the structure or domain defined by the first or the second amino acid sequence.

In other aspects, a nucleotide sequence encoding the polypeptide of the present is provided, wherein the polypeptide comprises a first amino acid sequence present in a vWF polypeptide and a second amino acid sequence heterologous to the first, wherein the polypeptide is capable of binding a FVIII. In one embodiment, the present invention provides an isolated nucleic acid molecule comprising the nucleotide sequence set forth in SEQ ID NO:23, SEQ ID NO:24, SEQ ID NO:25, SEQ ID NO:26, SEQ ID NO:27, SEQ ID NO:28, 37, 42, and 43.

The polynucleotides of the invention can include variants which have substitutions, deletions, and/or additions which can involve one or more nucleotides. The variants can be altered in coding regions, non-coding regions, or both. Alterations in the coding regions can produce conservative or non-conservative amino acid substitutions, deletions or additions. Especially preferred among these are silent substitutions, additions and deletions, which do not alter the properties and FVIII binding ability of the polypeptides of the present invention.

Further embodiments of the invention include nucleic acid molecules comprising a polynucleotide having a nucleotide sequence at least 90% identical, and more preferably at least 95%, 96%, 97%, 98% or 99% identical to (a) a nucleotide sequence encoding a polypeptide having the amino acid sequences set for herein; and (b) a nucleotide sequence complementary to any of the nucleotide sequences in (a) above.

By a polynucleotide having a nucleotide sequence at least, for example, 95% "identical" to a reference nucleotide sequence encoding a polypeptide is intended that the nucleotide sequence of the polynucleotide be identical to the reference sequence except that the polynucleotide sequence can include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

Two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An implementation of this algorithm for nucleic acid and peptide sequences is provided by the Genetics Computer Group (Madison, Wis.) in their BESTFIT utility application. The default parameters for this method are described in the Wisconsin Sequence Analysis Package Program Manual, Version 8 (1995) (available from Genetics Computer Group, Madison, Wis.).

For example, due to the degeneracy of the genetic code, one of ordinary skill in the art will recognize that a number of the nucleic acid molecules having a sequence at least 90%, 95%, 96%, 97%, 98%, or 99% identical to any one of the nucleic acid sequences described herein can encode the polypeptide.

In fact, because degenerate variants of these nucleotide sequences all encode the same polypeptide, this will be clear to the skilled artisan even without performing any functional assays or measurements described herein. It will be further recognized in the art that, for such nucleic acid molecules that are not degenerate variants, a reasonable number will also encode a polypeptide having FVIII binding capability. This is because the skilled artisan is fully aware of amino acid substitutions that are either less likely or not likely to significantly effect protein binding (e.g., replacing one aliphatic amino acid with a second aliphatic amino acid).

Recently, advances in the synthetic production of longer polynucleotide sequences have enabled the synthetic production of nucleic acids encoding significantly longer polypeptides without the use of traditional cloning techniques. Commercial providers of such services include Blue Heron, Inc., Bothell, Wash. (http://worldwideweb.blueheronbio.com). Technology utilized by Blue Heron, Inc. is described in U.S. Pat. Nos. 6,664,112; 6,623,928; 6,613,508; 6,444,422; 6,312,893; 4,652,639; U.S. Published Patent Application Nos. 20020119456A1; 20020077471A1; and Published International Patent Applications (Publications Nos) WO03054232A3; WO0194366A1; WO9727331A2; and WO9905322A1, all incorporated herein by reference.

Of course, traditional techniques of molecular biology, microbiology, and recombinant nucleic acid can also be used to produce the polynucleotides of the invention. These techniques are well known and are explained in, for example, Current Protocols in Molecular Biology, F. M. Ausebel, ed., Vols. I, II and III (1997); Sambrook et al., Molecular Cloning: A Laboratory Manual, 2$^{nd}$ Edition, Cold Spring Harbor Laboratory Press, Cold Spring Harbor, N.Y. (1989); DNA Cloning: A Practical Approach, D. N. Glover, ed., Vols. I and II (1985); Oligonucleotide Synthesis, M. L. Gait, ed. (1984); Nucleic Acid Hybridization, Hames and Higgins, eds. (1985); Transcription and Translation, Hames and Higgins, eds. (1984); Animal Cell Culture, R. I. Freshney, ed. (1986); Immobilized Cells and Enzymes, IRL Press (1986); Perbal, "A Practical Guide to Molecular Cloning"; the series, Methods in Enzymology, Academic Press, Inc. (1984); Gene Transfer Vectors for Mammalian Cells, J. H. Miller and M. P. Calos, eds., Cold Spring Harbor Laboratory (1987); and Methods in Enzymology, Wu and Grossman and Wu, eds., respectively, Vols. 154 and 155, all incorporated herein by reference.

Also provided, in other aspects, is an expression vector comprising the nucleic acid molecules encoding the polypeptides of the present invention. Host cells also are provided that express the polypeptides of the present invention. In one embodiment, the present invention provides a cell expressing a polypeptide comprising a first amino acid sequence present in a vWF polypeptide and a second amino acid sequence heterologous to the first, wherein the polypeptide is capable of binding a FVIII, wherein the cell further expresses the FVIII. In another embodiment, the FVIII is recombinant FVIII.

IV. Protein Complex

In another aspect, the present invention provides a protein complex comprising a polypeptide and a FVIII, wherein the polypeptide comprises a first amino acid sequence present in a vWF polypeptide and a second amino acid sequence heterologous to the first, wherein the polypeptide is capable of binding the FVIII. In one embodiment, the complex comprises two separate chains of the polypeptide in the form of a dimer in complex with the FVIII.

In another embodiment, the present invention provides for a homodimeric protein complex comprising two of the polypeptide chains of the present invention, wherein one or more disulfide bonds are formed between the chains. In one embodiment, one or more disulfide bonds form between the first amino acid sequences of two separate chains thereby creating a dimer In another embodiments, one or more disulfide bonds form between Fc regions of two separate chains thereby creating a dimer. In some embodiment, the homodimeric complex consists of or essentially consists of two of the polypeptide chains of the present invention. In still further embodiments, heterodimers also are within the scope of the present invention.

In another embodiment, the present invention provides oligomers, e.g. by further linking of the dimers. In some embodiments, differently sized oligomers are provided, preferably with formation of disulfide bridges at the amino-terminal ends of the polypeptides of the present invention. Thus, in other embodiments, differently sized oligomers ranging in size from a dimer of at least about: 100,000, 250,000, 500,000 daltons or more including large multimers of about: 5, 10, 20, 30, 40, or 50 million daltons or more are provided.

In still further embodiments, the oligomers are homo- or hetero-oligomers. In another embodiment, the dimer is a heterodimer.

In other embodiments, the protein complex is prepared from a cell or tissue culture expression system that expresses the polypeptide and the FVIII. In one embodiment, the polypeptide and the FVIII are co-expressed in the same cell.

In one embodiment, the present invention provides a soluble fusion protein comprising a first amino acid sequence fused to the N-terminus of an Fc polypeptide, wherein the first amino acid sequence is present in a vWF polypeptide, wherein the polypeptide is capable of binding a FVIII. In some embodiments, the polypeptide is capable of binding the FVIII as a dimer comprising two of the soluble fusion proteins joined by disulfide bonds.

In another embodiment, the present invention provides a dimer comprising two soluble fusion proteins joined by disulfide bonds, wherein each protein comprises a first amino acid sequence fused to the N-terminus of an Fc polypeptide, wherein the first amino acid sequence is present in a vWF polypeptide, wherein the dimer is capable of binding a FVIII.

In other aspects, the present invention provides a protein complex comprising disulfide-linked multimers comprising two or more of the polypeptide having the first and the second amino acid sequence.

In one embodiment, the disulfide-linked multimers are prepared by contacting the polypeptides with a vWF propeptide fragment whereby the vWF propeptide fragment acts in "trans" to direct the assembly of the disulfide-linked multimers.

In some embodiment, the vWF propeptide fragment comprises the amino acid sequence set forth in SEQ ID NO:31 or a variant thereof.

In another embodiment, the contacting comprises co-expressing the polypeptide with the vWF propeptide fragment.

For example, in one embodiment, the present invention provides a protein complex comprising disulfide-linked multimers comprising two or more of the polypeptide having the first and the second amino acid sequence, wherein the first amino acid sequence is set forth in SEQ ID NO:1, SEQ ID NO:4, or SEQ ID NO:7. In other embodiments, the first amino acid sequence is set forth in SEQ ID NO:3, SEQ ID NO:6, or SEQ ID NO:9. In some embodiments, the first amino acid sequence of the polypeptide is set forth in SEQ ID NO:17, SEQ ID NO:18, or SEQ ID NO:19. In another embodiment, the protein complex is prepared by co-expressing, using a recombinant expression system, the polypeptide with the vWF propeptide fragment comprising the amino acid sequence set forth in SEQ ID NO:31 whereby the fragment acts in "trans" to direct the assembly of disulfide-linked multimers comprising the polypeptides.

V. Methods

In still further aspects, the present invention provides a method for preparing a protein complex of the present invention. In some embodiments, an affinity column comprising a binding partner of the structure or domain defined by the second amino acid sequence is employed to affinity-purify the complex. For example, wherein the second amino acid sequence corresponds to an antibody Fc polypeptide, an affinity column comprising protein A or protein G can be used for affinity purification of the complex. In some embodiments, the binding partner is immobilized. Alternatively, the affinity column may comprise an antibody that binds the Fc portion of the polypeptide or that binds a structure or domain defined by the first amino acid sequence of the polypeptide. In some embodiments, the complex to be prepared comprises a dimer comprising two soluble fusion proteins joined by disulfide bonds, wherein each protein comprises a first amino acid sequence fused to the N-terminus of an Fc polypeptide, wherein the first amino acid sequence is present in a vWF polypeptide, wherein the dimer is capable of binding a FVIII.

In another embodiment, the complex further comprises FVIII bound to the dimer. FVIII can be removed/dissociated from the complex and, optionally, subjected to one or more additional purification steps to obtain partially pure, substantially pure, or pure FVIII.

In one aspect, the present invention provides a method for preparing a FVIII, the method comprising: contacting the FVIII with a polypeptide to form a protein complex comprising the FVIII and the polypeptide, wherein the polypeptide comprises a first amino acid sequence present in a vWF polypeptide and a second amino acid sequence heterologous to the first, wherein the polypeptide is capable of binding the FVIII to form the protein complex.

In one embodiment, the method further comprises selectively adhering the complex to a separation medium comprising a binding partner having affinity for a region or domain defined by the second amino acid sequence. In another embodiment, the second amino acid sequence corresponds to an immunoglobulin Fc region. In other embodiments, the binding partner is a protein A or a protein G. In one embodiment, the binding partner is an antibody. In some embodiments, the binding partner is an antibody against the immunoglobulin Fc region. In still further embodiments, the complex comprises two chains of the polypeptide in the form of a dimer, wherein the dimer is affinity-bound to the FVIII.

For immobilization of the binding partner, any number of different solid supports may be utilized. For example, the solid support material may be composed of polysaccharides, such as cellulose, starch, dextran, agar or agarose, or hydrophilic synthetic polymers, such as substituted or unsubstituted polyacrylamides, polymethacrylamides, polyacrylates, polymethacrylates, polyvinyl hydrophilic polymers, polystyrene, polysulfone or the like. Other suitable materials for use as the solid support material include porous mineral materials, such as silica, alumina, titania oxide, zirconia oxide and other ceramic structures. Alternatively, composite materials may be used as the solid support material. Such composite materials may be formed by the copolymerization of or by an interpenetrated network of two or more of the above-mentioned entities. Examples of suitable composite materials include polysaccharide-synthetic polymers and/or polysaccharide-mineral structures and/or synthetic polymer-mineral structures, such as are disclosed in U.S. Pat. Nos. 5,268,097, 5,234,991, and 5,075,371, each of which is herein incorporated by reference for its teaching of composite materials.

The solid support material of the present invention may take the form of beads or irregular particles ranging in size from about 0.1 mm to 1000 mm in diameter, fibers (hollow or otherwise) of any size, membranes, flat surfaces ranging in thickness from about 0.1 mm to 1 mm thick, and sponge-like materials with holes from a μm to several mm in diameter.

Preferably, the binding partners are chemically immobilized on the solid support material via a covalent bond framed between, e.g., a mercapto group of the binding partner and a reactive group present on the solid support. Reactive groups capable of reacting with the mercapto group of the present ligand include epoxy groups, tosylates, tresylates, halides and vinyl groups. Because many of the aforementioned solid support materials do not include one of the reactive groups recited above, bifunctional activating agents capable of both reacting with the solid support materials and providing the necessary reactive groups may be used. Examples of suitable activating agents include epichlorhydrin, epibromhydrin, dibromo- and dichloropropanol, dibromobutane, ethyleneglycol diglycidylether, butanediol diglycidylether, divinyl sulfone and the like.

Typical examples of suitable supports are Sepharose™, agarose, the resin activated-CH Sepharose™ 4B (N-hydroxysuccinimide containing agarose) from Pharmacia (Sweden), the resin NHS-activated Sepharose™ 4 Fast Flow (activated with 6-aminohexanoic acid to form active N-hydroxysuccinimide esters; Amersham Biosciences), the resin CNBr-activated Sepahrose™ Fast Flow (activated with cyanogen bromide; Amersham Biosciences) the resin PROTEIN PAK™ epoxy-activated affinity resin (Waters, USA), the resin EUPERGIT™ C30 N (Rohm & Haas, Germany), UltraLink Biosupport Medium (Pierce), Trisacryl GF-2000 (Pierce), or AFFI-GEL™ from BioRad (USA). Preferably, the support for affinity chromatography is preactivated with epoxyde groups for direct coupling to peptides and proteins.

The affinity chromatography resins useful for practicing the methods of the invention include, but are not limited to, any combination of ligand or compound described above with any of the supports described above. Non-limiting examples of specific affinity chromatography resins are Protein A-Sepharose™, Protein A-agarose, Protein A-agarose CL-4B, Protein G-Sepharose™, Protein G-agarose, Protein G-agarose CL-4B, Protein A/G agarose (various versions of all of the above are available from various manufacturers, e.g., Sigma-Aldrich, Amersham, and Pierce), Protein A Ultraflow™ (Sterogene), Protein A Cellthru™ 300 (Sterogene), QuickMab (Sterogene), QuickProtein A™ (Sterogene), Thruput™ and Thruput Plus (Sterogene), PROSEP-A or PROSEP-G (Millipore), and any variations of the above.

The methods used for the affinity chromatography can depend, at least in part, on the specific reagent used and are typically supplied by the manufacturer or known in the art. For example, the affinity chromatography reagent can be packed in a chromatographic column, equilibrated with a buffer capable of promoting an interaction between the protein complex and the binding partner, and then contacted with a composition comprising the complex. The column can then be washed with at least one solution capable of eluting the impurities without interfering with the interaction between the complex and the affinity ligand. The entire complex comprising the polypeptide and the FVIII can then be eluted using an appropriate eluent to obtain the complex. Alternatively, the FVIII can be dissociated from the complex whereby the complex remains bound to the binding partner.

For example, in a method for preparing a protein complex comprising the polypeptide (e.g., a dimer of the polypeptide) with or without the FVIII bound thereto, a composition comprising the complex can be contacted with at least one affinity chromatography resin that has Protein A as a ligand under conditions that allow binding of the complex to the resin. Desirably, the Protein A is a naturally occurring or a recombinant form of Protein A. The chromatography resin can then be washed with a series of wash buffers having increasing acidity (e.g. pH 7.0, 6.5, 6.0, 5.8, 5.5, 5.2, 5.0, 4.8, 4.6, 4.5, 4.4, or 4.0) such that the washing causes the dissociation of non-complex material from the resin but does not substantially dissociate the complex. The resin can be washed at least one time, preferably at least two times, and most preferably at least three times with wash buffers, where the first wash buffer has a pH of about 5.0 to 6.0, preferably about 5.2, and each subsequent wash buffer has a pH that is more acidic than the previous wash buffer. In preferred embodiments, the wash buffers will not dissociate more than 80%, 70%, 60%, 50%, 40%, 30%, 20%, 10%, or 5% of the complex from the resin.

In some embodiments, after washing the resin, the complex can be eluted from the chromatography resin using an eluent having an acidic pH of about 2.5 to 3.5 (e.g., pH 2.5, 3.0, 3.5) and being more acidic than any of the wash buffers. The eluate contains the purified, partially purified, or substantially purified complex with a preferred purity of at least 50%, 60%, 70%, 80%, 85%, 90%, or 95% or more.

In other embodiments, wherein the protein complex to be prepared comprises the FVIII bound to the dimeric form of the polypeptide, resin binding and washing conditions can be performed under conditions such that the FVIII remains affinity-bound to the dimer, which in turn can remain bound to the resin. Then, the FVIII can be separated from the resin-bound dimer to provide a composition comprising the FVIII, wherein the composition is partially, substantially, or completely free of the dimer.

Thus, in some embodiments, the polypeptide comprising the first and the second amino acid sequences can be employed for preparing FVIII by virtue of its ability to bind the FVIII to form a protein complex comprising the polypeptide and the FVIII. In some embodiments, such a protein complex can be subjected to affinity chromatography to prepare the complex and/or any FVIII associated therewith.

In other aspects, the present invention provides a composition comprising the FVIII, wherein the FVIII is prepared according to the methods described herein. Also provided are compositions comprising a protein complex comprising the polypeptide having the first and the second amino acid sequence, with or without FVIII bound to the polypeptide of the complex. In one embodiment, the composition comprises a protein complex comprising two of the polypeptides in the form of a dimer (e.g., homo- or hetero-dimer) bound with the FVIII.

Thus, in some aspects, the present invention provides compositions (e.g, truncated recombinant vWF fusion protein) and methods for enhancing expression of recombinant FVIII by mammalian cells by protecting it from removal and/or degradation, as well as to allow rapid chromatographic purification of the resulting FVIII:recombinant vWF complex by use of the fusion protein handle (e.g., the second amino acid sequence) incorporated into the recombinant vWF polypeptide of the present invention.

Accordingly, in various embodiments, a robust and simple method is provided for using a truncated version of vWF coupled to the Fc portion of immunoglobulin (e.g., immunoglobulin $G_1$) to complex with, and protect, FVIII during expression and production in a manner analogous to a complete vWF molecule. The unique approach described herein is more efficient at least because of the smaller size and easier expression of the vWF fusion polypeptides of the present invention, and/or (2) the ability to rapidly purify the FVIII: vWF fusion complex through the Fc region on the fusion protein, thus selectively enriching for the desired FVIII molecule with less contamination from other proteins as well as from vWF. In addition, the high-affinity binding of an Fc region provides that a FVIII:vWF fusion complex can also be removed in situ through an inline protein A cartridge, for example, in order to increase the yield and purity.

In one embodiment, the present invention provides a method using in-line purification during a perfusion process to continually purify the FVIII:recombinant vWF fusion complex through the selective affinity attachment of the vWF fusion Fc region to a protein A (or other similar) matrix.

The present invention, in some embodiments, takes advantage of at least two observations to create a superior method for FVIII purification: (a) using recombinant vWF polypeptides, in particular recombinant truncated vWF polypeptides that retain binding to FVIII but are significantly smaller than the full-length molecule, and (b) creating a fusion protein with the Fc region of an immunoglobulin (e.g., $IgG_1$) that binds with high affinity to the ligand, Protein A. This combination provides robust expression in mammalian cell systems while allowing a rapid method for collecting the FVIII: recvWF complex without regard to media or other components in the expression supernatant, as well as issues related to ionic strength, etc. It furthers allows a variety of reagents/solutions to be used to remove the FVIII while retaining full activity, and with superior recovery, of product. The high-affinity binding of the Fc portion to Protein A (or high-affinity antibody) column does not interfere with the FVIII:vWF interaction, as it is a separate and independent molecular entity.

In still further aspects, the present invention provides a method for recombinantly preparing the polypeptides of the present invention. In some embodiments, the method comprises: (a) generating a mammalian cell line by transforming the cell line with an expression vector encoding the polypeptide of the present invention; (b) growing the cell line under conditions sufficient for expressing the polypeptide; and (c) purifying the expressed protein from step (b) to obtain a vWF-Fc fusion protein, wherein the vWF portion of the fusion protein is a truncated vWF that lacks at least one domain of a mature full-length vWF polypeptide, wherein the fusion protein is capable of forming multimers that are capable of binding a FVIII protein. In one embodiment, the truncated vWF has domains D' and D3, with the proviso that the truncated vWF lacks domain A1, A2, A3, D4, B, C1, C2, CK, or a combination thereof In another embodiment, the truncated vWF has domains D', D3, and A1, with the proviso that the truncated vWF lacks domains A2, A3, D4, B, C1, C2, and CK. In some embodiments, the truncated vWF has domains D', D3, A1, and A2, with the proviso that the truncated vWF lacks domains A3, D4, B, C1, C2, and CK. In other embodiments, the truncated vWF has domains D', D3, A1, A2, and A3, with the proviso that the truncated vWF lacks domains D4, B, C1, C2, and CK. In still further embodiments, the truncated vWF lacks domains D4, B, C1, C2, and CK. In other embodiments, the method further comprises co-expressing a recombinant propeptide, wherein the vWF-Fc fusion protein is expressed as a recombinant fusion protein that further lacks a propeptide sequence, wherein the recombinant propeptide and the recombinant vWF-Fc fusion associate to form a propeptide/vWF-Fc complex following recombinant expression.

VI. Other Compositions and Methods

In other aspects, the present invention provides methods and compositions for FVIII having extended plasma half-life. For example, in some embodiments, the recombinant vWF-Fc fusion polypeptides of the present invention can be employed as an additive to a recombinant or a plasma-derived FVIII that may promote an extended half-life for the FVIII and/or combined complex. In accordance with the present invention, in some embodiments, the Fc region is fused to a truncated piece of vWF such that FVIII binding is provided and the Fc region further provides for additional half-life to the complex. For example, in one embodiment, the recombinant FVIII:recombinant vWF-Fc fusion complex can be either purified directly from expressed culture media, then injected (e.g., intravenously) into patients as a pharmaceutical formulation, e.g. with or without an excess of the recombinant vWF-Fc fusion (i.e., the polypeptide of the present invention). In some embodiments, supplementing the complex with excess vWF-Fc fusion (e.g., 2, 3, 4, 5, 6, 7, 8, 9, 10 fold or more on a mole basis) is provided in order to increase the fusion polypeptide concentration in plasma and provide for FVIII to re-bind to the vWF-Fc fusion protein, if it dissociates in the plasma.

In still further embodiments, the fusion polypeptides of the present invention can be formulated at high concentration with FVIII, administered to a human or non-human subject intravenously or by other routes thereby allowing the FVIII to be associated with vWF fusion protein during the course of its circulation and prior to cleavage by thrombin, released at the site of injury.

Accordingly, in some embodiments, the polypeptides of the present invention and/or protein complex comprising them, can be formulated for treatment. For example, the polypeptides and/or protein complexes of the present invention can be formulated according to known methods to prepare pharmaceutically useful compositions, preferably combined in admixture with a pharmaceutically acceptable carrier vehicle. Suitable vehicles and their formulation, inclusive of other human proteins, e.g. human serum albumin, are described for example in Remington's Pharmaceutical Sciences by E. W. Hartin, which is herein incorporated by reference. In one embodiment, such compositions will contain an effective amount of the FVIII protein in complex with a recombinant vWF polypeptide, together with a suitable amount of vehicle in order to prepare pharmaceutically acceptable compositions suitable for effective administration to a subject, for example parenterally administered to a subject suffering, e.g., from hemophilia A.

The average current dosage for the treatment of a hemophiliac varies with the severity of the bleeding episode. For example, the average doses administered intravenously may be in the range of: about 40 units per kilogram of FVIII for pre-operative indications, about 15 to about 20 units per kilogram for minor hemorrhaging, and about 20 to about 40 units per kilogram administered over an about 8-hour period for a maintenance dose. Other dosages and regimens can be readily determined by one of ordinary skill in the art of treating hemophiliacs.

VII. Kit

In still further aspects, kits comprising the polypeptides, nucleic acid sequences, protein complexes, and/or compositions of the present invention also are provided. The kits can have a single container, or they may have distinct container for each desired component. Kits comprising reagents necessary for preparing the recombinant polypeptides and/or the protein complexes derived therefrom also are contemplated, for example reagents such as, but not limited to, expression vectors, recombinant host cells comprising the expression vectors, and purification reagents. Further, wherein the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided.

The following examples are given only to illustrate the present process and are not given to limit the invention. One skilled in the art will appreciate that the examples given only illustrate that which is claimed and that the present invention is only limited in scope by the appended claims.

EXAMPLES

Example 1

Construction of Expression Plasmids for Truncated vWF-Fc Fusion Polypeptides Six DNA molecules, each having a nucleotide sequence that encodes a truncated vWF-Fc fusion polypeptide, were commercially synthesized (GENEART AG, Regensburg, Germany). The sequence identifiers for the nucleotide sequences of the DNA molecules and for the corresponding encoded amino acid sequences are shown in Table 1.

TABLE 1

Nucleotide and amino acid sequences for truncated vWF-Fc polypeptides.

| Polypeptide Name | Nucleotide Sequence | Amino Acid Sequence |
|---|---|---|
| D'-D3-Fc | SEQ ID NO: 37 | SEQ ID NO: 36 |
| Pro-D'-D3-Fc | SEQ ID NO: 24 | SEQ ID NO: 20 |
| D'-A1-Fc | SEQ ID NO: 42 | SEQ ID NO: 38 |
| Pro-D'-A1-Fc | SEQ ID NO: 28 | SEQ ID NO: 21 |
| D'-A3-Fc | SEQ ID NO: 43 | SEQ ID NO: 39 |
| Pro-D'-A3-Fc | SEQ ID NO: 23 | SEQ ID NO: 22 |

For each DNA molecule, the nucleotide sequence portion of the molecule encoding the truncated vWF region was codon-optimized using algorithms that account for codon usage, secondary structure, inhibitory sequences, and the like. The Fc DNA region of each molecule, which corresponds to the amino acid sequence shown in SEQ ID NO:16 and which is derived from $IgG_1$, was not subjected to sequence-optimization. Further, each DNA molecule contains a nucleotide sequence that encodes the signal peptide sequence shown as SEQ ID NO:40. SEQ ID NOs:20-22 additionally include the propeptide amino acid sequence shown as SEQ ID NO:41.

Restriction sites included in the synthetic genes were cleaved and re-cloned into the corresponding restriction sites in the plasmid expression vector pcDNA3002Neo (Crucell, Netherlands). Recombinant DNAs were prepared from clones by the SDS-alkaline lysis method according to commonly known protocols, e.g. as described by Sambrook et al., (1989) Molecular Cloning: A Laboratory Manual, CSH; Jones (1995) Gel Electrophoresis: Nucleic Acids Essential Techniques, Wiley. Restriction enzyme-digested DNAs were fractionated on 1% agarose gels to determine size and identity. Verification of plasmid clone sequences was performed by automated DNA sequencing using fluorescent deoxyribonucleotide primers (Applied Biosystems, Carlsbad, Calif.). The Prepared plasmid expression vector DNAs encoding the various truncated vWF-Fc constructs were each sterilized by a 70% ethanol wash after precipitation, and resuspended in sterile water to a final concentration of about 0.2 to about 1.0 micrograms per microliter.

Example 2

Electroporation of Expression Plasmids into PER.C6 Mammalian Cells

PER.C6 cells and cells of clonal line 078 (BDD-078 cells), which are PER.C6 cells expressing a B-domain-deleted FVIII (BDD-FVIII), were each maintained in continuous culture by routine (4 day) passaging in PER-MAb media (Hyclone, Logan, Utah). Forty-eight hours prior to electroporation, cells were refreshed by seeding cells at $1\times10^6$ cells/nil in fresh PER-MAb medium. On the day of the electroporation, $5\times10^6$ cells were resuspended into 100 microliters of Amaxa Nucleofector® Kit V Solution (Lonza Walkersville Inc., Walkersville, Md.).

For each electroporation, the cell suspension was mixed with about 2 to about 5 micrograms of expression plasmid DNA for expression of the polypeptides described in Table 1. The cell mixture was then transferred to the electroporation cuvette of an Amaxa Nucleofector® Device (Lonza Walkersville Inc., Walkersville, Md.); and a pre-set program X-001 was used to electroporate the DNA into cells. After electroporation, the cell suspension was transferred immediately into pre-warmed (37° C.) Mab media (SAFC Biosciences, Lenexa, Kans.) in the well of a 6-well plastic microplate. Cells were incubated without shaking in a humidified incubator chamber set at 37° C., with 5% $CO_2$ and 95% humidity.

After approximately 48 hours in culture, each electroporation reaction was removed from the 6-well microplate into a 125 culture flask with 20 ml of fresh MAb media (SAFC Bioscience, Lenexa, Kans.) containing appropriate selection antibiotic(s): Geneticin/G418 or Zeocin were used at final concentrations 125 or 100 micrograms/ml, respectively; Hygromycin was used at a final concentration of 50 micrograms/ml). Cells were then cultured at 37° C., in 5% $CO_2$ and 95% humidity without shaking. After 7-10 days, cells were then adapted to growth in PER-MAb media with shaking and routine passaging to prepare a polyclonal pool of transfected cells. Alternatively, selected cells were prepared for limited dilution cloning as described by, e.g., Harlow, E and Lane, D. (1988). Antibodies: A Laboratory Manual, pp. 116-117 and pp. 222-223. Cold Spring Harbor Laboratory Press, Cold Spring Harbor, N.Y. Cloned cells were checked regularly for growth and eventually were moved into shake flasks for expansion and growth as suspension cells in PER-MAb medium (Hyclone, Logan, Utah).

Example 3

Assays

FVIII: A commercial BDD-FVIII (a/k/a Xyntha®; Antihemophilic Factor (Recombinant)) (Wyeth (now a subsidiary of Pfizer Inc., New York, N.Y.)) protein was used as the standard for developing a robust linear assay using an enzyme-linked immunosorbent assay (ELISA). The capture antibody bound to the microplate wells was a commercial murine monoclonal antibody, namely clone GMA-012 (R8B12) (Green Mountain Antibodies, Inc., Burlington, Vt.), directed against the A2 domain of human FVIII; and the detection antibody was a commercial biotinylated sheep polyclonal antibody, namely SAF8C-APBIO, (Affinity Biologicals, Ontario, Canada) that recognizes human FVIII. Washing of microwells between antibody additions was done in the presence of Tris-buffered saline (TBS), pH 7.5. Colorimetric detection at 405 nm was by streptavidin-alkaline phosphatase mediated-cleavage of pNpp substrate. Alternatively, colorimetric FVIII unit activity determination was performed using a Beckman ACL Coagulation Analyzer, performed according to the manufacturer's specifications and using an internal plasma calibrator control, or by the Chromogenix Coatest SP4 FVIII kit (Diapharma Group, Columbus, Ohio) using a BDD-FVIII standard.

vWF: Research-grade plasma-derived vWF (Haemtech, Essex Junction, Vt.) was used as an antigen standard for ELISA measurements of protein content. The capture antibody used is a commercial murine monoclonal against human vWF protein; and for detection, an HRP-conjugated goat anti-human vWF antibody was used. Colorimetric detection at 450 nm is by incubation with the enzyme substrate, tetramethylbenzidine.

For the recombinant vWF-Fc fusion proteins, similar ELISA formats were used, such as capture of the Fc region by protein A or anti-human Fc antibody immobilized on a microplate, followed by detection with murine anti-human vWF polyclonal antibodies binding to the D'-D3, D'-A1 or D'-A3 domains of vWF, depending on the expression construct.

Example 3

Characterization of Truncated vWF-Fc Polypeptides

The recombinant polypeptides corresponding to the truncated vWF-Fc proteins (i.e., D'-D3-Fc, Pro-D'-D3-Fc, D'-A1-Fc, Pro-D'-A1-Fc, D'-A3-Fc, Pro-D'-A3-Fc; Table 1) that were expressed in PER.C6 cells were immunoprecipitated by incubation of 0.2-1 ml of cell supernatant with 20 microliters of protein G beads. Beads were concentrated by centrifugation, then washed with Tris buffer. Centrifuged beads were suspended in 25 microliters of Laemmli buffer and heated to 95° C. for 10 minutes before loading onto a 4-12% gradient Bis-Tris PAGE gel. Visualization of bands was by Coomassie Brilliant Blue staining/destaining.

For experiments involving either co-expression of BDD-FVIII and pro-D'-A3-Fc fusion or by mixing of commercial BDD-FVIII, Xyntha® (Wyeth), with PER.C6 cell supernatants expressing pro-D'-D3-Fc, samples eluted from affinity columns were electrophoretically separated on reducing and denaturing 7% NuPAGE Tris-acetate polyacrylamide gels, stained with Coomassie Blue dye, destained and photographed for comparison with known molecular weight markers run on the same gel.

Sequence Analysis

Recombinant polypeptides separated by polyacrylamide gel electrophoreses (PAGE) and were blotted onto PVDF membranes; protein bands visualized by rapid Ponceau S staining and de-staining were excised from the membranes in preparation for Edman degradation (AIBioTech, Richmond Va.) to yield N-terminal sequence information. The amino terminal sequences obtained were aligned with known sequences from either the mature N-terminus of vWF or from the N-terminal propeptide sequence that appeared in bands expected to represent incompletely processed vWF products.

In Vitro Association of BDD-FVIII and the Truncated vWF-Fc Proteins

Figure 8:
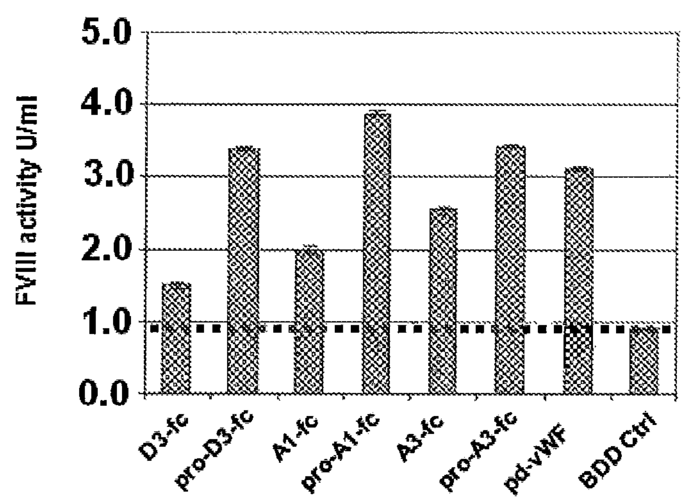
FIG. 8 is a bar chart showing recovered FVIII activity using vWF-Fc fusion proteins or plasma-derived vWF protein. The dashed bar indicates the increased recovery above the control (i.e., BDD-FVIII without added vWF proteins). Cell supernatants containing expressed, truncated vWF-Fc fusion proteins or full-length vWF were mixed with BDD-078 cells expressing recombinant FVIII. After two days, samples were analyzed for FVIII expression using a chromogenic FVIII assay.

Once cells expressing the D'-D3-Fc, Pro-D'-D3-Fc, D'-A1-Fc, Pro-D'-A1-Fc, D'-A3-Fc, and Pro-D'-A3-Fc proteins were selected and propagated, samples of cell supernatant were clarified and added to an actively-growing BDD-078 cells (a mammalian cell clone expressing B-domain-deleted FVIII). BDD-078 cells were seeded at $12.5\times10^6$ cells/ml with PER.C6 cell supernatants from cells transfected with the plasmid constructs for expression of the truncated vWF-Fc fusion proteins (i.e., D'-D3-Fc, Pro-D'-D3-Fc, D'-A1-Fc, Pro-D'-A1-Fc, D'-A3-Fc, Pro-D'-A3-Fc). For the "BDD Ctrl," conditioned medium was substituted. Cells were grown for 2 days with shaking at 37° C. as described. At that point, aliquots were removed, centrifuged and supernatants were tested for both FVIII activity as well as FVIII and vWF antigen. Only FVIII activity is shown in FIG. 8. The dash bar indicates the increase above the control BDD-FVIII without added vWF-Fc proteins.

Under normal conditions, the BDD-FVIII expressed from BDD-078 cells appeared to be catabolized or sequestered by the cells (Kalind et al., *J. Biotechnology,* 147:198-204 (2010)). However, addition of either plasma-derived vWF protein, or of supernatants of cells expressing one of the truncated vWF-Fc fusion proteins, resulted in higher recovery of FVIII activity, suggesting a protective effect against unwanted uptake or catabolism of FVIII by growing cells. This result demonstrates that the truncated vWF-Fc fusions can function to increase FVIII yield in culture. After 2 days in 37° C. culture with the expressed FVIII, aliquots were taken and evaluated for accumulation of FVIII activity. A substantial increase in recovered FVIII activity was observed (FIG. 8).

Multimer Analysis

Figure 9:
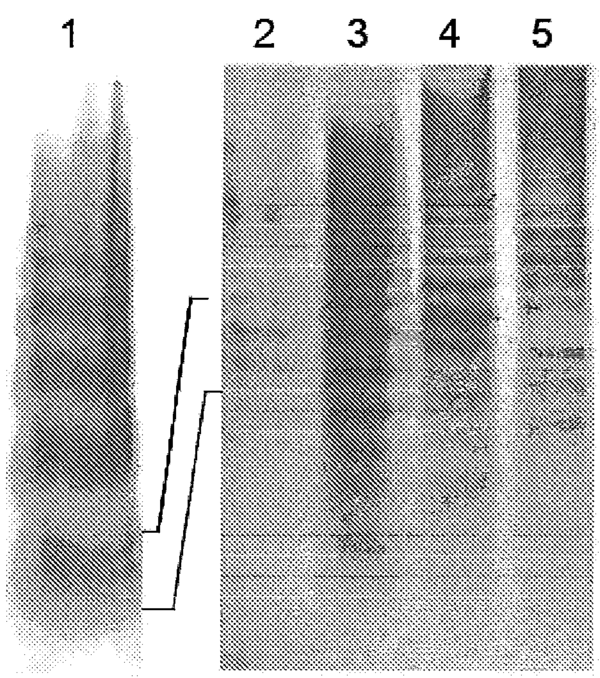
FIG. 9 is a gel showing multimerization of pro-vWF-Fc fusion proteins, with a comparison to normal, plasma-derived multimers of vWF. Plasma-derived factor VIII (Koate-DVI®) was run as a standard for multimerization on denaturing, but not reducing, 1.6% (lane 1) and 2% HGT(P) (lane2) agarose gels, while samples of pro-D'-D3-Fc (lane 3), pro-D'-A1-Fc (lane 4) and pro-D'-A3-Fc (lane 5) proteins were electrophoresed on 1.6% gels to visualize the differences in ladder sizes. Brackets identify the position of vWF dimer triplets in lane 1 and corresponding position in lane 2. As expected, the increasing sizer of the pro-vWF-Fc polypeptide chain results in creation of multimer bands of increasing molecular weight, in the order: pro-D'-D3-Fc<pro-D'-A1-Fc<pro-D'-A3-Fc.

Plasma-derived vWF (pd-vWF) and the recombinant polypeptides were evaluated for their ability to form high molecular weight complexes by electrophoretic analysis on non-reducing, 1.6 or 2% high-melting temperature (HGT-P) agarose gels (modified from Raines et al., *Thrombosis Res.,* 60:201-212 (1990), Plasma-derived FVIII (Koate-DVI®) was used as electrophoresis standard for evaluation of vWF-Fc multimers. Proteins were transferred by semi-dry blotting methods to nitrocellulose paper on an iBlot device (Invitrogen Corp., Rockville, Md.) and blocked using SuperBlock Solution (Pierce, Rockford, Ill.). Samples were incubated with a rabbit anti-human vWF polyclonal antibody (Abeam cat#ab6994) followed by an alkaline phosphatase-conjugated goat anti-rabbit IgG $F(ab')_2$ fragment (cat#A3937; Sigma); detection of bands was by incubation with Western Blue solution (Invitrogen Corp., Carlsbad, Calif.). A rinse in distilled water was used to quench the reaction; and bands were visualized on a BioRad Molecular Imager ChemiDoc $XRS^+$ Imaging System (Bio-Rad Laboratories Hercules, Calif.). The results are shown in FIG. 9.

Protein Purification and Chromatography on Protein A

Clarified supernatants from cell cultures expressing BDD-FVIII and pro-D'-A3-Fc protein were prepared by triple centrifugation and separation at 2,500×g for 7 minutes, followed by 2,500×g for 11 minutes. Supernatants were then filtered through a Sartobran 150 depth filter (0.45 micrometer), followed by a 0.2 micrometer, cellulose acetate filter (#5231307-H4-00) (Sartorius Stedim Stedim Biotech S.A., Aubagne, France). Filters were pre-wetted using a pump with 100-200 ml of 20 mM Tris, pH 7.0, followed by cell supernatant, and finally flushed with ca.25 ml of 20 mM Tris, pH 7.0. The final filtrate was two-fold-diluted cell supernatant and was the material used for column chromatography. Filtered supernatants were applied to a 5 or 10 milliliter Protein A-HiTrap column (part 17-1403-01) (GE Healthcare, Piscataway, N.J.) on an AKTA Explorer Chromatography System (GE Healthcare, Piscataway, N.J.). System tubing was pre-flushed with 20 mM Tris, pH 7.0, and the Protein A column was washed with five column volumes of 20 mM Tris, pH 7.0 to ensure a stable baseline before application of sample to the column. Filtered samples were run through the column at 5 milliliter/min, and the eluate was collected as "flow-through". Once all material was loaded, the Protein A-HiTrap column was additionally washed with five column volumes of 20 mM Tris, pH 7.0 until a stable baseline was achieved. At this point, the column was washed with four column volumes of 20 mM Tris, pH 7.0 containing 0.1 M $CaCl_2$ and eluted material was collected. The Factor VIII bound to the truncated vWF-Fc fusions was then eluted with 20 mM Tris, pH 7.0 containing 0.3 M $CaCl_2$ until the fraction eluted (approximately three column volumes). The column was then washed with five additional column volumes of 20 mM Tris, pH 7.0. The truncated vWF-Fc proteins remaining bound to protein A were stripped from the column by addition of 250 mM Glycine, 150 mM NaCl, pH 3.9. Alternative elution methods have been described, e.g., Arakawa et al., *Prot. Expr. Purif.,* 63:158-163 (2009). All collected samples from the Protein A-HiTrap column were saved, tested for Factor VIII activity using the chromogenic and/or clotting assay (described above) and aliquots were prepared for SDS-PAGE electrophoresis. In some cases, for example where FVIII peak activity was detected, the protein was loaded onto PD10 columns (GE Healthcare 45000148) that were pre-washed with 25 ml of desired FVIII storage buffer. Two and one-half milliliters of eluted BDD-FVIII was then applied to each column and the desalted BDD-FVIII was eluted with 3.5 ml FVIII storage buffer. Proteins were then placed at −80° C. for long-term storage; and, in some cases, serum albumin was added to 10 mg/ml.

Purification of FVIII from Pro-D'-A3-Fc/FVIII Binding Complex

Figure 10:
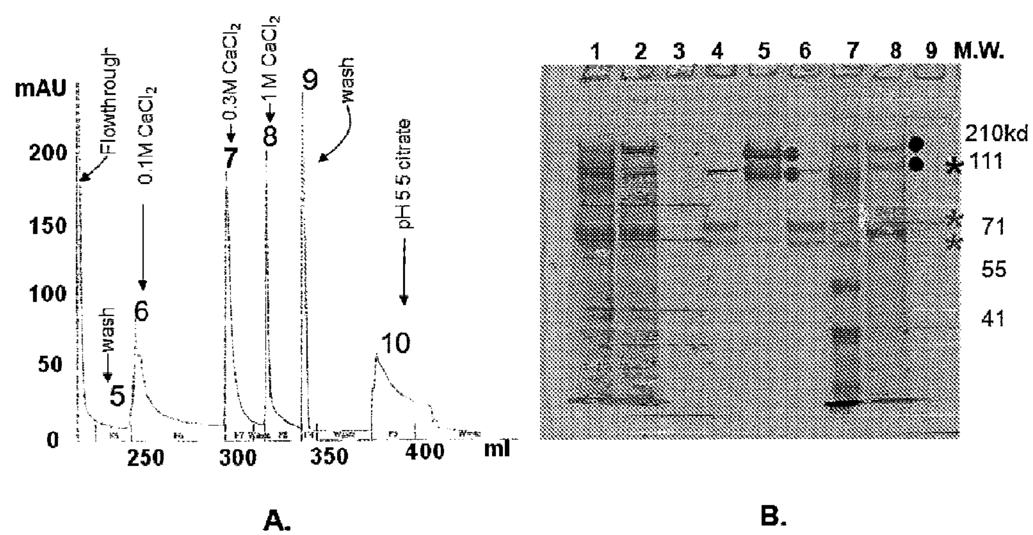
FIG. 10 shows purification of FVIII from supernatants containing pro-D'A3-Fc/FVIII complexes: (A) Chromatographic trace of peaks eluted during different buffer conditions; and (B) Coomassie-stained 7.5% PAGE gel with samples taken from the column trace represented in (A) shows the specific elution of FVIII from the pro-D'A3-Fc/FVIII complexes in lane 4. Lane Lanes 1-9 represent, respectively, (1) starting material, (2) flow-through, (3) 0.1M $CaCl_2$ eluate, (4) 0.3M $CaCl_2$ eluate, (5) pH 5.5 citrate eluate, (6) a concentrated BDD-FVIII preparation, (7) molecular weight markers (sizes on right side), (8) cell supernatant from pro-D'-A3-Fc expressing PER.C6 cells, (9) commercial BDD-FVIII (Xyntha®), asterisks showing three bands of approximately 170, 90, and 80 kd, corresponding to full-length BDD-FVIII, heavy chain and light chain(s), respectively.

To determine whether the truncated vWF-Fc polypeptides were capable of binding FVIII, cells co-expressing BDD-FVIII and pro-D'-A3-Fc were grown for 5 days in PER-MAb media with 125 micrograms/ml each of neomycin and zeocin. Supernatants were prepared and chromatographed substantially as described above. At various points during elution, samples were saved and electrophoresed (FIG. 10). In FIG. 10A, chromatographic trace of peaks eluted with different buffer conditions after application of 10 ml of BDD-FVIII/proD'A3-Fc PER.C6 cell supernatant onto a 5 ml HiTrap Protein A column is shown (step 5 is a wash step, step 6 is the eluate after 0.1 M $CaCl_2$, step 7 is the FVIII eluate after 0.3M $CaCl_2$ wash, step 8 is the eluate after 1 M $CaCl_2$ wash, step 9 is a low salt wash, and step 10 is the eluate after stripping the column with citrate, pH 5.5). FIG. 10B shows polyacrylamide gel electrophoresis of the elution samples. Lanes 1-9 represent, respectively, (1) starting material, (2) flow-through, (3) 0.1M $CaCl_2$ eluate, (4) 0.3M $CaCl_2$ eluate, (5) pH 5.5 citrate eluate, (6) a concentrated BDD-FVIII preparation, (7) molecular weight markers (sizes on right side), (8) cell supernatant from pro-D'-A3-Fc expressing PER.C6 cells, (9) commercial BDD-FVIII (Xyntha®), asterisks showing three bands of 170, 90, and 80 kd, corresponding to full-length BDD-FVIII, heavy chain and light chain(s), respectively.

Dots adjacent to bands in lanes 5 and 8 show migration of expected sizes for propeptide-containing proD'-A3-Fc and mature proD'-A3-Fc proteins (higher and lower molecular weights, respectively).

A substantially pure fraction of BDD-FVIII bound to pro-D'A3-Fc was captured on protein A matrix. The complex was stable to washing conditions before being separated and eluted from the vWF-Fc matrix only at the 0.3 M $CaCl_2$ elution step (FIG. 10A, step 7; and FIG. 10B, lane 4). The pro-D'-A3-Fc protein itself is only visualized by stripping the matrix under harsher washing conditions that included an acidic pH of 3.9 (FIG. 10A, step 10; and FIG. 10B, lane 5). The proteins eluted by the pH 3.9 wash co-migrate with a set of proteins that previously were prepared and identified as authentic truncated pro-D'-A3-Fc molecules (FIG. 10B, lane 8).

Purification of FVIII from D'-D3-Fc Binding Complex

Figure 11:
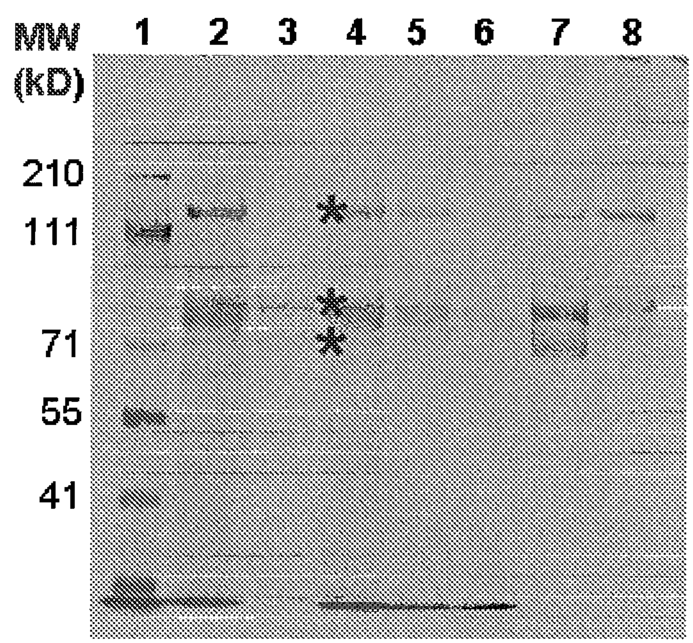
FIG. 11 shows purification of FVIII from supernatants containing commercial recombinant B-domain-deleted FVIII (Xyntha) with supernatant containing pro-D'D3-Fc protein After elution from gels with different buffer compositions, fractions were analyzed on 7% NuPAGE reducing/denaturing polyacrylamide gels and stained with Coomassie Brilliant Blue. Lane 7 shows essentially pure FVIII recovered after elution from pro-D'-D3-Fc/FVIII complexes bound to Protein A. Lanes 1-9 represent, respectively, (1) molecular weight polypeptide markers with molecular weights listed to the left, (2) pro-D'-D3-Fc cell supernatant, (3) commercial B-domain-deleted FVIII (Xyntha®), (4) Xyntha® mixed with pro-D'-D3 supernatant, (5) supernatant (pro-D'D3-Fc+ Xyntha®) load onto Protein A column, (6) flow-through wash with 20 mM Tris-HCl, pH 7.0, (7) 0.3M $CaCl_2$ eluate, and (8) pH 3.9 glycine wash that acts to strip the column of additional Protein A-binding proteins. The three asterisks in lane 3 align with proteins bands of approximately 170, 90, and 80 kd, corresponding to full-length BDD-FVIII, heavy chain and light chain(s), respectively.

A 10 ml solution of PER.C6 cell supernatant containing expressed pro-D'-D3-Fc protein (FIG. 11, lane 2) was added to 250 units of commercial BDD-FVIII (Xyntha®, lane 3) and incubated at 37° C. for 4 hours (lanes 4 and 5). The mixture was diluted two-fold with 20 mM Tris-HCl, pH 7.0 and applied to a 1 ml Protein A-HiTrap column, essentially as described for purification of FVIII from pro-D'-A3-Fc complexes above and shown in FIG. 10. Unbound proteins were washed off the column with 20 mM Tris-HCl, pH 7.0 (lane 6). There is clear retention of FVIII complexed with pro-D'-D3 protein, as seen by lack of FVIII and/or vWF-Fc polypeptides in FIG. 11, lane 6 (as compared to lane 7), followed by dramatic elution of FVIII (lane 7) with 0.3 M $CaCl_2$; this compares well with the FVIII eluted from FVIII/pro-D'-A3-Fc complexes (FIG. 10B, lane 4). Retained polypeptides representing truncated vWF-Fc are eluted with a low pH buffer, 0.1 M glycine, 0.15 M NaCl, pH 3.9 (FIG. 11, lane 8). The three asterisks in lane 3 align with proteins bands of approximately 170, 90, and 80 kd, corresponding to full-length BDD-FVIII, heavy chain and light chain(s), respectively. The results from pro-D'D3-Fc/FVIII purification demonstrate that addition of pro-D'D3-Fc with FVIII results in the capture, retention and subsequent specific elution of FVIII, with results virtually identical to those seen in FIG. 10

Pharmacokinetics

The purified recombinant vWF-Fc fusion proteins, bound to FVIII or as native protein, is injected intravenously into the tail vein of mice at ca. 5 micrograms/mouse in phosphate-buffered saline with a stabilizing agent, like albumin. As control articles, FVIII with/without vWF is similarly injected and evaluated for clearance in animals. Five to eight animals (either wild-type or having a bleeding disease due to genetic deficiency of either FVIII or vWF, or both) are used for examining blood loss. At different times points (e.g., 0 minutes, 3 min, 15 minutes, 30 minutes, 1 hr, 2 hr, 4 hr, 8 hr, 16 hr, 24 hr) post-injection, animals are sacrificed, blood is withdrawn through the inferior vena cava, and plasma is prepared and frozen. Plasma samples are then evaluated for antigen and/or functional activity by ELISA and/or chromogenic or clotting assays, respectively, depending on the genetic background of the animal. Plasma clearance is determined by pharmacokinetic analysis of antigen and/or activity vs. time (e.g. as described by Mordenti et al., Toxicol. Appl. Pharmacol., 137:75-78 (1996) and Lenting et al., J. Biol. Chem., 279:12102-12109 (2004), each of which is incorporated herein for its teaching of method for pharmacokinetic analysis), and by comparison with the control article.

I claim:

1. An isolated von Willebrand factor (vWF) polypeptide comprising a Factor VIII (FVIII) binding domain, with the proviso that the polypeptide lacks one of vWF domain A1, A2, A3, D4, B1, B2, B3, C1, C2, CK, or a combination thereof, wherein the polypeptide further comprises an immunoglobulin Fc amino acid sequence comprising at least a hinge region, wherein the polypeptide exhibits binding to the FVIII, wherein the Factor VIII (FVIII) binding domain comprises the amino acid sequence as set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:33, SEQ ID NO:34, or SEQ ID NO:35.

2. An isolated von Willebrand factor (vWF) polypeptide comprising a Factor VIII (FVIII) binding domain, with the proviso that the polypeptide lacks one of vWF domain A1, A2, A3, D4, B1, B2, B3, C1, C2, CK, or a combination thereof, wherein the polypeptide further comprises an immunoglobulin Fc amino acid sequence comprising at least a hinge region, wherein the polypeptide exhibits binding to the FVIII, wherein the polypeptide comprises the sequence set forth in SEQ ID NO:17, SEQ ID NO:18, SEQ ID NO:19, SEQ ID NO:20, SEQ ID NO:21, SEQ ID NO:22, SEQ ID NO:36, SEQ ID NO:38, or SEQ ID NO:39.

3. The polypeptide of claim 1, wherein the polypeptide is capable of forming a dimer.

4. The polypeptide of claim 1, wherein the immunoglobulin Fc amino acid sequence has the sequence set forth in SEQ ID NO:16.

5. A composition comprising the polypeptide of claim 1.

6. A protein complex comprising the polypeptide of claim 1 bound to the FVIII.

7. A composition comprising the protein complex of claim 6.

8. A cell expressing the polypeptide of claim 1.

9. A cell expressing the protein complex of claim 6.

10. A composition comprising the protein complex of claim 6, and a pharmaceutically acceptable carrier.

* * * * *